(12) United States Patent
Donovan et al.

(10) Patent No.: US 11,155,611 B2
(45) Date of Patent: Oct. 26, 2021

(54) COMPOSITIONS AND METHODS FOR MAKING AND USING ANTI-MYOSTATIN ANTIBODIES

(71) Applicant: Scholar Rock, Inc., Cambridge, MA (US)

(72) Inventors: Adriana Donovan, West Roxbury, MA (US); Stefan Wawersik, Westborough, MA (US); Yung Chyung, Lexington, MA (US); Micah Webster, Nashua, NH (US)

(73) Assignee: Scholar Rock, Inc., Cambridge, MA (US)

( * ) Notice: Subject to any disclaimer, the term of this patent is extended or adjusted under 35 U.S.C. 154(b) by 0 days.

(21) Appl. No.: 16/474,330

(22) PCT Filed: Jan. 5, 2018

(86) PCT No.: PCT/US2018/012686
§ 371 (c)(1),
(2) Date: Jun. 27, 2019

(87) PCT Pub. No.: WO2018/129395
PCT Pub. Date: Jul. 12, 2018

(65) Prior Publication Data
US 2019/0345239 A1 Nov. 14, 2019

Related U.S. Application Data

(60) Provisional application No. 62/608,069, filed on Dec. 20, 2017, provisional application No. 62/530,311, filed on Jul. 10, 2017, provisional application No. 62/443,455, filed on Jan. 6, 2017.

(30) Foreign Application Priority Data

Jan. 6, 2017 (EP) .................................. 17150586

(51) Int. Cl.
| | |
|---|---|
| *G01N 33/53* | (2006.01) |
| *G01N 33/50* | (2006.01) |
| *C07K 16/22* | (2006.01) |
| *A61K 39/395* | (2006.01) |
| *C12N 5/10* | (2006.01) |
| *C12N 5/00* | (2006.01) |
| *C12N 15/63* | (2006.01) |
| *A61P 21/00* | (2006.01) |
| *A61P 19/00* | (2006.01) |
| *A61P 25/00* | (2006.01) |

(52) U.S. Cl.
CPC .......... *C07K 16/22* (2013.01); *A61K 39/3955* (2013.01); *C12N 5/0018* (2013.01); *C12N 5/10* (2013.01); *C12N 15/63* (2013.01); *G01N 33/5023* (2013.01); *G01N 33/53* (2013.01); *A61P 19/00* (2018.01); *A61P 21/00* (2018.01); *A61P 25/00* (2018.01)

(58) Field of Classification Search
CPC ........ C07K 16/22; C07K 1/14; A61K 39/955; A61K 39/3955; C12N 5/10; C12N 15/63; G01N 33/33; G01N 33/5023
See application file for complete search history.

(56) References Cited

U.S. PATENT DOCUMENTS

| | | | |
|---|---|---|---|
| 6,096,506 A | 8/2000 | Lee et al. | |
| 6,656,475 B1 | 12/2003 | Lee et al. | |
| 6,858,208 B2 | 2/2005 | Lee et al. | |
| 7,138,501 B2 | 11/2006 | Ruben et al. | |
| 7,566,768 B1 | 7/2009 | Lee et al. | |
| 10,287,345 B2 | 5/2019 | Donovan et al. | |
| 10,307,480 B2 | 6/2019 | Straub et al. | |
| 10,751,413 B2 * | 8/2020 | Carven ................. | C07K 16/22 |
| 2002/0157126 A1 | 10/2002 | Lee et al. | |
| 2003/0167492 A1 | 9/2003 | Lee et al. | |
| 2005/0049402 A1 | 3/2005 | Babcook et al. | |
| 2005/0143306 A1 | 6/2005 | Junker et al. | |
| 2006/0216279 A1 | 9/2006 | Glass et al. | |
| 2007/0087000 A1 * | 4/2007 | Walsh ....................... | A61P 1/00 424/145.1 |
| 2007/0218067 A1 | 9/2007 | Buttner et al. | |
| 2008/0119426 A1 | 5/2008 | Dale | |
| 2008/0213251 A1 | 9/2008 | Sexton et al. | |
| 2009/0148436 A1 | 6/2009 | Lavallie et al. | |
| 2010/0080811 A1 | 4/2010 | Davies et al. | |
| 2010/0183616 A1 | 7/2010 | Green et al. | |
| 2010/0221777 A1 | 9/2010 | Choe et al. | |
| 2011/0165175 A1 | 7/2011 | Linhard et al. | |
| 2011/0239317 A1 | 9/2011 | Lee et al. | |

(Continued)

FOREIGN PATENT DOCUMENTS

| | | |
|---|---|---|
| AU | 2011244851 A1 | 11/2011 |
| EP | 2853898 A1 | 4/2015 |

(Continued)

OTHER PUBLICATIONS

Ferrara et al (2015. mAbs. 7(1): 32-41).*
Baranello et al., (2020) "Evaluation of body composition as a potential biomarker in spinal muscular atrophy", Muscle & Nerve, 61(4):530-534.
Burch et al., (2017) "Reduced serum myostatin concentrations associated with genetic muscle disease progression", Journal of Neurology, 264(3):541-553.
D'Ydewalle et al., (2015) "Spinal muscular atrophy therapeutics: where do we stand?", Neurotherapeutics 12(2):303-316.

(Continued)

*Primary Examiner* — Zachary C Howard
(74) *Attorney, Agent, or Firm* — Finnegan, Henderson, Farabow, Garrett & Dunner, LLP

(57) ABSTRACT

The present invention relates to antibodies, or antigen-binding fragments thereof, that specifically bind proMyostatin and/or latent Myostatin, and methods and uses thereof for treating metabolic diseases.

7 Claims, 39 Drawing Sheets

Specification includes a Sequence Listing.

(56) References Cited

U.S. PATENT DOCUMENTS

| | | |
|---|---|---|
| 2013/0209498 A1 | 8/2013 | Han et al. |
| 2013/0216548 A1 | 8/2013 | Neijssen et al. |
| 2013/0336982 A1 | 12/2013 | Mader et al. |
| 2014/0017262 A1 | 1/2014 | Sanicola-Nadel |
| 2014/0023638 A1 | 1/2014 | LaVallie et al. |
| 2017/0198032 A1 | 7/2017 | Donovan et al. |
| 2017/0333558 A1 | 11/2017 | Straub et al. |

FOREIGN PATENT DOCUMENTS

| | | |
|---|---|---|
| JP | 2017536354 | 12/2017 |
| WO | WO 1996/01845 A2 | 1/1996 |
| WO | WO 2002/009641 A2 | 2/2002 |
| WO | WO 2002/085306 A2 | 10/2002 |
| WO | WO 2003/027248 A2 | 4/2003 |
| WO | WO 2004/009776 A2 | 1/2004 |
| WO | WO 2004/024890 A2 | 3/2004 |
| WO | WO 2004/037861 A2 | 5/2004 |
| WO | WO 2005/066204 A2 | 7/2005 |
| WO | WO 2005/084699 A1 | 9/2005 |
| WO | WO 2005/103081 A2 | 11/2005 |
| WO | WO 2005/115439 A2 | 12/2005 |
| WO | WO 2006/116269 A2 | 11/2006 |
| WO | WO 2007/024535 A2 | 3/2007 |
| WO | WO 2007/044411 A3 | 4/2007 |
| WO | WO 2007/047112 A2 | 4/2007 |
| WO | WO 2007/061995 A2 | 5/2007 |
| WO | WO 2008/067480 A2 | 6/2008 |
| WO | WO 2008/119426 A1 | 10/2008 |
| WO | WO 2009/038760 A2 | 3/2009 |
| WO | WO 2010/070094 A1 | 6/2010 |
| WO | WO 2010/125003 A1 | 11/2010 |
| WO | WO 2010/144452 A1 | 12/2010 |
| WO | WO 2011/122011 A2 | 10/2011 |
| WO | WO 2011/150008 A1 | 12/2011 |
| WO | WO 20121024242 A1 | 2/2012 |
| WO | WO 2013/071056 A2 | 5/2013 |
| WO | WO 2013/072902 A1 | 5/2013 |
| WO | WO 2013/148284 A1 | 10/2013 |
| WO | WO 2013/165972 A2 | 11/2013 |
| WO | WO 2013/186719 A1 | 12/2013 |
| WO | WO 2014/074532 A2 | 5/2014 |
| WO | WO 2014/182676 A2 | 11/2014 |
| WO | WO 2015/070158 A1 | 5/2015 |
| WO | WO 2015/195094 A1 | 12/2015 |
| WO | WO 2016/073853 A1 | 5/2016 |
| WO | WO 2016/073879 A2 | 5/2016 |
| WO | WO 2016/073906 A2 | 5/2016 |
| WO | WO 2016/098357 A1 | 6/2016 |
| WO | WO 2016/168613 A1 | 10/2016 |
| WO | WO 2017/049011 A1 | 3/2017 |
| WO | WO 2017/120523 A2 | 7/2017 |
| WO | WO 2018/116201 A1 | 6/2018 |

OTHER PUBLICATIONS

Feng et al., (2016) "Pharmacologically induced mouse model of adult spinal muscular atrophy to evaluate effectiveness of therapeutics after disease onset", Human Molecular Genetics, 25(5):964-975.

Gonzalez et al., (2005) "BMP-1/Tolloid-like Metalloproteases Process Endorepellin, the Angiostatic C-terminal Fragment of Perlecan", The Journal of Biological Chemistry, 280(8):7080-7087.

Jiang et al., (2019) "Genomic analysis of a spinal muscular atrophy (SMA) discordant family identifies a novel mutation in TLL2, an activator of growth differentiation factor 8 (myostatin): a case report", BMC Medical Genetics, 20(1):204.

Kariya et al., (2014) "Requirement of enhanced Survival Motoneuron protein imposed during neuromuscular junction maturation", The Journal of Clinical Investigation, 124(2):785-800.

Latres et al., (2017) "Activin A more prominently regulates muscle mass in primates than does GDF8", Nature Communications, 8:15153.

Long et al., (2019) "Specific inhibition of myostatin activation is beneficial in mouse models of SMA therapy", Human Molecular Genetics, 28(7):1076-1089.

Mariot et al., (2017) "Downregulation of myostatin pathway in neuromuscular diseases may explain challenges of anti-myostatin therapeutic approaches", Nature Communications, 8(1):1859.

Pirruccello-Straub et al., (2018) "Blocking extracellular activation of myostatin as a strategy for treating muscle wasting", Scientific Reports, 8(1):2292.

Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pages).

Singapore Patent Application No. 11201805709R, filed Jan. 6, 2017, by Scholar Rock, Inc.: International Search Report and Written Opinion, dated Oct. 11, 2019 (12 pages).

Smith et al., (2013) "Myostatin inhibitors as therapies for muscle wasting associated with cancer and other disorders", Curr Opin Support Palliat Care, 7(4):352-360.

Sumner et al., (2009) "Inhibition of myostatin does not ameliorate disease features of severe spinal muscular atrophy mice", Human Molecular Genetics, 18(17):3145-3152.

Wang (2000) "Lyophilization and development of solid protein pharmaceuticals", International Journal of Pharmaceutics, 23(1-2):1-60.

Whittemore et al., (2003) "Inhibition of myostatin in adult mice increases skeletal muscle mass and strength", Biochemical and Biophysical Research Communications, 300(4):965-971.

Zhao et al., (2016) "Pharmacokinetics, pharmacodynamics, and efficacy of a small molecule SMN2 splicing modifier in mouse models of spinal muscular atrophy", Human Molecular Genetics, 25(10):1885-1899.

International Application No. PCT/US2018/012686, filed Jan. 5, 2018, by Scholar Rock, Inc., International Search Report and Written Opinion, dated Apr. 3, 2018.

Latres et al., (2015) "Myostatin blockade with a fully human monoclonal antibody induces muscle hypertrophy and reverses muscle atrophy in young and aged mice", Skeletal Muscle, Biomed Central Ltd., 5(1):34.

Szlama et al., (2013) "Latent myostatin has significant activity and this activity is controlled more efficiently by WFIKKN1 than by WFIKKN2", FEBS Journal, 280(16):3822-3839.

Anonymous (2017) SC 2. Anterolateral Systems—Deficits. Retrieved from the internet at: http://www.neuroanatomy.wisc.edu/sc97/text/p2/deficits.htm. Jul. 11, 2017 (1 page).

Anonymous (2019) "GDF-11/BMP-11 Mouse anti-Human, Clone: 743833, R&D Systems(TM)" [online]. Retrieved from: http://www.fishersci.co.uk/shop/products/gdf-11bpm-11-mouse-anti-human-clone-743833-r-d-systems/15724724; on Feb. 28, 2019 (4 pages).

Holzbaur et al., (2006) "Myostatin inhibition slows muscle atrophy in rodent models of amyotrophic lateral sclerosis", Neurobiol Dis., 23(3):697-707.

International Application No. PCT/US2016/043712, by Scholar Rock, Inc., International Search Report and Written Opinion, dated Jan. 13, 2017.

International Application No. PCT/US2017/012606, by Scholar Rock, Inc., International Search Report and Written Opinion, dated Jul. 24, 2017.

International Application No. PCT/US2017/012606, by Scholar Rock, Inc., Written Opinion dated Jan. 3, 2018 (18 pages).

International Application No. PCT/US2017/037332, by Scholar Rock, Inc., International Search Report and Written Opinion, dated Nov. 14, 2017.

International Application No. PCT/US2018/012686, by Scholar Rock, Inc., International Search Report and Written Opinion, dated Apr. 3, 2018.

International Preliminary Report on Patentability for Application No. PCT/US2015/059468, dated May 9, 2017 (12 pages).

International Preliminary Report on Patentability for Application No. PCT/US2016/052014, dated Mar. 29, 2018 (11 pages).

International Search Report and Written Opinion for Application No. PCT/US2016/052014, dated Jan. 9, 2017 (17 pages).

International Search Report for Application No. PCT/US2015/059468, dated Apr. 4, 2016 (6 pages).

(56) References Cited

OTHER PUBLICATIONS

International Search Report for Application No. PCT/US2015/059515, dated Mar. 25, 2016 (8 pages).

Loffredo et al., (2013) "Growth differentiation factor 11 is a circulating factor that reverses age-related cardiac hypertrophy", Cell, 153(4):828-839.

McPherron et al., (2010) "Metabolic Functions of Myostatin and GDF11", Immunol Endocr Metab Agents Med Chem., 10(4):217-231.

Morrison et al., (2009) "A soluble activin type IIB receptor improves function in a mouse model of amyotrophic lateral sclerosis", Exp Neurol, 217(2):258-268.

Mosler et al., (2012) "The anabolic steroid methandienone targets the hypothalamic-pituitary-testicular axis and myostatin signaling in a rat training model", Archives of Toxicology, 86(15):109-119.

Pandya et al., (2013) "Therapeutic neuroprotective agents for amyotrophic lateral sclerosis", Cell Mol Life Sci., 70(24):4729-4745.

Bräuninger et al., (2003) "Epstein-Barr virus (EBV)-positive lymphoproliferations in posttransplant patients show immunoglobulin V gene mutation patterns suggesting interference of EBV with normal B cell differentiation processes", Eur J Immunol., 33(6):1593-1602.

Breitbart et al., (2013) "Highly specific detection of myostatin prodomain by an immunoradiometric sandwich assay in serum of healthy individuals and patients", PLoS One, 8(11):e80454 (10 pages).

Brown et al., (1996) "Tolerance of single, but not multiple, amino acid replacements in antibody VH CDR 2: a means of minimizing B cell wastage from somatic hypermutation?", J Immunol., 156(9):3285-3291.

Ciciliot et al., (2013) "Muscle type and fiber type specificity in muscle wasting", Int J Biochem Cell Biol., 45(10):2191-2199.

Cohen et al., (2015) "Muscle wasting in disease: molecular mechanisms and promising therapies", Nat Rev Drug Discov., 14(1):58-74.

Dalbo et al., (2017) "Testosterone and trenbolone enanthate increase mature myostatin protein expression despite increasing skeletal muscle hypertrophy and satellite cell number in rodent muscle", Andrologia, 49(3):1-11.

Egerman et al., (2015) "GDF11 Increases with Age and Inhibits Skeletal Muscle Regeneration", Cell Metabolism, 22(1):164-174.

European Patent Application No. 16828657.3, by Scholar Rock, Inc: Supplementary European Search Report and Opinion, dated Mar. 20, 2019.

Ferrara et al., (2015) "Recombinant renewable polyclonal antibodies", MAbs, 7(1):32-41.

Ge et al., (2005) "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858.

Giangregorio et al., (2006) "Bone Loss and Muscle Atrophy in Spinal Cord Injury Epidemiology, Fracture Prediction, and Rehabilitation Strategies", J Spinal Cord Med., 29(5):489-500.

Graham et al., (2015) "A Soluble Myostatin Inhibitor Does Not Prevent Sublesional Muscle Atrophy 56 Days After Spinal Cord Injury in Mice", Medicine & Science in Sports & Exercise, Abstract No. 2219:587.

Guo et al., (2009) "Myostatin Inhibition in Muscle, but Not Adipose Tissue, Decreases Fat Mass and Improves Insulin Sensitivity", PLoS One, 4(3):e4937 (11 pages).

Pistilli et al., (2011) "Targeting Activin Type IIB Receptor to Improve Muscle Mass and Function in the mdx Mouse Model of Duchenne Muscular Dystrophy", Am J Pathol., 178(3):1287-1297.

Sgoutas et al., (1992) "Effect of Lyophilization on Determinations of Lipoprotein(a) in Serum", Clin Chem., 38(7)1355-1360.

Smith et al., (2015) "Myostatin Neutralization Results in Preservation of Muscle Mass and Strength in Preclinical Models of Tumor-Induced Muscle Wasting", Mol Cancer Ther., 14(7)1661-1670.

Suragani et al., (2014) "Transforming growth factor-β superfamily ligand trap ACE-536 corrects anemia by promoting late-stage erythropoiesis", Nature Medicine, 20(4):408-414.

Unknown (2000) American Spinal Injury Association (ASIA) Impairment Scale, Standard Neurological Classification of Spinal Cord Injury (2 pages).

Unknown (2013) "Myostatin Propeptide Human, Chicken Polyclonal Antibody", BioVendor, Research and Diagnostic Products, Data Sheet (2 pages).

Wintgens et al., (2012) "Plasma myostatin measured by a competitive ELISA using a highly specific antiserum", Clin Chim Acta., 413(15-16):1288-1294.

Wolfman et al., (2003) "Activation of latent myostatin by the BMP-1/tolloid family of metalloproteinases", Proc Natl Acad Sci U.S.A., 100(26):15842-15846.

Anderson et al., (2008) "Identification of a novel pool of extracellular pro myostatin in skeletal muscle", The Journal of Biological Chemistry, 283(11):7027-7035.

Australian Application No. 202010134, filed Jul. 27, 2020, for Scholar Rock, Inc.: Examination Report No. 1, dated Oct. 15, 2020.

Benatar (2007) "Lost in translation: Treatment trials in the SOD1 mouse and in human ALS", Neurobiology of Disease, 26:1-13.

Dibernardo et al., (2006) "Translating preclinical insights into effective human trials in ALS", Biochimica et Biophysica Acta, 1762:1139-1149.

Gogliotti et al., (2011) "Characterization of a commonly used mouse model of SMA reveals increased seizures susceptibility and heightened fear response in FVB/N mice", Neurobiol Dis. 43(1):142-151.

Liu et al., (2014) "The Smn-Independent Beneficial Effect of Trichostatin A on an Intermediate Mouse Model of Spinal Muscular Atrophy", PLOS ONE, 9(7):e101225. (9 pages).

Anonymous (2005) "Human Myostatin ELISA—Prodomain specific", Version 03151105, BioVendor Laboratory Medicine, Inc., XP055100354, Retrieved from the Internet: URL:http://deltaclon.es/pdf/RD193058100.pdf (10 pgs).

Biovendor (2013) Research and Diagnostics Products. Myostatin Propeptide Human, Chicken Polyclonal Antibody. Product Data Sheet (2 pgs.) Apr. 11, 2013.

Chen et al., (2016) "Considerations for Developing Combination Therapies in SMA" Cure SMA Researcher Meeting, Jun. 16, 2016 (57 pgs.).

Cully, M. (2014) Beefing up the right splice variant to treat spinal muscular atrophy, Nat Rev Drug Discov 13, 725. https://doi.org/10.1038/nrd4445 (1 pg.).

Dagbay et al., (2020) "Structural basis of specific inhibition of extracellular activation of pro- or latent myostatin by the monoclonal antibody SRK-015", J. Biol. Chem., 295(16):5404-5418.

Day et al., (2021) "Onasemnogene abeparvovec gene therapy for symptomatic infantile-onset spinal muscular atrophy in patients with two copies of SMN2 (STR1VE): an open-label, single-arm, multicentre, phase 3 trial", Lancet Neurol, 20:284-293.

European Patent Application No. 20179533.3, by Scholar Rock, Inc.: Partial European Search Report, dated Mar. 31, 2021 (12 pgs.).

European Patent Application No. 20193425.4, by Scholar Rock, Inc.: European Search Report, dated Apr. 1, 2021 (9 pgs.).

Farrar et al. (2017) "Emerging therapies and challenges in spinal muscular atrophy" Ann Neural 81(3): 355-368. Published online Feb. 17, 2017. doi: 10.1002/ana.24864. Publication details included.

Fidler (2016) "Scholar Rock Rolls Up $36M to Move Muscle Drug to Clinical Trials" https://xconomy.com/boston/2016/01/04/scholar-rock-rolls-up-36m-to-move-muscle-drug-to-clinical-trials/ ( 3 pgs.).

Heymsfield et al. (2021) "Effect of Bimagrumab vs Placebo on Body Fat Mass Among Adults With Type 2 Diabetes and Obesity: A Phase 2 Randomized Clinical Trial", Jan. 4, 2021;4(1):e2033457. doi: 10.1001/jamanetworkopen.2020.33457.

International Search Report for Application No. PCT/US2015/059557, dated May 19, 2016 (5 pgs.).

International Preliminary Report on Patentability for Application No. PCT/US2015/059468, dated May 9, 2017 (12 pgs.).

International Preliminary Report on Patentability for Application No. PCT/US2015/059515, dated May 9, 2017 (12 pgs.).

(56) References Cited

OTHER PUBLICATIONS

Japanese Patent Application No. 2019-517209, filed Jun. 13, 2017, by Scholar Rock, Inc., Decision to Grant a Patent, dated Dec. 8, 2020 (7 pgs).

Jarolim et al., (2013) "2013 AACC Annual Meeting Abstracts B-175 Determination of Cardiac Troponin with a Single-Molecule High-Sensitivity Assay and Outcomes in Patients with Stable Coronary Artery Disease: Analysis from PROVE IT-TIMI 22", XP055100559, Retrieved from the Internet: URL:http://www.aacc.org/events/Annual_Meeting/abstracts/Documents/AACC_13_AM_B175-13239.pdf (22 pgs).

Liu et al., (2016) "Activin Receptor Type 11B Inhibition Improves Muscle Phenotype and Function in a Mouse Model of Spinal Muscular Atrophy", PLoS One 11 (11): e0166803, published Nov. 21, 2016 (17 pgs.).

Muramatsu et al., (2021) "Novel myostatin-specific antibody enhances muscle strength in muscle disease models", Sci Rep, 11:2160, https://doi.org/10.1038/s41598-021-81669-8 (16 pgs).

Naryshkin et al. (2014) "SMN2 splicing modifiers improve motor function and longevity in mice with spinal muscular atrophy" Science, vol. 345, Issue 6197, pp. 688-693, DOI: 10.1126/science.1250127.

Ojala et al., (2021) "In Search of a Cure: The Development of Therapeutics to Alter the Progression of Spinal Muscular Atrophy", Brain Sci., 11:194 (39 pgs).

Opposition filed against EP Patent No. 3368069 on Apr. 28, 2021 (37pgs.).

Opposition filed against EP Patent No. 3368069 on May 4, 2021 (89 pgs.).

Reply to Examination Report dated Feb. 13, 2016 in EP Application No. 17732001.7, dated May 31, 2019 (3 pgs).

Request for early entry and processing of EP Application No. 17732001.7, on Jun. 1, 2018 (5 pgs).

Response to Communication dated Jul. 31, 2018 in EP Application No. 17732001.7, dated Dec. 10, 2018 (5 pgs).

Rodino-Klapac et al. (2009) "Inhibition of myostatin with emphasis on follistatin as a therapy for muscle disease" Muscle Nerve 39(3):283-96. doi: 10.1002/mus.21244.

Rose et al. (2009) "Delivery of recombinant follistatin lessens disease severity in a mouse model of spinal muscular atrophy" Hum Mol Genet. Mar. 15, 2009; 18(6): 997-1005, Published online Dec. 12, 2008. doi: 10.1093/hmg/ddn426.

Roth et al. (2004) "Myostatin: a therapeutic target for skeletal muscle wasting" Curr Opin Clin Nutr Metab Care 7(3):259-63. doi: 10.1097/00075197-200405000-00004.

Scholar Rock Announcement (2015) "Scholar Rock Presents First Data for Niche Modulator Inhibiting Myostatin Activation and Announces SRK-015 as Lead Drug Program" (1 pg.).

ScholarRock.com (2016) "Scholar Rock discovered SRK-015, a selective and local inhibitor or latent myostatin activation for the treatment of primary myopathies" (1 pg.).

Shorrock et al. (2016) "Development and Translation of Therapies for Spinal Muscular Atrophy" EMJ Neurol. 4(1):64-73.

SMA Annual Conference "The 2016 Annual SMA Conference is here", https://www.curesma.org/the-2016-annual-sma-conference-is-here/ (3 pgs.).

SMA Researcher Meeting Summary: The Changing Landscape of SMA 2016 (5 pgs).

SPINRAZA (Nusinersen) FDA label, Dec. 2016 (13 pgs.).

Sumner et al., (2016) "Spinal Muscular Atrophy, Disease Mechanisms and Therapy", First edition, Academic Press, Chapters 15, 16, 21, and 23. Publication details included (91 pgs.).

Sumner et al. (2016) "Spinal Muscular Atrophy, Disease Mechanisms and Therapy", Academic Press, pp. 6, 15-19 and 351-356. Publication details included (22 pgs).

Wagner (2020) "The elusive promise of myostatin inhibition for muscular dystrophy", Current Opinion in Neurology, 33(5):621-628.

Walker et al., (2016) "Biochemistry and Biology of GDF11 and Myostatin: similarities, differences and questions for future investigation", Cir. Res. 118(7): 1125-1142, published Apr. 1, 2016.

Walter et al., (2021) "Improving Care and Empowering Adults Living with SMA: A Call to Action in the New Treatment Era", Journal of Neuromuscular Diseases, DOI 10.3233/JND-200611 (9 pgs).

* cited by examiner

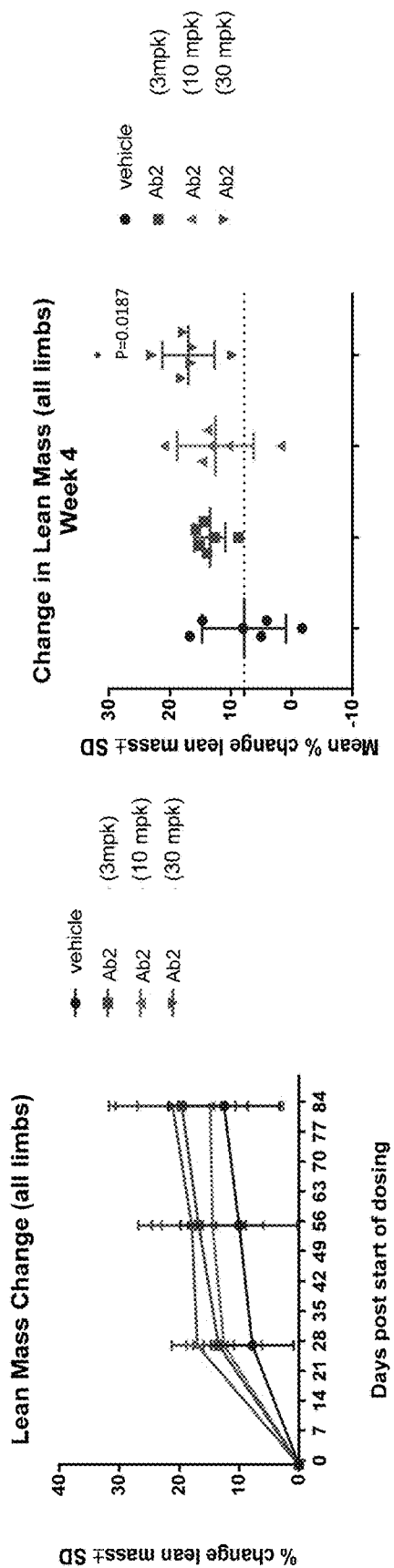
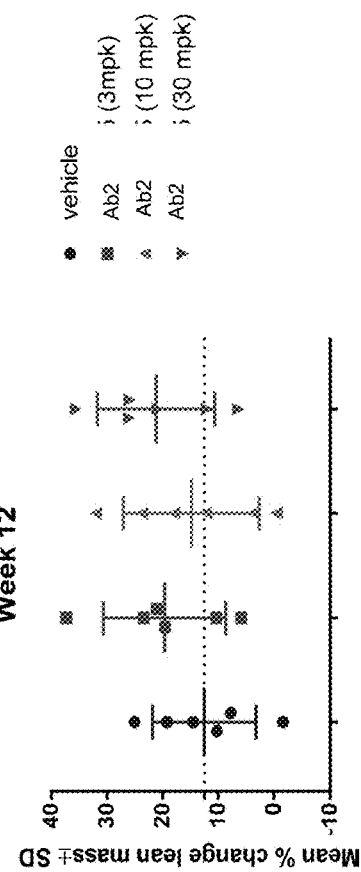
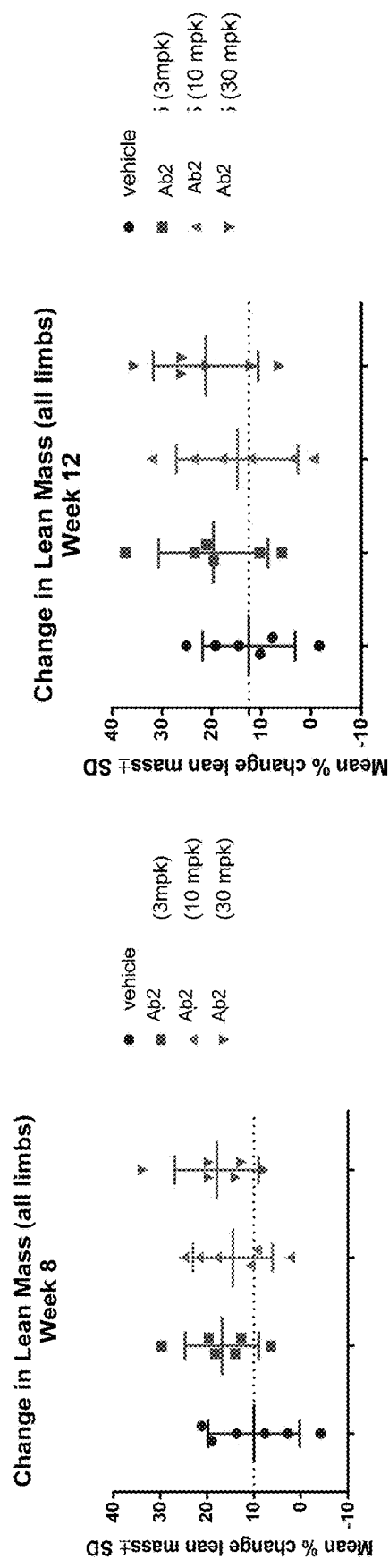
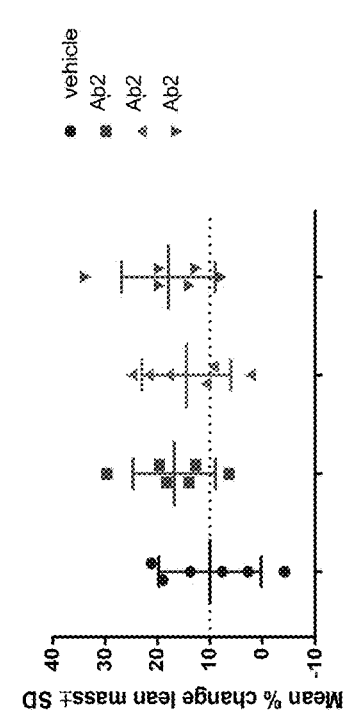
Figure 11A
Figure 11B
Figure 11C
Figure 11D \* = significance vs. vehicle

| Readouts | vehicle | Ab2 (3mpk) | Ab2 (10mpk) | Ab2 (30mpk) |
|---|---|---|---|---|
| Mean % change in lean mass @ 4 weeks | 7.8 | 13.5 | 12.6 | 17.0 |
| Mean % change in lean mass @ 8 weeks | 10.0 | 16.8 | 14.5 | 17.9 |
| Mean % change in lean mass @ 12 weeks | 12.5 | 19.6 | 14.8 | 21.2 |
| % difference in biceps weight vs. vehicle group | 0.0 | 18.0 | 13.0 | 25.5 |
| % difference in gastroc weight vs. vehicle group | 0.0 | 21.7 | 16.0 | 22.9 |

Tb.BV/TV = Trabecular bone volume/total volume
Tb.N = Trabecular Number
Tb.Th = Trabecular thickness
Tb.Sp = Trabecular spacing

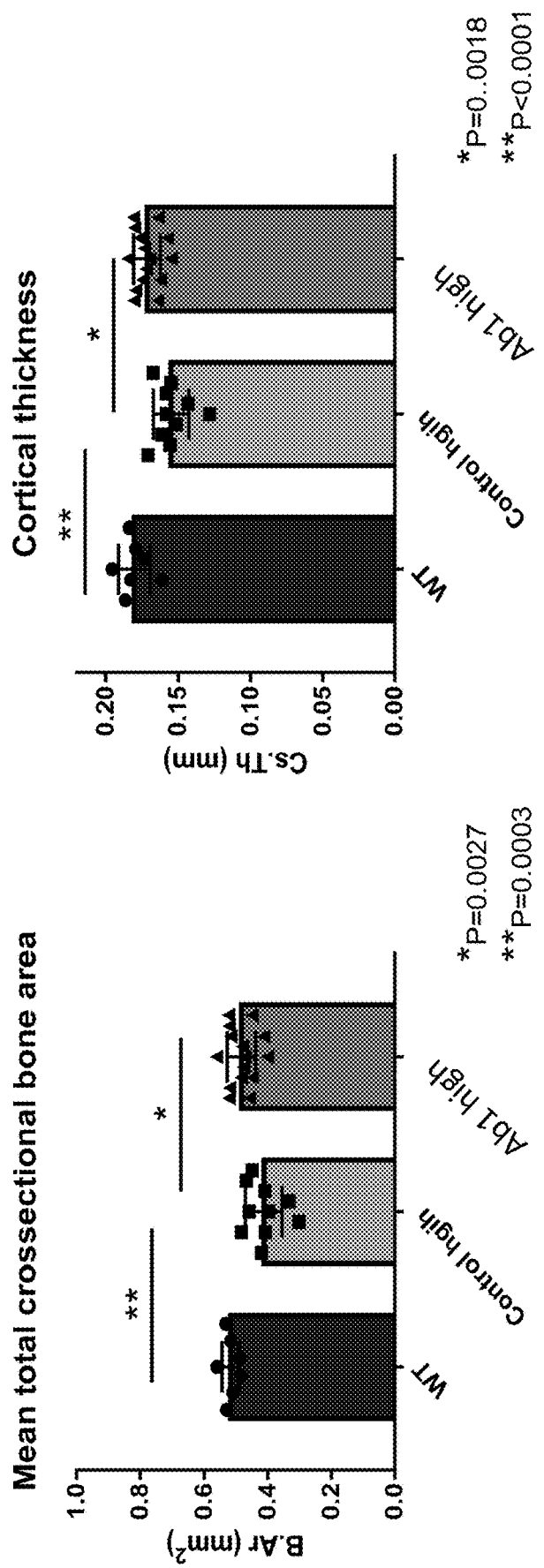
Figure 29 - Cortical Bone

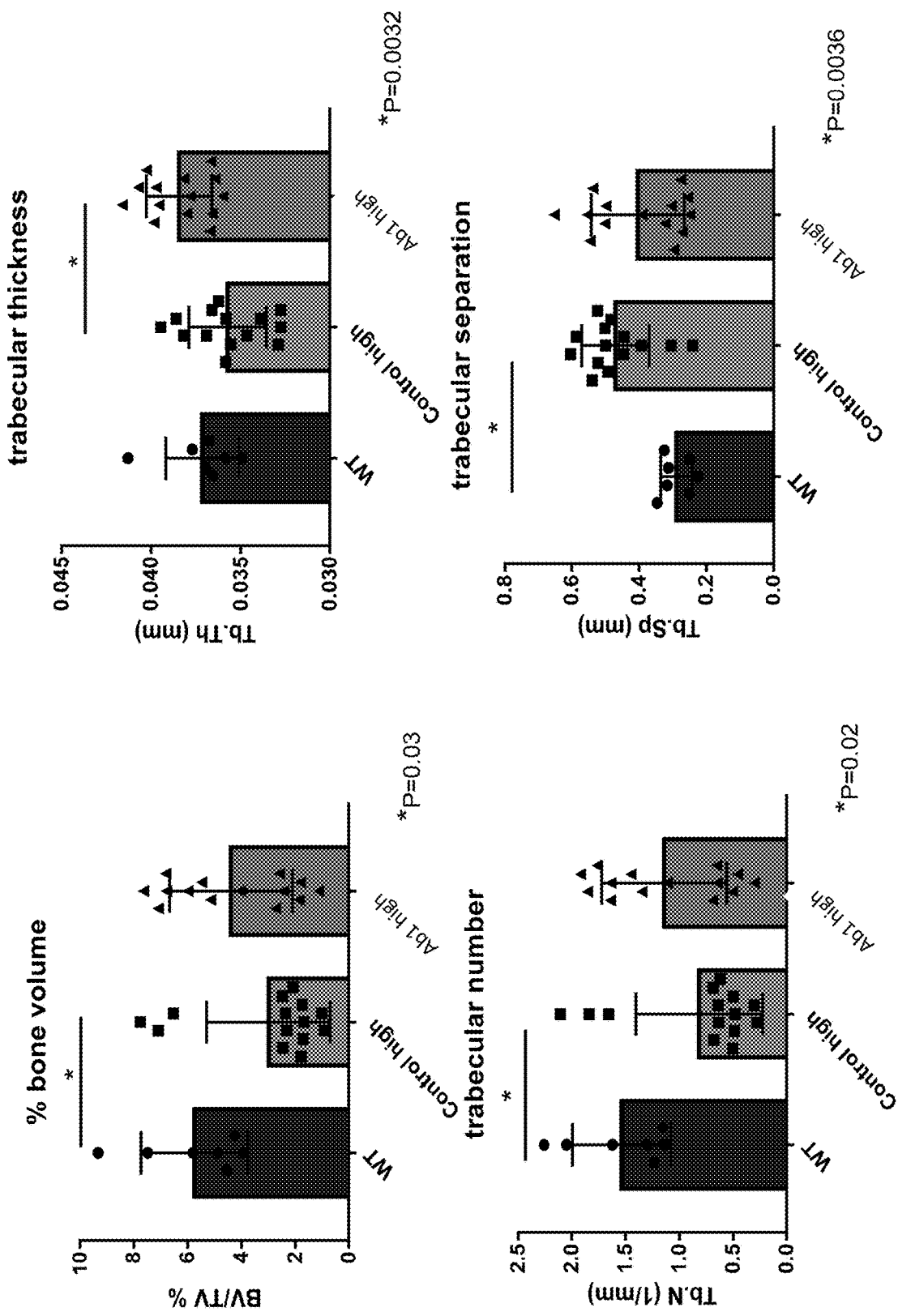

Ctrl High: SMA mice with high dose SMNC-1 + vehicle started at PND24, n = 15
Ctrl High + Ab1: SMA mice with high dose SMNC-1 + Ab1 started at PND24, n =15
WT: littermates, n = 16

Plantarflexor force

Masseter force

Ctrl High: SMA mice with high dose SMNC-1 + vehicle started at PND24, n = 14
Ctrl High + Ab1: SMA mice with high dose SMNC-1 + Ab1 started at PND24, n =15
WT: littermates, n = 16

SEQUENCE LISTING

```
<160> NUMBER OF SEQ ID NOS: 118

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Ser Ser Tyr Gly Met His
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Gly Phe Thr Phe Ser Ser Tyr Gly Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3
```

```
Gly Phe Ala Phe Ser Ser Tyr Gly Met His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 4

Val Ile Ser Tyr Asp Gly Ser Asn Lys Tyr Tyr Ala Asp Ser Val Lys
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Ile Ser Tyr Asp Gly Ser Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Val Ile Ser Tyr Asp Gly Ser Ile Lys Tyr Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Ile Ser Tyr Asp Gly Ser Ile
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 8

Val Ile Ser Tyr Asp Gly Asn Asn Lys Tyr Tyr Ala Asp Ser Val Lys
1               5                   10                  15

Gly

<210> SEQ ID NO 9
<211> LENGTH: 7
<212> TYPE: PRT
<213> ORGANISM: Artificial Sequence
```

<220> FEATURE:
<223> OTHER INFORMATION: Synthetic Polypeptide

<400> SEQUENCE: 9

Ile Ser Tyr Asp Gly Asn Asn
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Asp Leu Leu Val Arg Phe Leu Glu Trp Ser His Tyr Tyr Gly Met Asp
1               5                   10                  15

Val

<210> SEQ ID NO 11
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 11

Asp Leu Leu Val Arg Phe Leu Glu Trp Ser His Lys Tyr Gly Met Asp
1               5                   10                  15

Val

<210> SEQ ID NO 12
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 12

Ser Gly Ser Ser Ser Asn Ile Gly Ser Asn Thr Val His
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 13

Ser Ser Asn Ile Gly Ser Asn Thr
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 14

Ser Gly Ser Thr Ser Asn Ile Gly Ser Asn Thr Val His
1               5                   10

<210> SEQ ID NO 15

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Thr Ser Asn Ile Gly Ser Asn Thr
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 16

Ser Gly Ser Ser Ser Asn Ile Gly Gly Asn Thr Val His
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 17

Ser Ser Asn Ile Gly Gly Asn Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 18

Ser Asp Asn Gln Arg Pro Ser
1               5

<210> SEQ ID NO 19
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 19

Ser Asp Asn
1

<210> SEQ ID NO 20
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 20

Ser Asp Asp Gln Arg Pro Ser
1               5

<210> SEQ ID NO 21
<211> LENGTH: 3
```

```
<212> TYPE: PRT
<213> ORGANISM: Artificial Sequence
<220> FEATURE:
<223> OTHER INFORMATION: Synthetic Polypeptide

<400> SEQUENCE: 21

Ser Asp Asp
1

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

Ala Ala Trp Asp Asp Ser Leu Asn Gly Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 23

Ala Ala Trp Asp Glu Ser Leu Asn Gly Val
1               5                   10

<210> SEQ ID NO 24
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 24

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
        115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 25
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
            115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 26

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
            115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 28

Gln Ile Gln Leu Val Gln Ser Gly Gly Val Val Gln Pro Gly Arg
 1               5                  10                  15

Ser Leu Arg Leu Ser Cys Ala Ala Ser Gly Phe Ala Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Asn Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 29

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ala Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Asn Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Val Arg Phe Leu Glu Trp Ser His Lys Tyr Gly
            100                 105                 110
```

```
Met Asp Val Trp Gly Gln Gly Thr Thr Val Thr Val Ser Ser
            115                 120                 125
```

```
<210> SEQ ID NO 30
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 30

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu
            100                 105
```

```
<210> SEQ ID NO 31
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu
            100                 105
```

```
<210> SEQ ID NO 32
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 32

Gln Pro Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
```

```
                    20                  25                  30

Thr Val His Trp Tyr Gln Gln Leu Pro Gly Thr Ala Pro Lys Leu Leu
            35                  40                  45

Ile Tyr Ser Asp Asp Gln Arg Pro Ser Gly Val Pro Asp Arg Phe Ser
        50                  55                  60

Gly Ser Lys Ser Gly Thr Ser Ala Ser Leu Val Ile Ser Gly Leu Gln
 65                  70                  75                  80

Ser Asp Asp Glu Ala Asp Tyr Tyr Cys Ala Ala Trp Asp Glu Ser Leu
                    85                  90                  95

Asn Gly Val Phe Gly Gly Gly Thr Lys Leu Thr Val Leu
                100                 105

<210> SEQ ID NO 33
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 33

Gln Ser Val Leu Thr Gln Pro Pro Ser Ala Ser Gly Thr Pro Gly Gln
 1               5                  10                  15

Arg Val Thr Ile Ser Cys Ser Gly Ser Thr Ser Asn Ile Gly Ser Asn
                20                  25                  30

Thr Val His Trp Tyr Gln Gln Leu Pro Gly Thr Ala Pro Lys Leu Leu
            35                  40                  45

Ile Tyr Ser Asp Asp Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Glu Ser Leu
                    85                  90                  95

Asn Gly Val Phe Gly Gly Gly Thr Lys Leu Thr Val Leu
                100                 105

<210> SEQ ID NO 34
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 34

Gln Pro Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Gly Asn
                20                  25                  30

Thr Val His Trp Tyr Gln Gln Leu Pro Gly Thr Ala Pro Lys Leu Leu
            35                  40                  45

Ile Tyr Ser Asp Asp Gln Arg Pro Ser Gly Val Pro Asp Arg Phe Ser
        50                  55                  60

Gly Ser Lys Ser Gly Thr Ser Ala Ser Leu Val Ile Ser Gly Leu Gln
 65                  70                  75                  80

Ser Asp Asp Glu Ala Asp Tyr Tyr Cys Ala Ala Trp Asp Glu Ser Leu
                    85                  90                  95

Asn Gly Val Phe Gly Gly Gly Thr Lys Leu Thr Val Leu
                100                 105
```

```
<210> SEQ ID NO 35
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 36
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 37
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45
```

```
Ile Tyr Ser Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 38
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 38
cagatccagc tggtgcagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatcatatg atggaagtaa taatactat     180 gcagactccg tgaagggccg attcaccatc tccagagaca attccaagaa cacgctgtat     240
ctgcaaatga acagcctgag agccgaggac acggctgtgt attactgtgc gagagatctc     300
ctggtgcgat ttttggagtg gtcgcactac tacggtatgg acgtctgggg ccaagggacc     360
acggtcaccg tctcctca                                                  378

<210> SEQ ID NO 39
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 39
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatcatatg atggaagtaa taatactat     180 gcagactccg tgaagggccg attcaccatc tccagagaca attccaagaa cacgctgtat     240
ctgcaaatga acagcctgag agccgaggac acggctgtgt attactgtgc gagagatctc     300
ctggtgcgat ttttggagtg gtcgcactac tacggtatgg acgtctgggg ccaagggacc     360
acggtcaccg tctcctca                                                  378

<210> SEQ ID NO 40
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 40
cagatccagc tggtgcagtc tgggggaggc gtggtccagc ctggagggtc cctgagactc      60
tcctgtgcag cgtctggatt cgccttcagt agctatggca tgcactgggt ccgccaggct     120
ccaggcaagg ggctggagtg ggtggcagtt atatcatatg atggaagtat caatactat     180 gcagactccg tgaagggccg attcaccatc tccagagaca attccaagaa cacgctgtat     240
ctgcaaatga acagcctgag agccgaggac acggctgtgt attactgtgc gagagatctc     300
```
ctggtgcgat ttttggagtg gtcgcacaag tacggtatgg acgtctgggg ccaagggacc    360
acggtcaccg tctcctca                                                   378

<210> SEQ ID NO 41
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 41
caggtgcagc tggtggagtc tgggggaggc gtggtccagc ctgggaggtc cctgagactc    60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                   378

<210> SEQ ID NO 42
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 42
cagatccagc tggtgcagtc tgggggaggc gtggtccagc ctgggaggtc cctgagactc    60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                   378

<210> SEQ ID NO 43
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 43
caggtgcagc tggtggagtc tgggggaggc gtggtccagc ctgggaggtc cctgagactc    60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                   378

<210> SEQ ID NO 44

```
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 44
cagcctgtgc tgactcagcc accctcagcg tctgggaccc ccgggcagag ggtcaccatc      60
tcttgttctg gaagcagctc caacatcgga agtaatactg tccactggta ccagcaactc     120
ccaggaacgg cccccaaact cctcatctat agtgataatc agcgcccctc agggggtccct    180 gaccgattct ctggctccaa gtctggcacc tcagcctccc tggtcatcag tgggctccag     240
tctgacgatg aggctgatta ttactgtgca gcatgggatg acagcctgaa tggggtgttc     300
ggcggaggga ccaagctgac cgtccta                                         327

<210> SEQ ID NO 45
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 45
cagtctgtgc tgactcagcc accctcagcg tctgggaccc ccgggcagag ggtcaccatc      60
tcttgttctg gaagcagctc caacatcgga agtaatactg tccactggta ccagcaactc     120
ccaggaacgg cccccaaact cctcatctat agtgataatc agcgcccctc agggggtccct    180 gaccgattct ctggctccaa gtctggcacc tcagcctccc tggccatcag tgggctccag     240
tctgaggatg aggctgatta ttactgtgca gcatgggatg acagcctgaa tggggtgttc     300
ggcggaggga ccaagctgac cgtccta                                         327

<210> SEQ ID NO 46
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 46
cagcctgtgc tgactcagcc accctcagcg tctgggaccc ccgggcagag ggtcaccatc      60
tcttgttctg gaagcacctc caacatcgga agtaatactg tccagcaactc                120 ccaggaacgg cccccaaact cctcatctat agtgatgatc agcgcccctc agggggtccct    180 gaccgattct ctggctccaa gtctggcacc tcagcctccc tggtcatcag tgggctccag     240
tctgacgatg aggctgatta ttactgtgca gcatgggatg agagcctgaa tggggtgttc     300
ggcggaggga ccaagctgac cgtccta                                         327

<210> SEQ ID NO 47
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 47
cagtctgtgc tgactcagcc accctcagcg tctgggaccc ccgggcagag ggtcaccatc      60
tcttgttctg gaagcacctc caacatcgga agtaatactg tccactggta ccagcaactc     120
ccaggaacgg cccccaaact cctcatctat agtgatgatc agcgcccctc agggggtccct    180
```

```
gaccgattct ctggctccaa gtctggcacc tcagcctccc tggccatcag tgggctccag      240
tctgaggatg aggctgatta ttactgtgca gcatgggatg agagcctgaa tggggtgttc      300
ggcggaggga ccaagctgac cgtccta                                          327
```

<210> SEQ ID NO 48
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 48

```
cagcctgtgc tgactcagcc accctcagcg tctgggaccc ccgggcagag ggtcaccatc       60
tcttgttctg gaagcagctc caacatcgga ggaaatactg tccactggta ccagcaactc      120
ccaggaacgg cccccaaact cctcatctat agtgatgatc agcgcccctc aggggtccct      180
gaccgattct ctggctccaa gtctggcacc tcagcctccc tggtcatcag tgggctccag      240
tctgacgatg aggctgatta ttactgtgca gcatgggatg agagcctgaa tggggtgttc      300
ggcggaggga ccaagctgac cgtccta                                          327
```

<210> SEQ ID NO 49
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 49

```
cagtctgtgc tgactcagcc accctcagcg tctgggaccc ccgggcagag ggtcaccatc       60
tcttgttctg gaagcagctc caacatcgga ggaaatactg tccactggta ccagcaactc      120
ccaggaacgg cccccaaact cctcatctat agtgatgatc agcgcccctc aggggtccct      180
gaccgattct ctggctccaa gtctggcacc tcagcctccc tggccatcag tgggctccag      240
tctgaggatg aggctgatta ttactgtgca gcatgggatg agagcctgaa tggggtgttc      300
ggcggaggga ccaagctgac cgtccta                                          327
```

<210> SEQ ID NO 50
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Leu Leu Val Arg Phe Leu Glu Trp Ser His Tyr Tyr Gly
                100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450

<210> SEQ ID NO 51
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 51
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 52
<211> LENGTH: 352
<212> TYPE: PRT
<213> ORGANISM: Homo sapiens

<400> SEQUENCE: 52

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160
```

```
Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
                260                 265                 270

Asp Trp Ile Ile Ala Pro Lys Arg Tyr Lys Ala Asn Tyr Cys Ser Gly
            275                 280                 285

Glu Cys Glu Phe Val Phe Leu Gln Lys Tyr Pro His Thr His Leu Val
        290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
                340                 345                 350

<210> SEQ ID NO 53
<211> LENGTH: 352
<212> TYPE: PRT
<213> ORGANISM: Rattus rattus

<400> SEQUENCE: 53

Asn Glu Asp Ser Glu Arg Glu Ala Asn Val Glu Lys Glu Gly Leu Cys
1               5                   10                  15

Asn Ala Cys Ala Trp Arg Gln Asn Thr Arg Tyr Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Ala Ile Arg Gln Leu Leu Pro Arg Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Ala Asp Gly Lys Pro
                100                 105                 110

Lys Cys Cys Phe Phe Lys Phe Ser Ser Lys Ile Gln Tyr Asn Lys Val
            115                 120                 125

Val Lys Ala Gln Leu Trp Ile Tyr Leu Arg Ala Val Lys Thr Pro Thr
        130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
                165                 170                 175

Thr Gly Ile Trp Gln Ser Ile Asp Val Lys Thr Val Leu Gln Asn Trp
```

```
                180                 185                 190
Leu Lys Gln Pro Glu Ser Asn Leu Gly Ile Glu Ile Lys Ala Leu Asp
            195                 200                 205

Glu Asn Gly His Asp Leu Ala Val Thr Phe Pro Gly Pro Gly Glu Asp
        210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 54
<211> LENGTH: 352
<212> TYPE: PRT
<213> ORGANISM: Mus musculus

<400> SEQUENCE: 54

Asn Glu Gly Ser Glu Arg Glu Glu Asn Val Glu Lys Glu Gly Leu Cys
1               5                   10                  15

Asn Ala Cys Ala Trp Arg Gln Asn Thr Arg Tyr Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Ala Ile Arg Gln Leu Leu Pro Arg Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Ala Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Lys Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205
```

```
Glu Asn Gly His Asp Leu Ala Val Thr Phe Pro Gly Pro Gly Glu Asp
            210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
            275                 280                 285

Glu Cys Glu Phe Val Phe Leu Gln Lys Tyr Pro His Thr His Leu Val
290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 55
<211> LENGTH: 277
<212> TYPE: PRT
<213> ORGANISM: Macaca fascicularis

<400> SEQUENCE: 55

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
                20                  25                  30

Ile Lys Ile Gln Ile Leu Ser Lys Leu Arg Leu Glu Thr Ala Pro Asn
            35                  40                  45

Ile Ser Lys Asp Ala Ile Arg Gln Leu Leu Pro Lys Ala Pro Pro Leu
        50                  55                  60

Arg Glu Leu Ile Asp Gln Tyr Asp Val Gln Arg Asp Asp Ser Ser Asp
65                  70                  75                  80

Gly Ser Leu Glu Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
            210                 215                 220

Gly Leu Asn Pro Phe Leu Glu Val Lys Val Thr Asp Thr Pro Lys Arg
225                 230                 235                 240
```

```
Ser Arg Arg Asp Phe Gly Leu Asp Cys Asp Glu His Ser Thr Glu Ser
            245                 250                 255

Arg Cys Cys Arg Tyr Pro Leu Thr Val Asp Phe Glu Ala Phe Gly Trp
        260                 265                 270

Asp Trp Ile Ile Ala
        275

<210> SEQ ID NO 56
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 56

Arg Ser Arg Arg
1

<210> SEQ ID NO 57
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Arg Val Arg Arg
1

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Cys Pro Pro Cys Pro
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 59

His Tyr Tyr Gly Met Asp Val Trp Gly Gln Gly Thr Thr Val Thr Val
1               5                   10                  15

Ser

<210> SEQ ID NO 60
<211> LENGTH: 89
<212> TYPE: PRT
<213> ORGANISM: Artificial Sequence
<220> FEATURE:
<223> OTHER INFORMATION: Synthetic Polypeptide

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys
                85

<210> SEQ ID NO 61
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 61

Val Phe Gly Gly Gly Thr Lys Leu Thr Val Leu
1               5                   10

<210> SEQ ID NO 62
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 62

Pro Lys Ala Pro Pro Leu Arg Glu Leu Ile Asp Gln Tyr Asp Val Gln
1               5                   10                  15

Arg Asp Asp Ser Ser Asp Gly Ser Leu Glu Asp Asp Asp Tyr His Ala
            20                  25                  30

Thr

<210> SEQ ID NO 63
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 63

Gly Leu Asn Pro Phe Leu Glu Val Lys Val Thr Asp Thr Pro Lys Arg
1               5                   10                  15

Ser Arg Arg Asp Phe Gly Leu Asp Cys Asp Glu His Ser Thr Glu Ser
            20                  25                  30

Arg Cys

<210> SEQ ID NO 64
<211> LENGTH: 80
<212> TYPE: PRT
<213> ORGANISM: Artificial Sequence
<220> FEATURE:
<223> OTHER INFORMATION: Synthetic Polypeptide

<400> SEQUENCE: 64

Val Asp Leu Asn Glu Asn Ser Glu Gln Lys Glu Asn Val Glu Lys Glu
1               5                   10                  15

Gly Leu Cys Asn Ala Cys Thr Trp Arg Gln Asn Thr Lys Ser Ser Arg
            20                  25                  30

Ile Glu Ala Ile Lys Ile Gln Ile Leu Ser Lys Leu Arg Leu Glu Thr
```

```
              35                  40                  45
Ala Pro Asn Ile Ser Lys Asp Val Ile Arg Gln Leu Leu Pro Lys Ala
 50                  55                  60

Pro Pro Leu Arg Glu Leu Ile Asp Gln Tyr Asp Val Gln Arg Asp Asp
 65                  70                  75                  80

<210> SEQ ID NO 65
<211> LENGTH: 418
<212> TYPE: PRT
<213> ORGANISM: Artificial Sequence
<220> FEATURE:
<223> OTHER INFORMATION: Synthetic Polypeptide

<400> SEQUENCE: 65

Met Asp Met Arg Val Pro Ala Gln Leu Leu Gly Leu Leu Leu Leu Trp
  1               5                  10                  15

Phe Ser Gly Val Leu Gly Asp Tyr Lys Asp Asp Asp Asp Lys His His
                 20                  25                  30

His His His His Leu Glu Val Leu Phe Gln Gly Pro Ala Glu Gly Pro
             35                  40                  45

Ala Ala Ala Ala Ala Ala Ala Ala Ala Ala Ala Ala Gly Val Gly
 50                  55                  60

Gly Glu Arg Ser Ser Arg Pro Ala Pro Ser Val Ala Pro Glu Pro Asp
 65                  70                  75                  80

Gly Cys Pro Val Cys Val Trp Arg Gln His Ser Arg Glu Leu Arg Leu
                 85                  90                  95

Glu Ser Ile Lys Ser Gln Ile Leu Ser Lys Leu Arg Leu Lys Glu Ala
                100                 105                 110

Pro Asn Ile Ser Arg Glu Val Val Lys Gln Leu Leu Pro Lys Ala Pro
                115                 120                 125

Pro Leu Arg Glu Leu Ile Asp Gln Tyr Asp Val Gln Arg Asp Asp Ser
130                 135                 140

Ser Asp Gly Ser Leu Glu Asp Asp Tyr His Ala Thr Thr Glu Thr
145                 150                 155                 160

Ile Ile Thr Met Pro Thr Glu Ser Asp Phe Leu Met Gln Val Asp Gly
                165                 170                 175

Lys Pro Lys Cys Cys Phe Phe Lys Phe Ser Ser Lys Ile Gln Tyr Asn
                180                 185                 190

Lys Val Val Lys Ala Gln Leu Trp Ile Tyr Leu Arg Pro Val Glu Thr
            195                 200                 205

Pro Thr Thr Val Phe Val Gln Ile Leu Arg Leu Ile Lys Pro Met Lys
            210                 215                 220

Asp Gly Thr Arg Tyr Thr Gly Ile Arg Ser Leu Lys Leu Asp Met Asn
225                 230                 235                 240

Pro Gly Thr Gly Ile Trp Gln Ser Ile Asp Val Lys Thr Val Leu Gln
                245                 250                 255

Asn Trp Leu Lys Gln Pro Glu Ser Asn Leu Gly Ile Glu Ile Lys Ala
                260                 265                 270

Leu Asp Glu Asn Gly His Asp Leu Ala Val Thr Phe Pro Gly Pro Gly
            275                 280                 285

Glu Asp Gly Leu Asn Pro Phe Leu Glu Val Lys Val Thr Asp Thr Pro
            290                 295                 300

Lys Arg Ser Arg Arg Asn Leu Gly Leu Asp Cys Asp Glu His Ser Ser
305                 310                 315                 320

Glu Ser Arg Cys Cys Arg Tyr Pro Leu Thr Val Asp Phe Glu Ala Phe
```

```
                    325                 330                 335
Gly Trp Asp Trp Ile Ile Ala Pro Lys Arg Tyr Lys Ala Asn Tyr Cys
                340                 345                 350

Ser Gly Gln Cys Glu Tyr Met Phe Met Gln Lys Tyr Pro His Thr His
            355                 360                 365

Leu Val Gln Gln Ala Asn Pro Arg Gly Ser Ala Gly Pro Cys Cys Thr
        370                 375                 380

Pro Thr Lys Met Ser Pro Ile Asn Met Leu Tyr Phe Asn Asp Lys Gln
385                 390                 395                 400

Gln Ile Ile Tyr Gly Lys Ile Pro Gly Met Val Val Asp Arg Cys Gly
                405                 410                 415

Cys Ser

<210> SEQ ID NO 66
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 66

Ala Arg Asp Leu Leu Val Arg Phe Leu Glu Trp Ser His Tyr Tyr Gly
1               5                   10                  15

Met Asp Val

<210> SEQ ID NO 67
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 67

Ala Ala Trp Asp Asp Ser Leu Asn Gly Val
1               5                   10

<210> SEQ ID NO 68
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 68

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Gly Ser
```

<210> SEQ ID NO 69
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 69

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Ser Pro Ser Ser
        115                 120                 125
```

<210> SEQ ID NO 70
<211> LENGTH: 272
<212> TYPE: PRT
<213> ORGANISM: Artificial Sequence
<220> FEATURE:
<223> OTHER INFORMATION: Synthetic Polypeptide

<400> SEQUENCE: 70

```
Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Gly Ser
        115                 120                 125

Ala Ser Ala Pro Thr Leu Gly Gly Gly Ser Gly Gly Gly Gly Ser
    130                 135                 140

Ala Ala Ala Gln Pro Val Leu Thr Gln Pro Pro Ser Ala Ser Gly Thr
145                 150                 155                 160

Pro Gly Gln Arg Val Thr Ile Ser Cys Ser Gly Ser Ser Ser Asn Ile
                165                 170                 175
```

```
Gly Ser Asn Thr Val His Trp Tyr Gln Gln Leu Pro Gly Thr Ala Pro
                180                 185                 190

Lys Leu Leu Ile Tyr Ser Asp Asn Gln Arg Pro Ser Gly Val Pro Asp
            195                 200                 205

Arg Phe Ser Gly Ser Lys Ser Gly Thr Ser Ala Ser Leu Val Ile Ser
        210                 215                 220

Gly Leu Gln Ser Asp Asp Glu Ala Asp Tyr Tyr Cys Ala Ala Trp Asp
225                 230                 235                 240

Asp Ser Leu Asn Gly Val Phe Gly Gly Thr Lys Leu Thr Val Leu
                245                 250                 255

Gly Gln Pro Lys Ala Ala Pro Ser Val Thr Leu Phe Ser Pro Ser Ser
                260                 265                 270

<210> SEQ ID NO 71
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 71

Ala Arg Glu Ser Leu Ile Arg Phe Leu Glu Asp Pro Gln Gln Gly Gly
1               5                   10                  15

Met Asp Val

<210> SEQ ID NO 72
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 72

Asn Ser Trp Thr Arg Ser Asn Asn Tyr Ile
1               5                   10

<210> SEQ ID NO 73
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 73

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Leu Ile Arg Phe Leu Glu Asp Pro Gln Gln Gly Gly
            100                 105                 110

Met Asp Val Trp Gly Gln Gly Thr Thr Val Thr Val Ser Ser Gly Ser
        115                 120                 125
```

```
<210> SEQ ID NO 74
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 74

Gln Ser Ala Leu Thr Gln Pro Ala Ser Val Ser Gly Ser Pro Gly Gln
1               5                   10                  15

Ser Leu Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Ile Ile Tyr Asp Val Thr Asp Arg Pro Ser Gly Val Ser Gly Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Glu Tyr Phe Cys Asn Ser Trp Thr Arg Ser
                85                  90                  95

Asn Asn Tyr Ile Phe Gly Gly Gly Thr Lys Leu Thr Val Leu Gly Gln
            100                 105                 110

Pro Lys Ala Ala Pro Ser Val Thr Leu Phe Pro Pro Ser Ser
        115                 120                 125

<210> SEQ ID NO 75
<211> LENGTH: 273
<212> TYPE: PRT
<213> ORGANISM: Artificial Sequence
<220> FEATURE:
<223> OTHER INFORMATION: Synthetic Polypeptide

<400> SEQUENCE: 75

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Leu Ile Arg Phe Leu Glu Asp Pro Gln Gln Gly Gly
            100                 105                 110

Met Asp Val Trp Gly Gln Gly Thr Thr Val Thr Val Ser Ser Gly Ser
        115                 120                 125

Ala Ser Ala Pro Thr Leu Gly Gly Gly Ser Gly Gly Gly Gly Gly Ser
    130                 135                 140

Ala Ala Ala Gln Ser Ala Leu Thr Gln Pro Ala Ser Val Ser Gly Ser
145                 150                 155                 160

Pro Gly Gln Ser Leu Thr Ile Ser Cys Thr Gly Thr Ser Ser Asp Ile
                165                 170                 175

Gly Gly Tyr Asn Tyr Val Ser Trp Tyr Gln Gln His Pro Gly Lys Ala
```

```
                180                 185                 190
Pro Lys Leu Ile Ile Tyr Asp Val Thr Asp Arg Pro Ser Gly Val Ser
            195                 200                 205

Gly Arg Phe Ser Gly Ser Lys Ser Gly Asn Thr Ala Ser Leu Thr Ile
    210                 215                 220

Ser Gly Leu Gln Thr Glu Asp Glu Ala Glu Tyr Phe Cys Asn Ser Trp
225                 230                 235                 240

Thr Arg Ser Asn Asn Tyr Ile Phe Gly Gly Gly Thr Lys Leu Thr Val
                245                 250                 255

Leu Gly Gln Pro Lys Ala Ala Pro Ser Val Thr Leu Phe Pro Pro Ser
            260                 265                 270

Ser

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

Ala Arg Asp Arg Tyr Ser Ser Ser Trp Gly Gly Gly Phe Asp Tyr
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 77

Gln Ser Tyr Asp Ala Ser Ser Leu Trp Val
1               5                   10

<210> SEQ ID NO 78
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 78

Glu Val Gln Leu Val Gln Ser Gly Gly Gly Val Val Gln Ser Gly Arg
1               5                   10                  15

Ser Leu Arg Leu Ser Cys Val Ala Ser Gly Phe Ser Phe Ser Asn Tyr
            20                  25                  30

Gly Met His Trp Val Arg Gln Ala Pro Gly Lys Gly Leu Glu Trp Leu
        35                  40                  45

Ala Phe Ile Trp Tyr Asp Gly Ser Asn Lys Trp Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Ser Ser Trp Gly Gly Gly Phe Asp Tyr Trp
            100                 105                 110

Gly Gln Gly Thr Val Leu Thr Val Ser Ser Gly Ser
        115                 120
```

<210> SEQ ID NO 79
<211> LENGTH: 132
<212> TYPE: PRT
<213> ORGANISM: Artificial Sequence
<220> FEATURE:
<223> OTHER INFORMATION: Synthetic Polypeptide

<400> SEQUENCE: 79

```
Asn Phe Met Leu Thr Gln Pro His Ser Val Ser Glu Ser Pro Gly Arg
1               5                   10                  15

Thr Val Thr Ile Pro Cys Ser Gly Arg Gly Gly Ser Ile Ala Ser Asp
            20                  25                  30

Ser Val Gln Trp Tyr Gln Arg Pro Gly Ser Ala Pro Thr Thr Ile
        35                  40                  45

Ile Tyr Glu Asp Asn Gln Arg Pro Ser Gly Val Pro Asp Arg Phe Ser
    50                  55                  60

Gly Ser Val Asp Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Ala
                85                  90                  95

Ser Ser Leu Trp Val Phe Gly Gly Lys Thr Lys Leu Thr Val Leu Gly
            100                 105                 110

Gln Pro Lys Ala Ala Pro Ser Val Thr Leu Phe Pro Pro Ser Ser Lys
        115                 120                 125

Ala Ser Gly Ala
        130
```

<210> SEQ ID NO 80
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 80

```
Glu Val Gln Leu Val Gln Ser Gly Gly Gly Val Val Gln Ser Gly Arg
1               5                   10                  15

Ser Leu Arg Leu Ser Cys Val Ala Ser Gly Phe Ser Phe Ser Asn Tyr
            20                  25                  30

Gly Met His Trp Val Arg Gln Ala Pro Gly Lys Gly Leu Glu Trp Leu
        35                  40                  45

Ala Phe Ile Trp Tyr Asp Gly Ser Asn Lys Trp Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Ser Ser Ser Trp Gly Gly Gly Phe Asp Tyr Trp
            100                 105                 110

Gly Gln Gly Thr Val Leu Thr Val Ser Ser Gly Ser Ala Ser Ala Pro
        115                 120                 125

Thr Leu Gly Gly Gly Gly Ser Gly Gly Gly Ser Ala Ala Ala Asn
        130                 135                 140

Phe Met Leu Thr Gln Pro His Ser Val Ser Glu Ser Pro Gly Arg Thr
145                 150                 155                 160

Val Thr Ile Pro Cys Ser Gly Arg Gly Gly Ser Ile Ala Ser Asp Ser
                165                 170                 175
```

Val Gln Trp Tyr Gln Gln Arg Pro Gly Ser Ala Pro Thr Thr Ile Ile
            180                 185                 190

Tyr Glu Asp Asn Gln Arg Pro Ser Gly Val Pro Asp Arg Phe Ser Gly
            195                 200                 205

Ser Val Asp Ser Ser Asn Ser Ala Ser Leu Thr Ile Ser Gly Leu
    210                 215                 220

Arg Thr Glu Asp Glu Ala Asp Tyr Tyr Cys Gln Ser Tyr Asp Ala Ser
225                 230                 235                 240

Ser Leu Trp Val Phe Gly Gly Lys Thr Lys Leu Thr Val Leu Gly Gln
            245                 250                 255

Pro Lys Ala Ala Pro Ser Val Thr Leu Phe Pro Pro Ser Ser Lys Ala
            260                 265                 270

Ser Gly Ala
        275

<210> SEQ ID NO 81
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 81

Val Arg Asp Arg His Ser Leu Gly Asp Phe Asp Tyr
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 82

Gln Ala Trp Asp Ser Thr Thr Val Val
1               5

<210> SEQ ID NO 83
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 83

Gln Leu Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Asp Arg His Ser Leu Gly Asp Phe Asp Tyr Trp Gly Gln Gly
            100                 105                 110

```
Thr Leu Val Thr Val Ser Ser Gly Ser
        115                 120
```

<210> SEQ ID NO 84
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 84

```
Ser Ser Glu Leu Thr Gln Pro Ser Val Ser Val Ser Pro Gly Gln Thr
1               5                   10                  15

Ala Thr Ile Thr Cys Ser Gly Asp Lys Leu Gly Asp Lys Tyr Ala Ser
            20                  25                  30

Trp Tyr Gln Gln Lys Pro Gly Gln Ser Pro Val Leu Val Ile Tyr Gln
        35                  40                  45

Asp Thr Lys Arg Pro Ser Gly Ile Pro Ala Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Ala Tyr Tyr Cys Gln Ala Trp Asp Ser Thr Thr Val Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser
        115                 120
```

<210> SEQ ID NO 85
<211> LENGTH: 201
<212> TYPE: PRT
<213> ORGANISM: Artificial Sequence
<220> FEATURE:
<223> OTHER INFORMATION: Synthetic Polypeptide

<400> SEQUENCE: 85

```
Gln Leu Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Arg His Ser Leu Gly Asp Phe Asp Tyr Trp Gly Gln Gly
            100                 105                 110

Thr Leu Val Thr Val Ser Ser Gly Ser Ala Ser Ala Pro Thr Leu Gly
        115                 120                 125

Gly Gly Gly Ser Gly Gly Gly Ser Ala Ala Ala Ser Ser Glu Leu
    130                 135                 140

Thr Gln Pro Pro Ser Val Ser Val Ser Pro Gly Gln Thr Ala Thr Ile
145                 150                 155                 160

Thr Cys Ser Gly Asp Lys Leu Gly Asp Lys Tyr Ala Ser Trp Tyr Gln
                165                 170                 175
```

```
Gln Lys Pro Gly Gln Ser Pro Val Leu Val Ile Tyr Gln Asp Thr Lys
            180                 185                 190

Arg Pro Ser Gly Ile Pro Ala Arg Phe
        195                 200

<210> SEQ ID NO 86
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 86

Ala Asn His Gly Leu Met Asp Asp Ser Ser Gly Tyr Tyr Leu Ser Asn
1               5                   10                  15

Ala Phe Asp Ile
            20

<210> SEQ ID NO 87
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 87

Ala Thr Trp Asp Asp Ser Leu Thr Gly Val Val
1               5                   10

<210> SEQ ID NO 88
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn
            100                 105                 110

Ala Phe Asp Ile Trp Gly Gln Gly Thr Met Val Thr Val Ser Ser Gly
        115                 120                 125

Ser

<210> SEQ ID NO 89
<211> LENGTH: 126
<212> TYPE: PRT
<213> ORGANISM: Artificial Sequence
<220> FEATURE:
<223> OTHER INFORMATION: Synthetic Polypeptide
```

<400> SEQUENCE: 89

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Glu Trp Tyr Gln Gln Leu Pro Gly Thr Ala Pro Lys Leu Leu
        35                  40                  45

Ile His Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Phe Cys Ala Thr Trp Asp Asp Ser Leu
                85                  90                  95

Thr Gly Val Val Phe Gly Gly Gly Thr Thr Leu Thr Val Leu Gly Gln
            100                 105                 110

Pro Lys Ala Ala Pro Ser Val Thr Leu Phe Pro Ser Ser
        115                 120                 125
```

<210> SEQ ID NO 90
<211> LENGTH: 274
<212> TYPE: PRT
<213> ORGANISM: Artificial Sequence
<220> FEATURE:
<223> OTHER INFORMATION: Synthetic Polypeptide

<400> SEQUENCE: 90

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn
            100                 105                 110

Ala Phe Asp Ile Trp Gly Gln Gly Thr Met Val Thr Val Ser Ser Gly
        115                 120                 125

Ser Ala Ser Ala Pro Thr Leu Gly Gly Gly Ser Gly Gly Gly Gly
    130                 135                 140

Ser Ala Ala Ala Gln Pro Val Leu Thr Gln Pro Ser Ala Ser Gly
145                 150                 155                 160

Thr Pro Gly Gln Arg Val Thr Ile Ser Cys Ser Gly Ser Ser Ser Asn
                165                 170                 175

Ile Gly Ser Asn Thr Val Glu Trp Tyr Gln Gln Leu Pro Gly Thr Ala
            180                 185                 190

Pro Lys Leu Leu Ile His Ser Asn Asn Gln Arg Pro Ser Gly Val Pro
        195                 200                 205

Asp Arg Phe Ser Gly Ser Arg Ser Gly Thr Ser Ala Ser Leu Ala Ile
    210                 215                 220
```

Ser Gly Leu Gln Ser Glu Asp Glu Ala Asp Tyr Phe Cys Ala Thr Trp
225                 230                 235                 240

Asp Asp Ser Leu Thr Gly Val Val Phe Gly Gly Gly Thr Thr Leu Thr
            245                 250                 255

Val Leu Gly Gln Pro Lys Ala Ala Pro Ser Val Thr Leu Phe Pro Pro
        260                 265                 270

Ser Ser

<210> SEQ ID NO 91
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 91

Ala Lys Val Gly Thr Ala Ala Gly Asp Ala Phe Asp Ile
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 92

Ala Ala Trp Asp Asp Ser Leu Ser Gly Trp Val
1               5                   10

<210> SEQ ID NO 93
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 93

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Gly Thr Ala Ala Gly Asp Ala Phe Asp Ile Trp Gly
            100                 105                 110

Gln Gly Thr Met Val Thr Val Ser Ser Gly Ser
        115                 120

<210> SEQ ID NO 94
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 94

```
Gln Pro Val Leu Thr Gln Pro Pro Ser Ala Ser Gly Thr Pro Gly Gln
1               5                   10                  15

Arg Val Thr Ile Ser Cys Phe Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser
        115                 120                 125
```

<210> SEQ ID NO 95
<211> LENGTH: 268
<212> TYPE: PRT
<213> ORGANISM: Artificial Sequence
<220> FEATURE:
<223> OTHER INFORMATION: Synthetic Polypeptide

<400> SEQUENCE: 95

```
Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Gly Thr Ala Ala Gly Asp Ala Phe Asp Ile Trp Gly
            100                 105                 110

Gln Gly Thr Met Val Thr Val Ser Ser Gly Ser Ala Ser Ala Pro Thr
            115                 120                 125

Leu Gly Gly Gly Ser Gly Gly Gly Ser Ala Ala Ala Gln Pro
    130                 135                 140

Val Leu Thr Gln Pro Pro Ser Ala Ser Gly Thr Pro Gly Gln Arg Val
145                 150                 155                 160

Thr Ile Ser Cys Phe Gly Ser Ser Asn Ile Gly Ser Asn Tyr Val
            165                 170                 175

Tyr Trp Tyr Gln Gln Leu Pro Gly Thr Ala Pro Lys Leu Leu Ile Tyr
            180                 185                 190

Arg Asn Asn Gln Arg Pro Ser Gly Val Pro Asp Arg Phe Ser Gly Ser
            195                 200                 205

Lys Ser Gly Thr Ser Ala Ser Leu Ala Ile Ser Gly Leu Arg Ser Glu
        210                 215                 220

Asp Glu Ala Asp Tyr Tyr Cys Ala Ala Trp Asp Asp Ser Leu Ser Gly
```

```
                    225                 230                 235                 240
Trp Val Phe Gly Gly Gly Thr Lys Leu Thr Val Leu Gly Gln Pro Lys
                    245                 250                 255

Ala Ala Pro Ser Val Thr Leu Phe Pro Pro Ser Ser
                260                 265

<210> SEQ ID NO 96
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 96

Ala Arg Val Gly Phe Tyr Asp Tyr Val Trp Gly Ser Tyr Pro Tyr Asp
1               5                   10                  15

Ala Phe Asp Ile
            20

<210> SEQ ID NO 97
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 97

Gln Gln Tyr Gly Thr Ser Pro Leu Thr
1               5

<210> SEQ ID NO 98
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 98

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp
                100                 105                 110

Ala Phe Asp Ile Trp Gly Gln Gly Thr Met Val Thr Val Ser Ser Gly
            115                 120                 125

Ser

<210> SEQ ID NO 99
<211> LENGTH: 117
<212> TYPE: PRT
<213> ORGANISM: Artificial Sequence
<220> FEATURE:
```

<223> OTHER INFORMATION: Synthetic Polypeptide

<400> SEQUENCE: 99

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Leu Tyr Tyr Cys Gln Gln Tyr Gly Thr Ser Pro
                85                  90                  95

Leu Thr Phe Gly Gly Gly Thr Lys Leu Glu Ile Lys Arg Thr Val Ala
            100                 105                 110

Ala Pro Ser Val Phe
            115

<210> SEQ ID NO 100
<211> LENGTH: 265
<212> TYPE: PRT
<213> ORGANISM: Artificial Sequence
<220> FEATURE:
<223> OTHER INFORMATION: Synthetic Polypeptide

<400> SEQUENCE: 100

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp
            100                 105                 110

Ala Phe Asp Ile Trp Gly Gln Gly Thr Met Val Thr Val Ser Ser Gly
        115                 120                 125

Ser Ala Ser Ala Pro Thr Leu Gly Gly Gly Gly Ser Gly Gly Gly Gly
    130                 135                 140

Ser Ala Ala Ala Glu Ile Val Met Thr Gln Ser Pro Gly Thr Leu Ser
145                 150                 155                 160

Leu Ser Pro Gly Glu Arg Ala Thr Leu Ser Cys Arg Ala Ser Gln Ser
                165                 170                 175

Val Ser Ser Asn Tyr Leu Ala Trp Tyr Gln Gln Lys Pro Gly Gln Ala
            180                 185                 190

Pro Arg Leu Leu Ile Tyr Asp Ala Ser Asn Arg Ala Thr Gly Ile Pro
        195                 200                 205

Ala Arg Phe Ser Gly Ser Gly Ser Gly Thr Asp Phe Thr Leu Thr Ile
    210                 215                 220

```
Ser Ser Leu Glu Pro Glu Asp Phe Ala Leu Tyr Tyr Cys Gln Gln Tyr
225                 230                 235                 240

Gly Thr Ser Pro Leu Thr Phe Gly Gly Gly Thr Lys Leu Glu Ile Lys
            245                 250                 255

Arg Thr Val Ala Ala Pro Ser Val Phe
            260                 265
```

<210> SEQ ID NO 101
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 101

```
Ala Lys Asp Thr Ser Asn Gly Gly Tyr Ser Ser Ser Phe Asp Tyr
1               5                   10                  15
```

<210> SEQ ID NO 102
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 102

```
Ser Ser Tyr Thr Ser Ser Ser Thr Leu Val
1               5                   10
```

<210> SEQ ID NO 103
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 103

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Thr Ser Asn Gly Gly Tyr Ser Ser Ser Phe Asp Tyr
            100                 105                 110

Trp Gly Gln Gly Thr Leu Val Thr Val Ser Ser Gly Ser
        115                 120                 125
```

<210> SEQ ID NO 104
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 104

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Thr Ala Pro Lys Leu
         35                  40                  45

Met Ile Tyr Asp Val Ser Tyr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Thr Gly Thr Lys Val Thr Val Leu Gly Gln
             100                 105                 110

Pro Lys Ala Asn Pro Thr Val Thr Leu Phe Pro Pro Ser Ser
        115                 120                 125
```

<210> SEQ ID NO 105
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 105

```
Glu Val Gln Leu Val Gln Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Thr Ser Asn Gly Gly Tyr Ser Ser Ser Ser Phe Asp Tyr
             100                 105                 110

Trp Gly Gln Gly Thr Leu Val Thr Val Ser Ser Gly Ser Ala Ser Ala
             115                 120                 125

Pro Thr Leu Gly Gly Gly Gly Ser Gly Gly Gly Gly Ser Ala Ala Ala
     130                 135                 140

Gln Ser Ala Leu Thr Gln Pro Ala Ser Val Ser Gly Ser Pro Gly Gln
145                 150                 155                 160

Ser Ile Thr Ile Ser Cys Thr Gly Thr Ser Ser Asp Val Gly Gly Tyr
                165                 170                 175

Asn Tyr Val Ser Trp Tyr Gln Gln His Pro Gly Thr Ala Pro Lys Leu
             180                 185                 190

Met Ile Tyr Asp Val Ser Tyr Arg Pro Ser Gly Val Ser Asn Arg Phe
         195                 200                 205

Ser Gly Ser Lys Ser Gly Asn Thr Ala Ser Leu Thr Ile Ser Gly Leu
     210                 215                 220

Gln Ala Glu Asp Glu Ala Asp Tyr Tyr Cys Ser Ser Tyr Thr Ser Ser
225                 230                 235                 240
```

Ser Thr Leu Val Phe Gly Thr Gly Thr Lys Val Thr Leu Gly Gln
                245                 250                 255

Pro Lys Ala Asn Pro Thr Val Thr Leu Phe Pro Pro Ser Ser
            260                 265                 270

<210> SEQ ID NO 106
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 106

Ala Arg Leu Val Tyr Gly Gly Tyr Asp Glu Pro Gly Tyr Tyr Phe Asp
1               5                   10                  15

Tyr

<210> SEQ ID NO 107
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 107

Ala Ala Trp Asp Asp Ser Leu Asn Gly Trp Val
1               5                   10

<210> SEQ ID NO 108
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 108

Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Pro Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Tyr Gly Gly Tyr Asp Glu Pro Gly Tyr Tyr Phe Asp
            100                 105                 110

Tyr Trp Gly Gln Gly Thr Leu Val Thr Val Ser Ser Gly Ser
        115                 120                 125

<210> SEQ ID NO 109
<211> LENGTH: 131
<212> TYPE: PRT
<213> ORGANISM: Artificial Sequence
<220> FEATURE:
<223> OTHER INFORMATION: Synthetic Polypeptide

<400> SEQUENCE: 109

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Lys Ala
        115                 120                 125

Ser Gly Ala
    130

<210> SEQ ID NO 110
<211> LENGTH: 276
<212> TYPE: PRT
<213> ORGANISM: Artificial Sequence
<220> FEATURE:
<223> OTHER INFORMATION: Synthetic Polypeptide

<400> SEQUENCE: 110

Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Tyr Gly Tyr Asp Glu Pro Gly Tyr Tyr Phe Asp
            100                 105                 110

Tyr Trp Gly Gln Gly Thr Leu Val Thr Val Ser Ser Gly Ser Ala Ser
        115                 120                 125

Ala Pro Thr Leu Gly Gly Gly Ser Gly Gly Gly Ser Ala Ala
        130                 135                 140

Ala Gln Ser Val Leu Thr Gln Pro Pro Ser Ala Ser Gly Thr Pro Gly
145                 150                 155                 160

Gln Arg Val Thr Ile Ser Cys Ser Gly Ser Ser Ser Asn Ile Arg Ser
                165                 170                 175

Asn Thr Val Asn Trp Tyr Gln Gln Leu Pro Gly Thr Ala Pro Lys Leu
            180                 185                 190

Leu Ile Tyr Ser Asn Asn Gln Arg Pro Ser Gly Val Pro Asp Arg Phe
        195                 200                 205

Ser Gly Ser Lys Ser Gly Thr Ser Ala Ser Leu Ala Ile Ser Gly Leu
    210                 215                 220
```

Gln Ser Glu Asp Glu Ala Asp Tyr Tyr Cys Ala Ala Trp Asp Asp Ser
225                 230                 235                 240

Leu Asn Gly Trp Val Phe Gly Gly Gly Thr Lys Leu Thr Val Leu Gly
            245                 250                 255

Gln Pro Lys Ala Ala Pro Ser Val Thr Leu Phe Pro Pro Ser Ser Lys
            260                 265                 270

Ala Ser Gly Ala
        275

<210> SEQ ID NO 111
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 111

Ala Lys Val Asp Gly Leu Glu Tyr Ser Ser Gly His Asn Phe Asp Tyr
1               5                   10                  15

<210> SEQ ID NO 112
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 112

Ser Ser Tyr Ala Gly Ser Tyr Thr Trp Val
1               5                   10

<210> SEQ ID NO 113
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 113

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Leu Glu Tyr Ser Ser Gly His Asn Phe Asp Tyr
            100                 105                 110

Trp Gly Gln Gly Thr Leu Val Thr Val Ser Ser Gly Ser
        115                 120                 125

<210> SEQ ID NO 114
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 114

```
Gln Ser Ala Leu Thr Gln Pro Pro Ser Val Ser Gly Ser Pro Gly Gln
1               5                   10                  15

Ser Val Thr Ile Ser Cys Thr Gly Ser Ser Asp Val Gly Tyr Tyr
            20                  25                  30

Asp His Val Ser Trp Tyr Gln His Pro Gly Arg Ala Pro Lys Val
        35                  40                  45

Ile Ile Tyr Asp Val Thr Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Glu Leu Thr Val Leu Gly Gln
            100                 105                 110

Pro Lys Ala Ala Pro Ser Val Thr Leu Phe Pro Pro Ser Ser
        115                 120                 125
```

<210> SEQ ID NO 115
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 115

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Leu Glu Tyr Ser Ser Gly His Asn Phe Asp Tyr
            100                 105                 110

Trp Gly Gln Gly Thr Leu Val Thr Val Ser Ser Gly Ser Ala Ser Ala
        115                 120                 125

Pro Thr Leu Gly Gly Gly Ser Gly Gly Gly Ser Ala Ala Ala
        130                 135                 140

Gln Ser Ala Leu Thr Gln Pro Pro Ser Val Ser Gly Ser Pro Gly Gln
145                 150                 155                 160

Ser Val Thr Ile Ser Cys Thr Gly Ser Ser Asp Val Gly Tyr Tyr
            165                 170                 175

Asp His Val Ser Trp Tyr Gln His Pro Gly Arg Ala Pro Lys Val
        180                 185                 190

Ile Ile Tyr Asp Val Thr Lys Arg Pro Ser Gly Val Pro Asp Arg Phe
195                 200                 205

Ser Gly Ser Lys Ser Gly Asn Thr Ala Ser Leu Thr Ile Ser Gly Leu
        210                 215                 220
```

```
Gln Ala Glu Asp Glu Ala Asp Tyr Tyr Cys Ser Ser Tyr Ala Gly Ser
225                 230                 235                 240

Tyr Thr Trp Val Phe Gly Gly Gly Thr Glu Leu Thr Val Leu Gly Gln
                245                 250                 255

Pro Lys Ala Ala Pro Ser Val Thr Leu Phe Pro Pro Ser Ser
            260                 265                 270

<210> SEQ ID NO 116
<211> LENGTH: 323
<212> TYPE: PRT
<213> ORGANISM: Artificial Sequence
<220> FEATURE:
<223> OTHER INFORMATION: Synthetic Polypeptide

<400> SEQUENCE: 116

Ala Ser Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320
```

```
Ser Pro Gly

<210> SEQ ID NO 117
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 117

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 118
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 118

Lys Ala Leu Asp Glu Asn
1               5
```

COMPOSITIONS AND METHODS FOR MAKING AND USING ANTI-MYOSTATIN ANTIBODIES

RELATED APPLICATIONS

This application is a national stage application under 35 U.S.C. § 371 of international application PCT/US2018/012686, filed on Jan. 5, 2018, which designated the U.S. and claims priority to the following patent applications: U.S. provisional application 62/443,455 and EP priority application 17150586.0, each filed on Jan. 6, 2017, U.S. provisional application 62/530,311 filed on Jul. 10, 2017, and U.S. provisional application 62/608,069, filed on Dec. 20, 2017. The entire contents of these prior applications are incorporated herein by reference, including the Sequence Listing, which was submitted electronically in ASCII format.

SEQUENCE LISTING

The instant application contains a Sequence Listing which has been submitted electronically in ASCII format and is hereby incorporated by reference in its entirety. Said ASCII copy, created on Jan. 5, 2018, is named "SR16-WO-PCT_Sequence_Listing_127036-00220.txt" and is 108,914 bytes in size.

BACKGROUND OF THE INVENTION

Metabolic diseases affect millions of people worldwide, and patients with metabolic diseases generally experience a loss of fat-free or lean muscle mass, an excess gain of fat mass, a lower metabolic rate, insulin resistance, lack of ability to regulate blood sugar, weight gain, and increase in body mass index. Thus, these patients are at risk of developing major complications, such as diabetes, obesity, coronary artery disease, hypertension, stroke, atherosclerosis, heart failure such as chronic heart failure (CHF), including congestive heart failure, metabolic bone disorders, gallbladder disease, osteoarthritis, sleep apnea, reproductive disorders such as polycystic ovarian syndrome, cancers of the breast, prostate, and colon, and increased incidence of complications of general anesthesia.

In addition to the serious health consequences of these metabolic diseases, serious economic costs are associated with these diseases. For example, the total cost of treating diabetes and its complications in the United States has been estimated at $245 billion annually. The estimated annual health care costs of obesity-related illness are a staggering $190.2 billion or nearly 21% of annual medical spending. Substantial costs to both society and its citizens are incurred not only for direct costs of medical care for these metabolic diseases, but also for indirect costs, including lost productivity resulting from metabolic diseases-related morbidity and premature mortality.

Myostatin, also known as growth differentiation factor 8 or GDF-8, is a member of the transforming growth factor-β (TGF-β) superfamily. Myostatin is produced and released by myocytes, and is a critical autocrine/paracrine inhibitor of skeletal muscle growth (Mouisel et al. *Am J Physiol Regul Integr Comp Physiol.* 2014; 307(4): R444-54). Myostatin has been primarily evaluated for use in treating diseases associated with muscle function.

Until now, most of metabolic diseases remain poorly treated. Current treatments do not fully meet patient needs, and there are no effective treatments applicable to the large majority of the affected patient population. Accordingly, there exists an unmet need for therapies for subjects suffering from metabolic diseases.

SUMMARY OF THE INVENTION

The present disclosure encompasses the recognition that myostatin may act as a key regulator to directly mediate function of the muscle as an endocrine organ that controls metabolism, including body composition, and regulation thereof.

According to the invention, modulation of myostatin signaling can affect a number of metabolic parameters central to the regulation of energy production and consumption by selectively mobilizing body's three major energy pools: glucose, lipids and proteins. Without wishing to be bound by theory, it is contemplated that myostatin may play a role in the process both as a molecular sensor of energy expenditure and as an effector to affect metabolic normalization. The present invention implicates myostatin in a broader role in metabolic regulation including nitrogen mobilization, osmoregulation, calcium metabolism, as well as acid-base and electrolyte balance.

Thus, the present invention provides methods and compositions for treating or preventing metabolic diseases in human subjects using anti-pro/latent myostatin inhibitors, e.g., antibodies. The present invention is based, at least in part, on the discovery that administration of a myostatin inhibitor, e.g., an antibody, or antigen binding fragment thereof, that specifically binds to pro/latent myostatin to subjects having a metabolic disease, e.g., spinal cord injury (SCI), significantly improves both the physiological and the functional characteristics of the injured subjects. In particular, the present inventors have surprisingly discovered that administration of a myostatin inhibitor, e.g., an anti-pro/latent myostatin antibody significantly increases the metabolic rate or energy expenditure in subjects having a metabolic disease, e.g., spinal cord injury (SCI). Administration of a myostatin inhibitor, e.g., an anti-pro/latent myostatin antibody, also significantly attenuated SCI-induced reduction in sub-lesional muscle mass and overall body mass, while at the same time reducing the mass of undesirable adipose tissue such as white and visceral adipose tissue. In addition, subjects who received a myostatin inhibitor, e.g., an anti-pro/latent myostatin antibody treatment exhibited a significant improvement in their locomotor function, muscle strength, as well as motor coordination and balance skills.

The present invention is further based, at least on part, on the surprising discovery that administration of a myostatin inhibitor, e.g., an anti-pro/latent myostatin antibody or antigen-binding fragment thereof, not only increases bone volume in weight-bearing bone, but also increases bone volume in non-weight bearing bones, e.g., the vertebrae in rodents. It is well known in the art that weight-bearing activity is an important stimulus for bone mass accrual, which could potentially explain increases in bone volume in weight-bearing bones after administration of a myostatin inhibitor. However, the surprising increase observed in non-weight bearing bone volume demonstrated upon administration of the myostatin inhibitors disclosed herein further confirms that myostatin inhibitors have a broader metabolic effect, i.e., the myostatin inhibitors act not only to increase bone through, for example, increased muscle stimulation, but also act as a key regulator to increase general metabolic effects, including bone health.

Finally, the present invention provides methods for promoting improved body compositions, e.g., enhanced muscle-to-fat ratios. Such methods may be effective in achieving robust weight loss in both healthy subjects, e.g., bodybuilders, or in subjects having obesity, e.g., diet-induced obesity, metabolic syndrome, NASH, NAFLD, and/or diabetes. As compared to dieting alone, where weight loss occurs in both fat and muscle, administration of a myostatin inhibitor disclosed herein in combination with a diet leads to weight loss or greater muscle-to-fat ratios, due to preferential loss of fat stores, relative to loss of the muscle. Specifically, administration of a myostatin inhibitor in combination with a diet, e.g., a caloric restriction diet, results in more robust weight loss due in part to the maintenance of a higher metabolic rate; improved cardiometabolic benefits (such as lipid profile, glucose metabolism, cardiovascular risk, etc.); and higher reduction in visceral fat and other deleterious fat levels as compared to dieting, alone. Such beneficial effects may be further enhanced when combined with moderate exercise.

Accordingly, in one aspect, disclosed herein is a composition comprising a myostatin inhibitor, e.g., an antibody, or antigen-binding fragment thereof, that specifically binds pro/latent-myostatin and blocks release of mature myostatin, for use as a medicament in treatment or prevention of a metabolic disease in a human subject, comprising steps of: selecting a human subject suffering from, or at risk of developing, a metabolic disease; and, administering to the human subject the composition comprising an effective amount of the myostatin inhibitor, e.g., antibody, or antigen-binding fragment thereof. In one embodiment, the subject is a pediatric subject.

In some embodiments, the subject does not have a myopathy, optionally wherein the myopathy is a primary myopathy or a secondary myopathy. In some embodiments, the subject is an adult human subject suffering from growth hormone (GH) deficiency, optionally wherein the subject concurrently receives a recombinant GH therapy or a GH gene therapy.

In some embodiments, the metabolic disease is selected from the group consisting of type I diabetes, type II diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome. In some embodiments, the obesity is sarcopenic obesity.

In some embodiments, the hypo-metabolic state is selected from the group consisting of a state associated with prolonged immobilization, a state associated with bed-rest, a state associated with casting, a state associated with a stroke, a state associated with amputation, and a post-surgery state.

In some embodiments, the Cushings disease is selected from the group consisting of corticosteroid-induced Cushings disease and tumor-induced Cushings disease.

In some embodiments, the obesity syndrome is selected from the group consisting of Prader Willi, an obesity syndrome associated with a genetic disorder, and an obesity syndrome associated with a hypothalamic disorder.

In some embodiments, administration of the composition causes at least one, e.g., 2, 3, 4, 5, 6, 7, 2-4, 2-5, 2-6, 3-5 or 3-6, of the following:

a) increases mass and/or function of a muscle tissue in the human subject;
b) increases mass and/or function of a fast twitch muscle tissue in the human subject;
c) increases mass and/or function of a slow twitch muscle tissue in the human subject;
d) increases the metabolic rate of the human subject;
e) increases insulin sensitivity in the human subject;
f) increases the level of brown adipose tissue in the human subject;
g) increases the level of beige adipose tissue in the human subject;
h) decreases the level of white adipose tissue in the human subject;
i) decreases the level of visceral adipose tissue in the human subject;
j) decreases the ratio of adipose-to-muscle tissue in the human subject;
k) increases glucose uptake by a target tissue in the human subject, wherein the target tissue is selected from the group consisting of brown adipose tissue, beige adipose tissue, and muscle tissue;
l) decreases glucose uptake by a target tissue in the human subject, wherein the target tissue is selected from the group consisting of a white adipose tissue and a liver tissue;
m) decreases muscle catabolism of protein and/or muscle release of amino acids in the human subject;
n) increases insulin dependent glycemic control in the human subject;
o) decreases intramuscular fat infiltration in the human subject;
p) improves a standardized quality of life test score;
q) prevents muscle loss or atrophy in the human subject;
r) reduces bone loss;
s) increases crossectional bone area and/or cortical thickness;
t) reduces frequency or severity of hone fractures; and/or,
u) reduces fluid overload or edema in chronic heart failure (CHF).

In some embodiments, the antibody, or antigen-binding fragment thereof does not bind to GDF11 or Activin. In some embodiments, the antibody, or antigen-binding fragment thereof does not bind mature (fully processed, free and active) myostatin. In some embodiments, the antibody, or antigen binding fragment thereof, comprises a) a heavy chain variable region comprising an amino acid sequence of SEQ ID NO:25 and a light chain variable region comprising an amino acid sequence of SEQ ID NO:31; or b) a heavy chain comprising an amino acid sequence of SEQ ID NO:50 and a light chain comprising an amino acid sequence of SEQ ID NO:51.

In another aspect, the disclosure provides a method for treating or preventing a metabolic disease in a human subject, the method comprising steps of: selecting a human subject suffering from or at risk of developing a metabolic disease; and, administering to the human subject a composition comprising an effective amount of a myostatin inhibitor, e.g., an antibody, or antigen-binding fragment thereof, that specifically binds pro/latent-myostatin and blocks release of mature myostatin, thereby treating or preventing the metabolic disease in the human subject.

In one embodiment, the subject does not have a myopathy. In one embodiment, the myopathy is a primary myopathy or a secondary myopathy.

In one embodiment, the subject is an adult human subject suffering from growth hormone (GH) deficiency. In one embodiment, the subject concurrently receives a recombinant GH therapy or a GH gene therapy.

In one embodiment, the metabolic disease is selected from the group consisting of type I diabetes, type 11 diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome. In one embodiment, the obesity is sarcopenic obesity. In one embodiment, the hypo-metabolic state is selected from the group consisting of a state associated with prolonged immobilization, a state associated with bed-rest, a state associated with casting, a state associated with a stroke, a state associated with amputation, and a post-surgery state. In one embodiment, the Cushings disease is selected from the group consisting of corticosteroid-induced Cushings disease and tumor-induced Cushings disease. In one embodiment, the obesity syndrome is selected from the group consisting of Prader Willi, an obesity syndrome associated with a genetic disorder, and an obesity syndrome associated with a hypothalamic disorder.

In some embodiments, the hypo-metabolic state is a post-surgery state, e.g., paraspinal muscle atrophy after lumbar spine surgery. In one embodiment, the paraspinal muscle atrophy is a nerve injury-dependent muscle atrophy. In one embodiment, the surgery is a spinal surgery. In one embodiment, the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc.

In one embodiment, administration of the composition increases mass and/or function of a muscle tissue in the human subject. In one embodiment, administration of the composition increases mass and/or function of a fast twitch muscle tissue in the human subject. In one embodiment, administration of the composition increases mass and/or function of a slow twitch muscle tissue in the human subject. In one embodiment, administration of the composition increases the metabolic rate of the human subject. In one embodiment, administration of the composition increases insulin sensitivity in the human subject. In one embodiment, administration of the composition increases the level of brown adipose tissue in the human subject. In one embodiment, administration of the composition increases the level of beige adipose tissue in the human subject. In one embodiment, administration of the composition decreases the level of white adipose tissue in the human subject. In one embodiment, administration of the composition decreases the level of visceral adipose tissue in the human subject. In one embodiment, administration of the composition decreases the ratio of adipose-to-muscle tissue in the human subject. In one embodiment, the human subject is a pediatric human subject.

In one embodiment, administration of the composition increases glucose uptake by a target tissue in the human subject, wherein the target tissue is selected from the group consisting of brown adipose tissue, beige adipose tissue, and muscle tissue. In one embodiment, administration of the composition decreases glucose uptake by a target tissue in the human subject, wherein the target tissue is selected from the group consisting of a white adipose tissue and a liver tissue. In one embodiment, administration of the composition decreases muscle catabolism of protein and/or muscle release of amino acids in the human subject. In one embodiment, the human subject is a pediatric human subject.

In one embodiment, administration of the composition increases insulin dependent glycemic control in the human subject. In one embodiment, administration of the composition decreases intramuscular fat infiltration in the human subject. In one embodiment, administration of the composition achieves a clinically meaningful improvement in a quality of life score as assessed by a standardized quality of life test. In some embodiments, the clinically meaningful improvement is at least an 8 point increase in the SF-36 Quality of Life Scoring System. In one embodiment, administration of the composition prevents muscle loss or atrophy in the human subject. In one embodiment, the human subject is a pediatric human subject.

In one aspect, disclosed herein is a method for inhibiting myostatin activation in a subject, the method comprising a step of administering to the subject a composition comprising a myostatin inhibitor, e.g., an antibody, or antigen binding fragment thereof, that specifically binds pro/latent-myostatin and blocks release of mature myostatin, in an amount effective to cause two or more of the following in the subject: (a) an increase in mass and/or function of a muscle tissue in the subject; (b) an increase in the metabolic rate of the subject; (c) an increase in insulin sensitivity of the subject; (d) an increase in a level of brown adipose tissue in the subject; (e) an increase in a level of beige adipose tissue in the subject; (f) a decrease in a level of white adipose tissue in the subject; (g) a decrease in a level of visceral adipose tissue in the subject; (h) a decrease in ratio of adipose-to-muscle tissue in the subject; (i) an increase in glucose uptake by a brown adipose tissue, a beige adipose tissue, or a muscle tissue in the subject; (j) a decrease in glucose uptake by a white adipose tissue or a liver tissue; (k) a decrease in muscle catabolism of protein and/or muscle release of amino acids in the subject; (l) an increase in insulin dependent glycemic control in the subject; (m) a decrease in intramuscular fat infiltration in the subject; (n) a clinically meaningful improvement in a quality of life score as assessed by a standardized quality of life test (e.g., at least 8 points increase in SF-36 Quality of Life Scoring System); (o) prevention of muscle loss or atrophy in the subject; and/or, (p) prevention of developing a metabolic dysregulation associated with muscle dysfunction in the subject, wherein the subject is a human subject that benefits from reduced myostatin signaling. In one embodiment, the human subject is a pediatric human subject.

In one embodiment, the method further comprises a step of selecting the subject suffering from a muscle condition or disorder. In another embodiment, the method further comprises a step of selecting the subject suffering from, or at risk of developing, a metabolic disorder. In one embodiment, the method further comprises a step of selecting a pediatric human subject.

In one embodiment, the subject exhibits i) an increase in a level of proMyostatin in a target muscle, as compared to a control level of proMyostatin, or ii) a decrease in a level of latent myostatin in the circulation, as compared to a control level of latent myostatin. In one embodiment, the subject exhibits both i) and ii). In one embodiment, the human subject is a pediatric human subject.

In one embodiment, the subject has a muscle condition selected from the group consisting of: myopathy, muscular atrophy, muscular dystrophy, nerve injury. In one embodiment, the muscular atrophy is associated with a defect in motor neurons. In one embodiment, the defect comprises a genetic mutation. In another embodiment, the muscular atrophy is associated with spinal muscular atrophy (SMA), amyotrophic lateral sclerosis (ALS), or myasthenia gravis. In one embodiment, the nerve injury comprises partial denervation of neurons that innervate muscle, or impaired signaling between a motor neuron and a target muscle. In one embodiment, the nerve injury is SCI. In another embodiment, the SCI is partial/incomplete SCI. In one embodiment, the SCI in human subjects comprises a lesion between i) T1-T6; ii) T7-L5; iii) C6-C7; iv) C5-C6; or v) C3-C8. In one embodiment, the subject is in an acute phase of SCI;

sub-acute phase of SCI, or chronic phase of SCI. In one embodiment, the subject has, or at risk of developing, a metabolic disorder associated with the SCI. In one embodiment, the metabolic disorder is or comprises insulin resistance, inflammation, abnormal lipid metabolism, or an increase in intramuscular fat infiltration. In one embodiment, the muscle atrophy comprises glucocorticoid-induced muscle atrophy. In one embodiment, the human subject is a pediatric human subject.

In one embodiment, the subject has a metabolic disease selected from the group consisting of type I diabetes, type 11 diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome. In one embodiment, the human subject is a pediatric human subject.

In one embodiment, the subject is treated with a second therapy. In one embodiment, the second therapy comprises neuroprotective therapy. In another embodiment, the neuroprotective therapy comprises a stem cell therapy.

In another aspect, disclosed herein is a method of treating or preventing a disease associated with an impaired neurological signaling between a neuron and a target tissue in a human subject, the method comprising selecting the human subject suffering from a disease associated with an impaired neurological signaling between a neuron and a target tissue; and administering to the human subject a composition comprising a myostatin inhibitor, e.g., an antibody, or antigen binding fragment thereof, that specifically binds pro/latent-myostatin and blocks release of mature myostatin in an amount effective to treat or prevent the disease, thereby treating or preventing the disease associated with the impaired neurological signaling in the human subject. In one embodiment, the human subject is a pediatric human subject.

In some embodiments, the target tissue expresses myostatin (e.g., myostatin precursors, and/or mature myostatin). In one embodiment, the target tissue is selected from the group consisting of a muscle, an adipose tissue, a brain tissue, a liver tissue, and a blood vessel tissue. In one embodiment, the target tissue is a muscle.

In another aspect, disclosed herein is a method for treating a lesion that causes an impaired but not complete loss of signaling between a neuron and a target muscle in a subject. Such method includes a step of administering to the subject a composition comprising a myostatin inhibitor, e.g., an anti-pro/latent myostatin antibody, in an amount effective to treat the muscle located below the lesion in the subject. In some embodiments, the amount is an amount effective to prevent muscle loss or muscle atrophy below the lesion in the subject. In some embodiments, the amount is an amount effective to increase muscle mass and/or function below the lesion in the subject.

In some embodiments, the lesion is associated with incomplete spinal cord injury.

In one embodiment, the muscle contains fast-twitch muscle fibers. In another embodiment, the muscle located below the lesion is selected from the group of a soleus muscle, a gastrocnemius muscle, a bicep muscle and a tricep muscle. In one embodiment, the amount is effective to increase mass and/or function of a muscle above the lesion in the subject. In another embodiment, the myostatin inhibitor is an agent that blocks, antagonizes or inhibits myostatin signaling in vivo. In some embodiments, such agent is an antibody, or antigen-binding portion thereof, a small molecule, or gene therapy. In some embodiments, the antibody is an antibody that specifically binds pro/latent myostatin and blocks release of mature myostatin in vivo. In some embodiments, the antibody hinds mature myostatin. In some embodiments, the antibody selectively (e.g., preferentially) binds mature myostatin over mature GDF11. In some embodiments, the antibody specifically binds mature myostatin but does not bind mature GDF11. In some embodiments, the antibody binds and/or blocks a myostatin receptor.

In one embodiment, the subject has an incomplete spinal cord injury (SCI). In one embodiment, the incomplete SCI in human subjects comprises a lesion between: i) T1-T6; ii) T7-L5; iii) C6-C7; iv) C5-C6; or v) C3-C8.

In one embodiment, the amount is effective to treat a metabolic condition in the subject. In one embodiment, the amount is effective to cause in the subject: (a) an increase in mass and/or function of a muscle tissue in the subject; (b) an increase in the metabolic rate of the subject; (c) an increase in insulin sensitivity of the subject; (d) an increase in a level of brown adipose tissue in the subject; (e) an increase in a level of beige adipose tissue in the subject; (f) a decrease in a level of white adipose tissue in the subject; (g) a decrease in a level of visceral adipose tissue in the subject; (h) a decrease in ratio of adipose-to-muscle tissue in the subject; (i) an increase in glucose uptake by a brown adipose tissue, a beige adipose tissue, or a muscle tissue in the subject; (j) a decrease in glucose uptake by a white adipose tissue or a liver tissue; (k) a decrease in muscle catabolism of protein and/or muscle release of amino acids in the subject; (1) an increase in insulin dependent glycemic control in the subject; (m) a decrease in intramuscular fat infiltration in the subject; (n) at least 8 points increase in SF-36 Quality of Life Scoring System; (o) prevention of muscle loss or atrophy in the subject; and/or, (p) prevention of developing a metabolic dysregulation associated with muscle dysfunction in the subject. In one embodiment, the subject is a pediatric subject.

In another aspect, the disclosure provides a method of treating or preventing a metabolic disease in a human subject, the method comprising selecting a human subject suffering from a metabolic disease; and administering to the human subject an effective amount of an antibody, or antigen binding fragment thereof, that specifically binds pro/latent-myostatin, thereby treating or preventing the metabolic disease in the human subject. In one embodiment, the human subject is a pediatric human subject.

In one embodiment, the metabolic disease is selected from the group consisting of type I diabetes, type II diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome. In one embodiment, the obesity is sarcopenic obesity. In one embodiment, the hypo-metabolic state is selected from the group consisting of a state associated with prolonged immobilization, a state associated with bed-rest, a state associated with casting, a state associated with a stroke, a state associated with amputation, and a post-surgery state. In one embodiment, the Cushings disease is selected from the group consisting of corticosteroid-induced Cushings disease and tumor-induced Cushings disease. In one embodiment, the obesity syndrome is selected from the group consisting of Prader Willi, an obesity syndrome associated with a genetic disorder, and an obesity syndrome associated with a hypothalamic disorder.

In another aspect, the disclosure provides a method of treating or preventing a disease associated with an impaired neurological signaling between a neuron and a target tissue in a human subject, the method comprising selecting a human subject suffering from a disease associated with an impaired neurological signaling between a neuron and a target tissue; and administering to the human subject an effective amount of a myostatin inhibitor, e.g., an antibody, or antigen binding fragment thereof, that specifically binds pro/latent-myostatin, thereby treating or preventing the disease associated with the impaired neurological signaling in the human subject. In some embodiments, the target tissue expresses myostatin (e.g., myostatin precursors, and/or mature myostatin). In one embodiment, the human subject is a pediatric human subject.

In one embodiment, the disease associated with an impaired neurological signaling between a neuron and a target tissue is selected from the group consisting of spinal cord injury (SCI), myasthenia gravis, amyotrophic lateral sclerosis (ALS), and spinal muscular atrophy (SMA). In one embodiment, the disease associated with an impaired neurological signaling between a neuron and a target tissue is spinal cord injury (SCI). In one embodiment, the human subject is in an acute spinal cord injury (SCI) phase. In one embodiment, the human subject is in a sub-acute spinal cord injury (SCI) phase. In one embodiment, the human subject is in a chronic spinal cord injury (SCI) phase.

In one embodiment, the target tissue is selected from the group consisting of a muscle tissue, an adipose tissue, a brain tissue, a liver tissue, and a blood vessel tissue.

In one embodiment, administration of the myostatin inhibitor, e.g., antibody, or antigen binding fragment thereof, increases mass and/or function of a muscle tissue in the human subject. In one embodiment, administration of the myostatin inhibitor, e.g., antibody, or antigen binding fragment thereof, increases mass and/or function of a fast twitch muscle tissue in the human subject. In one embodiment, administration of the myostatin inhibitor, e.g., antibody, or antigen binding fragment thereof, increases mass and/or function of a slow twitch muscle tissue in the human subject. In one embodiment, the human subject is a pediatric human subject.

In one embodiment, administration of the myostatin inhibitor, e.g., antibody, or antigen binding fragment thereof, increases the metabolic rate of the human subject. In one embodiment, administration of the myostatin inhibitor, e.g., antibody, or antigen binding fragment thereof, increases insulin sensitivity in the human subject. In one embodiment, administration of the myostatin inhibitor, e.g., antibody, or antigen binding fragment thereof, increases the level of brown adipose tissue in the human subject. In one embodiment, administration of the myostatin inhibitor, e.g., antibody, or antigen binding fragment thereof, increases the level of beige adipose tissue in the human subject. In one embodiment, administration of the myostatin inhibitor, e.g., antibody, or antigen binding fragment thereof, decreases the level of white adipose tissue in the human subject. In one embodiment, administration of the myostatin inhibitor, e.g., antibody, or antigen binding fragment thereof, decreases the level of visceral adipose tissue in the human subject. In one embodiment, administration of the myostatin inhibitor, e.g., antibody, or antigen binding fragment thereof, decreases the ratio of adipose-to-muscle tissue in the human subject. In one embodiment, the human subject is a pediatric human subject.

In one embodiment, administration of the myostatin inhibitor, e.g., antibody, or antigen binding fragment thereof, increases glucose uptake by a muscle tissue in the human subject. In one embodiment, administration of the myostatin inhibitor, e.g., antibody, or antigen binding fragment thereof, decreases glucose uptake by a target tissue, wherein the target tissue is selected from the group consisting of a white adipose tissue, a liver tissue and a blood vessel tissue. In one embodiment, the human subject is a pediatric human subject.

In one embodiment, administration of the myostatin inhibitor, e.g., antibody, or antigen binding fragment thereof, decreases muscle catabolism of protein and/or muscle release of amino acids in the human subject. In one embodiment, administration of the myostatin inhibitor, e.g., antibody, or antigen binding fragment thereof, increases insulin dependent glycemic control in the human subject. In one embodiment, the human subject is a pediatric human subject.

In another aspect, disclosed herein is a method of increasing metabolic rate in a human subject, the method comprising selecting a human subject who would benefit from an increase in metabolic rate; and administering to the human subject an effective amount of a myostatin inhibitor, e.g., an antibody, or antigen binding fragment thereof, that specifically binds pro/latent-myostatin, thereby increasing the metabolic rate in the human subject.

In another aspect, disclosed herein is a method of increasing the level of brown adipose tissue in a human subject, the method comprising selecting a human subject who would benefit from an increase in the level of brown adipose tissue; and administering to the human subject an effective amount of a myostatin inhibitor, e.g., an antibody, or antigen binding fragment thereof, that specifically binds pro/latent-myostatin, thereby increasing the level of brown adipose tissue in the human subject.

In another aspect, disclosed herein is a method of increasing the level of beige adipose tissue in a human subject, the method comprising selecting a human subject who would benefit from an increase in the level of beige adipose tissue; and administering to the human subject an effective amount of a myostatin inhibitor, e.g., an antibody, or antigen binding fragment thereof, that specifically binds pro/latent-myostatin, thereby increasing the level of beige adipose tissue in the human subject.

In another aspect, disclosed herein is a method of increasing insulin dependent glycemic control in a human subject, the method comprising selecting a human subject who would benefit from an increase in insulin dependent glycemic control; and administering to the human subject an effective amount of a myostatin inhibitor, e.g., an antibody, or antigen binding fragment thereof, that specifically binds pro/latent-myostatin, thereby increasing insulin dependent glycemic control in the human subject.

In another aspect, disclosed herein is a method of decreasing muscle catabolism of protein and/or muscle release of amino acids in a human subject, the method comprising selecting a human subject who would benefit from a decrease in muscle catabolism of protein and/or muscle release of amino acids; and administering to the human subject an effective amount of a myostatin inhibitor, e.g., an antibody, or antigen binding fragment thereof, that specifically binds pro/latent-myostatin, thereby decreasing muscle catabolism of protein and/or muscle release of amino acids in the human subject.

In another aspect, disclosed herein is a method of decreasing glucose uptake by a target tissue in a human subject, the method comprising selecting a human subject who would benefit from a decrease in glucose uptake by a target tissue selected from the group consisting of a white adipose tissue, a liver tissue and a blood vessel tissue; and administering to the human subject an effective amount of a myostatin inhibitor, e.g., an antibody, or antigen binding fragment thereof, that specifically binds pro/latent-myostatin, thereby decreasing glucose uptake by the target tissue in the human subject.

In one embodiment, the target tissue comprises macrophages, smooth muscle cells and foam cells.

In another aspect, disclosed herein is a method of treating or preventing a metabolic disease in a human subject, the method comprising selecting a human subject suffering from a metabolic disease; and administering to the human subject an amount of a myostatin inhibitor, e.g., an antibody, or antigen binding fragment thereof, that specifically binds pro/latent-myostatin, effective to cause at least two or more of the following in the human subject: (a) an increase in mass and/or function of a muscle tissue in the human subject; (b) an increase in the metabolic rate of the human subject; (c) an increase in insulin sensitivity of the human subject; (d) an increase in the level of brown adipose tissue in the human subject; (e) an increase in the level of beige adipose tissue in the human subject; (f) a decrease in the level of white adipose tissue in the human subject; (g) a decrease in the level of visceral adipose tissue in the human subject; (h) a decrease in the ratio of adipose-to-muscle tissue in the human subject; (i) an increase in glucose uptake by a white adipose tissue, a liver tissue or a blood vessel tissue in the human subject; (j) a decrease in muscle catabolism of protein and/or muscle release of amino acids in the human subject; and/or (k) an increase in insulin dependent glycemic control in the human subject, thereby treating or preventing the metabolic disease in the human subject. In one embodiment, the human subject is a pediatric human subject.

In another aspect, disclosed herein is a method of increasing mass and/or function of a muscle located below a lesion in a subject who has suffered a lesion, the method comprising selecting a subject who has suffered a lesion; and administering to the human subject an effective amount of a myostatin inhibitor, e.g., an antibody, or antigen binding fragment thereof, that specifically hinds pro/latent-myostatin, thereby increasing the mass and/or function of the muscle located below a lesion in the human subject.

In one embodiment, the lesion is due to a spinal cord injury (SCI). In one embodiment, the human subject is in an acute spinal cord injury (SCI) phase. In one embodiment, the human subject is in a sub-acute spinal cord injury (SCI) phase. In one embodiment, the human subject is in a chronic spinal cord injury (SCI) phase.

In one embodiment, administration of the myostatin inhibitor, e.g., antibody, or antigen binding fragment thereof, further increases mass and/or function of a muscle above the lesion. In one embodiment, administration of the myostatin inhibitor, e.g., antibody, or antigen binding fragment thereof, increases mass and/or function of a fast switch muscle. In one embodiment, administration of the antibody, or antigen binding fragment thereof, increases mass and/or function of a slow switch muscle.

In some embodiments, the mass of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases locomotor function in the human subject. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, administration of the myostatin inhibitor, e.g., antibody, or antigen binding fragment thereof, increases motor coordination and balance in the human subject. In some embodiments, the motor ordination and balance of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the motor ordination and balance of the human subject is increased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, administration of the myostatin inhibitor, e.g., antibody, or antigen binding fragment thereof, increases muscle strength in the human subject. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, administration of the myostatin inhibitor, e.g., antibody, or antigen binding fragment thereof, increases grip strength in the human subject. In one embodiment, administration of the myostatin inhibitor, e.g., antibody, or antigen binding fragment thereof, decreases the level of white adipose tissue in the human subject. In some embodiments, the level of white adipose tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of white adipose tissue is decreased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, administration of the myostatin inhibitor, e.g., antibody, or antigen binding fragment thereof, increases total body mass of the human subject. In some embodiments, the level of total body mass is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of total body mass is increased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, administration of the myostatin inhibitor, e.g., antibody, or antigen binding fragment thereof, increases metabolic rate of the human subject. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%. In one embodiment, the human subject is a pediatric human subject.

In one embodiment, the muscle is selected from the group of a soleus muscle, a gastrocnemius muscle, a bicep muscle and a tricep muscle.

In one embodiment, the myostatin inhibitor, e.g., antibody, or antigen binding fragment thereof, is administered to the human subject within less than 5, 10, 20, 30, 40, 50, 60 minutes after the human subject has suffered the lesion. In one embodiment, the myostatin inhibitor, e.g., antibody, or antigen binding fragment thereof, is administered to the human subject at least 1, 2, 3, 4, 5, 6, 7, 8, 9, 10, 12 or 24 hours after the human subject has suffered the lesion. In one embodiment, the myostatin inhibitor, e.g., antibody, or antigen binding fragment thereof, is administered to the human subject within at least 1, 2, 3, 4, 5, 6, 7, 8, 9, 10 days or at least 1, 2, 3, 4, 5, 6, 7, 8, 9, 10, 11, 12, 24, 48 or 60 months after the human subject has suffered the lesion. In one embodiment, the myostatin inhibitor, e.g., antibody, or antigen binding fragment thereof, is administered to the human subject for about 1-30 days, about 1-50 days, about 1-100 days, about 1-200 days or about 1-300 days.

In one embodiment, the myostatin inhibitor, e.g., antibody, or antigen binding fragment thereof, is administered to the human subject chronically. In one embodiment, the myostatin inhibitor, e.g., antibody, or antigen binding fragment thereof, is administered to the human subject at a dose in a range of 0.01 mg/kg to 100 mg/kg. In one embodiment, the myostatin inhibitor, e.g., antibody, or antigen binding fragment thereof, is administered to the human subject intraperitoneally, intravenously, intramuscularly, locally or subcutaneously.

In one embodiment, the methods disclosed herein further comprise administering a second therapy to the human subject. In one embodiment, the second therapy is selected from the group consisting of insulin, insulin sensitivity enhancing agents, alpha-glucosidase inhibitors, biguanides, sulfonylureas, insulin secretion-promoting agents, amyrin agonist, phosphotyrosin phosphatase inhibitor, aldose reductase inhibitors, neurotrophic factors, PKC inhibitors, advanced glycation end-product (AGE) inhibitors, active oxygen quenching agents, statins, squalene synthetase inhibitors, fibrate, niacin, PCSK9 inhibitors, triglyceride lowing agents, cholesterol sequestering agents, angiotensin converting enzyme inhibitors, angiotensin II antagonists, calcium channel blockers, ursodiol, pioglitazone, orlistat, betaine, rosiglitazone, central anti-obesity agents, gastrointestinal lipase inhibitors, beta 3-adrenoceptor agonists, peptide-based appetite-suppressing agents, cholecystokinin agonists, dopamine agonists, DPP-4 inhibitors, glucagon-like peptides, meglitinides, sulfonylureas, sodium glucose transporter (SGLT) 2 inhibitors, cyclooxygenase inhibitors, progesterone derivatives, metoclopramide-based agents, tetrahydrocannabinol-based agents, and lipid metabolism improving agents.

In one embodiment, the myostatin inhibitor, e.g., antibody, or antigen-binding fragment thereof, is administered at a dose of about 0.01 mg/kg to about 30 mg/kg. In one embodiment, the myostatin inhibitor, e.g., antibody, or antigen-binding fragment thereof, is administered intraperitoneally, intravenously, intramuscularly, or subcutaneously.

In one embodiment, the antibody, or antigen-binding fragment thereof does not bind to GDF11 or Activin. In one embodiment, the antibody, or antigen-binding fragment thereof does not bind mature myostatin. In one embodiment, the antibody, or antigen binding fragment thereof, is cross-reactive with human and murine pro/latent myostatin. In one embodiment, the antibody, or antigen binding fragment thereof, inhibits proteolytic formation of mature myostatin by tolloid protease. In one embodiment, the antibody, or antigen binding fragment thereof, inhibits proteolytic formation of mature myostatin by tolloid protease with an IC50 of less than 1 μM.

In one embodiment, the antibody, or antigen binding fragment thereof, comprises a heavy chain variable domain comprising a complementarity determining region 3 (CDRH3) comprising a sequence as set forth in any one of SEQ ID NOs:10-11 and 66. In one embodiment, the antibody, or antigen binding fragment thereof, comprises a light chain variable domain comprising a complementarity determining region 3 (CDRL3) comprising a sequence as set forth in any one of SEQ ID NO: 22-23 and 67. In one embodiment, the antibody, or antigen binding fragment thereof, comprises six complementarity determining regions (CDRs): CDRH1, CDRH2, CDRH3, CDRL1, CDRL2, and CDRL3, wherein CDRH1 comprises a sequence as set forth in any one of SEQ ID NOs: 1-3, CDRH2 comprises a sequence as set forth in any one of SEQ ID NOs: 4-9, CDRH3 comprises a sequence as set forth in any one of SEQ ID NOs: 10-11 and 66, CDRL1 comprises a sequence as set forth in any one of SEQ ID NOs: 12-17, CDRL2 comprises a sequence as set forth in any one of SEQ ID NOs: 18-21, and CDRL3 comprises a sequence as set forth in any one of SEQ ID NOs: 22-23 and 67.

In one embodiment, CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 22.

In one embodiment, CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14 or 15, CDRL2 comprises a sequence as set forth in SEQ ID NO: 20 or 21, and CDRL3 comprises a sequence as set forth in SEQ ID NO: 23.

In one embodiment, CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 66, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 67.

In one embodiment, CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16 or 17, CDRL2 comprises a sequence as set forth in SEQ ID NO: 20 or 21, and CDRL3 comprises a sequence as set forth in SEQ ID NO: 23.

In one embodiment, the antibody, or antigen binding fragment thereof, wherein the antibody comprises a heavy chain variable domain sequence as set forth in any one of SEQ ID NOs: 24-29. In one embodiment, the antibody, or antigen binding fragment thereof, comprises a light chain variable domain sequence of as set forth in any one of SEQ ID NOs: 30-35. In one embodiment, the antibody, or antigen binding fragment thereof, comprises a heavy chain variable region comprising an amino acid sequence of SEQ ID NO:25 and a light chain variable region comprising an amino acid sequence of SEQ ID NO:31.

In one embodiment, the antibody, or antigen binding fragment thereof, comprises a heavy chain comprising an amino acid sequence of SEQ ID NO:50. In one embodiment, the antibody, or antigen binding fragment thereof, comprises a light chain comprising an amino acid sequence of SEQ ID NO:51.

In one embodiment, the antibody, or antigen binding fragment thereof, competes for binding to pro/latent myostatin with any other antibody described herein. In one embodiment, the antibody, or antigen binding fragment thereof, binds to pro/latent myostatin at the same epitope as an antibody described herein.

In one embodiment, the antibody, or antigen binding fragment thereof, competes for binding to pro/latent myostatin with an equilibrium dissociation constant, Kd, between the antibody and pro/latent myostatin of less than $10^{-6}$ M. In one embodiment, the Kd is in a range of $10^{-11}$ M to $10^{-6}$ M.

In one embodiment, the antibody, or antigen binding fragment thereof, is a human antibody, a humanized antibody, a diabody, a chimeric antibody, a Fab fragment, a F(ab')2 fragment, or an Fv fragment. In one embodiment, the antibody is a humanized antibody. In one embodiment, the antibody is a human antibody. In one embodiment, the antibody, or antigen binding fragment thereof, comprises a framework having a human germline sequence.

In one embodiment, the antibody, or antigen binding fragment thereof, comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In one embodiment, the antibody comprises a constant domain of IgG4. In one embodiment, the antibody comprises a constant domain of IgG4 having a backbone substitution of Ser to Pro that produces an IgG1-like hinge and permits formation of inter-chain disulfide bonds. In one embodiment, the antibody, or antigen-binding portion thereof, docs not bind to GDF11. In one embodiment, the antibody, or antigen-binding portion thereof, does not bind mature (fully processed, free/soluble, active) myostatin. In one embodiment, the antibody, or antigen-binding portion thereof, selectively or preferentially binds the tissue-bound myostatin (e.g., pro-form of myostatin; i.e., proMyostatin or pro-myostatin). In one embodiment, the antibody, or antigen-binding portion thereof, binds both the pro- and latent forms of myostatin (proMyostatin and latent Myostatin) but not mature myostatin.

BRIEF DESCRIPTION OF THE FIGURES

FIG. 1A shows myostatin secreted as a proprotein, with an inhibitory prodomain followed by a C-terminal growth factor domain, which exists as a disulfide-linked dimer. FIG. 1B shows precursor protein assembled in an inactive conformation where the prodomain (dark gray) encloses the growth factor (light gray) with a "straightjacket" assembly. This figure is an adaption from the structure of latent TGFβ1 (Shi et al. Nature 2011).

FIGS. 11A-11D show effects of treatment with Ab2 on change in lean mass in healthy Cynomolgus monkeys. Healthy male Cynomolgus monkeys were dosed by intravenous injection once weekly for 8 weeks at three different doses of Ab2, 3 mg/kg, 10 mg/kg, and 30 mg/kg, with a 4-week recovery phase. Control animals were administered vehicle control (20 mM Citrate and 150 mM Sodium Chloride USP, pH 5.5). Lean mass was measured by Dual Energy X-Ray Absorptiometry (DEXA). FIG. 11A is a graph showing mean percent change in lean mass in muscles from all limbs in Ab2-treated and control animals measured at Day 0, 4 weeks, 8 weeks, and 12 weeks. FIG. 11B is a graph showing mean percent change in lean mass in muscles from all limbs in Ab2-treated and vehicle control animals measured at week 4. FIG. 11C is a graph showing mean percent change in lean mass in limb muscles in Ab2-treated and vehicle control animals measured at week 8. FIG. 11D is a graph showing mean percent change in lean mass in limb muscles in Ab2-treated and vehicle control animals measured at week 12.

FIGS. 12A-2B are graphs showing effects of treatment with Ab2 on muscle weight in biceps brachii and gastrocnemius muscles collected from healthy Cynomolgus monkeys. Healthy male Cynomolgus monkeys were dosed by intravenous injection once weekly for 8 weeks at three different doses of Ab2, 3 mg/kg, 10 mg/kg, and 30 mg/kg, with a 4-week recovery phase to week 12. Control animals were administered vehicle control (20 mM Citrate and 150 mM Sodium Chloride USP, pH 5.5). Muscle weight was measured by tissue weight at week 12.

FIG. 13 shows mean percent change in lean mass from baseline (day 0) and in percent difference in muscle weight in healthy Cynomolgus monkeys treated with Ab2 compared to the vehicle control.

FIGS. 25A-25C show cross sections of tibilias anterior muscle probed with anti-pro/latent GDF8 antibody, Ab10, that had been incubated in blocking buffer alone (FIG. 25A), incubated in blocking buffer with 10-fold molar excess recombinant mouse GDF8 (FIG. 25B), or incubated in blocking buffer with 10-fold molar excess recombinant mouse GDF11 (FIG. 25C). FIGS. 25A-25C are counterstained with DAPI.

FIGS. 26A-26C show cross sections of tibilias anterior muscle probed with anti-pro/latent GDF8 antibody, Ab10, and anti-laminin, and counterstained with DAPI. Pro/latent GDF8 and laminin colocalize in the interstitial space at muscle fiber vertices (arrow), between muscle fibers (arrow head), and around interstitial nuclei (asterisk).

FIG. 29 demonstrates that antibody-treated animals showed a statistically significant increase in mean total crossectional bone area and cortical thickness as compared to control (PBS).

FIG. 30 demonstrates that antibody-treated animals showed an increase in trabecular bone volume, trabecular thickness, and trabecular number as compared to control. Additionally, antibody-treated animals showed a decrease in trabecular separation as compared to control.

DETAILED DESCRIPTION OF THE INVENTION

Figure 1A:
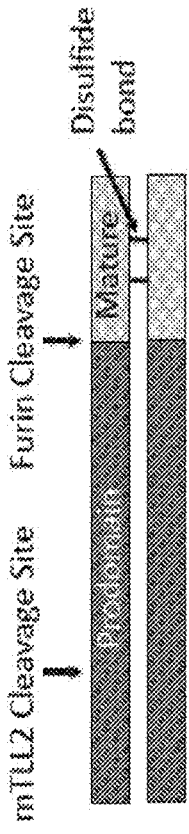
FIGS. 1A-1B depict myostatin (also known as GDF8) domain structure and pro-myostatin assembly.

The present invention is based, at least in part, on the discovery that administration of a myostatin inhibitor, e.g., an antibody, or antigen binding fragment thereof, that specifically binds to pro/latent myostatin to subjects having a metabolic disease, e.g., spinal cord injury (SCI), significantly improves both the physiological and the functional characteristics of the affected subjects. In particular, the present inventors have surprisingly discovered that administration of a myostatin inhibitor, e.g., an anti-pro/latent myostatin antibody or antigen-binding portion thereof, significantly enhances the metabolic rate or energy expenditure in subjects having metabolic disease or dysfunction. Administration of a myostatin inhibitor, e.g., an anti-pro/latent myostatin antibody also significantly attenuated SCI-induced reduction in sub-lesional muscle mass and overall body mass and, while at the same time reducing the mass of undesirable adipose tissue such as white and visceral adipose tissue. In addition, subjects who received a myostatin inhibitor, e.g., an anti-pro/latent myostatin antibody or antigen-binding portion thereof, treatment exhibited a significant improvement in their locomotor function, muscle strength, as well as motor coordination and balance skills.

Accordingly, the present invention provides methods for treating or preventing metabolic disease in a human subject using a myostatin inhibitor, e.g., anti-pro/latent myostatin antibodies or antigen-binding portions thereof. The present invention also provides methods for treating or preventing diseases associated with an impaired neurological signaling, increasing metabolic rate, increasing the level of brown adipose tissue, increasing the level of beige adipose tissue, increasing insulin dependent glycemic control, decreasing muscle catabolism of protein and/or muscle release of amino acids, decreasing glucose uptake by a target tissue in a human subject using a myostatin inhibitor, e.g., anti-pro/latent myostatin antibodies or antigen-binding portions thereof. The present invention further provides methods for increasing mass and/or function of a muscle located below a lesion in a subject who has suffered a lesion using a myostatin inhibitor, e.g., anti-pro/latent myostatin antibodies and antigen-binding portions thereof.

Thus, the present invention includes the use of antibodies and antigen-binding portions thereof that specifically bind proMyostatin and/or latent myostatin and block activation of mature myostatin in vivo in subjects, e.g., human subjects who benefit from reduced myostatin signaling. The invention includes methods of treating or preventing conditions associated with myostatin dysregulation using myostatin inhibitors, e.g., antibodies and antigen-binding portions thereof, that specifically bind proMyostatin and/or latent myostatin and block activation of myostatin in an amount effective to treat or prevent such conditions.

Definitions

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

The terms "administer", "administering" or "administration" include any method of delivery of an antibody or an antigen-binding fragment thereof, e.g., a pharmaceutical composition comprising such an antibody or antigen-binding fragment, or an agent, into a subject's system or to a particular region in or on a subject (systemic and local administration, respectively).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1 CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The antibodies of the invention are described in further detail in International Patent Application WO2016073853A1 and International Application No. PCT/US2016/052014, filed on Sep. 15, 2016, the entire contents of each of which are incorporated herein by reference. Antibody variants, as known in the art, are also encompassed by the present invention.

The term "antigen binding fragment", "antigen-binding fragment" or "antigen-binding portion" of an antibody (or simply "antibody fragment" or "antibody portion"), as used herein, refers to one or more fragments of an antibody that retain the ability to specifically bind to an antigen (e.g., pro/latent myostatin). It has been shown that the antigen-binding function of an antibody can be performed by fragments of a full-length antibody. Examples of binding fragments encompassed within the term "antigen binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) Proc. Natl. Acad. Sci. USA 90:6444-6448; Poljak, R. J. et al. (1994) Structure 2:1121-1123).

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

The term "control" or "control sample," as used herein, refers to any clinically or scientifically relevant comparative sample or counterpart, including, for example, a sample from a healthy subject, a sample from a subject having a deficiency that can cause or make the subject susceptible to a certain disease or condition, a subject with a disease or condition of interest, a sample from a subject treated with a pharmaceutical carrier, a sample from a subject prior to treatment, a sham or buffer treated subject or sample, an untreated subject or sample, and the like.

The term "control level" refers to an accepted or pre-determined level of a biological marker, e.g., a level of a marker obtained before treatment or the onset of disease or before administration of a drug, e.g., an antibody or an antigen-binding portion thereof. The level of a biological marker present in a subject or population of subjects having one or more particular characteristics, e.g., the presence or absence of a particular disease or condition.

The term "decrease", as used herein, in the context of a disease symptom refers to a statistically significant decrease in such level. The decrease can be, for example, at least 5%, 10%, 15%, 20%, 25%, 30%, 35%, 40%, 45%, 50%, 55%, 60%, 65%, 70%, 75%, 80%, 85%, 90%, or 95%, or below the level of detection for the detection method. The decrease can also be, for example, about 1-10%, 10-20%, 1-30%, 20-50%, 30-60%, 40-70%, 50-80%, or 60-90% below the level of detection for the detection method. In certain embodiments, the reduction is down to a level accepted as within the range of normal for an individual without such disorder which can also be referred to as a normalization of a level.

As used herein, the term "denervation" refers to loss or perturbation of nerve supply or neuronal input to its target tissue, such as a muscle tissue. Causes of denervation include disease (e.g., genetic disorders of motor neurons), chemical toxicity, physical injury, or intentional surgical interruption of a nerve and the like. Denervation may be partial denervation (also referred to as incomplete denervation) or complete denervation. Partial denervation can be, for example, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% loss or perturbation of nerve supply or neuronal input to its target tissue. In some embodiments, partial denervation includes about 1-10%, 10-20%, 1-30%, 20-50%, 30-60%, 40-70%, 50-80%, 60-90% of loss or perturbation of nerve supply or neuronal input to its target tissue.

"Determining" as used herein is understood as performing an assay or using a method to ascertain the state of someone or something, e.g., the presence, absence, level, or degree of a certain condition, biomarker, disease state, or physiological condition.

"Development" or "progression" of a disease means initial manifestations and/or ensuing progression of the disease. Development of the disease can be detectable and assessed using standard clinical techniques. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with myopathy includes initial onset and/or recurrence.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. The epitope can be a linear epitope or a conformational epitope.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the intended purpose may be to inhibit activation of myostatin in vivo, to achieve clinically meaningful outcome associated with the myostatin inhibition.

Measure of the relevant intended purpose may be objective (i.e., measurable by some assay or marker) or subjective (i.e., subject gives an indication of or feels an effect). In some embodiments, a therapeutically effective amount is an amount that, when administered to a patient population that meets certain clinical criteria for a disease, disorder or condition (for example, as determined by symptoms manifested, disease progression/stage, genetic profile, etc.), a statistically significant therapeutic response is obtained among the population.

In some embodiments, an effective amount is an amount that, when administered according to a particular regimen, produces a positive clinical outcome with a reasonably acceptable level of adverse effects (e.g., toxicity), such that the adverse effects, if present, are tolerable enough for a patient to continue with the therapeutic regimen, and the benefit of the therapy overweighs risk of toxicity. Those of ordinary skill in the art will appreciate that in some embodiments of the invention, a unit dosage may be considered to contain an effective amount if it contains an amount appropriate for administration in the context of a dosage regimen correlated with a positive outcome.

A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

The term "human antibody", as used herein, is intended to include antibodies having variable and constant regions derived from human germline immunoglobulin sequences and fragments thereof. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "increase" in the context, e.g., of a disease symptom, such as for example, a loss of function or loss of mass, e.g., muscle mass associated with a disease, refers to a statistically significant increase in such level. The increase can be, for example, at least 5%, 10%, 15%, 20%, 25%, 30%, 35%, 40%, 45%, 50%, 55%, 60%, 65%, 70%, 75%, 80%, 85%, 90%, or 95%, or above the level of detection for the detection method. The increase can also be, for example, about 1-10%, 10-20%, 1-30%, 20-50%, 30-60%, 40-70%, 50-80%, or 60-90% above the level of detection for the detection method. In certain embodiments, the increase is up to a level accepted as within the range of normal for an individual without such disorder which can also be referred to as a normalization of a level. In certain embodiments, the increase is the normalization of the level of a sign or symptom of a disease, an increase in the difference between the subject level of a sign of the disease and the normal level of the sign for the disease. In certain embodiments, the methods include an increase in the mass and/or function of the muscle tissue after treatment of a subject with an antibody that specifically binds pro/latent myostatin. In certain embodiments, the methods include an increase in a level of pro-myostatin in a target muscle, as compared to a control level of pro-myostatin.

An "isolated antibody", as used herein, is intended to refer to an antibody that is substantially free of other antibodies having different antigenic specificities (e.g., an isolated antibody that specifically binds pro/latent-myostatin is substantially free of antibodies that specifically bind antigens other than pro/latent-myostatin). An isolated antibody that specifically binds pro/latent-myostatin may, however, have cross-reactivity to other antigens, such as pro/latent-myostatin molecules from other species. Moreover, an isolated antibody may be substantially free of other cellular material and/or chemicals.

Unless explicitly stated otherwise, the term "mature myostatin" refers to a fully processed, biologically active form of myostatin, unless explicitly stated otherwise. A biologically active form of myostatin is capable of myostatin receptor binding and/or activation. Wild type sequence of mature myostatin is provided as SEQ ID NO: 52. In some cases, mature myostatin may contain one or more mutations, which may exhibit altered structure/function or stability.

As used herein, the term "myostatin inhibitor" refers to any compound that inhibits or antagonizes the activity or expression level of myostatin, e.g., pro/latent myostatin. In some embodiments, the myostatin inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin, an Affibody, a DARPin, an Anticalin, an Avimer, a Versabody or a gene therapy. The antibody, or antigen binding fragment thereof, may bind mature myostatin, a myostatin receptor, and/or GDF11. In some embodiments, the myostatin inhibitor is a small molecule inhibitor. In other embodiments, the myostatin inhibitor refers to a gene therapy. In one embodiment, the myostatin inhibitor binds specifically to myostatin, but not GDF11. In one embodiment, the myostatin inhibitor can be used to treat a metabolic disease, a muscle condition or disorder, a disease or disorder associated with an impaired neurological signaling or partial denervation or other condition described herein. In another embodiment, the myostatin inhibitor can be used to treat a disease involving fast twitch fibers, as described herein. In another embodiment, a myostatin inhibitor can be used to provide therapeutic effects below a lesion, as described herein.

As used herein, the phrase "latent myostatin in the circulation" or "circulating latent myostatin" refers to latent myostatin in the blood, plasma, or serum.

As used herein, the term "pro/latent-myostatin" refers to pro-myostatin, latent myostatin, or both (i.e., pro-forms or precursors of myostatin).

"Specific" and "specificity" in the context of an interaction between members of a specific binding pair (e.g., a ligand and a binding site, an antibody and an antigen, biotin and avidin) refer to the selective reactivity of the interaction. The phrase "specifically binds to" and analogous phrases refer to the ability of antibodies (or antigenically reactive fragments thereof) to bind specifically to an antigen (or a fragment thereof) and not bind specifically to other entities. Specific binding is understood as a preference for binding a certain antigen, epitope, receptor ligand, or binding partner with, for example, at least 2-fold, 5-fold, 10-fold, 50-fold, 100-fold, 200-fold, 500-fold, or 1,000-fold preference over a control non-specific antigen, epitope, receptor ligand, or binding partner. "Specific binding" as used herein can also refer to binding pairs based on binding kinetics such as $K_{on}$, $K_{off}$, and $K_D$. For example, a ligand can be understood to bind specifically to its target site if it has a $K_{off}$ of $10^{-2}$ sec$^{-1}$ or less, $10^{-3}$ sec$^{-1}$ or less, $10^{-4}$ sec$^{-1}$ or less, $10^{-5}$ sec$^{-1}$ or less, or $10^{-6}$ sec$^{-1}$ or less; and/or a $K_D$ of $10^{-6}$ M or less, $10^{-7}$M or less, $10^{-8}$ M or less, $10^{-9}$M or less, $10^{-10}$ M or less, or $10^{-11}$ M or less, or $10^{-12}$ M or less. It is understood that various proteins can share common epitopes or other binding sites (e.g., kinase reactive sites). In certain embodiments, binding sites may bind more than one ligand, but still can be considered to have specificity based on binding preference as compared to a non-specific antigen and/or by having certain binding kinetic parameters. Methods of selecting appropriate non-specific controls are within the ability of those of skill in the art. Binding assays are typically performed under physiological conditions.

As used herein, the term "slow-twitch", "slow twitch" "Type 1" or "Type I" muscle refers to a muscle enriched in Type I muscle fibers and is used frequently, more postural, and help enable long-endurance feats such as distance running. As used herein, the term "fast-twitch", "fast twitch" "Type 2" or "Type II" muscle refers to a muscle that provides higher energy output and strength and is used in powerful bursts of movements like sprinting, but such a muscle fatigue faster and cannot be used repeatedly. Fast-twitch muscles break down into two categories of fiber types: moderate fast-twitch fibers (Type IIA) and fast-twitch fibers (Type IIB or IIx). Moderate fast-twitch fibers are thicker, quicker to contract, and wear out more rapidly than slow-twitch fibers. Fast-twitch fibers, the most powerful and lowest in endurance, are activated when the body nears maximum exertion. While most muscles tend to be comprised of a mixture of various fiber types, different muscles contain different ratios of fiber types. During development or in response to certain events (e.g., exercise, disease, injury, etc.), fiber types within a muscle or muscle group may undergo fiber type switching, resulting in an altered phenotype in muscle physiology.

As used herein, the term "subject" and "patient" may be used interchangeably. In one embodiment, a subject refers to a vertebrate, in particular a mammal, in need of treatment, e.g., companion animals (e.g., dogs, cats and the like), farm animals (e.g., cows, pigs, horses, sheep, goats, poultry and the like) and laboratory animals (e.g., rats, mice, guinea pigs and the like). In some embodiments, the subject is a human who will benefit from or in need of treatment. In one embodiment, a subject is a human subject. In one embodiment, the subject is a pediatric subject.

As used herein, the phrase "sustained increase" in the context of increase of muscle mass refers to an increase of muscle mass for a specified time after the administration a therapeutically effective amount of a myostatin inhibitor, e.g., an anti-pro/latent-myostatin antibody, as described herein. Sustained increase may be continuous or non-continuous, but overall results in an increase in muscle mass for the specified time.

By "treating" or "preventing" a disease or disorder is meant delaying or preventing the onset of such a disease or disorder, reversing, alleviating, ameliorating, inhibiting, slowing down or stopping the progression, aggravation or deterioration, the progression or severity of a condition associated with such a disease or disorder, but not necessarily require a complete treatment or prevention of the disease or disorder. In one embodiment, the symptoms of a disease or disorder are alleviated by at least 5%, at least 10%, at least 20%, at least 30%, at least 40%, or at least 50%.

Myostatin

Figure 1B:
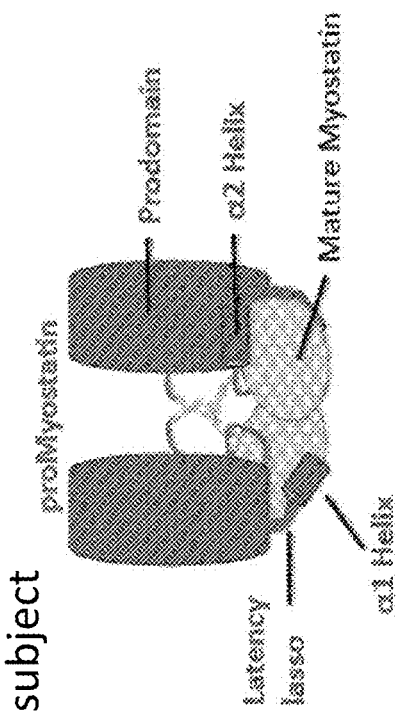
Figure 2:
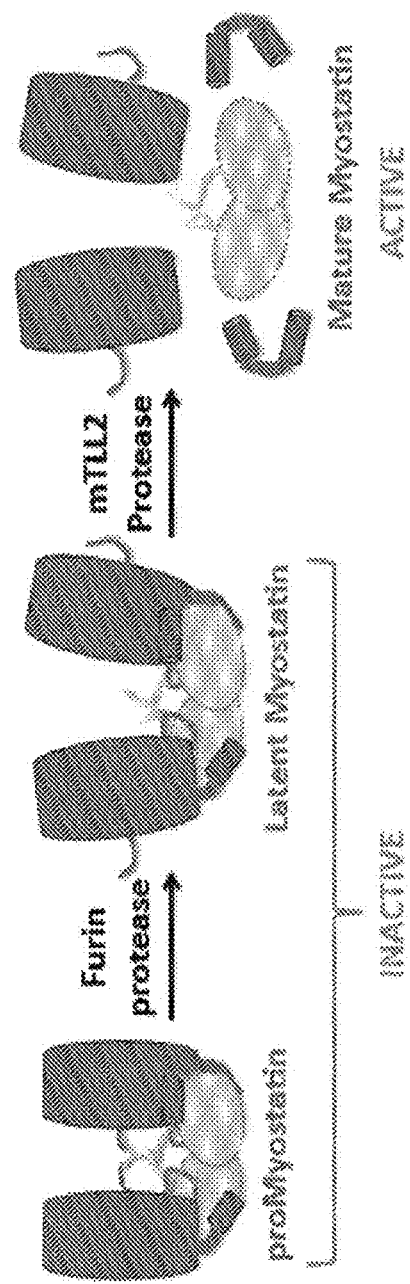
FIG. 2 demonstrates that the activation of myostatin involves two distinct protease events, generating three major myostatin species. The biosynthetic precursor protein, pro-myostatin, is processed by two separate proteases. Cleavage of pro-myostatin (and pro-GDF11) is carried out by a proprotein convertase, such as Furin/PACE3 (Paired Basic Amino acid Cleaving Enzyme 3) or PCSK5 (Proprotein Convertase Subtilisin/Kexin type 5), which cuts at a conserved RXXR site between the prodomain and mature growth factor. This cleavage produces a latent complex, in which the mature growth factor is shielded from binding to its receptors by the prodomain Activation and release of the active growth factor is accomplished after cleavage by an additional protease from the BMP/tolloid family, such as TLL-2 (Tolloid-like protein 2) or BMP1 (Bone Morphogenetic Protein 1). These cleavage events yield a mature form of myostatin, which may be referred to as active myostatin or mature myostatin.

Myostatin, also known as GDF8, is a member of the TGFβ superfamily, and belongs to a subfamily including two members: myostatin and GDF11. Like other members of the TGFβ superfamily, myostatin and GDF11 are both initially expressed as inactive precursor polypeptides (termed pro-myostatin and proGDF11, respectively). The domain structure and nomenclature are shown in FIG. 1A. FIG. 1B illustrates a cartoon model of the overall structure of pro-myostatin, where the mature growth factor is held locked in a cage comprised of two alpha helices connected by a loop termed the "latency lasso".

Myostatin is a well-characterized negative regulator of skeletal muscle mass that is released from an autoinhibitory N-terminal prodomain by two separate protease cleavage steps. These cleavage events, within the muscle fiber microenvironment, for example, may be referred to as supracellular activation. Following activation, mature myostatin signals by binding to a complex of Type I and II cell surface receptors (Alk4/5 and ActRIIB) whose downstream signaling induces muscle atrophy. There is interest in myostatin as a target for the treatment of muscle wasting. A number of therapeutics targeting the ActRIIB signaling pathway are completing early- to mid-stage clinical trials in muscle wasting conditions including sarcopenia, muscular dystrophies, cachexia, and hip replacement/hip fracture. To date, the primary clinical strategy has focused on blocking the interaction between mature myostatin and cell surface receptors. However, several therapeutic programs have been discontinued due to lack of specificity (leading to unacceptable toxicities) and/or efficacy. In vivo, myostatin is primarily in complex with its inhibitory prodomain.

Aspects of the disclosure provided herein relate to an assessment of the extent to which blocking the supracellular activation of myostatin from these inhibitory prodomain complexes provides a means for specifically blocking myostatin pathway signaling. Further aspects of the disclosure relate to an evaluation of a panel of human monoclonal antibodies that selectively bind the myostatin precursor forms, including a subset that inhibit proteolytic activation in vitro. In some embodiments, it has been found that antibodies that block activation are capable of protecting mice from dexamethasone-induced muscle atrophy. Assessment of serum and muscle samples from healthy animals and from those undergoing dexamethasone-induced atrophy demonstrated altered biodistribution of precursor forms during atrophy, a unique finding with important implications in understanding muscle wasting pathologies. Furthermore, treatment of healthy mice with a murine version of a potent activation-blocking antibody promoted robust muscle growth and resulted in significant gains in muscle function. Results provided herein provide insights into the significance of myostatin processing in skeletal muscle protein homeostasis. In addition, blocking the supracellular activation of the growth factor from precursor forms is a potent method for preventing myostatin signaling, a technique offering a novel therapeutic strategy that can also be applied to other members of the TGFβ superfamily.

Activation and release of mature myostatin is accomplished by several discrete protease cleavage events. The first cleavage step of pro-myostatin and proGDF11 is carried out by a proprotein convertase, which cuts at a conserved RXXR site between the prodomain and mature growth factor. This cleavage produces a "latent-myostatin," in which the mature myostatin is shielded from binding to its receptors by the prodomain. Activation and release of the mature, active myostatin growth factor is accomplished after cleavage of latent-myostatin by an additional protease from the BMP/tolloid family, such as mTLL-2. As used herein, the term "mature myostatin" can refer to both full-length mature myostatin, as well as fragments of the full-length mature myostatin which retain biological activity.

The term "pro-myostatin," also known as "proGDF8," refers to an inactive precursor of mature myostatin which comprises a disulfide-linked homodimer, each molecule of the homodimer comprising the amino terminal prodomain covalently bound to the carboxyl terminal mature myostatin domain. In one embodiment, "pro-myostatin" has not been cleaved by either a proprotein convertase, or a protease from the BMP/tolloid family. Exemplary pro-myostatin sequences, variants thereof, and methods of generating pro-myostatin are well known in the art and described in more detail herein.

As used herein the term "latent-myostatin" refers to an inactive precursor of mature myostatin which comprises a disulfide-linked homodimer, each molecule of the homodimer comprising the amino terminal prodomain non-covalently bound to the carboxyl terminal mature myostatin domain. In one embodiment, "latent-myostatin" is generated from a pro-myostatin that has been cleaved by a proprotein convertase, but which has not been cleaved by a protease from the BMP/tolloid family. In another embodiment, "latent-myostatin" can be generated by combining the prodomain and the carboxy terminal mature myostatin domain in vitro and allowing them to fold properly. See, for example, Sengle et al., J. Biol. Chem., 286(7):5087-5099, 2011. Exemplary latent-myostatin sequences, variants thereof, and methods of generating latent-myostatin are well known in the art and described in more detail herein.

Exemplary proGDF8 sequences in the human, rat, mouse and cynomolgus are provided below. In these proGDF8 sequences, a proprotein convertase cleavage site is indicated in bold and a tolloid protease site is indicated by underlining. In some embodiments, the proprotein convertase cleavage site comprises amino acid residues 240 to 243 of SEQ ID NOs: 52-55. In some embodiments, the tolloid protease site comprises amino acid residues 74-75 of SEQ ID NOs: 52-55. It should be appreciated that the exemplary proGDF8 sequences provided herein are not intended to be limiting and additional proGDF8 sequences from other species, including any isoforms thereof, are within the scope of this disclosure.

proGDF8 (human):
(SEQ ID NO: 52)
NENSEQKENVEKEGLCNACTWRQNTKSSRIEAIKIQILSKLRLETAPNIS

KDVIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (rat):
(SEQ ID NO: 53)
NEDSEREANVEKEGLCNACAWRQNTRYSRIEAIKIQILSKLRLETAPNIS

KDAIRQLLPRAPPLRELIDQYDVQRDDSSDGSLEDDDYAHTTETIITMPT

ESDFLMQADGKPKCCFFKFSSKIQYNKVVKAQLWIYLRAVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (mouse):
(SEQ ID NO: 54)
NEGSEREENVEKEGLCNACAWRQNTRYSRIEAIKIQILSKLRLETAPNIS

KDAIRQLLPRAPPLRELIDQYDVQRDDSSDGSLEDDDYAHTTETIITMPT

ESDFLMQADGKPKCCFFKFSSKIQYNKVVKAQLWIYLRPVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVGRCG

CS.

proGDF8 (cynomolgus):
(SEQ ID NO: 55)
NENSEQKENVEKEGLCNACTWRQNTKSSRIEAIKIQILSKLRLETAPNIS

KDAIRQLLPKAPPLRELIDQYDVQRDDSSDGSLEDDDYAHTTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIA.

The prodomain of the myostatin polypeptide is comprised of several structural domains as described previously (WO 2014/182676). These include, for example, Straight Jacket region, Fastner region, Arm region, Fingers region 1, Fingers region 2, Latency Loop, Alpha-1 Helical region, and Bowtie region. In some embodiments, preferred antibodies or fragments thereof binds an epitope within the Arm region of the myostatin prodomain. In some embodiments, the epitope includes at least one amino acid residue from the "KALDEN" (SEQ ID NO: 118) polypeptide stretch within the Arm region of the prodomain. In some embodiments, the amino acid residue within the Arm region of the prodomain making contact with the antibody when bound to the antigen is a residue that is not conserved between myostatin and GDF11. In some embodiments, such residue(s) is/are K, E, and/or N of the polypeptide stretch (shown in bold type above).

Myostatin and GDF11 share a relatively high degree of conservation between their mature growth factor domains, with ninety percent identity, but are much less well conserved in their prodomain regions with less than fifty percent amino acid identity between the two. Myostatin and GDF11 bind and signal through the same receptors consisting of a Type I receptor (ALK4/5) in association with a type II receptor (ACTRIIA/B). Engagement of myostatin with Type I and Type II receptors initiates a signaling cascade leading to SMAD phosphorylation and transcriptional activation of muscle atrophy genes. The relatively high degree of conservation in the mature growth factors has made it challenging to identify reagents, such as monoclonal antibodies, that can differentiate between mature myostatin and GDF11.

In some embodiments, pro/latent-myostatin antibodies are provided herein that specifically bind to a chimeric construct that contains the growth factor domain and N terminal propeptide portion of GDF11 and the C terminal portion of the propeptide of GDF8. This chimeric construct, as forth below, is referred as GDF11 Arm8.

>GDF11 Arm8
(SEQ ID NO: 65)
MDMRVPAQLLGLLLLWFSGVLGDYKDDDDKHHHHHHLEVLFQGPAEGPAA

AAAAAAAAAAGVGGERSSRPAPSVAPEPDGCPVCVWRQHSRELRLESIK

SQILSKLRLKEAPNISREVVKQLLPKAPPLRELIDQYDVQRDDSSDGSLE

DDDYHATTETIITMPTESDFLMQVDGKPKCCFFKFSSKIQYNKVVKAQLW

IYLRPVETPTTVFVQILRLIKPMKDGTRYTGIRSLKLKMNPGTGIWQSID

VKTVLQNWLKQPESNLGIEIKALDENGHDLAVTFPGPGEDGLNPFLEVKV

TDTPKRSRRNLGLDCDEHSSESRCCRYPLTVDFEAFGWDWIIAPKRYKAN

YCSGQCEYMFMQKYPHTHLVQQANPRGSAGPCCTPTKMSPINMLYFNDKQ

QIIYGKIPGMVVDRCGCS

Role of Myostatin in Muscle Homeostasis and Metabolic Regulation

Skeletal muscle accounts for approximately 40% of body mass and is a dynamic organ, turning over at a rate of 1-2% per day. Myostatin is believed to play a pivotal role in maintaining the homeostasis of muscle both in healthy and disease conditions. Myostatin is capable of inducing muscle atrophy via its inhibition of myoblast proliferation, increasing ubiquitin-proteasomal activity and downregulating activity of the IGF-Akt pathway. These well-recognized effects are seen in multiple atrophy causing situations, including injury, diseases such as cachexia, disuse and space flight, demonstrating the importance of the myostatin signaling mechanism. Based on this central role, significant work has been pursued to inhibit myostatin's actions in viva. Indeed, antagonizing myostatin signaling has shown to favor muscle growth/increase.

In addition, muscle is known to be the major protein reservoir of the body and therefore contributes to amino acid homeostasis/metabolism. Along with glucose (made and stored as glycogen primarily in the liver and the muscles) and lipids (stored in fat tissues), proteins in muscles can act as an energy source (i.e., broken down to generate energy). Impairment or imbalance in the utilization or mobilization of these energy sinks in the body may, at least in part, underlie various types of metabolic dysregulation. It is therefore contemplated that myostatin may play a direct role in the regulation of metabolism by coordinating the balance between breakdown vs. synthesis/storage of glucose, fats and/or muscles in the body. Indeed, while myostatin has been primarily considered as a key regulator of muscle growth/loss since its discovery in 1997, findings presented in more detail herein suggest a broader role of myostatin as a metabolic regulator.

Because muscle homeostasis is correlated with amino acid/protein metabolism, it is further contemplated that myostatin inhibition may in turn regulate nitrogen metabolism and nitrogen mobilization in the body. In muscle catabolism, a muscle tissue breaks down into its building blocks, amino acids, which may be considered as a major reservoir (and thus a source) of nitrogen. Nitrogen is an element of ammonia, which is highly toxic to the body and is excreted in a form of urea in humans. When nitrogen metabolism is dysregulated, possible outcome includes an imbalance in fluid retention, which may manifest as systemic or local edema (e.g., congestion; fluid overload). Pulmonary edema, as well as renal congestion, for example, is frequently observed in patients with heart failure, associated with decreased cardiac output. Pulmonary congestion is in fact the most frequent cause of hospitalization in this clinical setting and correlates with poor prognosis.

Similarly, in pathologic conditions that involve impaired osmoregulation, the affected individual may be particularly sensitive to salt intake, which may cause or exacerbate fluid overload.

Therefore, for subjects with fluid retention or volume-overload, such as subjects having impaired osmoregulation and subjects with heart failure, e.g., chronic heart failure, current guidelines suggest that decongestion should be attempted using diuretic therapy (see, e.g., Regolisti et al., Nephrology @ Point of Cre 2016; 2(1):e73-e87). However, in many cases, diuretic treatment is ineffective, or the subject is refractory to diuretic therapy. Myostatin inhibition according to the present disclosure may provide such patients with clinical benefits. Specifically, the methods of the present invention are suitable for increasing responsiveness of subjects who are refractory to diuretic treatment, or poorly responsive to diuretic treatment.

For example, administration of a myostatin inhibitor reduces the diuretic dose needed and/or offers improved control of symptoms, such as CHF symptoms; improves cardiac function; and/or prevents pathologic cardiac remodeling or other worsening of cardiac function chronically. Myostatin inhibition using an inhibitor described herein also reduces the risk of CHF exacerbations, such as episodes of acute pulmonary edema.

For other volume-overload states, e.g., renal failure or liver disease, which require high-dose diuretics, a myostatin inhibitor disclosed herein reduces the diuretic dose needed; offer improved control of symptoms, such as peripheral edema or congestion within the body internally (including pleural effusions, ascites, hepatic congestion, or eyes-volume overload within the eyes, which can lead to retinal detachment); and/or reduce the risk of pulmonary edema.

For subjects at higher risk for developing acute pulmonary edema, such as subjects receiving IV fluids, blood transfusions, or fluid shifts, the myostatin inhibitors disclosed herein may be administered prophylactically. For example, a subject with congestive heart failure who needs to receive a blood transfusion can be prophylactically administered a myostatin inhibitor during the blood transfusion to prevent the onset of acute pulmonary edema during the transfusion.

For subjects having CHF and/or other volume-overload states who develop hyponatremia, either due to the volume-overload, itself, or from diuretics used to treat the volume-overload, myostatin inhibitors disclosed herein can be administered to treat the hyponatremia and/or enable higher doses of diuretics to be used, when diuretic dosing is limited by hyponatremia as a side effect. Generally speaking, however, the myostatin inhibitors disclosed herein may be used to treat hyponatremia, irrespective of the underlying etiology.

Myostatin Pathway Inhibition

There are several myostatin pathway inhibitors, such as small molecules, antibodies or antigen-binding portions thereof, and gene therapies, in various stages of clinical development towards the treatment of muscle-related conditions. Such pathway antagonists target either the mature growth factor or its type II receptor. Notably, most of these antagonists are not myostatin-specific, such that they antagonize the signaling of multiple TGFβ family members. For example, a number of current clinical candidates block additional growth factors such as Activin A, GDF11, and BMPs 9 and 10, which are regulators of reproductive biology, wound healing, erythropoiesis and blood vessel formation, respectively. Aspects of this disclosure relate to a recognition that the lack of specificity observed in these myostatin antagonists described elsewhere may pose a greater risk to certain patient populations because they block additional biological pathways such as those listed above in addition to myostatin. This may therefore potentially limit the population of patients who can safely undergo therapy due to unacceptable adverse-effects such as abnormal bleeding, wound healing, or reproductive problems caused by off-target antibody binding (Campbell, et al. *Muscle Nerve* (2016); David, L., *Blood* 109, 1953-1961 (2007)). For example, Activin A is involved in both wound healing and reproductive biology, and binding to Activin A would therefore limit use in patients who have recently undergone surgery or injury, or in women of reproductive age. Such increased risk of adverse effects or toxicity may be particularly concerning where i) a patient population requires a long-term treatment (such as chronic conditions); and/or, ii) a patient population is or includes pediatric patients, who may be susceptible to such adverse effects and/or toxicity. Accordingly, the present invention includes a novel approach to inhibiting myostatin signaling in vivo with potentially greater safety profiles.

Accordingly, provided herein are myostatin inhibitors, such as antibodies, or antigen binding fragments thereof, capable of binding to pro-myostatin and/or latent myostatin, thereby inhibiting myostatin activation, and uses thereof for treating diseases and disorders associated with myopathy. In some embodiments, given the prevalence of the latent complex in circulation, treatments are provided herein that specifically target more abundant and longer-lived myostatin precursors e.g., pro-myostatin and latent myostatin, rather than the mature growth factor. Without wishing to be bound by any particular theory, myostatin inhibitors, such as antibodies, or antigen binding fragments thereof, provided herein may prevent the proteolytic activation of pro-myostatin and/or latent myostatin into mature myostatin which is considered the "active" form of myostatin, capable of activating the myostatin pathway, e.g., by binding Type I (ALK4/5) and Type II (ACTRIIA/B) receptors.

As used herein, the term "pro/latent-myostatin" refers to pro-myostatin, latent myostatin, or both. In some embodiments, an anti-pro/latent myostatin antibody, or antigen binding fragment thereof, binds specifically to pro-myostatin. In some embodiments, an anti-pro/latent myostatin antibody, or antigen binding fragment thereof, binds specifically to latent myostatin. In some embodiments, an anti-pro/latent myostatin antibody, or antigen binding fragment thereof, binds specifically to both latent myostatin and pro-myostatin. In preferred embodiments, the anti-pro/latent myostatin antibody, or antigen binding fragment thereof, that binds specifically to pro-myostatin and/or latent myostatin does not bind mature myostatin. In preferred embodiments, the anti-pro/latent myostatin antibody, or antigen binding fragment thereof, that binds specifically to pro-myostatin and/or latent myostatin does not bind pro/latent GDF11 or mature GDF11.

Anti-Pro/Latent Myostatin Antibodies, or Antigen-Binding Fragments thereof, and Production Thereof The present disclosure is based, at least in part, on the surprising discovery that blocking the activation step of myostatin, rather than targeting already active myostatin, may provide an advantageous mode of selectively inhibiting myostatin signaling in vivo. Thus, the invention may have utility as a therapeutic in any condition where selective reduction of myostatin signaling in vivo is beneficial. More specifically, the invention includes surprising findings that specific inhibition of myostatin activation can effectuate not only muscle mass increase but also enhanced muscle function, as well as prevention of metabolic dysregulation. Unexpectedly, beneficial therapeutic effects can also be achieved even below a lesion in a subject having impaired but not complete loss of signaling between a neuron and a target tissue, such as a target muscle.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Antibodies, or antigen binding fragments thereof, described herein are capable of binding to a pro/latent-myostatin, thereby inhibiting the proteolytic activation of pro/latent-myostatin into mature myostatin. In some instances, antibodies, or antigen binding fragments thereof, described herein can inhibit the proteolytic activation of pro/latent-myostatin by at least 20%, e.g., 30%, 40%, 50%, 60%, 70%, 80%, 90%, 95%, or higher. In some instances, antibodies described herein can inhibit the proteolytic cleavage of pro-myostatin by a proprotein convertase (e.g., furin) by at least 20%, e.g., 30%, 40%, 50%, 60%, 70%, 80%, 90%, 95%, or higher. In some instances, antibodies, or antigen binding fragments thereof, described herein can inhibit the proteolytic cleavage of pro-myostatin or latent myostatin by a tolloid protease (e.g., mTLL2) by at least 20%, e.g., 30%, 40%, 50%, 60%, 70%, 80%, 90%, 95%, or higher.

In some embodiments, inhibition of proteolytic cleavage of pro-myostatin or latent myostatin by a tolloid protease results in a progressive increase in muscle mass. In some embodiments, a subject exhibits a progressive increase in muscle mass for at least 2 weeks, 4 weeks, 6 weeks, 8 weeks, 10 weeks, 12 weeks, 14 weeks, 16 weeks, 18 weeks, or 20 weeks (or any range bracketed by any of the values). The inhibitory activity of an anti-pro/latent-myostatin antibody can be measured by routine methods, for example, by Western blot analysis as described in Example 1 and FIG. 3 disclosed in WO 2016/073853, the entire contents of which are expressly incorporated herein by reference. However, it should be appreciated that additional methods may be used for measuring the inhibitory activity of an anti-pro/latent-myostatin antibody on proteolytic cleavage of pro/latent-myostatin. In some embodiments, inhibition of pro/latent-myostatin cleavage (e.g., by a proprotein convertase and/or tolloid protease) may be reflected as an inhibition constant ($K_i$), which provides a measure of inhibitor potency, and which it is the concentration of inhibitor (e.g., an anti-pro/latent-myostatin antibody) required to reduce protease activity (e.g., of a proprotein convertase or tolloid protease) by half and is not dependent on enzyme or substrate concentrations.

In some embodiments, a proprotein convertase comprises (i) a catalytic domain that hydrolyzes a peptide bond of a protein containing a proprotein convertase cleavage site, and (ii) a binding pocket that binds to an rTGF with a proprotein convertase cleavage site. Examples of proprotein convertases for use in accordance with the present disclosure include, without limitation, PCSK5/6, PACE4, PACE7 and PACE3 (e.g., furin). A proprotein convertase, in some embodiments, is obtained, e.g., purified from, any mammal including, without limitation, humans, monkeys or rodents (e.g., mice, rats, hamsters). In another embodiment, a proprotein convertase is produced recombinantly.

In some embodiments, a proprotein convertase is homologous to a proprotein convertase selected from the group consisting of: PCSK5/6, PACE4, PACE7 and PACE3 (e.g., furin). For example, a proprotein convertase may be at least 70% identical, at least 80% identical, at least 90% identical, at least 95% identical, at least 96% identical, at least 97% identical, at least 98% identical, at least 99% identical, at least 99.5% identical, or at least about 99.9% identical to PCSK5/6, PACE4, PACE7 or PACE3 (e.g., furin).

A proprotein convertase cleavage site, in some embodiments, is an amino sequence that can be cleaved by a proprotein convertase (e.g., PCSK5/6, PACE4, PACE7 and PACE3). In some embodiments, the proprotein convertase cleavage site comprises the amino acid sequence R-X-X-R, where R is arginine and X is any amino acid. In some embodiments, the proprotein convertase cleavage site comprises the amino acid sequence R-X-(K/R)-R, where R is arginine, K is lysine and X is any amino acid. In some embodiments, the proprotein convertase cleavage site comprises the amino acid sequence is R-V-R-R (SEQ ID NO: 57), where R is arginine and V is valine Exemplary proprotein convertase cleavage sites for human, rat, mouse, and cynomolgus myostatin are shown, in bold, in SEQ ID NOs: 52-55. In some embodiments, the proprotein convertase cleavage site comprises the amino acid sequence RSRR (SEQ ID NO: 56).

In some embodiments, tolloid proteases for use in accordance with the present disclosure include, without limitation, BMP-1, mTLL-1 and mTLL-2. A tolloid protease may be obtained from any mammal including, without limitation, humans, monkeys, or rodents (e.g., mice, rats, hamsters).

In some embodiments, a tolloid protease is homologous to a tolloid protease selected from the group consisting of: BMP-1, mTLL-1 and mTLL-2. For example, a tolloid protease may be at least 70% identical, at least 80% identical, at least 90% identical, at least 95% identical, at least 96% identical, at least 97% identical, at least 98% identical, at least 99% identical, at least 99.5% identical, or at least about 99.9% identical to BMP-1, mTLL-1 and mTLL-2.

A tolloid protease cleavage site, in some embodiments, is an amino sequence that can be cleaved by a tolloid (e.g., BMP-1, mTLL-1 and mTLL-2). Exemplary tolloid protease cleavage sites for human, rat, mouse, and cynomolgus myostatin are shown, in underlining, in SEQ ID NOs: 52-55. In some embodiments, the tolloid cleavage site comprises the amino acid sequence QR, where Q is glutamine and R is arginine.

In some embodiments, antibodies, or antigen binding fragments thereof, described herein are capable of binding to a pro/latent-myostatin, thereby inhibiting myostatin activity. In some instances, the antibodies, or antigen binding fragments thereof, described herein can inhibit myostatin signaling by at least 20%, e.g., 30%, 40%, 50%, 60%, 70%, 80%, 90%, 95%, or higher. In some embodiments, inhibition of Myostatin signaling can be measured by routine methods, for example, using a myostatin activation assay as described in Example 1 disclosed in WO 2016/073853, the entire contents of which are expressly incorporated herein by reference. However, it should be appreciated that additional methods may be used for measuring myostatin signaling activity.

It should be appreciated that the extent of proteolytic cleavage of myostatin, e.g., by a proprotein convertase and/or a tolloid protease, can be measured and/or quantified using any suitable method. In some embodiments, the extent of proteolytic cleavage of myostatin is measured and/or quantified using an enzyme-linked immunosorbent assay (ELISA). For example, an ELISA may be used to measure the level of released growth factor (e.g., mature myostatin). As another example, an antibody, or antigen binding fragment thereof, that specifically binds to pro-myostatin, latent myostatin and/or mature myostatin can be used in an ELISA to measure the level of a specific form of myostatin (e.g., pro/latent/mature-myostatin), to quantify the extent of proteolytic cleavage of myostatin. In some embodiments, the extent of proteolytic cleavage of myostatin is measured and/or quantified using immunoprecipitation followed by SDS-PAGE or mass spectrometry of tryptic peptides, fluorescence anisotropy-based techniques, FRET assays, hydrogen-deuterium-exchange mass spectrometry, and/or NMR spectroscopy.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H$1. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

Anti-pro/latent-myostatin antibodies, or antigen binding fragments thereof, suitable for use in the methods of the present invention include those described in International Patent Application Nos. PCT/US15/59468 and PCT/US16/52014. The entire contents of each of the foregoing applications are incorporated herein by reference in their entireties.

In some embodiments, anti-pro/latent-myostatin antibodies, or antigen binding fragments thereof, of the present disclosure and the nucleic acid molecules of the present disclosure that encode the antibodies, or antigen binding fragments thereof, include the CDR amino acid sequences shown in Tables 1-3.

TABLE 1

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Ab1 Kabat: IMGT: | SSYGMH (SEQ ID NO: 1) GFTFSSYGMH (SEQ ID NO: 2) | VISYDGSNK YYADSVKG (SEQ ID NO: 4) ISYDGSN (SEQ ID NO: 5) | DLLVRFLEWSH YYGMDV (SEQ ID NO: 10) | SGSSSNIGSNT VH (SEQ ID NO: 12) SDN SSNIGSNT (SEQ ID NO: 13) | SDNQRPS (SEQ ID NO: 18) SDN (SEQ ID NO: 19) | AAWDDSLNGV (SEQ ID NO: 22) |

TABLE 1-continued

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Ab2 Kabat: IMGT: | SSYGMH (SEQ ID NO: 1) GFTFSSYGMH (SEQ ID NO: 2) | VISYDGSNK YYADSVKG (SEQ ID NO: 4) ISYDGSN (SEQ ID NO: 5) | DLLVRFLEWSH YYGMDV (SEQ ID NO: 10) | SGSSSNIGSNT VH (SEQ ID NO: 12) SSNIGSNT (SEQ ID NO: 13) | SDNQRPS (SEQ ID NO: 18) SDN (SEQ ID NO: 19) | AAWDDSLNGV (SEQ ID NO: 22) |
| Ab3 Kabat: IMGT: | SSYGMH (SEQ ID NO: 1) GFAFSSYGMH (SEQ ID NO: 3) | VISYDGSIK YYADSVKG (SEQ ID NO: 6) ISYDGSI (SEQ ID NO: 7) | DLLVRFLEWSH KYGMDV (SEQ ID NO: 11) | SGSTSNIGSVT VH (SEQ ID NO: 14) TSNIGSNT (SEQ ID NO: 15) | SDDQRPS (SEQ ID NO: 20) SDD (SEQ ID NO: 21) | AAWDESLNGV (SEQ ID NO: 23) |
| Ab4 Kabat: IMGT: | SSYGMH (SEQ ID NO: 1) GFAFSSYGMH (SEQ ID NO: 3) | VISYDGSIK YYADSVKG (SEQ ID NO: 6) ISYDGSI (SEQ ID NO: 7) | DLLVRFLEWSH KYGMDV (SEQ ID NO: 11) | SGSTSNIGSVT VH (SEQ ID NO: 14) TSNIGSNT (SEQ ID NO: 15) | SDDQRPS (SEQ ID NO: 20) SDD (SEQ ID NO: 21) | AAWDESLNGV (SEQ ID NO: 23) |
| Ab5 Kabat: IMGT: | SSYGMH (SEQ ID NO: 1) GFAFSSYGMH (SEQ ID NO: 3) | VISYDGNNK YYADSVKG (SEQ ID NO: 8) ISYDGNN (SEQ ID NO: 9) | DLLVRFLEWSH KYGMDV (SEQ ID NO: 11) | SGSSSNIGGVT VH (SEQ ID NO: 16) SSNIGGNT (SEQ ID NO: 17) | SDDQRPS (SEQ ID NO: 20) SDD (SEQ ID NO: 21) | AAWDESLNGV (SEQ ID NO: 23) |

In Table 1, the single sequences of CDRH3 and CDRL3 reflect Kabat and IMGT.

TABLE 2

| Description | Amino Acid Sequence (SEQ ID NO) | Nucleic Acid Sequence (SEQ ID NO) |
|---|---|---|
| Heavy chain variable region - Ab1 parental | QIQLVQSGGGVVQPGRSLR LSCAASGFTFSSYGMHWVR QAPGKGLEWVAVISYDGSN KYYADSVKGRFTISRDNSK NTLYLQMNSLRAEDTAVYY CARDLLVRFLEWSHYYGMD VWGQGTTVTVSS (SEQ ID NO: 24) | CAGATCCAGCTGGTGCAGTCTGGGGGAGGCG TGGTCCAGCCTGGGAGGTCCCTGAGACTCTC CTGTGCAGCGTCTGGATTCACCTTCAGTAGC TATGGCATGCACTGGGTCCGCCAGGCTCCAG GCAAGGGGCTGGAGTGGGTGGCAGTTATATC ATATGATGGAAGTAATAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACTACTACGGTATGGA CGTCTGGGGCCAAGGGACCACGGTCACCGTC TCCTCA (SEQ ID NO: 38) |
| Heavy chain variable region - Ab2 germline | QVQLVESGGGVVQPGRSLR LSCAASGFTFSSYGMHWVR QAPGKGLEWVAVISYDGSN KYYADSVKGRFTISRDNSK NTLYLQMNSLRAEDTAVYY CARDLLVRFLEWSHYYGMD VWGQGTTVTVSS (SEQ ID NO: 25) | CAGGTGCAGCTGGTGGAGTCTGGGGGAGGCG TGGTCCAGCCTGGGAGGTCCCTGAGACTCTC CTGTGCAGCGTCTGGATTCACCTTCAGTAGC TATGGCATGCACTGGGTCCGCCAGGCTCCAG GCAAGGGGCTGGAGTGGGTGGCAGTTATATC ATATGATGGAAGTAATAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACTACTACGGTATGGA CGTCTGGGGCCAAGGGACCACGGTCACCGTC TCCTCA (SEQ ID NO: 39) |

TABLE 2-continued

| Description | Amino Acid Sequence (SEQ ID NO) | Nucleic Acid Sequence (SEQ ID NO) |
|---|---|---|
| Heavy chain variable region - Ab3 parental | QIQLVQSGGGVVQPGRSLR LSCAASGFAFSSYGMHWVR QAPGKGLEWVAVISYDGSI KYYADSVKGRFTISRDNSK NTLYLQMNSLRAEDTAVYY CARDLLVRFLEWSHKYGMD VWGQGTTVTVSS (SEQ ID NO: 26) | CAGATCCAGCTGGTGCAGTCTGGGGGAGGCG TGGTCCAGCCTGGGAGGTCCCTGAGACTCTC CTGTGCAGCGTCTGGATTCGCCTTCAGTAGC TATGGCATGCACTGGGTCCGCCAGGCTCCAG GCAAGGGGCTGGAGTGGGTGGCAGTTATATC ATATGATGGAAGTATCAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACAAGTACGGTATGGA CGTCTGGGGCCAAGGGACCACGGTCACCGTC TCCTCA (SEQ ID NO: 40) |
| Heavy chain variable region - Ab4 germline | QVQLVESGGGVVQPGRSLR LSCAASGFAFSSYGMHWVR QAPGKGLEWVAVISYDGSI KYYADSVKGRFTISRDNSK NTLYLQMNSLRAEDTAVYY CARDLLVRFLEWSHKYGMD VWGQGTTVTVSS (SEQ ID NO: 27) | CAGGTGCAGCTGGTGGAGTCTGGGGGAGGCG TGGTCCAGCCTGGGAGGTCCCTGAGACTCTC CTGTGCAGCGTCTGGATTCGCCTTCAGTAGC TATGGCATGCACTGGGTCCGCCAGGCTCCAG GCAAGGGGCTGGAGTGGGTGGCAGTTATATC ATATGATGGAAGTATCAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACAAGTACGGTATGGA CGTCTGGGGCCAAGGGACCACGGTCACCGTC TCCTCA (SEQ ID NO: 41) |
| Heavy chain variable region - Ab5 parental | QIQLVQSGGGVVQPGRSLR LSCAASGFAFSSYGMHWVR QAPGKGLEWVAVISYDGNN KYYADSVKGRFTISRDNSK NTLYLQMNSLRAEDTAVYY CARDLLVRFLEWSHKYGMD VWGQGTTVTVSS (SEQ ID NO: 28) | CAGATCCAGCTGGTGCAGTCTGGGGGAGGCG TGGTCCAGCCTGGGAGGTCCCTGAGACTCTC CTGTGCAGCGTCTGGATTCGCCTTCAGTAGC TATGGCATGCACTGGGTCCGCCAGGCTCCAG GCAAGGGGCTGGAGTGGGTGGCAGTTATATC ATATGATGGAAATAATAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACAAGTACGGTATGGA CGTCTGGGGCCAAGGGACCACGGTCACCGTC TCCTCA (SEQ ID NO: 42) |
| Heavy chain variable region - Ab6 germline | QVQLVESGGGVVQPGRSLR LSCAASGFAFSSYGMHWVR QAPGKGLEWVAVISYDGNN KYYADSVKGRFTISRDNSK NTLYLQMNSLRAEDTAVYY CARDLLVRFLEWSHKYGMD VWGQGTTVTVSS (SEQ ID NO: 29) | CAGGTGCAGCTGGTGGAGTCTGGGGGAGGCG TGGTCCAGCCTGGGAGGTCCCTGAGACTCTC CTGTGCAGCGTCTGGATTCGCCTTCAGTAGC TATGGCATGCACTGGGTCCGCCAGGCTCCAG GCAAGGGGCTGGAGTGGGTGGCAGTTATATC ATATGATGGAAATAATAAATACTATGCAGAC TCCGTGAAGGGCCGATTCACCATCTCCAGAG ACAATTCCAAGAACACGCTGTATCTGCAAAT GAACAGCCTGAGAGCCGAGGACACGGCTGTG TATTACTGTGCGAGAGATCTCCTGGTGCGAT TTTTGGAGTGGTCGCACAAGTACGGTATGGA CGTCTGGGGCCAAGGGACCACGGTCACCGTC TCCTCA (SEQ ID NO: 43) |
| Light chain variable region - Ab1 parental | QPVLTQPPSASGTPGQRVT ISCSGSSSNIGSNTVHWYQ QLPGTAPKLLIYSDNQRPS GVPDRFSGSKSGTSASLVI SGLQSDDEADYYCAAWDDS LNGVFGGGTKLTVL (SEQ ID NO: 30) | CAGCCTGTGCTGACTCAGCCACCCTCAGCGT CTGGGACCCCCGGGCAGAGGGTCACCATCTC TTGTTCTGGAAGCAGCTCCAACATCGGAAGT AATACTGTCCACTGGTACCAGCAACTCCCAG GAACGGCCCCCAAACTCCTCATCTATAGTGA TAATCAGCGCCCTCAGGGGTCCCTGACCGA TTCTCTGGCTCCAAGTCTGGCACCTCAGCCT CCCTGGTCATCAGTGGGCTCCAGTCTGACGA TGAGGCTGATTATTACTGTGCAGCATGGGAT GACAGCCTGAATGGGGTGTTCGGCGGAGGGA CCAAGCTGACCGTCCTA (SEQ ID NO: 44) |
| Light chain variable region - Ab2 germline | QSVLTQPPSASGTPGQRVT ISCSGSSSNIGSNTVHWYQ QLPGTAPKLLIYSDNQRPS GVPDRFSGSKSGTSASLAI | CAGTCTGTGCTGACTCAGCCACCCTCAGCGT CTGGGACCCCCGGGCAGAGGGTCACCATCTC TTGTTCTGGAAGCAGCTCCAACATCGGAAGT AATACTGTCCACTGGTACCAGCAACTCCCAG |

TABLE 2-continued

| Description | Amino Acid Sequence (SEQ ID NO) | Nucleic Acid Sequence (SEQ ID NO) |
| --- | --- | --- |
| | SGLQSEDEADYYCAAWDDSLNGVFGGGTKLTVL (SEQ ID NO: 31) | GAACGGCCCCCAAACTCCTCATCTATAGTGATAATCAGCGCCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGGGTGTTCGGCGGAGGGACCAAGCTGACCGTCCTA (SEQ ID NO: 45) |
| Light chain variable region - Ab3 parental | QPVLTQPPSASGTPGQRVTISCSGSTSNIGSNTVHWYQQLPGTAPKLLIYSDDQRPSGVPDRFSGSKSGTSASLVISGLQSDDEADYYCAAWDESLNGVFGGGTKLTVL (SEQ ID NO: 32) | CAGCCTGTGCTGACTCAGCCACCCTCAGCGTCTGGGACCCCCGGGCAGAGGGTCACCATCTCTTGTTCTGGAAGCACCTCCAACATCGGAAGTAATACTGTCCACTGGTACCAGCAACTCCCAGGAACGGCCCCCAAACTCCTCATCTATAGTGATGATCAGCGCCCCTCAGGGGTCCCTGACCGATTCTCTGGCTCCAAGTCTGGCACCTCAGCCTCCCTGGTCATCAGTGGGCTCCAGTCTGACGATGAGGCTGATTATTACTGTGCAGCATGGGATGAGAGCCTGAATGGGGTGTTCGGCGGAGGGACCAAGCTGACCGTCCTA (SEQ ID NO: 46) |
| Light chain variable region - Ab4 germline | QSVLTQPPSASGTPGQRVTISCSGSTSNIGSNTVHWYQQLPGTAPKLLIYSDDQRPSGVPDRFSGSKSGTSASLAISGLQSEDEADYYCAAWDESLNGVFGGGTKLTVL (SEQ ID NO: 33) | CAGTCTGTGCTGACTCAGCCACCCTCAGCGTCTGGGACCCCCGGGCAGAGGGTCACCATCTCTTGTTCTGGAAGCACCTCCAACATCGGAAGTAATACTGTCCACTGGTACCAGCAACTCCCAGGAACGGCCCCCAAACTCCTCATCTATAGTGATGATCAGCGCCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGAGAGCCTGAATGGGGTGTTCGGCGGAGGGACCAAGCTGACCGTCCTA (SEQ ID NO: 47) |
| Light chain variable region - Ab5 parental | QPVLTQPPSASGTPGQRVTISCSGSSSNIGGNTVHWYQQLPGTAPKLLIYSDDQRPSGVPDRFSGSKSGTSASLVISGLQSDDEADYYCAAWDESLNGVFGGGTKLTVL (SEQ ID NO: 34) | CAGCCTGTGCTGACTCAGCCACCCTCAGCGTCTGGGACCCCCGGGCAGAGGGTCACCATCTCTTGTTCTGGAAGCAGCTCCAACATCGGAGGAAATACTGTCCACTGGTACCAGCAACTCCCAGGAACGGCCCCCAAACTCCTCATCTATAGTGATGATCAGCGCCCCTCAGGGGTCCCTGACCGATTCTCTGGCTCCAAGTCTGGCACCTCAGCCTCCCTGGTCATCAGTGGGCTCCAGTCTGACGATGAGGCTGATTATTACTGTGCAGCATGGGATGAGAGCCTGAATGGGGTGTTCGGCGGAGGGACCAAGCTGACCGTCCTA (SEQ ID NO: 48) |
| Light chain variable region - Ab6 germline | QSVLTQPPSASGTPGQRVTISCSGSSSNIGGNTVHWYQQLPGTAPKLLIYSDDQRPSGVPDRFSGSKSGTSASLAISGLQSEDEADYYCAAWDESLNGVFGGGTKLTVL (SEQ ID NO: 35) | CAGTCTGTGCTGACTCAGCCACCCTCAGCGTCTGGGACCCCCGGGCAGAGGGTCACCATCTCTTGTTCTGGAAGCAGCTCCAACATCGGAGGAAATACTGTCCACTGGTACCAGCAACTCCCAGGAACGGCCCCCAAACTCCTCATCTATAGTGATGATCAGCGCCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGAGAGCCTGAATGGGGTGTTCGGCGGAGGGACCAAGCTGACCGTCCTA (SEQ ID NO: 49) |
| Ab2-Heavy Chain | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARDLLVRFLEWSHYYGMDVWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVICVVVDVSQEDPEVQFNWYVDGVEVHNAKTKPREEQFNSTYRVVSVLTVLHQDWLNGK | |

TABLE 2-continued

| Description | Amino Acid Sequence (SEQ ID NO) | Nucleic Acid Sequence (SEQ ID NO) |
|---|---|---|
| | EYKCKVSNKGLPSSIEKTI SKAKGQPREPQVYTLPPSQ EEMTKNQVSLTCLVKGFYP SDIAVEWESNGQPENNYKT TPPVLDSDGSFFLYSRLTV DKSRWQEGNVFSCSVMHEA LHNHYTQKSLSLSLG (SEQ ID NO: 50) | |
| Ab2-Light Chain | QSVLTQPPSASGTPGQRVT ISCSGSSSNIGSNTVHWYQ QLPGTAPKLLIYSDNQRPS GVPDRFSGSKSGTSASLAI SGLQSEDEADYYCAAWDDS LNGVFGGGTKLTVLGQPKA APSVTLFPPSSEELQANKA TLVCLISDFYPGAVTVAWK ADSSPVKAGVETTTPSKQS NNKYAASSYLSLTPEQWKS HRSYSCQVTHEGSTVEKTV APTECS (SEQ ID NO: 51) | |

TABLE 3

| | CDR-H3 | CDR-L3 | VH | VL | scFV | SEQ ID NOs: from left to right |
|---|---|---|---|---|---|---|
| Ab7 | ESLIRF LEDPQQ GGMDV | NSWTRS NNYI | QVQLQQSGAEVKKPG ASVKVSCKASGYTFT SYYMHWVRQAPGQGL EWMGIINPSGGSTSY AQKFQGRVTMTRDTS TSTVYMELSSLRSED TAVYYCARESLIRFL EDPQQGGMDVWGQGT TVTVSS | QSALTQPASVSGSPGQSL TISCTGTSSDIGGYNYVS WYQQHPGKAPKLIIYDVT DRPSGVSGRFSGSKSGNT ASLTISGLQTEDEAEYFC NSWTRSNNYIFGGGTKLT VLGQPKAAPSVTL | QVQLQQSGAEVKKPGASVKVSC KASGYTFTSYYMHWVRQAPGQG LEWMGIINPSGGSTSYAQKFQG RVTMTRDTSTSTVYMELSSLRS EDTAVYYCARESLIRFLEDPQQ GGMDVWGQGTTVTVSSGSASAP TLGGGGSGGGGSAAAQSALTQP ASVSGSPGQSLTISCTGTSSDI GGYNYVSWYQQHPGKAPKLIIY DVTDRPSGVSGRFSGSKSGNTA SLTISGLQTEDEAEYFCNSWTR SNNYIFGGGTKLTVLGQPKAAP SVTLFPPSS | 71-75 |
| Ab10 | DRYSSS WGGGFD Y | QSYDAS SLWV | EVQLVQSGGGVVQSG RSLRLSCVASGFSFS NYGMHWVRQAPGKGL EWLAFIWYDGSNKWY ADSVKGRFTISRDNS KNALYLQMNSLRAED TAVYYCARDRYSSSW GGGFDYWGQGTVLTV SS | NFMLTQPHSVSESPGRTV TIPCSGRGGSIASDSVQW YQQRPGSAPTTIIYEDNQ RPSGVPDRFSGSVDSSSN SASLTISGLRTEDEADYY CQSYDASSLWVFGGKTKL TVLGQPKAAPSVTL | EVQLVQSGGGVVQSGRSLRLSC VASGFSFSNYGMHWVRQAPGKG LEWLARIWYDGSNKWYADSVKG RFTISRDNSKNALYLQMNSLRA EDTAVYYCARDRYSSSWGGGFD YWGQGTVLTVSSGSASAPTLGG GGSGGGGSAAANFMLTQPHSVS ESPGRTVTIPCSGRGGSIASDS VQWYQQRPGSAPTTIIYEDNQR PSGVPDRFSGSVDSSSNSASLT ISGLRTEDEADYYCQSYDASSL WVFGGKTKLTVLGQPKAAPSVT LFPPSSKASGA | 76-80 |
| Ab11 | DRHSLG DFDY | QAWDST TVV | QLQLQQSGGGLVKPG GSLRLSCAASGFTFS SYSMNWVRQAPGKGL EWVSSISSSSSYIYY ADSVKGRFTISRDNA KNSLYLQMNSLRAED TAVYYCVRDRHSLGD FDYWGQGTLVTVSSG S | SSELTQPSVSVSPGQTAT ITCSGDKLGDKYASWYQQ KPGQSPVLVIYQDTKRPS GIPARFSGSNSGNTATLT ISGTQAMDEAAYYCQAWD STTVVFGGGTKLTVLGQP KAAPSVTLFPPSS | QLQLQQSGGGLVKPGGLSLRLS CAASGFTFSSYSMNWVRQAPGK GLEWVSSISSSSSYIYYADSVK GRFTISRDNAKNSLYLQMNSLR AEDTAVYYCVRDRHSLGDFDYW GQGTLVTVSSGSASAPTLGGGG SGGGGSAAASSELTQPPSVSVS PGQTATITCSGDKLGDKYASWY QQKPGQSPVLVIYQDTKRPSGI PARF | 81-85 |
| Ab9 | HGLMDD SSGYYL SNAFDI | ATWDDS LTGVV | QVQLVQSGAEVKKPG SSVKVSCKASGGTFS SYAISWVRQAPGQGL EWMGGIIPIFGTANY AQKFQGRVTITADES | QPVLTQPPSASGTPGQRV TISCSGSSSNIGSNTVEW YQQLPGTAPKLLIHSNNQ RPSGVPDRFSGSRSGTSA SLAISGLQSEDEADYFCA | QVQLVQSGAEVKKPGSSVKVSC KASGGTFSSYAISWVRQAPGQG LEWMGGIIPIFTANYAQKFQGR VTITADESTSTAYMELSSLRSE DTAVYYCANHGLMDDSSGYYLS | 86-90 |

TABLE 3-continued

| | CDR-H3 | CDR-L3 | VH | VL | scFV | SEQ ID NOs: from left to right |
|---|---|---|---|---|---|---|
| | | | TSTAYMELSSLRSED TAVYYCANHGLMDDS SGYYLSNAFDIWGQG TMVTVSSGS | TWDDSLTGVVFGGGTTLT VLGQPKAAPSVTLFPPSS | NAFDIWGQGTMVTVSSGSASAP TLGGGGSGGGGSAAAQPVLTQP PSASGTPGQRVTISCSGSSSNI GSNTVEWYQQLPGTAPKLLIHS NNQRPSGVPDRFSGSRSGTSAS LAISGLQSEDEADYFCATWDDS LTGVVFGGGTTLTVLGQPKAAP SVTLFPPSS | |
| Ab12 | VGTAAA GDAFDI | AAWDDS LSGWV | QVQLVQSGGGLIQPG GSLRLSCAASGFTVS SYSMNWVRQAPGKGL EWVSYISSSGSTIYY ADSVKGRFTISRDNA KNSLYLQMNSLRAED TALYYCAKVGTAAAG DAFDIWGQGTMVTVS SGS | QPVLTQPPSASGTPGQRV TISVFGSSSNIGSNYVYW YQQLPGTAPKLLIYRNNQ RPSGVPDRFSGSKSGTSA SLAISGLRSEDEADYYCA AWDDSLSGWVFGGGTKLT VLGQPKAAPSVTLFPPSS | QVLQVSGGGLIQPGGSLRLSC AASGFTVSSYSMNWVRQAPGKG LEWVSYISSSGSTIYYADSVKG RFTISRDNAKNSLYLQMNSLRA EDTALYYCAKVGTAAAGDAFDI WGQGTMVTVSSGSASAPTLGGG GSGGGGSAAAQPVLTQPPSASG TPGQRVTISCFGSSSNIGSNYV YWYQQLPGTAPKLLIYRNNQRP SGVPDRFSGSKSGTSASLAISG LRSEDEADYYCAAWDDSLSGWV FGGGTKLTVLGQPKAAPSVTLF PPSS | 91-95 |
| Ab8 | VGFYDY VWGSYP YDAFDI | QQYGTS PLT | QIQLVQSGAEVKKPG ASVKVSCKASGYTFT SYGISWVRQAPGQGL EWMGWISAYNGNTNY AQKLQGRVTMTTDTS TSTAYMELSSLRSED TAVYYCARVGFYDYV WGSYPYDAFDIGSYP YDAFDIWGQGTMVTV SS | EIVMTQSPGTLSLSPGER ATLSCRASQSVSSNYLAW YQQKPGQAPRLLIYDASN RATGIPARFSGSGSGTDF TLTISSLEPEDFALYYCQ QYGTSPLTFGGGTKLEIK | QIQLVQSGAEVKKPGASVKVSC KASGYTFTSYGISWVRQAPGQG LEWMGWISAYNGNTNYAQKLQG RVTMTTDTSTSTAYMELSSLRS EDTAVYYCARVGFYDYVWGSYP YDAFDIWGQGTMVTVSSGSASA PTLGGGGSGGGGSAAAEIVMTQ SPGTLSLSPGERATLSCRASQS VSSNYLAWYQQKPGQAPRLLIY DASNRATGIPARFSGSGSGTDF TLTISSLEPEDFALYYCQQYGT SPLTFGGGTKLEIKRTVAAPSV F | 96-100 |
| Ab13 | DTSNGG YSSSSF DY | SSYTSS STLV | EVQLVQSGGGLVQPG RSLRLSCAASGFTFD DYAMHWVRQAPGKGL EWVSGISWNSGSIGY ADSVKGRFTISRDNA KNSLYLQMNSLRAED TALYYCAKDTSNGGY SSSSFDYWGQGTLVT VSS | QSALTQPASVSGSPGQSI TISCTGTSSDVGGYNYVS WYQQHPGTAPKLMIYDVS YRPSGVSNRFSGSKSGNT ASLTISGLQAEDEADYYC SSYTSSSTLVFGTGTKVT VL | EVQLVQSGGGLVQPGRSLRLSC AASGFTFDDYAMHWVRQAPGKG LEWVSGISWNSGSIGYADSVKG RFTISRDNAKNSLYLQMNSLRA EDTALYYCAKDTSNGGYSSSSF DYWGQGTLVTVSSGSASAPTLG GGGSGGGGSAAAQSALTQPASV SGSPGQSITISCTGTSSDVGGY NYVSWYQQHPGTAPKLMIYDVS YRPSGVSNRFSGSKSGNTASLT ISGLQAEDEADYYCSSYTSSST LVFGTGTKVTVLGQPKANPTVT LFPPSS | 101-105 |
| Ab14 | LVYGGY DEPGYY FDY | AAWDDS LNGWV | EVQLLESRAEVKKPG ESLKISCKGSGYSFT SYWIGWVRQMPGKGP EWMGIIYPGDSDTRY SPSFQGQVTISADKS ISTAYLQWSSLKASD TAMYYCARLVYGGYD EPGYYFDYWGQGTLV TVSS | QSVLTQPPSASGTPGQR VTISCSGSSSNIRSNTV NWYQQLPGTAPKLLIYS NNQRPSGVPDRFSGSKS GTSASLAISGLQSEDEA DYYCAAWDDSLNGWVFG GGTKLTVL | EVQLLERSRAEVKKPGESLKIS CKGSGYSFTSYWIGWVRQMPSF QGPEWMGIIYPGDSDTRYSPFQ GQVTISADKSISTAYLQWSSLK ASDTAMYYCARLVYGGYDEPGY YFDYWGQGTLVTVSSGSASAPT LGGGGSGGGGSAAAQSVLTQPP SASGTPGQRVTISCSGSSSNIR SNTVNWYQQLPGTAPKLLIYSN NQRPSGVPDRFSGSKSEDEADY YCAAWDDSLNGWVFGGGTKLTV LGQPKAAPSVTLFPPSSKASGA | 106-110 |
| Ab15 | VDGLEY SSGHNF DY | SSYAGS YTWV | EVQLVQSGGGLVQPG RSLRLSCAASGFTFD DYAMHWVRQAPGKGL EWVSGISWNSGSIGY ADSVKGRFTISRDNS KNTLYLQMNSLRAED TAVYYCAKVDGLEYS SGHNFDYWGQGTLVT VSS | QSALTQPPSVSGSPGQSV TISCTGSSSDVGYYDHVS WYQHHPGRAPKVIIYDVT KRPSGVPDRFSGSKSGNT ASLTISGLQAEDEADYYC SSYAGSYTWVFGGGTELT VL | EVQLVQSGGGLVQPGRSLRLS CAASGFTFDDYAMHWVRQAPGK GLEWVSGISWNSGSIGYADSVK GRFTISRDNKNTLYLQMNSLR AEDTAVYYCAKVDGLEYSSGHN FDYWGQGTLVTVSSGSASAPTL GGGGSGGGGSAAAQSALTQPPS VSGSPGQSVTISCTGSSSDVGY YDHVSWYQHHPGRAPKVIIYDV TKRPSGVPDRFSGSKSGNTASL | 111-115 |

TABLE 3-continued

| CDR-H3 | CDR-L3 | VH | VL | scFV | SEQ ID NOs: from left to right |
|---|---|---|---|---|---|
| | | | | TISGLQAEDEADYYCSSYAGSY TWVFGGGTELVTVLGQPKAAPS VTLFPPSS | |

In some embodiments, anti-pro/latent-myostatin antibody, or antigen-binding portion thereof, of the disclosure include any antibody, or antigen binding fragment thereof, that includes a CDRH1, CDRH2, CDRH3, CDRL1, CDRL2, or CDRL3, or combinations thereof, as provided for any one of the antibodies shown in Tables 1-3. In some embodiments, anti-pro/latent-myostatin antibodies, or antigen-binding portions thereof, comprise the CDRH1, CDRH2, CDRH3, CDRL1, CDRL2, and CDRL3 of any one of the antibodies shown in Tables 1-3. The disclosure also includes any nucleic acid sequence that encodes a molecule comprising a CDRH1, CDRH2, CDRH3, CDRL1, CDRL2, or CDRL3 as provided for any one of the antibodies shown in Tables 1-3. Antibody heavy and light chain CDR3 domains may play a particularly important role in the binding specificity/affinity of an antibody for an antigen. Accordingly, the anti-pro/latent myostatin antibodies, or antigen-binding portions thereof, of the disclosure, or the nucleic acid molecules thereof, may include at least the heavy and/or light chain CDR3s of antibodies as shown in Tables 1-3.

Aspects of the disclosure relate to a monoclonal antibody, or antigen binding fragment, that binds to pro/latent-myostatin protein and that comprises six complementarity determining regions (CDRs): CDRH1, CDRH2, CDRH3, CDRL1, CDRL2, and CDRL3.

In some embodiments, CDRH1 comprises a sequence as set forth in any one of SEQ ID NOs: 1-3. In some embodiments, CDRH2 comprises a sequence as set forth in any one of SEQ ID NOs: 4-9. In some embodiments, CDRH3 comprises a sequence as set forth in any one of SEQ ID NOs: 10-11, 66, 71, 76, 81, 86, 91, 96, 101, 106 and 111. CDRL1 comprises a sequence as set forth in any one of SEQ ID NOs: 12-17. In some embodiments, CDRL2 comprises a sequence as set forth in any one of SEQ ID NOs: 18-21. In some embodiments, CDRL3 comprises a sequence as set forth in any one of SEQ ID NOs: 22-23, 67, 72, 77, 82, 87, 92, 97, 102, 107 and 112.

In some embodiments (e.g., as for anti-pro/latent-myostatin antibody Ab1, shown in Table 1, or an antigen-binding portion thereof), CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 22, and the antibody, or an antigen-binding portion thereof, binds to pro/latent-myostatin.

In some embodiments (e.g., as for anti-pro/latent-myostatin antibody Ab2, shown in Table 1, or an antigen-binding portion thereof), CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 66, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 67, and the antibody, or an antigen-binding portion thereof, binds to pro/latent-myostatin.

In some embodiments (e.g., as for anti-pro/latent-myostatin antibody Ab3, shown in Table 1, or an antigen-binding portion thereof), CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14, or 15, CDRL2 comprises a sequence as set forth in SEQ ID NO: 20 or 21, and CDRL3 comprises a sequence as set forth in SEQ ID NO: 23, and the antibody, or an antigen-binding portion thereof, binds to pro/latent-myostatin.

In some embodiments (e.g., as for anti-pro/latent-myostatin antibody Ab5, shown in Table 1, or an antigen-binding portion thereof), CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16, or 17, CDRL2 comprises a sequence as set forth in SEQ ID NO: 20 or 21, and CDRL3 comprises a sequence as set forth in SEQ ID NO: 23, and the antibody, or an antigen-binding portion thereof, binds to pro/latent-myostatin.

In some examples, any of the anti-pro/latent-myostatin antibodies, or antigen-binding portions thereof, of the disclosure include any antibody or antigen binding fragment having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Tables 1-3 (SEQ ID NOs: 1-23, 66, 67, 71, 72, 76, 77, 81, 82, 86, 87, 91, 92, 96, 97, 101, 102, 106, 107, 111 and 112) containing up to 5, 4, 3, 2, or 1 amino acid residue variations as compared to the corresponding CDR region in any one of SEQ ID NOs: 1-23, 66, 67, 71, 72, 76, 77, 81, 82, 86, 87, 91, 92, 96, 97, 101, 102, 106, 107, 111 and 112.

In some embodiments, anti-pro/latent-myostatin antibodies, or antigen-binding portions thereof, of the disclosure include any antibody that includes a heavy chain variable domain of any one of SEQ ID NOs: 24-29, 73, 78, 83, 88, 93, 98, 103, 108 and 113 or a light chain variable domain of any one of SEQ ID NOs: 30-35, 74, 79, 84, 89, 94, 99, 104, 109 and 114. In some embodiments, anti-pro/latent-myostatin antibodies, or antigen-binding portions thereof, of the disclosure include any antibody that includes the heavy chain variable and light chain variable pairs of SEQ ID NOs: 24 and 30; 25 and 31; 26 and 32; 27 and 33; 28 and 34; or 29 and 35).

Aspects of the disclosure provide anti-pro/latent-myostatin antibodies, or antigen-binding portions thereof, having a heavy chain variable and/or a light chain variable amino acid sequence homologous to any of those described herein. In some embodiments, the anti-pro/latent-myostatin antibody, or antigen-binding portions thereof, comprises a heavy chain variable sequence or a light chain variable sequence that is at least 75% (e.g., 80%, 85%, 90%, 95%, 98%, or 99%) identical to the heavy chain variable sequence of any of SEQ ID NOs: 24-29, 73, 78, 83, 88, 93, 98, 103, 108 and 113 or a light chain variable sequence of any one of SEQ ID NOs: 30-35, 74, 79, 84, 89, 94, 99, 104, 109 and 114. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, conservative mutations can be introduced into the CDRs or framework sequences at positions where the residues are not likely to be involved in interacting with pro/latent-myostatin as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies, or antigen binding fragments thereof, provided herein comprise mutations that confer desirable properties to the antibodies, or antigen binding fragments thereof. For example, to avoid potential complications due to Fab-arm exchange, which is known to occur with native IgG4 mAbs, the antibodies, or antigen binding fragments thereof, provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 58)) hinge sequence. Accordingly, any of the antibodies may include a stabilizing 'Adair' mutation or the amino acid sequence CPPCP (SEQ ID NO: 58).

Anti-pro/latent-myostatin antibodies, or antigen-binding portions thereof, of this disclosure may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with any suitable constant regions.

In certain embodiments, the $V_H$ and/or $V_L$ domains may be reverted to germline sequence, e.g., the FR of these domains are mutated using conventional molecular biology techniques to match those produced by the germline cells. For example, the $V_H$ and/or $V_L$ domains may be reverted to germline sequence of IgHV3-30 (SEQ ID NO: 36) and/or IgLV1-44 (SEQ ID NO: 37), respectively. It should be appreciated that any of the $V_H$ and/or $V_L$ domains may be reverted to any suitable germline sequence. In other embodiments, the FR sequences remain diverged from the consensus germline sequences.

```
IgHV3-30
                                          (SEQ ID NO: 36)
QVQLVESGGGVVQPGRSLRLSCAASGFTFSSYGMHWVRQAPGKGLEWVA

VISYDGSNKYYADSVKGRFTISRDNSKNTLYLQMNSLRAEDTAVYYCAR

IgL V1-44
                                          (SEQ ID NO: 37)
QSVLTQPPSASGTPGQRVTISCSGSSSNIGSNTVNWYQQLPGTAPKLLI

YSNNQRPSGVPDRFSGSKSGTSASLAISGLQSEDEADYYCAAWDDSLNG
```

In some embodiments, anti-pro/latent-myostatin antibodies or antigen binding fragments may or may not include the framework region of the antibodies shown in SEQ ID NOs: 24-35. In some embodiments, anti-pro-latent-myostatin antibodies are murine antibodies and include murine framework region sequences.

In some embodiments, an anti-pro/latent-myostatin antibodies, or antigen binding fragments thereof, can bind to pro/latent-myostatin with relatively high affinity, e.g., with a Kd less than $10^{-6}$ M, $10^{-7}$ M, $10^{-8}$ M, $10^{-9}$ M, $10^{-10}$ M, $10^{-11}$ M or lower. For example, anti-pro/latent-myostatin antibodies, or antigen binding fragments thereof, can bind to pro/latent-myostatin with an affinity between 5 pM and 500 nM, e.g., between 50 pM and 100 nM, e.g., between 500 pM and 50 nM. The invention also includes antibodies or antigen binding fragments that compete with any of the antibodies described herein for binding to pro/latent-myostatin and that have an affinity of 50 nM or lower (e.g., 20 nM or lower, 10 nM or lower, 500 pM or lower, 50 pM or lower, or 5 pM or lower). The affinity and binding kinetics of the anti-pro/latent-myostatin antibody can be tested using any suitable method including but not limited to biosensor technology (e.g., OCTET or BIACORE). When such binding profiles are measured with the use of OCTET or BIACORE, the assay is performed typically in accordance with the manufacturer's instructions, unless otherwise specified.

In some embodiments, antibodies, or antigen binding fragments thereof, are disclosed herein that specifically bind pro/latent-myostatin. In some embodiments, any of the antibodies, or antigen binding fragments thereof, provided herein bind at or near a tolloid cleavage site or at or near a tolloid docking site of pro/latent-myostatin. In some embodiments, an antibody binds near a tolloid cleavage site or near a tolloid docking site if it binds within 15 or fewer amino acid residues of the tolloid cleavage site or tolloid docking site. In some embodiments, any of the antibodies, or antigen binding fragments thereof, provided herein bind within 1, 2, 3, 4, 5, 6, 7, 8, 9, 10, 11, 12, 13, 14 or 15 amino acid residues of a tolloid cleavage site or tolloid docking site. In some embodiments, an antibody binds at or near a tolloid cleavage site of GDF8. For example, an antibody may bind an amino acid sequence as set forth in SEQ ID NO: 62 PKAPPLRELIDQYDVQRDDSSDGSLEDDDYHAT (SEQ ID NO: 62). In other embodiments, any of the antibodies, or antigen binding fragments thereof, provided herein bind at or near a proprotein convertase cleavage site or at or near a proprotein convertase docking site of pro/latent-myostatin. In some embodiments, an antibody binds near a proprotein convertase cleavage site or near a proprotein convertase docking site if it binds within 15 or fewer amino acid residues of the proprotein convertase cleavage site or proprotein convertase docking site. In some embodiments, any of the antibodies, or antigen binding fragments thereof, provided herein bind within 1, 2, 3, 4, 5, 6, 7, 8, 9, 10, 11, 12, 13, 14 or 15 amino acid residues of a proprotein convertase cleavage site or proprotein convertase docking site. In some embodiments, an antibody binds at or near a proprotein convertase cleavage site of GDF8. For example, an antibody may bind an amino acid sequence as set forth in SEQ ID NO: 63 (GLNPFLEVKVTDTPKRSRRDFGLDCDEHSTESRC).

In one example, the anti-pro/latent-myostatin antibodies, or antigen binding fragments thereof, described herein specifically bind pro/latent-myostatin as compared to other forms of Myostatin and/or other members of the TGFβ family of growth factors. Members of the TGFβ family of growth factors include, without limitation AMH, ARTN, BMP10, BMP15, BMP2, BMP3, BMP4, BMP5, BMP6, BMP7, BMP8A, BMP8B, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, NODAL, NRTN, PSPN, TGFβ1, TGFβ2, and TGFβ3 protein. Such antibodies, or antigen binding fragments thereof, may bind pro/latent-myostatin at a much higher affinity as compared to other members of the TGFβ family of growth factors (e.g., at least 2-fold, 5-fold, 10-fold, 50-fold, 100-fold, 200-fold, 500-fold, or 1,000-fold higher). In some embodiments, such antibodies, or antigen binding fragments thereof, may bind pro/latent-myostatin with an affinity of at least 000-fold higher as compared to other members of the TGFβ family of growth factors. In some embodiments, antibodies, or antigen binding fragments thereof, provided herein may bind to pro/latent-myostatin at a much higher affinity as compared to one or more forms of GDF11 or mature myostatin (e.g., at least 2-fold, 5-fold, 10-fold, 50-fold, 100-fold, 200-fold, 500-fold, or 1,000-fold higher). In some embodiments, antibodies, or antigen binding fragments thereof, provided herein may bind to pro/latent-myostatin with an affinity of at least 1,000-fold higher as compared to one or more forms of GDF11 (e.g., proGDF11, latent GDF11 or mature GDF11) or mature myostatin. Alternatively, or in addition, antibodies, or antigen binding fragments thereof, may exhibit a much higher inhibitory activity against proteolytic cleavage of pro/latent-myostatin (e.g., by a proprotein convertase or tolloid protease) as compared with other members of the TGFβ family, such as pro/latent GDF11 (e.g., at least 2-fold, 5-fold, 10-fold, 50-fold, 100-fold, 200-fold, 500-fold, 1,000-fold higher). In another embodiment, the antibodies, or antigen binding fragments thereof, disclosed herein do not bind to GDF11. This avoids potential toxicity issues associated with antibodies that cross-react with both myostatin and GDF11.

In some embodiments, antibodies bind an antigen but cannot effectively eliminate the antigen from the plasma. Thus, in some embodiments, the concentration of the antigen in the plasma may be increased by reducing the clearance of the antigen. However, in some embodiments, antibodies (e.g., sweeping antibodies) provided herein have an affinity to an antigen that is sensitive to pH. Such pH sensitive antibodies may bind to the antigen in plasma at neutral pH and dissociate from the antigen in an acidic endosome, thus reducing antibody-mediated antigen accumulation and/or promoting antigen clearance from the plasma.

Aspects of the disclosure relate to sweeping antibodies. As used herein "sweeping antibodies" or antigen-binding fragments thereof refer to antibodies, or antigen-binding fragments thereof, having both pH-sensitive antigen binding and at least a threshold level of binding to cell surface neonatal Fc receptor (FcRn) at neutral or physiological pH. In some embodiments, sweeping antibodies, or an antigen-binding portion thereof, bind to the neonatal Fc receptor FcRn at neutral pH. For example, sweeping antibodies may bind to the FcRn at a pH ranging from 7.0 to 7.6. In some embodiments, sweeping antibodies, or an antigen-binding portion thereof, can bind to an antigen at an antigen binding site and bind to a cellular FcRn via an Fc portion of the antibody. In some embodiments, sweeping antibodies, or an antigen-binding portion thereof, may then be internalized, releasing antigen in an acidic endosome, which may be degraded. In some embodiments, a sweeping antibody, or an antigen-binding portion thereof, no longer bound to the antigen, may then be released (e.g., by exocytosis) by the cell back into the serum.

In some embodiments, FcRn in the vascular endothelia (e.g., of a subject) extends the half-life of a sweeping antibody, or an antigen-binding portion thereof. In some embodiments, vascular endothelial cells internalize sweeping antibodies, or antigen-binding portions thereof, which in some embodiments are hound to an antigen such as myostatin (e.g., pro-myostatin, latent myostatin or primed myostatin). In some embodiments, a sweeping antibody, or an antigen-binding portion thereof, is recycled back into the bloodstream. In some embodiments, a sweeping antibody, or an antigen-binding portion thereof, has an increased half-life (e.g., in the serum of a subject) as compared to its conventional counterpart. In some embodiments, a conventional counterpart of a sweeping antibody refers the antibody, or an antigen-binding portion thereof, from which the sweeping antibody, or an antigen-binding portion thereof, was derived (e.g., prior to engineering the Fc portion of the conventional antibody to bind FcRn with greater affinity at pH 7). In some embodiments, a sweeping antibody, or an antigen-binding portion thereof, has a half-life in the serum of a subject that is at least 1%, 5%, 10%, 15%, 20%, 25%, 35%, 50%, 75%, 100%, 150%, 200% or 250% longer as compared to its conventional counterpart.

In some embodiments, an Fc portion of a sweeping antibody binds FcRn. In some embodiments, the Fe portion of a sweeping antibody binds to FcRn at a pH of 7.4 with a Kd ranging from $10^{-3}$ M to $10^{-8}$ M. In some embodiments, a sweeping antibody binds to FcRn at a pH of 7.4 with a Kd ranging from $10^{-3}$ M to $10^{-7}$ M, from $10^{-3}$ M to $10^{-6}$M, from $10^{-3}$ M to $10^{-5}$ M, from $10^{-3}$ M to $10^{-4}$ M, from $10^{-4}$ M to $10^{-8}$ M, from $10^{-4}$ M to $10^{-7}$ M, from $10^{-4}$ M to $10^{-6}$ M, from $10^{-4}$ M to $10^{-5}$ M, from $10^{-5}$ M to $10^{-8}$ M, from $10^{-5}$ M to $10^{-7}$ M, from $10^{-5}$ M to $10^{-6}$ M, from $10^{-6}$ M to $10^{-8}$ M, from $10^{-6}$ M to $10^{-7}$ M, or from $10^{-7}$ M to $10^{-8}$M. In some embodiments, FcRn binds to the CH2-CH3 hinge region of a sweeping antibody. In some embodiments, FcRn binds to the same region as protein A or protein G. In some embodiments, FcRn binds to a different binding site from FcγRs. In some embodiments, the amino acid residues AA of a sweeping antibody Fc region are required for binding to FcRn. In some embodiments, the amino acid residues AA of a sweeping antibody Fc region affect binding to FcRn.

In some embodiments, any of the antibodies, or antigen binding fragments thereof, provided herein are engineered to bind FcRn with greater affinity. In some embodiments, any of the antibodies, or antigen binding fragments thereof, provided herein are engineered to bind FcRn with greater affinity at pH 7.4. In some embodiments, the affinity of antibodies, or antigen binding fragments thereof, to FcRn is increased to extend their pharmacokinetic (PK) properties as compared to their conventional counterparts. For example, in some embodiments, sweeping antibodies elicit less adverse reactions due to their efficacy at lower doses. In some embodiments, sweeping antibodies, or an antigen-binding portion thereof, are administered less frequently. In some embodiments, transcytosis of sweeping antibodies, or an antigen-binding portion thereof, to certain tissue types are increased. In some embodiments, sweeping antibodies, or antigen-binding portions thereof, enhance efficiency of trans-placental delivery. In some embodiments, sweeping antibodies, or antigen-binding portions thereof, are less costly to produce.

In some embodiments, any of the antibodies, or antigen binding fragments thereof, provided herein are engineered to bind FcRn with lower affinity. In some embodiments, any of the antibodies, or antigen binding fragments thereof, provided herein are engineered to bind FcRn with lower affinity at pH 7.4. In some embodiments, the affinity of sweeping antibodies, or an antigen-binding portion thereof, to FcRn is decreased to shorten their pharmacokinetic (PK) properties as compared to their conventional counterparts. For example, in some embodiments, sweeping antibodies, or an antigen-binding portion thereof, are more rapidly cleared for imaging and/or radioimmunotherapy. In some embodiments, sweeping antibodies, or an antigen-binding portion thereof, promote clearance of endogenous pathogenic antibodies as a treatment for autoimmune diseases. In some embodiments, sweeping antibodies, or antigen-binding portions thereof, reduce the risk of adverse pregnancy outcome, which may be caused by trans-placental transport of material fetus-specific antibodies.

In some embodiments, sweeping antibodies, or an antigen-binding portion thereof, have decreased affinity to an antigen at low pH as compared to a neutral or physiological pH (e.g., pH 7.4). In some embodiments, sweeping antibodies, or an antigen-binding portion thereof, have a decreased affinity to an antigen at an acidic pH (e.g. a pH ranging from 5.5 to 6.5) as compared to a physiological pH (e.g., pH 7.4).

It should be appreciated that any of the antibodies, or antigen binding fragments thereof, provided herein can be engineered to dissociate from the antigen depending on changes in pH (e.g., pH-sensitive antibodies). In some embodiments, sweeping antibodies, or an antigen-binding portion thereof, provided herein are engineered to bind antigen in a pH-dependent manner. In some embodiments, sweeping antibodies, or an antigen-binding portion thereof, provided herein are engineered to bind FcRn in a pH-dependent manner. In soma embodiments, sweeping antibodies, or an antigen-binding portion thereof, provided herein are internalized by endocytosis. In some embodiments, sweeping antibodies, or an antigen-binding portion thereof, provided here are internalized by FcRn binding. In some embodiments, endocytosed sweeping antibodies, or antigen-binding portion thereof, release antigen in an endosome. In some embodiments, sweeping antibodies, or antigen-binding portions thereof, are recycled back to the cell surface. In some embodiments, sweeping antibodies remain attached to cells. In some embodiments, endocytosed sweeping antibodies, or an antigen-binding portion thereof, are recycled back to the plasma. It should be appreciated that the Fc portion of any of the antibodies, or antigen binding fragments thereof, provided herein may be engineered to have different FcRn binding activity. In some embodiments, FcRn binding activity affects the clearance time of an antigen by a sweeping antibody. In some embodiments, sweeping antibodies may be long-acting or rapid-acting sweeping antibodies.

In some embodiments, converting a conventional therapeutic antibody, or an antigen-binding portion thereof, into a sweeping antibody, or an antigen-binding portion thereof, reduces the efficacious dose. In some embodiments, converting a conventional therapeutic antibody, or an antigen-binding portion thereof, into a sweeping antibody, or an antigen-binding portion thereof, reduces the efficacious dose by at least 1%, 2%, 5%, 10%, 20%, 30%, 40%, 50%, 60%, 70%, 80%, 90%, 95%, or 99%. In some embodiments, converting a conventional therapeutic antibody, or an antigen-binding portion thereof, into a sweeping antibody, or an antigen-binding portion thereof, reduces the efficacious dose by at least 1.5-fold, 2-fold, 3-fold, 4-fold, 5-fold, 6-fold, 8-fold, 10-fold, 15-fold, 20-fold, 50-fold or 100-fold.

In some embodiments, selecting an appropriate dose of a sweeping antibody, or an antigen-binding portion thereof, for therapy may be performed empirically. In some embodiments, a high dose of a sweeping antibody, or an antigen-binding portion thereof, may saturate FcRn, resulting in antibodies which stabilize antigen in serum without being internalized. In some embodiments, a low dose of a sweeping antibody, or an antigen-binding portion thereof, may not be therapeutically effective. In some embodiments, sweeping antibodies, or antigen-binding portions thereof, are administered once a day, once a week, once every two weeks, once every three weeks, once every four weeks, once every 6 weeks, once every 8 weeks, once every 10 weeks, once every 12 weeks, once every 16 weeks, once every 20 weeks, or once every 24 weeks.

In some embodiments, any of the antibodies, or antigen binding fragments thereof, provided herein may be modified or engineered to be sweeping antibodies. In some embodiments, any of the antibodies, or antigen binding fragments thereof, provided herein may be converted into a sweeping antibody using any suitable method. For example, suitable methods for making sweeping antibodies, or antigen-binding portions thereof, have been previously described in Igawa et al., (2013) "Engineered Monoclonal Antibody with Novel Antigen-Sweeping Activity In vivo," *PLoS ONE* 8(5): e63236; and Igawa et al., "pH-dependent antigen-binding antibodies as a novel therapeutic modality," *Biochimica et Biophysica Acta* 1844 (2014) 1943-1950; the contents of each of which are hereby incorporated by reference. It should be appreciated, however, that the methods for making sweeping antibodies, or an antigen-binding portion thereof, as provided herein are not meant to be limiting. Thus, additional methods for making sweeping antibodies, or an antigen-binding portion thereof, are within the scope of this disclosure.

Some aspects of the disclosure are based on the recognition that the affinity (e.g., as expressed as Kd) of any of the anti-pro/latent-myostatin antibodies, or antigen binding fragments thereof, provided herein are sensitive to changes in pH. In some embodiments, the antibodies, or antigen binding fragments thereof, provided herein have an increased Kd of binding to pro/latent-myostatin at a relatively low pH (e.g., a pH ranging from 4.0-6.5) as compared to a relatively high pH (e.g., a pH ranging from 7.0-7.4). In some embodiments, the antibodies, or antigen binding fragments thereof, provided herein have a Kd of binding to pro/latent-myostatin ranging from $10^{-3}$ M, $10^{-4}$ M, $10^{-5}$ M, $10^{-6}$ M, $10^{-7}$ M, $10^{-8}$ M when the pH is between 4.0 and 6.5. In some embodiments, the antibodies, or antigen binding fragments thereof, provided herein have a Kd of binding to pro/latent-myostatin ranging from $10^{-6}$ M, $10^{-7}$ M, $10^{-8}$ M, $10^{-9}$ M, $10^{-10}$ M, $10^{-11}$ M when the pH is between 7.0 and 7.4. In some embodiments, the antibodies, or antigen binding fragments thereof, provided herein have a Kd of binding to pro/latent-Myostatin that is at least 2-fold, at least 10-fold, at least 50-fold, at least 100-fold, at least 500-fold, at least 1000-fold, at least 5000-fold, or at least 10000-fold greater at a pH between 4.0 and 6.5 as compared to a pH between 7.0 and 7.4.

In some embodiments, pro/latent-myostatin antibodies, or antigen binding fragments thereof, are provided herein that do not specifically bind to an epitope within the amino acid sequence set forth as (SEQ ID NO: 64). In some embodiments, pro/latent-myostatin antibodies, or antigen binding fragments thereof, provided herein do not specifically bind to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not compete or do not cross-compete for binding to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not specifically bind to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not compete or do not cross-compete for binding to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/J P2015/006323, which was filed on Dec. 18, 2015.

Polypeptides

Some aspects of the disclosure relate to a polypeptide having a sequence selected from the group consisting of SEQ ID NO: 24, SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32, SEQ ID NO: 33, SEQ ID NO: 34, or SEQ ID NO 35.

Antibodies, and Antigen-Binding Fragments, that Compete with Anti-Pro/Latent-Myostatin Antibodies, or Antigen Binding Fragments Thereof Aspects of the disclosure relate to antibodies, and antigen-binding fragments thereof, that compete or cross-compete with any of the antibodies, or antigen binding fragments thereof, provided herein. The term "compete", as used herein with regard to an antibody, means that a first antibody binds to an epitope of a protein (e.g., latent myostatin) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies, or antigen-binding portions thereof, that compete or cross-compete with any of the antibodies, or antigen binding fragments thereof, provided herein. In some embodiments, an antibody, or an antigen-binding portion thereof, binds at or near the same epitope as any of the antibodies provided herein. In some embodiments, an antibody, or an antigen-binding portion thereof, binds near an epitope if it binds within 15 or fewer amino acid residues of the epitope. In some embodiments, any of the antibodies, or antigen binding fragments thereof, provided herein bind within 1, 2, 3, 4, 5, 6, 7, 8, 9, 10, 11, 12, 13, 14 or 15 amino acid residues of an epitope that is bound by any of the antibodies, or antigen binding fragments thereof, provided herein.

In another embodiment, an antibody, or an antigen-binding portion thereof, competes or cross-competes for binding to any of the antigens provided herein (e.g., pro/latent-myostatin) with an equilibrium dissociation constant, Kd, between the antibody and the protein of less than $10^{-6}$ M. In other embodiments, an antibody, or an antigen-binding portion thereof, competes or cross-competes for binding to any of the antigens provided herein with a Kd in a range from $10^{-11}$ M to $10^{-6}$ M.

Aspects of the disclosure relate to antibodies, or antigen-binding portions thereof, that compete for binding to pro/latent-myostatin with any of the antibodies, or antigen binding fragments thereof, provided herein. In some embodiments, the antibody, or an antigen-binding portion thereof, binds to pro/latent-myostatin at the same epitope as any of the antibodies, or antigen-binding portions thereof, provided herein. For example, in some embodiments any of the antibodies provided herein bind at or near a tolloid cleavage site or at or near a tolloid docking site of pro/latent-myostatin. In other embodiments, any of the antibodies, or antigen binding fragments thereof, provided herein bind at or near a proprotein convertase cleavage site or at or near a proprotein convertase docking site of pro/latent-myostatin. In another embodiment, an antibody, or an antigen-binding portion thereof, competes for binding to pro/latent-myostatin with an equilibrium dissociation constant, Kd, between the antibody, or antigen-binding portion thereof, and pro/latent-myostatin of less than $10^{-6}$ M. In other embodiments, the antibody, or antigen-binding portion thereof, that competes with any of the antibodies, or antigen-binding portions thereof, provided herein binds to pro/latent-myostatin with a Kd in ranging from $10^{-11}$ M to $10^{-6}$ M.

Any of the antibodies, or antigen binding fragments thereof, provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody, or an antigen-binding portion thereof, binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody, or an antigen-binding portion thereof, binds can be determined in a systematic screen by using overlapping peptides derived from the target antigen sequence and determining binding by the antibody, or an antigen-binding portion thereof. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody, or an antigen-binding portion thereof, to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody, or an antigen-binding portion thereof, in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the pro/latent-myostatin polypeptide have been replaced (swapped) with sequences from a closely related, but antigenically distinct protein, such as another member of the TGFβ protein family (e.g., GDF11). By assessing binding of the antibody, or antigen-binding portion thereof, to the mutant pro/latent-myostatin, the importance of the particular antigen fragment to antibody, or antigen-binding portion thereof, binding can be assessed.

Alternatively, competition assays can be performed using other antibodies known to bind to the same antigen to determine whether an antibody, or an antigen-binding portion thereof, binds to the same epitope as the other antibodies, or antigen-binding portions thereof. Competition assays are well known to those of skill in the art.

Any of the suitable methods, e.g., the epitope mapping methods as described herein, can be applied to determine whether an anti-pro/latent-myostatin antibody, or an antigen-binding portion thereof, binds one or more of the specific residues/segments in pro/latent-myostatin as described herein. Further, the interaction of the antibody, or an antigen-binding portion thereof, with one or more of those defined residues in pro/latent-myostatin can be determined by routine technology. For example, a crystal structure can be determined, and the distances between the residues in pro/latent-myostatin and one or more residues in the antibody, or antigen-binding portion thereof, can be determined accordingly. Based on such distance, whether a specific residue in pro/latent-myostatin interacts with one or more residues in the antibody, or antigen-binding portion thereof, can be determined. Further, suitable methods, such as competition assays and target mutagenesis assays can be applied to determine the preferential binding of a candidate anti-pro/latent-myostatin antibody, or n antigen-binding portion thereof, to pro/latent-myostatin as compared to another target such as a mutant pro/latent-myostatin.

Production of Anti-Pro/Latent-Myostatin Antibodies or Antigen Binding Fragments Thereof Numerous methods may be used for obtaining antibodies, or antigen binding fragments thereof, of the disclosure. For example, antibodies, and antigen-binding fragments thereof, can be produced using recombinant DNA methods. Monoclonal antibodies, and antigen-binding fragments thereof, may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody, or an antigen-binding portion thereof, that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies, and antigen-binding portions thereof, includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597; WO92/18619; WO 91/17271; WO 92/20791; WO 92/15679; WO 93/01288; WO 92/01047; WO 92/09690; and WO 90/02809.

In addition to the use of display libraries, the specified antigen (e.g., pro-myostatin) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies, and antigen-binding portions thereof.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotide(s) may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies and antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of pro/latent-myostatin. The detectable substance may be coupled or conjugated either directly to the polypeptides of the disclosure or indirectly, through an intermediate (such as, for example, a linker) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the anti-pro/latent-myostatin antibodies, or antigen-binding portions thereof, of the disclosure or indirectly, through an intermediate (such as, for example, a linker) using suitable techniques. Anti-pro/latent-myostatin antibodies, or antigen-binding portions thereof, conjugated to a detectable substance may be used for diagnostic assays as described herein.

Biological Effects of Myostatin Inhibitors, Such as Anti-Pro/Latent Myostatin Antibodies and Antigen Binding Fragments Thereof Myostatin inhibitors, such as antibodies and antigen-binding fragments thereof, which are encompassed by the present disclosure can be used as a medicament to effectuate beneficial effects (e.g., therapeutic effects) in a subject when administered to the subject in an effective amount. Exemplary such biologically beneficial effects are provided herein. Beneficial biological effects in a subject can be achieved by administration of myostatin inhibitors, e.g., antibodies, or antigen binding fragments thereof, as described herein, that specifically bind pro/latent myostatin. In some embodiments, the antibody, or antigen-binding portion thereof, is administered in an amount effective to cause two or more of the biological effects described below. In some embodiments, the myostatin inhibitor, e.g., antibody, or antigen-binding portion thereof, is administered in an amount effective to cause three or more of the biological effects described below. In some embodiments, the myostatin inhibitor, e.g., the antibody, or antigen-binding portion thereof, is administered in an amount effective to cause four or more of the biological effects described below. In some embodiments, the myostatin inhibitor, e.g., the antibody, or antigen-binding portion thereof, is administered in an amount effective to cause five or more of the biological effects described below. In some embodiments, the myostatin inhibitor, e.g., the antibody, or antigen-binding portion thereof, is administered in an amount effective to cause six or more of the biological effects described below. In some embodiments, the myostatin inhibitor, e.g., the antibody, or antigen-binding portion thereof, is administered in an amount effective to cause seven or more of the biological effects described below. In some embodiments, the myostatin inhibitor, e.g., the antibody, or antigen-binding portion thereof, is administered in an amount effective to cause eight, nine, ten, eleven, twelve, thirteen, fourteen, fifteen, or sixteen of the biological effects described below.

A. Effect on Mass and/or Function of Muscle Tissue in the Human Subject

Administration of a myostatin inhibitor, e.g., an antibody, or antigen binding fragment thereof, that specifically binds pro/latent myostatin increases mass and/or function of a muscle tissue in the human subject. In some embodiments, the muscle tissue is selected from the group consisting of a smooth muscle tissue, a skeletal muscle tissue and a cardiac muscle tissue. Smooth muscle tissue is made up from long tapering cells, generally involuntary and differs from striated muscle in the much higher actin/myosin ratio, the absence of conspicuous sarcomeres and the ability to contract to a much smaller fraction of its resting length. Smooth muscle cells are found particularly in blood vessel walls, surrounding the intestine and in the uterus. Cardiac muscle tissue is a striated but involuntary tissue responsible for the pumping activity of the vertebrate heart. The individual cardiac muscle cells are not fused together into multinucleate structures as they are in striated muscle tissue. Skeletal muscle tissue is under voluntary control. The muscle fibers are syncytial and contain myofibrils, tandem arrays of sarcomeres. There are two general types of skeletal muscle fibers: slow-twitch (type I) and fast-twitch (type II) according to the expression of their particular myosin heavy chain (MHC) isoform. Slow-twitch muscles are better equipped to work aerobically and help enable long-endurance feats such as distance running, while fast-twitch muscles fatigue faster but are better equipped to work anaerobically and are used in powerful bursts of movements like sprinting. The differentiation between slow and fast twitch muscle fibers is based on histochemical staining for myosin adenosine-triphosphatase (ATPase) and the type of myosin heavy chain. The slow twitch muscle fiber (type I fiber) is MHC isoform I and the three fast twitch isoforms (type II fibers) are MHC isoform IIa, MHC isoform IId, and MHC isoform IIb (S. Schiaffino, *J. Muscle Res. Cell. Motil.*, 10 (1989), pp. 197-205). In some embodiments, the mass and/or function of a fast twitch muscle tissue in the human subject is increased. In other embodiments, the mass and/or function of a slow twitch muscle tissue in the human subject is increased.

Biological effects of an effective amount of the pharmaceutical compositions provided herein may be associated with a phenotypic change of muscle fiber types, which is a process referred to as fiber type switch. In some embodiments, fiber type switch is triggered by an event, such as an injury and starvation.

In one aspect, the disclosure provides a method for promoting fiber type switch in a subject. The method comprises administering to the subject a composition comprising a myostatin inhibitor, e.g., an antibody, or antigen binding fragment thereof, that specifically binds pro/latent-myostatin and blocks release of mature myostatin in an amount effective to promote fiber type switch, thereby promoting fiber type switch in the subject.

In another aspect, the disclosure provides a method for preferentially increasing type II or fast twitch fibers over type I or slow twitch fibers in a subject. The method comprises administering to the subject a composition comprising a myostatin inhibitor, e.g., an antibody, or antigen binding fragment thereof, that specifically binds pro/latent-myostatin and blocks release of mature myostatin in an amount effective to preferentially increase type II or fast twitch fibers over type I or slow twitch fibers fiber type switch, thereby preferentially increasing type II or fast twitch fibers over type I or slow twitch fibers in the subject.

In some embodiments, administration of an effective amount of a myostatin inhibitor, e.g., an antibody, or antigen-binding fragment thereof, described herein to a subject can cause an increase in muscle mass. Preferably, such an increase in muscle mass is clinically meaningful to benefit or otherwise improve the health status of the subject. For example, clinically meaningful changes in muscle mass may improve the patient's mobility, self-care, metabolism, etc. In some embodiments, the increase in muscle mass is an increase in lean muscle or lean muscles. In some embodiments, such increase in muscle mass is a systemic effect such that muscles in the whole body or substantially whole body show the measurable effect. In other embodiments, effects are localized to certain group/type of muscles. In some embodiments, the mass of the muscle tissue, e.g., lean muscle tissue, is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue, e.g., lean muscle tissue, is increased by at least about 1-5%, 5-10%, 10-20%, 1-30%, 1-40%, 1-50%, 10-50%, 20-30%, 20-60%, 30-80%, 40-90%, or 50-100%. Such increase in muscle mass may be deduced or measured by any suitable known methods, including measurement of cross-sectional area via MRI (e.g., forearm cross section), circumference, diaphragm width (e.g., via ultrasound), etc.

In some embodiments, administration of an effective amount of an antibody or antigen-binding fragments thereof described herein to a subject can cause an enhancement in muscle function. Muscle function may be assessed by a variety of measures, including, without limitation: force generation, grip strength (e.g., maximum grip strength), endurance, muscle oxidative capacity, dynamic grip endurance, etc. In some embodiments, serum creatinine levels are used as a validated biomarker indicative of muscle mass, albeit with limited sensitivity.

In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, increased muscle function comprises improved rating, for example, from 1 to 2, 2 to 3, 3 to 4, 4 to 5, 5 to 6, 6 to 7, 7 to 8, 8 to 9, or 9 to 10.

In some embodiments, the myostatin inhibitors, e.g., anti-pro/latent myostatin antibodies, or antigen binding fragments thereof, for use in the methods of the present invention may increase the mass and/or function of the muscle tissue in the subject suffering from a lesion, e.g., due to a spinal cord injury. In some embodiments, the subject is in an acute spinal cord injury phase immediately after injury, where diagnosis between complete and incomplete injury is generally difficult. In other embodiments, the subject is in a sub-acute spinal cord injury phase, where there is a distinction between complete and incomplete spinal cord injury, and recovery is possible through ongoing rehab. In yet another embodiment, the subject is in a chronic spinal cord injury phase. The chronic SCI phase occurs around 4 or 6 month from the date of injury, where patients have demonstrated substantial decrease in rate of recovery or when rehab efforts have reached a plateau despite the ongoing standard of care efforts.

In some embodiments, the mass and/or function of the muscle tissue below a lesion is increased in a subject suffering from a lesion, e.g., a spinal cord injury. In other embodiments, the mass and/or function of the muscle tissue above a lesion is increased in a subject suffering from a lesion, e.g., a spinal cord injury. In some embodiment, the muscle is selected from the group consisting of a soleus muscle, a gastrocnemius muscle, a bicep muscle and a tricep muscle. In some embodiments, the mass of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin increases locomotor function in the human subject, e.g., in a subject suffering from a lesion. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin increases the motor ordination and balance in the human subject, e.g., in a subject suffering from a lesion. In some embodiments, the motor ordination and balance of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the motor ordination and balance of the human subject is increased by at least about 1-5%, 5-10%, 10-20%, 1-30%, 1-40%, 1-50%, 10-50%, 20-30%, 20-60%, 30-80%, 40-90%, or 50-100%.

In another embodiment, administration of the myostatin inhibitor, e.g., antibody, or antigen binding fragment thereof, that specifically binds pro/latent myostatin increases the muscle strength in the human subject, e.g., in a subject suffering from a lesion. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin can cause clinically meaningful changes in muscle function which corresponds to enhanced functionality of the patient. In some embodiments, enhanced functionality includes improvement in the patient's mobility, self-care, metabolism, etc. In some embodiments, administration of an effective amount of the myostatin inhibitor, e.g., antibody, or antigen binding fragment thereof, that specifically binds pro/latent myostatin facilitates or accelerates recovery from a condition, such as injuries, surgeries and other medical procedures. Suitable such conditions may involve a condition that is associated with a nerve damage (whether resulting from an injury or a surgical or other clinical procedure).

For example, suitable subjects include generally healthy individuals, such as a patient who: i) has sustained an acute injury involving a nerve damage that affects muscle function; ii) is scheduled to undergo a surgical procedure (therapeutic or corrective) that may cause an unintended nerve injury (e.g., motor neuron injury); iii) has undergone a surgical procedure that has caused an unintended muscle dysfunction; iv) receives a treatment that involves immobilization of a particular muscle or muscle groups (e.g., cast, etc.); v) is on ventilator (e.g., as a result of acute injury). The administration of the myostatin inhibitor described herein may accelerate recovery in such patients. In some embodiments, such administration may be prophylactic. For example, prior to undergoing or immediately following a surgical procedure that may cause a nerve damage and associated muscle dysfunction, the antibody may be administered to prevent muscle dysfunction. Prevention includes alleviating or lessening the severity of such dysfunction. In these embodiments, administration may be a local administration at or near the site of the affected area, e.g., injury, surgery, etc.

B. Effect on the Metabolic Rate of the Human Subject

Administration of the myostatin inhibitor, e.g., antibody, or antigen binding fragment thereof, that specifically binds pro/latent myostatin increases the metabolic rate of the human subject. In some embodiments, administration of an effective amount of such myostatin inhibitor, e.g., antibody, or antigen-binding fragment thereof, can increase the basal metabolic rate in the subject. Metabolic rates can be calculated by any methods known in the art, for example, by examining the oxygen input and carbon dioxide output, or by indirect calorimetry as demonstrated by Example 11 of the present application. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

C. Effect on Insulin Sensitivity of the Human Subject

Administration of the myostatin inhibitor, e.g., antibody, or antigen binding fragment thereof, that specifically binds pro/latent myostatin increases insulin sensitivity of the human subject. Methods for measuring insulin sensitivity are known in the art, for example, glucose tolerance test, and fasting insulin or glucose test. During a glucose tolerance test, a fasting patient takes a 75-gram oral dose of glucose, and then blood glucose levels are measured over the following two hours. A glycemia less than 7.8 mmol/L (140 mg/dl) is considered normal, a glycemia of between 7.8 and 11.0 mmol/L (140 to 197 mg/dl) is considered as impaired glucose tolerance (TGT), and a glycemia of greater than or equal to 11.1 mmol/L (200 mg/dl) is considered diabetes mellitus. For fasting insulin test, a fasting serum insulin level greater than 25 mIU/L or 174 pmol/L is considered insulin resistance. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

D. Effect on the Level of Adipose Tissue in the Human Subject

Administration of the myostatin inhibitor, e.g., antibody, or antigen binding fragment thereof, that specifically binds pro/latent myostatin affects the level of adipose tissue in the human subject. As used herein, the term "adipose tissue" refers to fat including the connective tissue that stores fat. Adipose tissue is derived from preadipocytes. Its main role is to store energy in the form of lipids, although it also cushions and insulates the body. The two types of adipose tissue are white adipose tissue (WAT), which stores energy, and brown adipose tissue (BAT), which generates body heat.

Brown adipose tissue (BAT) is known to function in the dissipation of chemical energy in response to cold or excess feeding, and also has the capacity to modulate energy balance. Activation of brown adipose tissue have been shown to improve glucose homeostasis and insulin sensitivity in humans suggesting that anyone with impaired insulin function might benefit from BAT activation (Stanford et al., *J Clin Invest*. 2013, 123(1): 215-223).

Beige adipose tissues are generated as a result of browning of WAT, also known as beiging. This occurs when adipocytes within WAT depots develop features of BAT. Beige adipocytes take on a multilocular appearance (containing several lipid droplets) and increase expression of uncoupling protein 1 (UCP1). In doing so, these normally energy-storing white adipocytes become energy-releasing adipocytes (Harms et al. Nature Medicine. 2013, 19 (10): 1252-63).

Visceral fat or abdominal fat (also known as organ fat or intra-abdominal fat) is located inside the abdominal cavity, packed between the organs (stomach, liver, intestines, kidneys, etc.). Visceral fat is different from subcutaneous fat underneath the skin, and intramuscular fat interspersed in skeletal muscles. Fat in the lower body, as in thighs and buttocks, is subcutaneous and is not consistently spaced tissue, whereas fat in the abdomen is mostly visceral and semi-fluid. An excess of visceral fat is known as central obesity, or "belly fat", in which the abdomen protrudes excessively and new developments such as the Body Volume Index (BVI) are specifically designed to measure abdominal volume and abdominal fat. Excess visceral fat is also linked to type 2 diabetes, insulin resistance, inflammatory diseases and other obesity-related diseases (Mokdad et al., *JAMA: The Journal of the American Medical Association*. 2001, 289 (1): 76-9).

Mass of adipose tissue can be determined by any method known to a person of ordinary skill in the art. For example, adipose tissue may be measured by dual-energy X-Ray absorptiometry (DXA), as demonstrated in Example 11 of the present application. Administration of the myostatin inhibitor, e.g., antibody, or antigen binding fragment thereof, that specifically binds pro/latent myostatin increases the level of brown adipose tissue and/or the level of beige adipose tissue in the human subject. On the other hand, administration of the myostatin inhibitor, e.g., anti-pro/latent myostatin antibody, or antigen-binding portion thereof, decreases the level of white adipose tissue and visceral adipose tissue in the human subject.

In some embodiments, the level of brown or beige adipose tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of brown or beige adipose tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, the level of white or visceral adipose tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of white or visceral adipose tissue is decreased by at least about 1-5%, 5-10%, 10-20%, 1-30%, 1-40%, 1-50%, 10-50%, 20-30%, 20-60%, 30-80%, 40-90%, or 50-100%.

E. Effect on the Ratio of Adipose-to-Muscle Tissue in the Human Subject

Administration of the myostatin inhibitor, e.g., antibody, or antigen binding fragment thereof, that specifically binds pro/latent myostatin decreases the ratio between adipose-to-muscle tissue in the human subject. In some embodiments, the ratio between adipose-to-muscle tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio between adipose-to-muscle tissue is decreased by at least about 1-5%, 5-10%, 10-20%, 1-30%, 1-40%, 1-50%, 10-50%, 20-30%, 20-60%, 30-80%, 40-90%, or 50-100%.

Administration of the myostatin inhibitor, e.g., antibody, or antigen binding fragment thereof, that specifically binds pro/latent myostatin also increases the ratio of muscle tissue to adipose in the human subject. In some embodiments, the ratio between muscle tissue-to-adipose is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio between muscle tissue-to-adipose is increased by at least about 1-5%, 5-10%, 10-20%, 1-30%, 1-40%, 1-50%, 10-50%, 20-30%, 20-60%, 30-80%, 40-90%, or 50-100%.

F. Effect on Glucose Uptake in the Human Subject

Administration of the myostatin inhibitor, e.g., antibody, or antigen binding fragment thereof, that specifically binds pro/latent myostatin affects glucose uptake by tissues in the human subject. In some embodiments, glucose uptake by muscle tissue is increased. For example, glucose uptake by the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, glucose uptake by the muscle tissue is increased by at least about 1-5%, 5-10%, 10-20%, 1-30%, 1-40%, 1-50%, 10-50%, 20-30%, 20-60%, 30-80%, 40-90%, or 50-100%.

In other embodiments, glucose uptake by white adipose tissue, liver tissue and blood vessel tissue are reduced. In some embodiments, glucose uptake by white adipose tissue, liver tissue and blood vessel tissue are reduced by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, glucose uptake by white adipose tissue, liver tissue and blood vessel tissue are reduced by at least about 1-5%, 5-10%, 10-20%, 1-30%, 1-40%, 1-50%, 10-50%, 20-30%, 20-60%, 30-80%, 40-90%, or 50-100%.

G. Effect on Muscle Catabolism of Protein and/or Muscle Release of Amino Acids in the Human Subject Administration of the myostatin inhibitor, e.g., antibody, or antigen binding fragment thereof, that specifically binds pro/latent myostatin decreases muscle catabolism of protein and/or muscle release of amino acids in the human subject. In some embodiments, muscle catabolism of protein and/or muscle release of amino acids is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle catabolism of protein and/or muscle release of amino acids is decreased by at least about 1-5%, 5-10%, 10-20%, 1-30%, 1-40%, 1-50%, 10-50%, 20-30%, 20-60%, 30-80%, 40-90%, or 50-100%.

H. Effect on Insulin Dependent Glycemic Control in the Human Subject

Administration of the myostatin inhibitor, e.g., antibody, or antigen binding fragment thereof, that specifically binds pro/latent myostatin increases insulin dependent glycemic control in the human subject. In some embodiments, insulin dependent glycemic control is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, insulin dependent glycemic control is increased by at least about 1-5%, 5-10%, 10-20%, 1-30%, 1-40%, 1-50%, 10-50%, 20-30%, 20-60%, 30-80%, 40-90%, or 50-100%.

I. Effect on Intramuscular Fat Infiltration in the Human Subject

Administration of the myostatin inhibitor, e.g., antibody, or antigen binding fragment thereof, that specifically binds pro/latent myostatin decreases intramuscular fat infiltration in the human subject. In some embodiments, intramuscular fat infiltration is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, intramuscular fat infiltration is decreased by at least about 1-5%, 5-10%, 10-20%, 1-30%, 1-40%, 1-50%, 10-50%, 20-30%, 20-60%, 30-80%, 40-90%, or 50-100%.

J. Effect on Life Quality of the Human Subject

Assessment of the quality of life in patients with severe or chronic conditions, such as SCI patients, may involve integrated approaches to evaluate various aspects of physical, mental, social and other parameters. Generally, a greater degree of quality of life is associated with factors such as: accessibility to assistive technology; community reintegration; functionality with lower limb and walking and/or wheeled mobility; mental health; severity in neurological impairment and autonomic dysfunction; pain management; functional independence and self-care; upper limb strength; and spasticity control. Administration of the antibody, or antigen binding fragment thereof, that specifically binds pro/latent myostatin increases the quality of life of the human subject to achieve a clinically meaningful improvement as measured by a standardized quality-of-life test/system. A number of suitable tests for assessing the quality of life in patients are known in the art, including: Incontinence Quality of Life Questionnaire (I-QOL); Life Satisfaction Questionnaire (LISAT-9, LISAT-11); Quality of Life Index (QLI)—SCI Version; Quality of Life Profile for Adults with Physical Disabilities (QOLP-PD); Quality of Well Being (QWB) and Quality of Well Being-Self-Administered (QWB-SA); Qualiveen; Satisfaction with Life Scale (SWLS, Deiner Scale); Short Form 36 (SF-36); Sickness Impact Profile 68 (SIP 68); and World Health Organization Quality of Life-BREF (WHOQOL-BREF).

In some embodiments, quality of life is assessed in accordance with the SF-36 Quality of Life Scoring System, which is a validated scoring system, in which an 8-point change is considered clinically meaningful. Typically, for SCI patients, values are in the low 50's. In some embodiments, administration of an effective amount of the antibody, or antigen binding fragment thereof, that specifically binds pro/latent myostatin results in a clinically meaningful improvement in a standardized quality-of-life test score. As used the herein, the term "clinically meaningful improvement" refers to a significant improvement over a standard level. In some embodiments, an SCI patient's SF-36 Quality of Life scores are increased by at least 8 points, following treatment with an effective amount of an antibody or antigen-binding fragments thereof described herein, as compared to the patient's score prior to the treatment. In some embodiments, patients achieve higher scores as assessed by the SF-36 Quality of Life Test, for example, at least 9, 10, 11, 12, 13, 14, 15, 16, 17, 18, 19, 20, 30, 40, or 50 points increase in the scores from the SF-36 Quality of Life Scoring System. In other embodiments, the scores from the SF-36 Quality of Life Scoring System is increased by at least about 8-10, 10-15, 15-20, 20-30, 30-40, 40-50, 8-20, 8-30, 8-40, or 8-50.

In some embodiments, the SCI Neurological Quality of Life Test is employed to assess patients' quality of life before and after treatment with the inhibitors of myostatin signaling disclosed herein. Advantages of this test include: i) it is easy to administer; ii) it assesses both physical function and mental health; and, iii) it is highly validated for a number of clinical indications.

K. Effect on Preventing Muscle Loss or Atrophy in the Human Subject

Administration of an effective amount of the myostatin inhibitor, e.g., antibody, or antigen binding fragment thereof, that specifically binds pro/latent myostatin prevents muscle loss or atrophy in the human subject at risk of developing muscle loss and/or atrophy. In some embodiments, muscle loss or atrophy is decreased or prevented by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle loss or atrophy is decreased or prevented by at least about 1-5%, 5-10%, 10-20%, 1-30%, 1-40%, 1-50%, 10-50%, 20-30%, 20-60%, 30-80%, 40-90%, or 50-100%.

In some embodiments, a suitable subject is a subject who has not developed atrophy but is considered at risk of developing atrophy. In some embodiments, a subject has a disease or condition associated with a neurological defect that impairs motor neuron function. In some embodiments, such conditions are caused by muscular dystrophy or atrophy. In some embodiments, the neurological defect is caused by a nerve injury. In some embodiments, the nerve injury involves partial denervation of motor neurons, which causes partial impairment of function in the affected muscle. In some embodiments, such condition is caused by SCI. In some embodiments, the subject with SCI is in an acute or sub-acute phase of SCI (e.g., not yet reached a chronic phase).

In some embodiments, when a composition comprising an effective amount of an inhibitor of myostatin signaling described herein is administered to a population of patients who are at risk of developing muscle atrophy associated with partial denervation of motor neurons, the composition i) prevents manifestation or aggravation of the muscle atrophy in a statistically significant fraction of the patient population; or, ii) lessens the severity of the muscle atrophy in the statistically significant fraction of the patient population.

Prevention of muscle loss or atrophy by the use of a myostatin inhibitor, e.g., an antibody or antigen-binding fragment thereof, described herein can be readily monitored or assessed by any suitable methods to evaluate motor function involving affected muscles.

In some embodiments, administration of an effective amount of such antibody also prevents or lessens an early-onset axonal polyneuropathy in affected limbs.

L. Effect on Preventing Development of Metabolic Disease in the Subject

Administration of an effective amount of the myostatin inhibitor, e.g., antibody, or antigen binding fragment thereof, that specifically binds pro/latent myostatin prevents development of metabolic disease in the subject, e.g., a human subject. In some embodiments, development of metabolic disease is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, development of metabolic disease is decreased by at least about 1-5%, 5-10%, 10-20%, 1-30%, 1-40%, 1-50%, 10-50%, 20-30%, 20-60%, 30-80%, 40-90%, or 50-100%.

In some embodiments, a suitable subject is a subject who has not fully developed a metabolic disease but is considered at risk of developing such a condition. In some embodiments, a subject has a disease or condition associated with muscle dysfunction. In some embodiments, the muscle dysfunction is associated with partial denervation of motor neurons, which causes partial impairment of function in the affected muscle. In some embodiments, such conditions are caused by muscular dystrophy or atrophy. In some embodiments, such condition is caused by SCI. In some embodiments, the subject with SCI is in an acute or sub-acute phase of SCI (e.g., not yet reached a chronic phase).

In some embodiments, when a composition comprising an effective amount of an inhibitor of myostatin signaling described herein is administered to a population of patients who are at risk of developing a metabolic disorder associated with muscle dysfunction, the composition i) prevents manifestation or aggravation of the metabolic disorder in a statistically significant fraction of the patient population; or, ii) lessens the severity of the metabolic disease in the statistically significant fraction of the patient population.

In some embodiments, effects on metabolism may be monitored or measured by insulin resistance, lipid panel/markers (e.g., leptin), inflammatory markers and oxidative stress markers, including, but are not limited to: IL-6, TNF, CRP, plasma total antioxidant status, lipid oxidation and erythrocyte glutathione peroxidase activity.

Pharmaceutical Compositions

Myostatin inhibitors, e.g., antibodies, or antigen binding fragments thereof, described herein may be formulated into pharmaceutical compositions suitable for administration in human or non-human subjects. Such pharmaceutical compositions may be intended for therapeutic use, or prophylactic use. One or more of the myostatin inhibitors, e.g., anti-pro/latent-myostatin antibodies can be mixed with a pharmaceutically acceptable carrier (excipient), including buffer, to form a pharmaceutical composition for administering to a patient who may benefit from reduced myostatin signaling in vivo. "Pharmaceutically acceptable" means that the carrier must be compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In one example, a pharmaceutical composition described herein contains more than one myostatin inhibitor, e.g., more than one anti-pro/latent-myostatin antibody, or antigen-binding portion thereof, that recognize different epitopes/residues of the target antigen.

In some examples, the pharmaceutical composition described herein comprises emulsion-based or lipid-based formulations, such as liposomes containing a myostatin inhibitor, e.g., anti-pro/latent-myostatin antibody or antigen-binding portion thereof, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The myostatin inhibitor, e.g., anti-pro/latent-myostatin antibody, or antigen-binding portion thereof, may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, sec, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, or antigen-binding portion thereof, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an anti-pro-myostatin antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner The Subject Pharmaceutical compositions described herein are suitable for administration in human or non-human subjects. Accordingly, the myostatin inhibitor, e.g., anti-pro/latent-myostatin antibodies, and antigen-binding portions thereof, described herein are useful as medicament for administering to a subject who is likely to benefit from reduced myostatin signaling. In some embodiments, suitable subjects include healthy individuals who may nonetheless benefit from enhanced muscle mass/function, as well as improved metabolism. In some embodiments, suitable subjects have an existing muscle condition and/or associated metabolic dysfunction. In some embodiments, suitable subjects are at risk of developing such condition(s). In some embodiments, suitable subjects are those on a therapy comprising another therapeutic agent to treat a muscle/metabolic condition, but which is associated with adverse effects or toxicity. In some embodiments, the subject is a pediatric subject, e.g., human patients of between birth and <18 years of age.

In some embodiments, preferred subjects meet at least two of the following criteria: i) the subject has a condition associated with partial denervation of a motor neuron; ii) the condition involves a muscle containing or enriched with fast twitch fibers; and, iii) the subject retains an anabolic capability (e.g., generally healthy adults with injury) and/or is in a growth phase (e.g., young children, etc.).

In some embodiments, such medicament is suitable for administration in a pediatric population, an adult population, and/or an elderly population.

The pediatric population in need for the myostatin inhibitor, e.g., anti-pro/latent-myostatin antibodies and antigen-binding portions thereof, described herein may range between 0 and 6 months of age, between 0 and 12 months of age, between 0 and 18 months of age, between 0 and 24 months of age, between 0 and 36 months of age, between 0 and 72 months of age, between 6 and 36 months of age, between 6 and 36 months of age, between 6 and 72 months of age, between 12 and 36 months of age, between 12 and 72 months of age. In some embodiments, the pediatric population suitable for receiving the myostatin inhibitor, e.g., antibody or antigen-binding fragment, described herein who is likely to benefit from such treatment may range between 0 and 6 years of age, between 0 and 12 years of age, between 3 and 12 years of age, between 0 and 17 years of age. In some embodiments, the population has an age of at least 5 years, e.g., 6, 7, 8, 9, 10, 11, 12, 13, 14, 15, 16, or 17 years. In some embodiments, the pediatric population may be aged below 18 years old. In some embodiments, the pediatric population may be (a) at least 5 years of age and (b) below 18 years of age.

The adult population in need for the myostatin inhibitor, e.g., anti-pro/latent-myostatin antibodies and antigen-binding portions thereof, described herein may have an age of at least 18 years, e.g., at least 19, 20, 25, 30, 35, 40, 45, 50, 55, 60 or 65 years. In some embodiments, the adult population may be below 65 years of age. In some embodiments, the adult population may of (a) at least 18 years of age and (b) below 65 years of age.

The elderly population in need for the myostatin inhibitor, e.g., anti-pro/latent-myostatin antibodies and antigen-binding portions thereof, described herein may have an age of 65 years or older (i.e., ≥65 years old), e.g., at least 70, 75 or 80 years.

A human subject who is likely to benefit from the treatment may be a human patient having, at risk of developing, or suspected of having a metabolic disease/disorder associated with impaired neurological signaling, such as those described below. A subject having a pro/latent-myostatin-associated disease or disorder can be identified by routine medical examination, e.g., laboratory tests, organ functional tests, CT scans, or ultrasounds. A subject suspected of having any of such disease/disorder might show one or more symptoms of the disease/disorder. A subject at risk for the disease/disorder can be a subject having one or more of the risk factors for that disease/disorder.

A control subject, as described herein, is a subject who provides an appropriate reference for evaluating the effects of a particular treatment or intervention of a test subject or subject. Control subjects can be of similar age, race, gender, weight, height, and/or other features, or any combination thereof, to the test subjects.

In some embodiments, a myostatin assay (e.g., myostatin ELISA) is used to determine a subject requiring treatment of an anti-pro/latent myostatin antibody. Methods for assaying myostatin can be found in Lakshman et al. Molecular and Cell Endocrinology (2009) 302:26-32 (myostatin ELISA) and Bergen et al. Skeletal Muscle (2015) 5:21 (liquid chromatography with tandem mass spectrometry, both of which are incorporated by reference herein.

In some embodiments, methods are provided for improving muscle performance in a subject. The subject may or may not have or be at risk of having a condition associated with decreased muscle mass and/or decreased muscle function. As used herein, the term "muscle performance" generally refers to the capacity of the muscle to contract and/or to apply a force (e.g., to an external object). In some embodiments, muscle performance may relate to the capacity of the muscle to consume energy. For example, in some embodiments, muscle performance may relate to the capacity of the muscle to produce and/or consume adenosine triphosphate (ATP) molecules to facilitate muscle contraction. In some embodiments, muscle performance refers to the capacity of the muscle to contract repeatedly for a particular duration of time. In some embodiments, muscle performance refers to the capacity of the muscle to apply a force to an object, e.g., to move the object over a measurable distance. In some embodiments, muscle performance refers to the capacity of the muscle to apply a force to an object for a particular duration of time (e.g., to move the object over a measurable distance for a particular duration of time).

In some embodiments, the myostatin inhibitor, e.g., anti-pro/latent-myostatin antibody and antigen-binding portions thereof, described herein is administered to a subject in need of the treatment at an amount sufficient to inhibit the proteolytic activation of pro/latent-myostatin to active myostatin by at least 20% (e.g., 30%, 40%, 50%, 60%, 70%, 80%, 90% or greater) in vivo. In other embodiments, a myostatin inhibitor, e.g., antibody or antigen-binding portion thereof, is administered in an amount effective in reducing the pro/latent-myostatin or latent myostatin level by at least 20% (e.g., 30%, 40%, 50%, 60%, 70%, 80%, 90% or greater).

In some embodiments, the myostatin inhibitor, e.g., anti-pro/latent-myostatin antibody or antigen-binding portion thereof, described herein is administered to a subject who will benefit from increased muscle mass. In some embodiments, the myostatin inhibitor, e.g., anti-pro/latent-myostatin antibody or antigen-binding portion thereof, described herein is administered to a subject who will benefit from increased muscle-to-fat ratios. In some embodiments, the myostatin inhibitor, e.g., anti-pro/latent-myostatin antibody or antigen-binding portion thereof, described herein is administered to a subject who will benefit from increased muscle function. In some embodiments, the subject may or may not have or be at risk of having a condition associated with decreased muscle mass and/or decreased muscle function. In some embodiments, the subject has or is at risk of having a condition associated with decreased muscle mass and/or decreased muscle function.

The methods of the present invention further comprising selecting a subject. In some embodiment, the subject suffer from or is at risk of developing a muscle condition or disorder. In some embodiment, the subject suffer from or is at risk of developing a metabolic disorder. In some embodiment, the subject suffer from or is at risk of developing a disease or disorder associated with impaired neurological signaling.

Routes of Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-pro/latent-myostatin antibodies can be aerosolized using a fluorocarbon formulation and a metered dose inhaler, or inhaled as a lyophilized and milled powder.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, a myostatin inhibitor, e.g., anti-pro/latent-myostatin antibody or antigen-binding portion thereof, is administered via site-specific or targeted local delivery techniques. Examples of site-specific or targeted local delivery techniques include various implantable depot sources of the myostatin inhibitor, e.g., anti-pro/latent-myostatin antibody or antigen-binding portion thereof, or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The particular dosage regimen, e.g., dose, timing and repetition, used in the method described herein will depend on the particular subject and that subject's medical history.

Treatment efficacy for a disease/disorder associated with myopathy can be assessed using any suitable methods. For example, treatment efficacy for a disease/disorder associated with myopathy can be assessed by evaluating muscle weakness (e.g., assessing the pattern and severity of weakness), electromyography, evaluating blood chemistries (e.g., assessing electrolytes, assessing endocrine causes, measuring creatinine kinase level, determining erythrocyte sedimentation rate and performing antinuclear antibody assays), and evaluating biopsies (e.g., by histologic, histochemical, electron microscopic, biochemical, and genetic analysis).

"An effective amount" as used herein refers to the amount of each active agent required to confer a therapeutic effect on the subject, either alone or in combination with one or more other active agents. For example, an effective amount refers to the amount of a myostatin inhibitor, e.g., an antibody, or antigen binding fragment thereof, of the present disclosure which is sufficient to achieve a biological effect, e.g., an increase in muscle mass or muscle fiber diameter, a switch in muscle fiber type, an increase in the amount of force generated by the muscle, an increase in mass and/or function of a muscle tissue in the subject; an increase in the metabolic rate of the subject; an increase in insulin sensitivity of the subject; an increase in a level of brown adipose tissue in the subject; an increase in a level of beige adipose tissue in the subject; a decrease in a level of white adipose tissue in the subject; a decrease in a level of visceral adipose tissue in the subject; a decrease in ratio of adipose-to-muscle tissue in the subject; an increase in glucose uptake by a brown adipose tissue, a beige adipose tissue, or a muscle tissue in the subject; a decrease in glucose uptake by a white adipose tissue or a liver tissue; a decrease in muscle catabolism of protein and/or muscle release of amino acids in the subject; an increase in insulin dependent glycemic control in the subject; or a decrease in intramuscular fat infiltration in the subject; or a clinically significant outcome, e.g., a partial or complete recovery of the ability to perform physical tasks after injury; a clinically meaningful improvement in quality of life as assessed by a standardized system, such as SF-36 Quality of Life Scoring System; prevention of muscle loss or atrophy in the subject; and/or prevention of developing a metabolic disease in the subject.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, in the context of an increase in the level of pro-myostatin in the target muscle, the increase is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of pro-myostatin. In one embodiment, the increase in the level of pro-myostatin in the target muscle is an increase in a range of 1-fold to 3-fold, 1.2-fold to 10-fold, 2-fold to 9-fold, 3-fold to 8-fold, 4-fold to 7-fold, 2-fold to 7-fold, etc. compared to the control level of pro-myostatin.

In some embodiments, in the context of an increase in latent myostatin in the target muscle after the administering step, the increase is detectable within 4 hours, 24 hours, 48 hours, 7 days, 14 days, 21 days, 28 days or 30 days (or any time range bracketed by any of the listed duration of times) after the administering step. In one embodiment, an increase in latent myostatin in the target muscle after the administering step is detectable for at least 5 days, 7 days, 14 days, 21 days, 28 days, or 30 days (or any time range bracketed by any of the listed duration of times) after the administering step. In one embodiment, an increase in the level of latent myostatin in the target muscle after the administering step is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to the level of latent myostatin in the target muscle before the administering step. In one embodiment, an increase in the level of latent myostatin in the target muscle after the administering step is an increase in a range of 1-fold to 3-fold, 1.2-fold to 10-fold, 2-fold to 9-fold, 3-fold to 8-fold, 4-fold to 7-fold, 2-fold to 7-fold, etc., compared to the level of latent myostatin in the target muscle before the administering step.

In some embodiment, in the context of an increase in latent myostatin in the circulation after the administering step, an increase is detectable within 4 hours, 24 hours, 48 hours, 7 days, 14 days, 21 days, 28 days, or 30 days (or any time range bracketed by any of the listed duration of times) after the administering step. In one embodiment, an increase in latent myostatin in the circulation after the administering step is detectable for at least 5 days, 7 days, 14 days, 21 days, 28 days, or 30 days (or any time range bracketed by any of the listed duration of times) after the administering step. In one embodiment, an increase in the level of latent myostatin in the circulation after the administering step is at least 1-fold, 2-fold, 3-fold, 5-fold, 10-fold, 15-fold, 20-fold, 25-fold, 30-fold, 35-fold, 40-fold, 45-fold, or 50-fold or more (or any range bracketed by any of the values), compared to the level of latent myostatin in the circulation before the administering step. In one embodiment, an increase in the level of latent myostatin in the target muscle after the administering step is an increase in a range of 1-fold to 3-fold, 1.2-fold to 10-fold, 2-fold to 9-fold, 3-fold to 8-fold, 4-fold to 7-fold, 2-fold to 7-fold, etc., compared to the level of latent myostatin in the target muscle before the administering step.

In some embodiments, in the context of a decrease in the level of latent myostatin in the circulation, the decrease is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of latent myostatin. In one embodiment, a decrease in the level of latent myostatin in the circulation is a decrease in a range of 1-fold to 3-fold, 1.2-fold to 10-fold, 2-fold to 9-fold, 3-fold to 8-fold, 4-fold to 7-fold, 2-fold to 7-fold, etc. compared to the control level of latent myostatin.

As discussed above, in some embodiments, in the context of administration of a myostatin inhibitor, e.g., a pro/latent-myostatin antibody, or antigen binding fragment thereof, to a subject, an effective amount is an amount effective to increase mass of a target muscle in the subject compared with a control muscle mass. In some embodiments, muscle treated with an effective amount of the antibody is increase by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, etc. as compared with a control muscle mass that is not treated with an effective amount of the antibody. In some embodiments, such muscle mass increase is achieved in a select group or type of muscles in the subject.

In some embodiments, in the context of administration of a myostatin inhibitor, e.g., pro/latent-myostatin antibody, or antigen binding fragment thereof, to a subject, an effective amount is an amount effective to switch fiber types in the subject. In some embodiments, an effective amount of the antibody can promote a fiber type switch from type I to type II. In some embodiments, an effective amount of the myostatin inhibitor, e.g., antibody or antigen-binding portion thereof, can promote a fiber type switch from type I to type IIB. In some embodiments, an effective amount of the myostatin inhibitor, e.g., antibody or antigen-binding portion thereof, can promote type II fibers, relative to other types of fibers. In some embodiments, an effective amount of the myostatin inhibitor, e.g., antibody or antigen-binding portion thereof, can promote type JIB fibers, relative to other types of fibers. In some embodiments, such phenotypic switch in fibers may occur without significant change in overall muscle mass. In other embodiments, such phenotypic switch in fibers may coincide an increase in overall muscle mass.

In some embodiments, in the context of administration of a myostatin inhibitor, e.g., pro/latent-myostatin antibody, or antigen binding fragment thereof, to a subject, an effective amount is an amount effective to increase diameter of muscle fiber in the subject compared with a control muscle fiber. In some embodiments, the increase in the diameter of the muscle fiber is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle fiber. In some embodiments, the increase in the diameter of muscle fiber is an increase in a range of 1-fold to 5-fold, 2-fold to 10-fold, 1-fold to 1.5-fold, 1-fold to 2-fold, etc. compared with a control muscle fiber.

In some embodiments, in the context of administration of a myostatin inhibitor, e.g., pro/latent-myostatin antibody, or antigen binding fragment thereof, to a subject, an effective amount is an amount effective to increase muscle-to-fat ratio in the subject compared with a control muscle mass. In some embodiments, the increase in the muscle-to-fat ratio is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the increase in the muscle-to-fat ratio is an increase in a range of 1-fold to 5-fold, 2-fold to 10-fold, 1-fold to 1.5-fold, 1-fold to 2-fold, etc. compared with a control subject.

In some embodiments, in the context of administration of a myostatin inhibitor, e.g., a pro/latent-myostatin antibody, or antigen binding fragment thereof, to a subject, an effective amount is an amount effective to decrease intramuscular fat infiltration in the subject compared with a control muscle mass. In some embodiments, the decrease in the intramuscular fat infiltration is a decrease of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the decrease in intramuscular fat infiltration is a decrease in a range of 1-fold to 5-fold, 2-fold to 10-fold, 1-fold to 1.5-fold, 1-fold to 2-fold, etc. compared with a control subject.

In some embodiments, a method of preventing a reduction of and/or increasing muscle mass in a human subject includes administering a myostatin inhibitor, e.g., a pro/latent-myostatin antibody, or antigen binding fragment thereof, to a subject that inhibits proteolytic formation of mature myostatin by a tolloid protease. In one embodiment, inhibition of proteolytic cleavage of pro-myostatin or latent myostatin by a tolloid protease results in a progressive increase in muscle mass. In one embodiment, a subject exhibits a progressive increase in muscle mass for at least 2 weeks, 4 weeks, 6 weeks, 8 weeks, 10 weeks, 12 weeks, 14 weeks, 16 weeks, 18 weeks, or 20 weeks (or any range bracketed by any of the values). In some embodiments, a method of preventing a reduction of and/or increasing muscle mass in a human subject includes administering a myostatin inhibitor, e.g., a pro/latent-myostatin antibody, or antigen binding fragment thereof, to a subject comprising more than two doses. In one embodiment, administering a myostatin inhibitor, e.g., a pro/latent-myostatin antibody, or antigen binding fragment thereof, comprises at least a first dose and a second dose, the first dose and the second dose are administered to the subject at least about 2 weeks apart, 4 weeks apart, 6 weeks apart, 8 weeks apart, or 12 weeks apart.

In some embodiments, in the context of administration of a myostatin inhibitor, e.g., a pro/latent-myostatin antibody, or antigen binding fragment thereof, to a subject, an effective amount is an amount effective to increase function of a target muscle in the subject compared with a control muscle function. In some embodiments, the increase in muscle function is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle function. In some embodiments, the increase in muscle function is an increase in a range of 1-fold to 5-fold, 2-fold to 10-fold, 1-fold to 1.5-fold, 1-fold to 2-fold, etc. compared with a control muscle function.

As used herein, the term "control muscle mass" refers to a reference standard useful for evaluating effects of a condition (e.g., treatment with a myostatin inhibitor, e.g., a pro/latent-myostatin antibody, or antigen binding fragment thereof) on the mass of a target muscle in a subject. In some embodiments, a control muscle mass is a predetermined value. In some embodiments, a control muscle mass is experimentally determined. In some embodiments, a control muscle mass is the mass of a target muscle in a subject who has not been administered the myostatin inhibitor, e.g., pro/latent-myostatin antibody, or antigen binding fragment thereof. In some embodiments, a control muscle mass is the mass (e.g., the average mass) of a target muscle in a population of subjects who have not been administered the myostatin inhibitor, e.g., pro/latent-myostatin antibody, or antigen binding fragment thereof. In some embodiments, a control muscle mass is the mass of a target muscle in a subject prior to (e.g., immediately prior to) being administered the myostatin inhibitor, e.g., pro/latent-myostatin antibody, or antigen binding fragment thereof. In some embodiments, a control muscle mass is the mass of a target muscle in a subject who has been administered, in place of the myostatin inhibitor, e.g., pro/latent-Myostatin antibody, or antigen binding fragment thereof, a normal antibody (e.g., of the same isotype as the pro/latent-Myostatin antibody) that has been obtained from an animal that has not been exposed to the antigen to which the pro/latent-myostatin antibody, or antigen binding fragment thereof, is directed. In some embodiments, a control muscle mass is the mass of a target muscle in a subject who has been administered, in place of the myostatin inhibitor, e.g., pro/latent-myostatin antibody, or antigen binding fragment thereof, a vehicle, e.g., saline.

In some embodiments, in the context of administration of a myostatin inhibitor, e.g., pro/latent-myostatin antibody, or antigen binding fragment thereof, to a subject, an effective amount is an amount effective to increase force generation capacity (e.g., a maximal force generation as determined in vitro with a muscle lever system adapted with a horizontal perfusion bath) of a target muscle in the subject compared with a control force generation capacity. In some embodiments, the increase in force generation capacity is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control force generation capacity. In some embodiments, the increase in force generation capacity is an increase in a range of 1-fold to 5-fold, 2-fold to 10-fold, 1-fold to 1.5-fold, 1-fold to 2-fold, etc. compared with a control force generation capacity.

As used herein, the term "control force generation capacity" refers to a reference standard useful for evaluating effects of a condition (e.g., treatment with a pro/latent-myostatin antibody, or antigen binding fragment thereof) on the force generation capacity of a muscle in a subject. In some embodiments, a control force generation capacity is a predetermined value. In some embodiments, a control force generation capacity is experimentally determined. In some embodiments, a control force generation capacity is the force generation capacity of a target muscle in a subject who has not been administered the myostatin inhibitor, e.g., pro/latent-myostatin antibody, or antigen binding fragment thereof. In some embodiments, a control force generation capacity is the force generation capacity (e.g., the average force generation capacity) of a target muscle in a population of subjects who have not been administered the myostatin inhibitor, e.g., pro/latent-myostatin antibody, or antigen binding fragment thereof. In some embodiments, a control force generation capacity is the force generation capacity of a target muscle in a subject prior to (e.g., immediately prior to) being administered the myostatin inhibitor, e.g., pro/latent-myostatin antibody, or antigen binding fragment thereof. In some embodiments, a control force generation capacity is the force generation capacity of a target muscle in a subject who has been administered, in place of the myostatin inhibitor, e.g., pro/latent-myostatin antibody, a normal antibody (e.g., of the same isotype as the pro/latent-myostatin antibody) that has been obtained from an animal that has not been exposed to the antigen to which the pro/latent-myostatin antibody is directed. In some embodiments, a control force generation capacity is the force generation capacity of a target muscle in a subject who has been administered, in place of the myostatin inhibitor, e.g., pro/latent-myostatin antibody, or antigen binding fragment thereof, a vehicle, e.g., saline.

In some embodiments, the target muscle is a plantarflexor muscle. In some embodiments, the target muscle is a muscle containing type 2 fibers. In some embodiments, the target muscle is a muscle containing fast oxidative fibers or fast glycolytic fibers. In some embodiments, the target muscle is a muscle containing type IIB fibers. In some embodiments, the administration of myostatin inhibitor, e.g., pro/latent-myostatin antibody, or antigen binding fragment thereof, results in increase in type IIB fiber cross-sectional area by at least 1%, 5%, 10%, 15%, 20%, 25%, 30%, 35%, 40%, 45%, or 50% (or any range bracketed by any of the values), compared to the cross-sectional area before the administering step.

Dosages

Empirical considerations, such as the half-life, generally will contribute to the determination of the dosage. For example, antibodies and antigen-binding portions thereof that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with myopathy. Alternatively, sustained continuous release formulations of a myostatin inhibitor, e.g., an anti-pro/latent-myostatin antibody, or antigen-binding portion thereof, may be appropriate. Various formulations and devices for achieving sustained release would be apparent to the skilled artisan and are within the scope of this disclosure.

In one example, dosages for a myostatin inhibitor, e.g., an anti-pro/latent-myostatin antibody, or antigen binding fragment thereof, as described herein may be determined empirically in individuals who have been given one or more administration(s) of the myostatin inhibitor, e.g., antibody, or antigen binding fragment thereof. Individuals are given incremental dosages of the antagonist. To assess efficacy of the antagonist, an indicator of the disease/disorder can be followed.

Generally, for administration of any of the antibody, or antigen binding fragment thereof, described herein, an initial candidate dosage can be about 2 mg/kg. For the purpose of the present disclosure, a typical daily dosage might range from about any of 0.1 pg/kg to 3 µg/kg to 30 pg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a disease or disorder associated with pro/latent-myostatin, or a symptom thereof. An exemplary dosing regimen comprises administering an initial dose of about 2 mg/kg, followed by a weekly maintenance dose of about 1 mg/kg of the antibody, or antigen binding fragment thereof, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 pg/mg, about 30 pg/mg, about 100 pg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, every 4 months, every 5 months, every 6 months, every 8 months, every 10 months, every year, or longer. The progress of this therapy is easily monitored by conventional techniques and assays. The dosing regimen (including the antibody used) can vary over time.

In some embodiments, the administration of any of the myostatin inhibitors, e.g., antibodies, or antigen binding fragments thereof, described herein comprises a single dose. In some embodiments, the administration of any of the myostatin inhibitors, e.g., antibodies, or antigen binding fragments thereof, described herein comprises multiple doses (e.g., at least 2, 3, 4, 5, 6, 7, 8, 9, or 10 doses). Administering may comprise more than two doses. In some embodiments, the administration comprises at least a first dose and a second dose of a therapeutically effective amount of the myostatin inhibitor, e.g., antibody or antigen-binding portion thereof. In one embodiment, the first dose and the second dose are administered to the subject at least about 4 weeks apart, 6 weeks apart, 8 weeks apart, or 12 weeks apart.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of a myostatin inhibitor, e.g., an anti-pro/latent-myostatin antibody, or antigen binding fragment thereof, will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. In some embodiments, a clinician will administer a myostatin inhibitor, e.g., an anti-pro/latent-myostatin antibody or antigen-binding portion thereof, until a dosage is reached that achieves the desired result. Administration of a myostatin inhibitor, e.g., an anti-pro/latent-myostatin antibody or antigen-binding portion thereof, can be continuous or intermittent, depending, for example, upon the recipient's physiological condition, whether the purpose of the administration is therapeutic or prophylactic, and other factors known to skilled practitioners. The administration of a myostatin inhibitor, e.g., an anti-pro/latent-myostatin antibody, or antigen binding fragment thereof, may be essentially continuous over a preselected period of time or may be in a series of spaced dose, e.g., either before, during, or after developing a disease or disorder associated with pro/latent-myostatin.

As used herein, the term "treating" refers to the application or administration of a composition including one or more active agents to a subject, who has a disease/disorder associated with myopathy, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Alleviating a disease/disorder associated with pro/latent-myostatin includes delaying the development or progression of the disease, or reducing disease severity. Alleviating the disease does not necessarily require curative results. As used therein, "delaying" the development of a disease/disorder associated with pro/latent-myostatin means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

Combination Therapies

The invention encompasses pharmaceutical compositions and related methods used as combination therapies for treating subjects who may benefit from myostatin inhibition in vivo. In any of these embodiments, such subjects may receive combination therapies that include a first composition comprising at least one myostatin inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat myopathy associated with a disease, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the enhancement of muscle mass/function and for the treatment or prevention of metabolic diseases or diseases associated with an impaired neurological signaling, including diabetes, obesity and spinal cord injury. Accordingly, the methods or the pharmaceutical compositions further comprise a second therapy. In some embodiments, the second therapy may be useful in treating or preventing metabolic diseases or diseases associated with an impaired neurological signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more anti-myostatin antibodies or other myostatin inhibitors of the invention may be used in combination with one or more of additional therapeutic agents. Examples of the additional therapeutic agents which can be used with an anti-myostatin antibody of the invention include, but are not limited to, diabetes mellitus-treating agents, diabetic complication-treating agents, cardiovascular diseases-treating agents, anti-hyperlipemic agents, hypotensive or anti-hypertensive agents, anti-obesity agents, nonalcoholic steatohepatitis (NASH)-treating agents, chemotherapeutic agents, immunotherapeutic agents, immunosuppressive agents, and the like. Such combination therapies may advantageously utilize lower dosages of the administered therapeutic agents, thus avoiding possible toxicities or complications associated with the various monotherapies. Examples of agents for treating diabetes mellitus include insulin formulations (e.g., animal insulin formulations extracted from a pancreas of a cattle or a swine; a human insulin formulation synthesized by a gene engineering technology using microorganisms or methods), insulin sensitivity enhancing agents, pharmaceutically acceptable salts, hydrates, or solvates thereof (e.g., pioglitazone, troglitazone, rosiglitazone, netoglitazone, balaglitazone, rivoglitazone, tesaglitazar, farglitazar, CLX-0921, R-483, NIP-221, NIP-223, DRF-2189, GW-7282TAK-559, T-131, RG-12525, LY-510929, LY-519818, BMS-298585, DRF-2725, GW-1536, GI-262570, KRP-297, TZD18 (Merck), DRF-2655, and the like), alpha-glycosidase inhibitors (e.g., voglibose, acarbose, miglitol, emiglitate and the like), biguanides (e.g., phenformin, metformin, buformin and the like) or sulfonylureas (e.g., tolbutamide, glibenclamide, gliclazide, chlorpropamide, tolazamide, acetohexamide, glyclopyramide, glimepiride and the like) as well as other insulin secretion-promoting agents (e.g., repaglinide, senaglinide, nateglinide, mitiglinide, GLP-1 and the like), amyrin agonist (e.g., pramlintide and the like), phosphotyrosin phosphatase inhibitor (e.g., vanadic acid and the like) and the like.

Examples of agents for treating diabetic complications include, but are not limited to, aldose reductase inhibitors (e.g., tolrestat, epalrestat, zenarestat, zopolrestat, minalrestat, fidareatat, SK-860, CT-112 and the like), neurotrophic factors (e.g., NGF, NT-3, BDNF and the like), PKC inhibitors (e.g., LY-333531 and the like), advanced glycation end-product (AGE) inhibitors (e.g., ALT946, pimagedine, pyradoxamine, phenacylthiazolium bromide (ALT766) and the like), active oxygen quenching agents (e.g., thioctic acid or derivative thereof, a bioflavonoid including flavones, isoflavones, flavonones, procyanidins, anthocyanidins, pycnogenol, lutein, lycopene, vitamins E, coenzymes Q, and the like), cerebrovascular dilating agents (e.g., tiapride, mexiletene and the like).

In one embodiment, remission of diabetes can be induced by administration of a myostatin inhibitor in combination with a caloric restriction diet, or other diet.

Anti-hyperlipemic agents include, for example, statin-based compounds which are cholesterol synthesis inhibitors (e.g., pravastatin, simvastatin, lovastatin, atorvastatin, fluvastatin, rosuvastatin and the like), squalene synthetase inhibitors or fibrate compounds having a triglyceride-lowering effect (e.g., fenofibrate, gemfibrozil, bezafibrate, clofibrate, sinfibrate, clinofibrate and the like), niacin, PCSK9 inhibitors, triglyceride lowering agents or cholesterol sequesting agents.

Hypotensive agents include, for example, angiotensin converting enzyme inhibitors (e.g., captopril, enalapril, delapril, benazepril, cilazapril, enalapril, enalaprilat, fosinopril, lisinopril, moexipril, perindopril, quinapril, ramipril, trandolapril and the like) or angiotensin II antagonists (e.g., losartan, candesartan cilexetil, olmesartan medoxomil, eprosartan, valsartan, telmisartan, irbesartan, tasosartan, pomisartan, ripisartan forasartan, and the like) or calcium channel blockers (e.g., amlodipine) or aspirin.

Nonalcoholic steatohepatitis (NASH)-treating agents include, for example, ursodiol, pioglitazone, orlistat, betaine, rosiglitazone. In one embodiment, steatosis, resulting liver inflammation, and fibrosis in NAFLD and/or NASH subjects can be treated by administration of a myostatin inhibitor in combination with a caloric restriction diet, or other diet.

Anti-obesity agents include, for example, central antiobesity agents (e.g., dexfenfluramine, fenfluramine, phentermine, sibutramine, amfepramone, dexamphetamine, mazindol, phenylpropanolamine, clobenzorex and the like), gastrointestinal lipase inhibitors (e.g., orlistat and the like), beta 3-adrenoceptor agonists (e.g., CL-316243, SR-58611-A, UL-TG-307, SB-226552, AJ-9677, BMS-196085 and the like), peptide-based appetite-suppressing agents (e.g., leptin, CNTF and the like), cholecystokinin agonists (e.g., lintitript, FPL-15849 and the like) and the like.

Chemotherapeutic agents include, for example, alkylating agents (e.g., cyclophosphamide, iphosphamide and the like), metabolism antagonists (e.g., methotrexate, 5-fluorouracil and the like), anticancer antibiotics (e.g., mitomycin, adriamycin and the like), vegetable-derived anticancer agents (e.g., vincristine, vindesine, taxol and the like), cisplatin, carboplatin, etoposide and the like. Among these substances, 5-fluorouracil derivatives such as furtulon and ncofurtulon are preferred.

Immunotherapeutic agents include, for example, microorganisms or bacterial components (e.g., muramyl dipeptide derivative, picibanil and the like), polysaccharides having immune potentiating activity (e.g., lentinan, sizofilan, krestin and the like), cytokines obtained by a gene engineering technology (e.g., interferon, interleukin (IL) and the like), colony stimulating factors (e.g., granulocyte colony stimulating factor, crythropoctin and the like) and the like, among these substances, those preferred are IL-1, IL-2, IL-12 and the like.

Immunosuppressive agents include, for example, calcineurin inhibitor/immunophilin modulators such as cyclosporine (Sandimmune, Gengraf, Neoral), tacrolimus (Prograf, FK506), ASM 981, sirolimus (RAPA, rapamycin, Rapamune), or its derivative SDZ-RAD, glucocorticoids (prednisone, prednisolone, methylprednisolone, dexamethasone and the like), purine synthesis inhibitors (mycophenolate mofetil, MMF, CellCept®, azathioprine, cyclophosphamide), interleukin antagonists (basiliximab, daclizumab, deoxyspergualin), lymphocyte-depleting agents such as antithymocyte globulin (Thymoglobulin, Lymphoglobuline), anti-CD3 antibody (OKT3), and the like.

In addition, agents whose cachexia improving effect has been established in an animal model or at a clinical stage, such as cyclooxygenase inhibitors (e.g., indomethacin and the like), progesterone derivatives (e.g., megestrol acetate), glucosteroid (e.g., dexamethasone and the like), metoclopramide-based agents, tetrahydrocannabinol-based agents, lipid metabolism improving agents (e.g., eicosapentanoic acid and the like), growth hormones, IGF-1, antibodies against TNF-α, LIF, IL-6 and oncostatin M may also be employed concomitantly with an anti-myostatin antibody according to the present invention. Additional therapeutic agents for use in the treatment of diseases or conditions related to metabolic disorders and/or impaired neurological signaling would be apparent to the skilled artisan and are within the scope of this disclosure.

In some embodiments, second agents suitable for administration as a combination therapy in conjunction with the antibodies described herein are anti-fibrotic agents, such as TGFβ1 inhibitors.

In some embodiments, second agents suitable for administration as a combination therapy in conjunction with the antibodies described herein are modulators (e.g., agonists and antagonists) of certain members of the TGFβ super family of growth factors, such as BMP6, BMP7, GDF11, TGFβ2, TGFβ3, RGMc, etc.

Any of the above-mentioned agents can be administered in combination with the myostatin antibody of the invention to treat a metabolic disease, or a disease associated with an impaired neurological signaling between a neuron and a target tissue, e.g., spinal cord injury, muscular atrophy, and muscular dystrophy.

Use of Anti-Pro/Latent-Myostatin Antibodies or Antigen Binding Fragments Thereof for Treating Diseases/Disorders Pharmaceutical compositions described herein are suitable for administration to human patients for the treatment or prevention of diseases and conditions where reduced myostatin signaling is desirable. Such diseases and conditions include, but are not limited to: metabolic disorders, and diseases associated with impaired neurological signaling, e.g., spinal cord injury. Exemplary conditions for which the compositions and methods of the present invention may be useful are further described below.

A. Metabolic Disorders and Diseases

The invention provides methods for treating or preventing a metabolic disease in a subject. As used herein, the term "metabolic disease" refers to any undesirable condition involving perturbation of the normal physiological state of homeostasis due to an alteration in metabolism (anabolism and/or catabolism). Metabolic disorders affect how the body processes substances needed to carry out physiological functions and are generally associated with aberrant glucose, lipid/fat and/or protein/nitrogen metabolism, or osmotic dysregulation, and pathological consequences arising from such condition. A number of metabolic disorders of the invention share certain characteristics, e.g., they are associated with a loss of fat-free or lean muscle mass, an excess of fat mass, a lower metabolic rate, insulin resistance, lack of ability to regulate blood sugar, weight gain, and/or increase in body mass index. In some cases, such metabolic conditions may be triggered or exacerbated by medication that the patients receive. As discussed in more detail herein, metabolic disorders can occur secondarily to, or occur as a result of, a muscle condition or disorder.

The present invention is based, at least in part, on the discovery that administration of a myostatin inhibitor, e.g., an antibody, or antigen binding fragment thereof, that specifically binds to pro/latent myostatin, to subjects having a metabolic disease significantly improves both the physiological and the functional characteristics of the injured subjects. In particular, the present inventors have surprisingly discovered that administration of a myostatin inhibitor, e.g., an anti-myostatin antibody or antigen-binding portion thereof, significantly increases the metabolic rate or energy expenditure in subjects having metabolic disease. Administration of a myostatin inhibitor, e.g., an anti-myostatin antibody or antigen-binding portion thereof, also significantly attenuated SCI-induced reduction in sub-lesional muscle mass and overall body mass and, while at the same time reducing the mass of undesirable adipose tissue such as white and visceral adipose tissue. In addition, subjects who received a myostatin inhibitor, e.g., an anti-myostatin antibody or antigen-binding portion thereof, treatment exhibited a significant improvement in their locomotor function, muscle strength, as well as motor coordination and balance skills.

Accordingly, the present invention provides methods for treating or preventing metabolic diseases in a human subject. The methods include selecting a human subject suffering from a metabolic disease, and administering to the human subject an effective amount of a myostatin inhibitor, e.g., an antibody, or antigen binding fragment thereof, that specifically binds myostatin, thereby treating or preventing the metabolic disease in the human subject. Preferably, the antibody, or antigen binding fragment thereof, specifically binds to pro/latent myostatin, but docs not bind to GDF11. Antibodies that specifically recognize pro/latent myostatin, but not GDF11, are beneficial and avoid undesirable toxicity caused by off-target binding of antibodies to GDF11 in the subject. In one embodiment, the subject is a pediatric subject.

Examples of metabolic diseases that may be treated or prevented by the methods of the present invention include but are not limited to, type 1 diabetes, type 2 diabetes, metabolic syndrome, pre-diabetes, obesity, cardiovascular diseases (such as congestive heart failure), non-alcoholic stetohepatitis (NASH), spinal cord injury (SCI) (e.g., complete or incomplete/partial SCI), hypo-metabolic states, double diabetes, Cushings disease (also referred to as Cushing's syndrome), obesity syndrome (e.g., diet-associated or diet-induced obesity), insulin resistance, insulin insufficiency, hyperinsulinemia, impaired glucose tolerance (IGT), abnormal glycogen metabolism, hyperlipidemia, hypoalbuminemia, hypertriglyceridemia, syndrome X, fatty liver disease and metabolic bone diseases. In some embodiments, metabolic diseases include diseases associated with impaired neurological signaling or partial denervation. In some embodiments, metabolic diseases include conditions triggered by or associated with certain medication (e.g., side effects).

Additional diseases or conditions related to metabolic disorders and/or body composition that would be apparent to the skilled artisan and are within the scope of this disclosure.

Diabetes refers to a group of metabolic diseases characterized by high blood sugar (glucose) levels which result from defects in insulin secretion or action, or both. There are two most common types of diabetes, namely type 1 diabetes and type 2 diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDDM, and juvenile onset diabetes. People with type I diabetes (insulin-dependent diabetes) produce little or no insulin at all. Although about 6 percent of the United States population has some form of diabetes, only about 10 percent of all diabetics have type I disorder. Most people who have type I diabetes developed the disorder before age 30. Type 1 diabetes represents is the result of a progressive autoimmune destruction of the pancreatic β-cells with subsequent insulin deficiency. More than 90 percent of the insulin-producing cells (beta cells) of the pancreas are permanently destroyed. The resulting insulin deficiency is severe, and to survive, a person with type I diabetes must regularly inject insulin.

In type II diabetes (also referred to as noninsulin-dependent diabetes mellitus, NDDM), the pancreas continues to manufacture insulin, sometimes even at higher than normal levels. However, the body develops resistance to its effects, resulting in a relative insulin deficiency. Type 11 diabetes may occur in children and adolescents but usually begins after age 30 and becomes progressively more common with age: about 15 percent of people over age 70 have type II diabetes. Obesity is a risk factor for type II diabetes, and 80 to 90 percent of the people with this disorder are obese.

In some embodiments, diabetes includes pre-diabetes. "Pre-diabetes" refers to one or more early diabetic conditions including impaired glucose utilization, abnormal or impaired fasting glucose levels, impaired glucose tolerance, impaired insulin sensitivity and insulin resistance. Prediabetes is a major risk factor for the development of type 2 diabetes mellitus, cardiovascular disease and mortality. Much focus has been given to developing therapeutic interventions that prevent the development of type 2 diabetes by effectively treating prediabetes.

In some embodiments, diabetes includes double diabetes, which is a combination of type 1 diabetes with features of insulin resistance and type 2 diabetes.

Diabetes can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependent diabetes mellitus (type 2 IDDM), non-autoimmune diabetes mellitus, non-insulin-dependent diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14th ed., New York, McGraw-Hill).

Obesity is another prevalent metabolic disease that can be treated or prevented by the methods of the present invention. "Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese. Obesity can be defined using any clinically relevant definitions. For example, in adults, body mass index (BMI, $kg/m^2$) is frequently used as a measure of overweight and obesity, with overweight being defined as a BMI 25-29.9 $kg/m^2$, obesity as a BMI equal to or greater than 30 $kg/m^2$, and morbid obesity being defined as BMIs over 40 $kg/m^2$. Obesity can also be defined in adults by central adiposity as measured by waist circumference, with raised waist circumference defined as equal to or greater than 102 cm in men and equal to or greater than 88 cm in women. Subject with obesity may exhibit other symptoms such as increased fasting plasma glucose, increased fasting plasma triglycerides, decreased fasting high density lipoprotein (HDL) level, and increased blood pressure. Obesity may also cause various orthopedic problems, skin disorders and swelling of the feet and ankles Severe complications of obesity include a much higher risk of coronary artery disorder and of its major risk factors type II diabetes, hyperlipidemia and hypertension. Much of the morbidity associated with obesity is associated with type II diabetes, as poorly controlled diabetes and obesity lead to a constellation of symptoms that are together known as syndrome X, or metabolic syndrome. In some embodiments, the obesity is sarcopenic obesity. In some embodiments, the subject having obesity is on a caloric restriction regimen.

The methods of the present invention are also suitable for treating or preventing metabolic disease such as metabolic syndromes. As used herein, "metabolic syndrome" refers to the concept of a clustering of metabolic risk factors that come together in a single individual and lead to a high risk of developing diabetes and/or cardiovascular diseases. The main features of metabolic syndrome include insulin resistance, hypertension (high blood pressure), cholesterol abnormalities, dyslipidemia, triglyceride abnormalities, an increased risk for clotting and excess body weight, especially in the abdomen, or obesity. The American Heart Association suggests that metabolic syndrome be diagnosed by the presence of three or more of the following components: (1) an elevated waist circumference (men, equal to or greater than 40 inches (102 cm); women, equal to or greater than 35 inches (88 cm)); (2) elevated triglycerides (equal to or greater than 150 mg/dL); (3) reduced High Density Lipoprotein cholesterol or HDL (men, less than 40 mg/dL; women, less than 50 mg/dL); (4) elevated blood pressure (equal to or greater than 130/85 mm Hg); and (5) elevated fasting glucose (equal to or greater than 100 mg/dL).

In another aspect, the methods of the present invention are suitable for treating or preventing metabolic disease such as obesity syndromes. The term "obesity syndrome" refers any disorder or conditions causing a subject to be grossly fat or overweight. Like other metabolic diseases, people with obesity syndrome are usually associated a loss of fat-free or lean muscle mass, an excess of fat mass, a lower metabolic rate, insulin resistance, lack of ability to regulate blood sugar, weight gain, and increase in body mass index. In some embodiments, the obesity syndrome is selected from the group consisting of Prader Willi, an obesity syndrome associated with a genetic disorder, and an obesity syndrome associated with a hypothalamic disorder.

The methods of the present invention are also suitable for treating or preventing metabolic diseases associated with a hypo-metabolic state. The term "a hypo-metabolic state" refers to a state of reduced metabolism or metabolic activity, where the body is not producing enough energy. Patients with a hypo-metabolic state generally have a lower metabolic rate, a loss of fat-free or lean muscle mass, an excessive gain of fat mass, insulin resistance, lack of ability to regulate blood sugar, weight gain, and an increase in body mass index. In some embodiments, the hypo-metabolic state is selected from the group consisting of a state associated with prolonged immobilization, a state associated with bedrest, a state associated with casting, a state associated with a stroke, a state associated with amputation, and a post-surgery state. In some embodiments, the hypo-metabolic state is a post-surgery state, e.g., paraspinal muscle atrophy after lumbar spine surgery. In one embodiment, the paraspinal muscle atrophy is a nerve injury-dependent muscle atrophy. In one embodiment, the surgery is a spinal surgery. In one embodiment, the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc.

In another aspect, the methods of the present invention are suitable for treating or preventing metabolic diseases such as Cushings disease, which is also referred to as Cushing's syndrome or Cushing syndrome. The term "Cushings disease" refers to a collection of signs and symptoms due to prolonged exposure to cortisol. This may stem from endogenous causes, such as a condition in which the pituitary gland releases too much adrenocorticotropic hormone (ACTH), or exogenous causes, such as the use of oral corticosteroid medication. Some of the hallmark signs and symptoms of Cushing disease may include: progressive obesity, such as weight gain and fatty tissue deposits, particularly around the midsection and upper back and between the shoulders (buffalo hump) (upper body obesity above the waist); thin arms and legs, round, red, full face (moon face); changes in the skin, such as pink or purple stretch marks (striae) on the skin of the abdomen, thighs, breasts and arms, thinning, fragile skin that bruises easily, low healing of cuts, insect bites and infections, and acne. Patients with Cushing disease may also experience severe fatigue, muscle weakness, depression, anxiety and irritability, loss of emotional control, cognitive difficulties, new or worsened high blood pressure, headache, type 2 diabetes, and/or bone loss which may lead to fractures over time. In children, Cushing disease may cause impaired growth (slow growth rate). In some embodiments, the Cushings disease is selected from the group consisting of corticosteroid-induced Cushings disease and tumor-induced Cushings disease.

To date, standard treatments for Cushing disease are designed to lower the high level of cortisol in the body, whether the source is endogenous overproduction of the hormones or due to medication. The best treatment for a particular patient depends on the cause of the syndrome. Treatment options that are currently available include, for example, reducing corticosteroid use, surgery, radiation therapy, and medications.

Thus, the use of inhibitors of myostatin activation described herein presents an alternative or additive treatment option for patients suffering from Cushing's disease.

Where the cause of Cushing disease is long-term use of corticosteroid medications, controlled reduction of the dosage of the drug over a period of time, while still adequately managing the underlining disease or condition for which the drug is being administered, may be considered. Thus, in some embodiments, the patient who is on a corticosteroid therapy has one or more autoimmune or inflammatory diseases, such as rheumatoid arthritis, lupus and asthma. Corticosteroid may also be prescribed to patients to suppress the body's immunity in order to prevent the body from rejecting an allograft transplant, such as a transplanted organ or tissue.

In some embodiments, patients receiving a corticosteroid therapy include a sub-population of individuals who do not tolerate well, who are poorly responsive or not responsive, to other treatment options, such as non-corticosteroid medications. In such situations, the physician may continue to prescribe corticosteroid medication. In some embodiments, surgery may be considered as an alternative option.

If the cause of Cushing syndrome is a tumor, complete surgical removal and/or radiation therapy can be considered. In some embodiments, patients have a tumor in the pituitary, adrenal glands, lungs or pancreas. After the operation, cortisol replacement therapy is typically administered to provide the body with the correct amount of adrenal hormone production.

In some embodiments, patients with Cushing syndrome never experience a resumption of normal adrenal function and therefore may require lifelong replacement therapy. The inhibitors of myostatin activation described herein may be suitable to treat such patients.

In some embodiments, medication can be used to control cortisol production when surgery and/or radiation don't work. Medications may also be used before surgery in patients who have become very sick with Cushing syndrome. The inhibitors of myostatin activation encompassed by the present disclosure may be used to treat such patients prior to surgery to improve signs and symptoms and minimize surgical risk.

Medications currently used to control excessive production of cortisol at the adrenal gland include ketoconazole (Nizoral), mitotane (Lysodren) and metyrapone (Metopirone). Mifepristone (Korlym) is approved for patients with Cushing syndrome who have type 2 diabetes or glucose intolerance. Mifepristone does not decrease cortisol production, but it blocks the effect of cortisol on the tissues. Side effects from these medications may include fatigue, nausea, vomiting, headaches, muscle aches, high blood pressure, low potassium and swelling. Some have more serious side effects, such as neurological side effects and liver toxicity. The inhibitors of myostatin activation encompassed by the present disclosure may be used alone (in lieu of) or in combination with any of these therapeutics.

More recently, pasireotide (Signifor) has become available for the treatment of Cushings, which works by decreasing ACTH production from a pituitary tumor. This medication is given as an injection twice daily. It is typically recommended when pituitary surgery is unsuccessful or cannot be done. Side effects associated with this medication are fairly common, and may include diarrhea, nausea, high blood sugar, headache, abdominal pain and fatigue. The inhibitors of myostatin activation encompassed by the present disclosure may be used alone (in lieu of) or in combination with any of such therapeutics.

In some embodiments, the tumor or its treatment will cause other hormones produced by the pituitary or adrenal gland to become deficient, which may require hormone replacement therapy. In some embodiments, none of these currently available treatment options are appropriate or effective, surgical removal of the adrenal glands (bilateral adrenalectomy) may be considered, which will require lifelong replacement medications. Patients who are candidates for such option may benefit from a myostatin inhibition therapy described herein, before and/or after adrenalectomy.

In yet another aspect, the methods of the present invention are suitable for treating or preventing metabolic diseases such as cardiovascular disease. The term "cardiovascular disease" refers to any disease of the heart or blood vessels. Cardiovascular or heart disease includes but is not limited to, for example, angina, arrhythmia, coronary artery disease (CAD), coronary heart disease, cardiomyopathy (including dilated cardiomyopathy, restrictive cardiomyopathy, arrhythmogenic right ventricular cardiomyopathy, and diabetic cardiomyopathy), heart attack (myocardial infarction), heart failure (e.g., CHF), hypertrophic cardiomyopathy, mitral regurgitation, mitral valve prolapse, pulmonary stenosis, etc. Blood vessel disease includes but is not limited to, for example, peripheral vascular disease, artery disease, carotid artery disease, deep vein thrombosis, venous diseases, and atherosclerosis. In some embodiments, a subject having heart failure is resistant to diuretic therapy. In another embodiment, a subject having heart failure responds poorly to diuretic therapy.

Another aspect of the disclosure includes a method of treating a subject having a metabolic disease or condition related to aging. Exemplary diseases and conditions related to ageing include, without limitation, sarcopenia (age-related muscle loss), frailty, and androgen deficiency.

Another aspect of the disclosure includes a method of treating a subject having a metabolic disease or condition related to disuse or genetic atrophy/trauma, e.g., atrophy caused by disuse, atrophy caused by genetic mutation(s), atrophy resulting from an injury. Exemplary such diseases and conditions include, without limitation, muscle weakness related to time spent in an intensive care unit (ICU), hip/joint replacement, hip fracture, stroke, bed rest, SCI, rotator cuff injury, knee replacement, bone fracture, and burns.

The present disclosure includes beneficial effects of myostatin inhibition on bone homeostasis. In the musculoskeletal system (defined as the bones of the skeleton, muscles, cartilage, tendons, ligaments, joints, and other connective tissue that supports and binds tissues and organs together), the homeostasis of muscle and bone is intimately connected. Bone grows in response to muscle growth is a mechanosensitive process that is regulated by endocrine signaling.

Like muscle, bone homeostasis involves a dynamic processes of balancing bone growth (bone formation) and bone loss (bone resorption). Parameters that may be used to assess bone homeostasis include but are not limited to: bone mass, volume, density, cross section area, strength, frequency of fractures, rate of bone repair, etc. Factors (e.g., cytokines, hormones) that are known to play a role in this process include, but are not limited to: parathyroid hormone, 1,25-dihydroxyvitamin D3, T4, corticosteroids, prostaglandins such as prostaglandin E2, Interleukin-4, Interleukin-18, Interferon-γ, Interleukin-17, Interleukin-6, Interleukin-1, RANKL, CSFs, TGFβ, osteoprotegerin, BMPs, IGFs and FGFs. Osteoclasts and osteoblasts contribute to bone resorption and growth, respectively.

From a structural point of view, bone strength is determined by combination of trabecular and cortical bone architecture and composition. Generally, decreased bone strength is observed with age, e.g., osteopenia and osteoporosis. In some circumstances, bone loss is due to other factors, such as medication. For example, glucocorticoid treatment may cause bone loss. Medical conditions that may be associated with bone loss include, without limitation, cancer and muscle/metabolic disorders with comorbid bone loss. In some embodiments, such conditions are associated with spinal cord injury (SCI), muscular dystrophy such as DMD, obesity, and/or Cushing disease.

Bone loss can be measured using assays well known to one of ordinary skill in the art (sec Shanmugarajan et al., *J. Pathol.*, 2009: 219(1):52-60 and Wasserman et al., *Neuromuscular Disorders*, 2017, 27(4):331-337). For example, bone mineral density, e.g., areal bone mineral density, can be measured using a DXA scan of the lumbar spine, whole body, and lateral distal femur in accordance with ISCD recommendations (Wasserman et al., *Neuromuscular Disorders*, 2017, 27(4):331-337). After scanning, bone mineral density can be calculated using reference data from Henderson et al., *Am. J. Roentgenol*, 2002, 178:439-443; Kalkwarf et al., *J. Bone Miner. Res.*, 2013, 28:206-212; Kelly et al., *J. Pediatr. Hematol. Oncol.*, 2005, 27:248-253; and Zemel et al., *J. Clin. Endocrinol. Metab.*, 2011, 96:3160-3169. Fracture history of patients can also be collected, including age at fracture, number of fractures, and location of fractures. Osteoporosis is typically measured using the 2013 ISCD criteria, which includes vertebral compression fractures in the absence of high energy trauma or infiltrative disease; or a BMD Z-score of ≤2.0 SD, and two or more long bone fractures by 10 years of age, or three or more long bone fractures by 19 years of age (see, e.g., Bishop et al., *J. Clin. Densitom*, 2014, 17:275-280).

Several therapeutics are currently available for the treatment of bone loss. Agents used to slow the rate of bone loss include Bisphosphenates and Denosumab. Bisphosphenates block osteoclast recruitment and induce osteoclast apoptosis. These are often used in treatment of post-menopausal and glucocorticoid induced osteoporosis, Paget's disease, and malignant hypercalcemia. Denosumab, developed by Amgen, is a monoclonal antibody that blocks RANKL (osteoclast development). It is used to treat osteoporosis, metastases to bone, other bone tumors.

Agents used to grow new bone include Teriparatide and Romosozumab. Forteo is a Teriparatide marketed by Eli Lilly, which is a recombinant protein fragment comprising the first 34 amino acid residues of parathyroid hormone. It is typically used to treat osteoporosis, and patients who are at high risk for bone fracture, as well as patients who are intolerant to other therapies. Romosozumab, available from Amgen, is a monoclonal antibody that blocks sclerostin (a Wnt pathway antagonist). To date, there is no drug that can increase both bone and muscle.

Several groups are carrying out preclinical and clinical studies with agents that at least in part affect the myostatin pathway. For example, Acceleron has developed ActRIIA and ActRIIB ligand trap agents (e.g., ACE-011, ACE-536, ACE-031 and ACE-2494), at least some of which are said to increase bone mass when administered in vivo. None of these agents appears to be specific to myostatin/GDF8 but also affects one or more of the other pathways. Eli Lilly's monoclonal antibody LY2495655 (Landogrozumab) did not increase bone mass in humans undergoing elective hip replacement, as measured by dexa. This antibody binds both GDF8 and GDF11.

Unlike these agents that affect myostatin as well as additional pathway(s), monoclonal antibodies encompassed by the present disclosure specifically bind and inhibit the activation step of myostatin/GDF8. In some embodiments, such antibodies bind proMyostatin and/or latent myostatin, thereby inhibiting activation and subsequent release of mature myostatin, but do not bind mature myostatin that is not associated with a latent (inactive) complex. In some embodiments, the antibodies or fragments thereof bind tethered forms (e.g., intramuscular) of inactive myostatin (e.g., pro-myostatin), which have the ability to locally act upon tissue-associated myostatin within a disease niche. In some embodiments, the antibodies or fragments thereof bind soluble forms (e.g., in circulation) of inactive myostatin (e.g., latent-myostatin), which have the ability to act upon circulating latent myostatin that may have endocrine or systemic effects. In any of such embodiments, preferred inhibitors of myostatin for carrying out the methods of the present invention are those that are selective for myostatin that do not antagonize other members of the TGFβ superfamily of growth factors/cytokins, such as GDF11. Such selectivity is advantageous particularly in pediatric patient populations and/or patient populations requiring a long-term care (e.g., chronic therapy), where inhibiting other pathways, such as GDF11, may produce harmful or unwanted side effects or adverse events. The inventors of the present disclosure have shown that such antibodies can effectively inhibit myostatin activation and cause beneficial muscle effects and metabolic effects. Furthermore, evidence provided herein shows that such antibodies can also cause beneficial biological effects on bone homeostasis in viva (see FIGS. 28-31).

Accordingly, the present invention includes the use of an inhibitor of myostatin activation for enhancing one or more parameters of bone homeostasis, including: relative bone volume (e.g., as measured by bone volume over total volume of the corresponding tissue or sample); trabecular bone volume, trabecular number; trabecular thickness; trabecular spacing/separation; bone cross section (e.g., as measured by cortical cross sectional area); cortical bone area; cortical endosteal perimeter; cortical periosteal perimeter; cortical porosity; and cortical cross section thickness. In some embodiments, the inhibitor of myostatin activation described herein can produce a clinically meaningful bone effects. In some embodiments, administration of the inhibitor causes at least a 10% increase in one or more of the parameters listed above, e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, and at least 25%.

The present invention also includes the use of an inhibitor of myostatin activation for increasing one or more of these parameters in weight-hearing hone or in non-weight hearing hone. As discussed in more detail in the Examples, weight-bearing activity is an important stimulus for bone mass accrual. Surprisingly, a myostatin inhibitor may be used to not only enhance bone parameters in weight-bearing bone, but may also be used to enhance these parameters in non-weight bearing bone. Clearly, weight-bearing and non-weight-bearing bones differ among species. In rodents, for example, non-weight-bearing bone includes the vertebrae. An increase in non-weight bearing bone parameters further demonstrates that myostatin inhibitors disclosed herein not only act to increase bone through, for example, increased muscle stimulation, but also act as a key regulator to increase the general metabolism and bone health of the treated animals.

Thus, preferred inhibitors of myostatin activation described herein are characterized by two or more of the following attributes: a) the ability to enhance muscle mass, b) the ability to prevent muscle loss, c) the ability to enhance motor function, d) the ability to prevent or ameliorate metabolic dysregulation, e) the ability to enhance bone mass, f) the ability to reduce bone loss, g) the ability to increase bone mineral density; without directly inhibiting any other members of the TGFβ super family of growth factors, such as GDF11 and Activin.

Accordingly, such an inhibitor can be used in human patients for: i) the prevention of bone fracture (e.g., reducing the frequency of such incidents and/or severity or degree of fracture); ii) the treatment of bone fractures (e.g., to facilitate bone healing, growth or regeneration); and enhancement of bone strength (to strengthen weakened bones, such as age-related, injury-associated or disease-associated). In some embodiments, such use can be combined with additional agent(s) intended to enhance bone (bone-enhancing or bone-protective agents), such TGFβ antagonists (preferably TGFβ1 inhibitors), bisphosphonates, calcium, vitamin D, RANKL inhibitors, etc.

In some embodiments, suitable patient populations include those with Cushing's syndrome.

B. Diseases Associated with Impaired Neurological Signaling

The present disclosure is based, at least in part, on the surprising discovery that inhibition of myostatin signaling may be particularly useful for the intervention of conditions involving defects in communication between muscle and its innervating neurons. The findings point to a close coordination/relationship between the musculoskeletal system and the nervous system. Needless to say, the spinal cord houses major nerves that control motor function. Thus, the disclosure provides methods for treating or preventing diseases associated with impaired neurological signaling between a neuron and a target tissue that expresses myostatin in subjects, e.g., human subjects. A disorder may be, for example, injury-based (e.g., a spinal cord injury) or genetic (e.g., resulting from a genetic mutation, e.g., SMA).

In some embodiments, the methods include administering to a subject suffering from a disease associated with an impaired neurological signaling between a neuron and a target tissue an effective amount of a myostatin inhibitor, e.g., an antibody, or antigen binding fragment thereof, that specifically hinds myostatin and inhibits myostatin signaling, thereby treating or preventing the disease associated with the impaired neurological signaling in the subject. Preferably, the antibody, or antigen binding fragment thereof, specifically binds to pro/latent myostatin, but does not bind to mature GDF11. In some embodiments, such antibody or fragment does not bind mature myostatin/GDF8.

As used herein, term "disease with an impaired neurological signaling" refers to any disease or disorder that is caused by, or associated with, a disrupted signal transduction or a breakdown in communication between a neuron and its target tissue(s), e.g., a muscle tissue, a brain tissue, a liver tissue, a blood vessel tissue, or an adipose tissue. In some embodiments, the impaired neurological signaling occurs due to a damage in the neuron structure, where neurons are incapable of transmitting signals towards their targets. In other embodiments, the structures of neurons remain intact, but there are functional disruption or defects, for example, a blockage at the neuromuscular junction, such that the ability of neurons to transmit signals is affected.

In some embodiments, "disease with an impaired neurological signaling" refers to disease or condition associated with denervation, e.g., a partial loss or perturbation of nerve supply or neuronal input to its target, such as muscle. In some embodiments, denervation is induced by injury. In some embodiments, denervation is associated with a disease, such as a genetic disease. In cases of genetic diseases, in some embodiments, the patient may be diagnosed with the genetic disease by genetic screening. In some embodiments, such genetic screening may be performed in a fetal, neonatal or pediatric subject. Non-limiting examples of diseases with an impaired neurological signaling include, for example, vocal cord paresis/paralysis, spinal cord injury (SCI), myasthelia gravis, amyotrophic lateral sclerosis (ALS), and spinal muscular atrophy (SMA).

Spinal Cord Injury

The methods of the present invention are also suitable for treating or preventing conditions with an impaired neurological signaling due to nerve injury. In some embodiments, such condition is spinal cord injury (SCI). As used herein, the term "spinal cord injury" refers to damages to any part of the spinal cord or nerves at the end of the spinal canal. Spinal cord injury often causes permanent changes in strength, sensation and other body functions below the site of the injury. Each year, it is estimated that there are 12,500 new cases of spinal cord injury (US). Prevalence is 275,000 cases in the US and roughly 60% have paraplegia. There are no therapies in development directed at reversing or reducing muscle atrophy in SCI and this represents a large unmet need. While there is significant patient heterogeneity based on time since injury, level and completeness of injury, and extent of disability, physical rehabilitation to improve muscle function and metabolic outcomes is standard of care.

SCI patients are stratified based on the level (paraplegia vs. tetraplegia) and the completeness of the lesion (complete vs incomplete). This stratification has been developed into the ASIA scale, with two broad groups based on level of paralysis: complete (AIS grades A/B) and incomplete (AIS grades C/D/E), defined below:
 A: Complete motor and sensory loss
 B: Motor loss with retained sensory perception (still can feel touch, pressure)
 C and D: Incomplete motor loss
 E: Most function is regained: this represents a low proportion of the population.

There are 7 cervical (neck), 12 thoracic (chest), 5 lumbar (back), and 5 sacral (tail) vertebrae. A lesion in SCI may occur at any location along the vertebrae. The key muscles that need to be tested to establish neurologic level are as follows:
 C5: Elbow flexors (biceps, brachialis)
 C6: Wrist extensors (extensor carpi radialis longus and brevis)
 C7: Elbow extensors (triceps)
 C8: Long finger flexors (flexor digitorum profundus)
 T1: Small finger abductors (abductor digiti minimi)
 L2: Hip flexors (iliopsoas)
 L3: Knee extensors (quadriceps)
 L4: Ankle dorsiflexors (tibialis anterior)
 L5: Long toe extensors (extensor hallucis longus)
 S1: Ankle plantar flexors (gastrocnemius, soleus)

With a complete spinal cord injury, the cord can't send signals below the level of the injury. As a result, patients are paralyzed below the injury. With an incomplete injury, patients will have some movement and sensation below the injury.

There are multiple phases associated with spinal cord injury. Subjects may be in an acute spinal cord injury phase immediately after injury, where diagnosis between complete and incomplete injury is generally difficult, due in part to the trauma and associated inflammation. Typically, the acute phase is defined as the initial in-hospital period following the event/injury in acute medical/surgical care, which is generally around ~2 weeks. A subject may be in a sub-acute spinal cord injury phase, where there is a distinction between complete and incomplete spinal cord injury, and recovery is possible through ongoing rehab. Typically the sub-acute phase constitutes ~2 weeks up to ~18 months post injury (e.g., 3-6 months post-injury). Yet further, a subject may be in a chronic spinal cord injury phase which generally starts around 6-12 months after the time of injury, where patients have demonstrated substantial decrease in rate of recovery or when rehab efforts have reached a stable phase (e.g., plateau) despite the ongoing standard of care efforts.

Muscle strength always should be graded according to the maximum strength attained, no matter how briefly that strength is maintained during the examination. The muscles are tested with the patient supine. Motor level is determined by the most caudal key muscles that have muscle strength of 3 or above while the segment above is normal (=5).

Motor index scoring uses the 0-5 scoring of each key muscle, with total points being 25 per extremity and with the total possible score being 100.

Lower extremities motor score (LEMS) uses the ASIA key muscles in both lower extremities, with a total possible score of 50 (i.e., maximum score of 5 for each key muscle [L2, L3, L4, L5, and S1] per extremity). A LEMS of 20 or less indicates that the patient is likely to be a limited ambulator. A LEMS of 30 or more suggests that the individual is likely to be a community ambulator.

ASIA recommends use of the following scale of findings for the assessment of motor strength in spinal cord injury:
 0: No contraction or movement
 1: Minimal movement
 2: Active movement, but not against gravity
 3: Active movement against gravity
 4: Active movement against resistance
 5: Active movement against full resistance Monitoring functional outcomes and quality of life in SCI patients is a complex task as selection of the appropriate functional measure depends upon the completeness and level of injury. One common measure which is applicable to all patients is the functional independence measure (FIM) which is a 7-point scale designed to quantify the dependence of a patient on a caregiver. An additional metric for measuring quality of life which has had recent attention is the SCI-QOL, which integrates both functional skills and emotional health of the patient (Tulsky 2015, *J Spinal Cord Med.* 38(3): 257-69). Many other functional outcome measures have been outlined by the SCIRE project.

In some embodiments, meaningful clinical effects achieved by administration of an effective amount of the myostatin inhibitor described herein to SCI patients may correspond to at least a 6 point (≥6) increase from baseline in total motor score of ASIA at, e.g., week 24. In some embodiments, meaningful clinical effects achieved by administration of an effective amount of the myostatin inhibitor described herein to SCI patients may correspond to statistically significant difference in the meantotal SCIM III score between treated and untreated/control groups at Day 112 (+/−7 days). In some embodiments, meaningful clinical effects achieved by administration of an effective amount of the myostatin inhibitor described herein to SCI patients may correspond to greater than a 4 point (>4) increase in Functional Independence Measure for Locomotion (FIM-L) score.

Individuals with spinal cord injury have an increased prevalence of abnormalities in carbohydrate and lipid metabolism associated with immobilization, muscle atrophy, and increased adiposity. The body composition is substantially altered and typified by rapid and long-term decline in metabolically active muscle mass and bone with stark increases in central adiposity. The latter contributes to a maladaptive metabolic profile favoring substantial gain in body mass occurring 2-7 months following injury. Occurring together these co-morbid risk factors incite all-cause cardiovascular disease, diabetes, and risk clustering as cardiometabolic disease, the latter including component hazards for dyslipidemia, glucose intolerance and insulin resistance.

Rapid and profound muscle wasting affects those with a spinal cord injury and impacts the entire body, not just the denervated limbs. Muscle loss is believed to be due to a combination of factors including denervation (of the paretic limbs), immobilization, inflammation, factors released by the paralyzed muscle, steroid use, infections, and lack of nutrition. A large percentage (~30%) of lean muscle mass is lost in the first six weeks following injury (the acute phase). This accelerated rate of lean mass loss continues on into chronic conditions with a decrease in lean mass (per decade) of 3% for tetraplegia and 2.4% for paraplegia (as compared to a decline of 1% seen in healthy controls) (Spungen 2003). This accelerated muscle atrophy contributes to premature sarcopenia.

An SCI patient experiences profound changes in total body composition. In particular, lean muscle mass is replaced with fat mass, on average an SCI patient has 13% more fat tissue per unit BMI than a healthy control, with a significant increase in intramuscular fat (Spungen 2003, Gorgey 2007). This whole-body change in composition (~60-70% are obese) has profound impacts on metabolism which is evidenced by increased prevalence of cardiovascular disease, type II diabetes, and thyroid disorders.

Mechanical unloading following spinal cord injury also translates into disruptions in bone homeostasis. SCI patients have reduced bone mineral content, develop osteoporosis, and suffer from increased rates of fractures (as many as 50% of SCI patients will experience a fracture post injury) (Battaglino 2013). A fracture leads to hospitalization and can have profound consequences by increasing the risk for developing pressure ulcers, contractures of the knee and hip, and for experiencing a hypertensive crisis.

Overall increases in lean mass and decrease in fat mass in SCI patients can be monitored by several well-validated methods, such as thigh or upper arm muscle volume by magnetic resonance imaging, or total body composition by dual-energy x-ray absorptiometry or DEXA. Such measurements are routinely performed in the field.

Outcome or progress of therapy (e.g., overall clinical effects) may be measured by using any of well-characterized tests commonly employed for evaluating SCI clinical practice. These tests are useful for i) providing information on each measure's clinical utility and psychometric properties; ii) assisting clinicians to select appropriate measures tailored to particular patient(s); iii) identifying individuals who may benefit from a certain therapy; iv) monitoring progress; v) evaluating whether treatments are effective; and/or, vi) help programs improve services to patients and medical professionals. Suitable clinical evaluation tools/tests available for patients include, but are not limited to the following:

For evaluating Assistive Technology, useful tests include: Assistive Technology Device Predisposition Assessment (ATD-PA); Quebec User Evaluation of Satisfaction with Assistive Technology (QUEST 2.0); and Wingate Anaerobic Testing (WAnT).

For evaluating Community Reintegration, useful tests include: Assessment of Life Habits Scale (LIFE-H); Community Integration Questionnaire (CIQ); Craig Handicap Assessment & Reporting Technique (CHART); Impact on Participation and Autonomy Questionnaire (IPAQ); Physical Activity Recall Assessment for People with Spinal Cord injury (PARA-SCI); Physical Activity Scale for Individuals with Physical Disabilities (PASIPD); and Reintegration to Normal Living (RNL) Index.

For evaluating Lower Limb & Walking, useful tests include: 10 Meter Walking Test (10 MWT); 6-Minute Walk Test (6MWT); Berg Balance Scale (BBS); Clinical Outcome Variables Scale (COVS); Functional Standing Test (FST); Spinal Cord Injury Functional Ambulation Inventory (SCI-FAI); Timed Up and Go Test (TUG); and Walking Index for Spinal Cord Injury (WISCI) and WISCI II.

For evaluating Mental Health, useful tests include: Beck Depression Inventory (BDI); Brief Symptom Inventory (BSI); CAGE Questionnaire; Center for Epidemiological Studies Depression Scale (CES-D and CES-D-10); Depression Anxiety Stress Scale-21 (DASS-21); Fatigue Severity Scale (FSS); Hospital Anxiety and Depression Scale (HADS); Patient Health Questionnaire-9 (PHQ-9); Scaled General Health Questionnaire-28 (GHQ-28); Symptom Checklist-90-Revised (SCL-90-R); and Zung Self-Rating Depression Scale (SDS).

For evaluating Neurological Impairment and Autonomic Dysfunction, useful tests include: American Spinal Injury Association Impairment Scale (AIS): International Standards for Neurological Classification of Spinal Cord Injury; and Surface Electromyography (sEMG).

Other useful evaluation systems for Affected Physiological Systems include: Exercise Self-Efficacy Scale (ESES); Moorong Self-Efficacy Scale (MSES); Spinal Cord Injury Secondary Conditions Scale (SCI-SCS); Spinal Cord Lesion Coping Strategies Questionnaire (SCL CSQ); Spinal Cord Lesion Emotional Wellbeing Questionnaire (SCL EWQ); and Wingate Anaerobic Testing (WAnT).

For assessing Pain, useful tests include: Brief Pain Inventory (BPI); Classification System for Chronic Pain in SCI; Donovan SCI Pain Classification System; Multidimensional Pain Inventory (MPI)—SCI version; Multidimensional Pain Readiness to Change Questionnaire (MPRCQ2); Quantitative Sensory Testing (QST); Tunk's Classification Scheme; and Wheelchair Users Shoulder Pain Index (WUSPI).

For evaluating Quality of Life and Health Status, useful tests include: Incontinence Quality of Life Questionnaire (I-QOL); Life Satisfaction Questionnaire (LISAT-9, LISAT-11); Quality of Life Index (QLI)—SCI Version; Quality of Life Profile for Adults with Physical Disabilities (QOLP-PD); Quality of Well Being (QWB) and Quality of Well Being-Self-Administered (QWB-SA); Qualiveen; Satisfaction with Life Scale (SWLS, Deiner Scale); Short Form 36 (SF-36); Sickness Impact Profile 68 (SIP 68); and World Health Organization Quality of Life-BREF (WHOQOL-BREF).

For evaluating Self Care & Daily Living, useful tests include: Appraisals of DisAbility: Primary and Secondary Scale (ADAPSS); Barthel Index (BT); Frenchay Activities Index (FAT); Functional Independence Measure (FIM); Functional Independence Measure Self-Report (FIM-SR); Klein-Bell Activities of Daily Living Scale (K-B Scale); Lawton Instrumental Activities of Daily Living scale (IADL); Quadriplegia Index of Function (QIF); Quadriplegia Index of Function Modified (QIF-Modified); Quadriplegia Index of Function-Short Form (QIF-SF); Rivermead Mobility Index (RMI); Self Care Assessment Tool (SCAT); Self Reported Functional Measure (SRFM); Spinal Cord Independence Measure (SCIM); and Spinal Cord Injury Lifestyle Scale (SCILS).

For Sexuality and Reproduction, useful tests include: Emotional Quality of the Relationship Scale (EQR); Knowledge, Comfort, Approach and Attitude towards Sexuality Scale (KCAASS); Sexual Attitude and Information Questionnaire (SAIQ); Sexual Behaviour Scale (SBS); Sexual Interest and Satisfaction Scale (SIS); Sexual Interest, Activity an; and Satisfaction (SIAS)/Sexual Activity and Satisfaction (SAS) Scales.

For evaluating Skin Health, useful tests include: Abruzzese Scale; Braden Scale; Gosnell Measure; Norton Measure; Skin Management Needs Assessment Checklist (SMNAC); Spinal Cord Injury Pressure Ulcer Scale-Acute (SCIPUS-A); Spinal Cord Injury Pressure Ulcer Scale (SCIPUS) Measure; Stirling's Pressure Ulcer Severity Scale; and. Waterlow Scale.

For evaluating Spasticity, useful tests include: Ashworth and Modified Ashworth Scale (MAS); Pendulum Test (Wartenberg); Penn Spasm Frequency Scale (PSFS); Spinal Cord Assessment Tool for Spastic Reflexes (SCATS); Spinal Cord Injury Spasticit; and Evaluation Tool (SCI-SET).

For evaluating Upper Limb Functionality, useful tests include: Box and Block Test (BBT); Capabilities of Upper Extremity Instrument (CUE); Graded Redefined Assessment of Strength, Sensibility and Prehension (GRASSY); Grasp and Release Test (GRT); Hand-Held Myometer; Jebsen Hand Function Test (JHFT); Modified Functional Reach Test (mFRT); Six-Minute Arm Test (6-MAT); Sollerman Hand Function Test; Tetraplegia Hand Activity Questionnaire (THAQ); and Van Licshout Test Short Version (VLT-SV).

And, for evaluating Wheeled Mobility, useful tests include: 4 Functional Tests for Persons who Self-Propel a Manual Wheelchair (4FTPSMW); Timed Motor Test (TMT); Tool for assessing mobility in wheelchair-dependent paraplegics; Wheelchair Circuit (WC); and Wheelchair Skills Test (WST).

Based on the effects of myostatin on muscle mass and metabolism, a myostatin inhibitor, e.g., an anti-myostatin antibody or antigen-binding portion thereof, can potentiate a number of long-term health consequences (which may be measured by one or more standardized tests/tools such as those listed above) which affect those living with SCI, and would cause clinically meaningful benefits to patients at the time of injury and/or in chronic conditions. Indeed, the present inventors surprisingly discovered that specific inhibition of myostatin activation by a myostatin inhibitor, e.g., an anti-pro/latent myostatin antibody had a positive impact on muscle function in the subjects, including in muscles below the injury or lesion. Specifically, administration of the myostatin inhibitor, e.g., anti-pro/latent myostatin antibody, to a partial denervation animal model not only prevented muscle atrophy and increased muscle mass in the injured subjects, but also enhanced the function of the injured muscle, as well as prevented metabolic dysregulation associated with neuron injuries and, thus, improving the overall metabolic health of the subjects which may provide significant long term benefits.

Whilst myostatin inhibition is effective in treating muscle atrophy and metabolic dysfunction caused by partial/incomplete SCI (such as severe contusion SCI) as described above, where the function of innervating motor neurons is at least partially intact, the inventors of the present disclosure further contemplate the use of a myostatin inhibitor, such as those described herein, in the treatment of complete SCI (e.g., complete transection), used in conjunction with a nerve stimulator.

Previously published work indicated that myostatin inhibition was ineffective in ameliorating complete transection injuries of the spinal cord or sciatic nerve. For example, it has been reported that prophylactic administration of a soluble ActRIIB ligand trap showed no therapeutic effect on muscle atrophy or bone loss in sublesional hind limbs in a complete transection model of SCI in mice (Graham 2015). The same study still showed increased mass of supralesional muscle, suggesting that myostatin inhibition is ineffective in the context of denervated muscle. In support of this, a separate study showed that prophylactic administration of soluble ActRIIB ligand trap failed to prevent muscle atrophy following complete transection of the sciatic nerve (MacDonald 2014).

Nevertheless, based on Applicant's previous recognition that effectiveness of myostatin inhibition at least in part depends on neuronal signaling from the innervating motor neurons (see, for example, PCT/US2017/037332), it is contemplated that myostatin inhibitor therapy, in conjunction with neuronal stimulation, may enhance therapeutic effects in complete SCI. Studies in rats and human patients with complete transection SCI suggest that a therapeutic neuronal stimulation regimen may protect against sublesional muscle atrophy, the conversion from slow twitch to fast fatigable muscle, and bone loss, while increasing muscle strength and decreasing blood glucose and insulin compared to control (Wu 2013; Adams 2011; Shields 2006; Griffin 2007). Thus, contrary to the general consensus in the art that myostatin inhibition appears ineffective in treating complete transection nerve injuries, it is contemplated herein to use a myostatin inhibitor, preferably an inhibitor of myostatin activation, in the treatment of patients inflicted with complete SCI to enhance clinical benefits of nerve stimulation.

In some embodiments, suitable neuronal stimulation comprises electrical stimulation, such as functional electrical stimulation or neuromuscular electrical stimulation. In some embodiments, one or more agents that simulate nerve stimulation or effects thereof in vivo may be employed. In some embodiments, such agents cause depolarization at the neuromuscular junction, such as voltage-sensitive sodium channel agonists. In some embodiments, such agents cause elevated calcium concentrations in the target muscle to mimic membrane potentiation. In some embodiments, such agents potentiate neurotransmission. In some embodiments, such agents are neurotransmitter agonists, such as acetylcholine or derivative thereof. In some embodiments, such agents activate postsynaptic receptors on the target muscle, e.g., acetylcholine receptors. In some embodiments, such agents induce phosphorylation of postsynaptic component(s) so as to mimic neurotransmission at the neuromuscular junction. In some embodiments, such agents regulate ECM assembly that promote postsynaptic function. For example, the agents may facilitate interactions of extracellular components such as synaptic integrins, laminins, collagens, as well as their receptors on the target muscle, such as agrin and MuSK.

Such combination therapy may be effective to prevent or ameliorate muscle atrophy, bone loss, and/or metabolic dysregulation, in patients suffering from severe SCI, such as injuries involving complete or almost complete transection SCI.

Spinal Muscular Atrophy (SMA)

Myostatin inhibition has been shown to be an effective approach to enhance motor function in SMA, which is a genetic disease associated with impaired neuromuscular signaling due to mutations in the Smn1 gene. This concept is captured in more detail in, for example, PCT/US2017/037332 and PCT/US2017/012606. The present disclosure expands this notion and encompasses the recognition that clinical benefits of myostatin inhibition in SMA may further include prevention or amelioration of bone loss or fracture. In some embodiments, subjects with SMA who receives myostatin inhibitor therapy, such as those described herein, may show beneficial clinical effects, as measured by one or more parameters, which include but are not limited to: cross-sectional bone area, cortical thickness, trabecular thickness, trabecular number, and trabecular separation.

Whether or not inhibition of myostatin provides a direct benefit to bone, as opposed to indirect, muscle-driven effects, has been unclear. Data presented herein supports the idea that myostatin inhibition can surprisingly exert beneficial effects even on non-weight-bearing bone, suggesting that myostatin inhibitors such as those described herein may at least in part directly target the bone, in addition to muscle-mediated effects. Thus, the present invention includes the use of myostatin inhibitors in the treatment of SMA in an amount effective to protect against (e.g., prevent or retard) bone loss, and/or reduce the frequency and/or degree of bone fracture in these patients. In some embodiments, SMA patients include those on neuronal corrector therapy. In some embodiments, SMA patients have not received or are not candidates for a neuronal corrector therapy. In some embodiments, the SMA patients who are not candidates for a neuronal corrector therapy have undergone a spinal fusion procedure. In some embodiments, SMA patients have ambulatory SMA (such as Type III). In some embodiments, SMA patients are non-ambulatory (such as Type I and severe forms of Type II).

C. Other Diseases and Disorders

Another aspect of the disclosure includes a method of treating a subject having a disease or condition related to Cachexia. Exemplary diseases and conditions related to cachexia include, without limitation, cancer, chronic heart failure (CHF), acquired immune deficiency syndrome (AIDS), chronic obstructive pulmonary disease (COPD), and chronic kidney disease (CKD).

A significant fraction of cancer patients suffers from cachexia and/or bone loss/frequent bone fractures. Myostatin inhibitors such as those described herein may provide clinically beneficial effects in cancer patients to not only prevent muscle loss but also prevent bone loss and reduce the frequency and/or severity of bone fractures.

In some embodiments, any metabolic bone diseases or diseases associated with bone loss (such as cancer) may be treated with a combination of a myostatin inhibitor and at least one other therapy, such as TGFβ inhibitor (preferably a TGFβ1 inhibitor) and/or other bone-protective agents, e.g., bisphosphonates, calcium, vitamin D, RANKL inhibitors, etc.

Another aspect of the disclosure includes a method of treating a subject having a disease or condition related to rare diseases. Exemplary rare diseases and conditions include, without limitation, osteogenesis imperfecta, sporadic inclusion body myositis, and acute lymphoblastic leukemia.

D. Weight Loss

The present invention further provides methods for promoting robust weight loss in both healthy subjects, e.g., bodybuilders, or in subjects having metabolic diseases, such as obesity, e.g., diet-induced obesity, metabolic syndrome, NASH/NAFLD, and/or diabetes. As compared to dieting alone (e.g., dieting by caloric restriction, low-carbohydrate diet, ketogenic diet, vegan diet, etc.), where weight loss occurs in both fat stores and muscle during dieting, administration of a myostatin inhibitor disclosed herein in combination with a diet leads to weight loss in fat stores, while sparing the muscle. Specifically, administration of a myostatin inhibitor in combination with a diet results in more robust weight loss due to the maintenance of a higher metabolic rate; improved cardiometabolic benefits (such as lipid profile, glucose metabolism, cardiovascular risk, etc.); and higher reduction in visceral fat and other deleterious fat levels as compared to dieting, alone. Additionally, administration of a myostatin inhibitor prevents or reduces muscle atrophy and/or bone loss which can occur concomitantly with a diet, e.g., a caloric restriction diet, a low-carbohydrate diet, a ketogenic diet, etc. Overall, administration of a myostatin inhibitor, e.g., an antibody or antigen-binding portion thereof, in combination with a diet increases the ratio of muscle to fat in the subject.

In subjects with metabolic diseases, e.g., obesity, metabolic syndrome, NASH/NAFLD, and/or diabetes, the combination of a myostatin inhibitor with a moderate diet enables the same metabolic benefits as a more aggressive diet, alone. A more moderate diet, e.g., caloric restriction diet, provides for better patient compliance and better long-term outcomes since subjects do not have to adhere to austere, aggressive diets, e.g., aggressive caloric restriction diets.

Such treatments are particularly useful for subjects who have limitations on physical activity, e.g., subjects having an orthopedic injury, spinal cord injury, musculoskeletal disease, a pulmonary disorder, a cardiac disorder, a neurologic disorder, severe obesity, etc. In such subjects, administration of a myostatin inhibitor in combination with a diet, e.g., a caloric restriction diet, prevents muscle atrophy and/or bone loss which are more prominent in these subjects due to their limitations on physical activity. In some embodiments, such a treatment enables subjects with limitations on physical activity to undergo a more robust diet, e.g., caloric restriction diet, because they are no longer limited by concerns regarding muscle loss or bone loss due to the administration of the myostatin inhibitor.

In some embodiments, the subject is on a diet, e.g., a caloric restriction regimen, but is not on an exercise regimen. In some embodiments, the subject is on a diet, e.g., a caloric restriction regimen, and an exercise regimen.

Kits

The present disclosure also provides kits for use in alleviating diseases/disorders associated with myopathy. Such kits can include one or more containers comprising a myostatin inhibitor, e.g., an anti-pro/latent-myostatin antibody, or antigen binding fragment thereof, e.g., any of those described herein.

In some embodiments, the kit can comprise instructions for use in accordance with any of the methods described herein. The included instructions can comprise a description of administration of the myostatin inhibitor, e.g., anti-pro/latent-myostatin antibody, or antigen binding fragment thereof, to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of a myostatin inhibitor, e.g., an anti-pro/latent-myostatin antibody, or antigen binding fragment thereof, generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with myopathy. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-pro/latent-myostatin antibody, or antigen binding fragment thereof, as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Assays for Detecting Pro/Latent-Myostatin

In some embodiments, methods and compositions provided herein relate to a method for detecting pro/latent-myostatin in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer. In some embodiments, the subject is a "healthy subject" (e.g., who is not at risk of developing a muscle condition, such as muscle atrophy, but may nevertheless benefit from increased muscle mass and/or function). In some embodiments, the subject has or at risk of developing muscle atrophy or weakness. In some embodiments, the subject has or at risk of developing muscle atrophy or weakness and will benefit from increased muscle mass and/or function.

In some embodiments, a method for detecting a pro/latent-myostatin in a sample obtained from a subject involves (a) contacting the sample with the anti-pro/latent-myostatin antibody, or antigen binding fragment thereof, under conditions suitable for binding of the antibody to the antigen, if the antigen is present in the sample, thereby forming binding complexes; and (b) determining the level of the antibody or antigen binding fragment bound to the antigen (e.g., determining the level of the binding complexes).

As used herein a binding complex refers to a biomolecular complex of antibody (including antigen binding fragments) bound to antigen (e.g., pro/latent-myostatin protein). Binding complexes may comprise antibodies with a single specificity or two or more antibodies or antigen binding fragments with different specificities. In one embodiment, a binding complex comprises two or more antibodies recognizing different antigenic sites on the same antigen. In some instances, an antibody may be bound to an antigen, having bound to it other biomolecules such as RNA, DNA, polysaccharides or proteins. In one embodiment, a binding complex comprises two or more antibodies recognizing different antigens. In some embodiments, an antibody in a binding complex (e.g., an immobilized antibody bound to antigen), may itself by bound, as an antigen, to an antibody (e.g., a detectably labeled antibody). Thus, binding complexes may, in some instances, comprise multiple antigens and multiple antibodies or antigen binding fragments.

Antigens present in binding complexes may or may not be in their native in situ conformation. In some embodiments, a binding complex is formed between an antibody and a purified protein antigen, or isolated proteins comprising antigen, in which the antigen is not in its native in situ conformation. In some embodiments, a binding complex is formed between an antibody and a purified protein antigen, in which the antigen is not in its native in situ conformation and is immobilized on solid support (e.g., a PVDF membrane). In some embodiments, a binding complex is formed with an antibody and, for example, a cell surface protein that is present in situ in a native confirmation (e.g., on the surface of a cell).

Antibodies in binding complexes may or may not be detectably labeled. In some embodiments, binding complexes comprise detectably labeled antibodies and non-labeled antibodies. In some embodiments, binding complexes comprise detectably labeled antigen. In some embodiments, antibodies, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

In any of the detection, diagnosis, and monitoring methods, the antibody, (including antigen binding fragments) or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G—antibody interactions, and streptavidin-biotin interactions. Other methods of conjugation will be readily apparent to one of ordinary skill in the art.

In some aspects, detection, diagnosis, and monitoring methods include comparing the level of the antibody (including antigen binding fragments) bound to the antigen (e.g., pro/latent-myostatin) to one or more reference standards. The reference standard may be, for example, the level of a corresponding pro/latent-myostatin in a subject that does or does not have a pro/latent-myostatin. In one embodiment, the reference standard is the level of pro/latent-myostatin detected in a sample that does not contain pro/latent-myostatin (e.g., a background level). Alternatively, a background level can be determined from a sample that contains a particular pro/latent-myostatin, by contacting the sample with non-specific antibodies (e.g., antibodies obtained from non-immune serum). Then again, the reference standard may be the level of pro/latent-myostatin detected in a sample that does contain pro/latent-myostatin (e.g., a positive control). In some cases, the reference standard may be a series of levels associated with varying concentrations of pro/latent-myostatin in a sample and useful for quantifying the concentration of pro/latent-myostatin in the test sample. The foregoing examples of reference standards are not limiting and other suitable reference standard will be readily apparent to one of ordinary skill in the art. In some embodiments, the level of the antibody bound to pro/latent-Myostatin is compared to the level of mature myostatin. In some instances, the level of pro/latent myostatin is compared to mature myostatin to determine the ratio of inactive to active myostatin in the sample.

The level of pro/latent-myostatin may be measured, as provided herein, from a biological sample. A biological sample refers to any biological material which may be obtained from a subject or cell. For example, a biological sample may be whole blood, plasma, serum, saliva, cerebrospinal fluid, urine, cells (or cell lysate) or tissue (e.g., normal tissue or tumor tissue). In some embodiments, a biological sample is a fluid sample. In some embodiments, a biological sample is a solid tissue sample. For example, a tissue sample may include, without limitation skeletal muscle, cardiac muscle, adipose tissue as well as tissue from other organs. In some embodiments, a biological sample is a biopsy sample. In some embodiments, a solid tissue sample may be made into a fluid sample using routine methods in the art.

A biological sample may also include one or more cells of a cell line. In some embodiments, a cell line includes human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells.

A further embodiment relates to a method for monitoring a disease, a condition, or any treatment thereof (e.g., myopathy or myopathy treatment) in a subject having, or at risk of having, the disease or condition comprising: (a) obtaining a biological sample from the subject, (b) determining the level of a pro/latent-myostatin in the biological sample using an antibody that detects pro/latent-myostatin, and (c) repeating steps (a) and (b) on one or more occasions. Myostatin has been used as a biomarker for muscle atrophy, however, the currently available commercial methods and reagents (e.g., antibodies used in ELISAs and Western Blots) are either not specific for myostatin, detect only mature myostatin or do not detect myostatin at all. Thus, provided herein are methods and reagents (e.g., antibodies) for detecting pro/latent-myostatin in the context of diseases and/or conditions (e.g., muscle atrophy) for diagnostic purposes. As one example, the level of pro/latent-myostatin may be measured in a subject, or biological sample therefrom, to detect or monitor the progression of a disease or condition. As another example, the level of pro/latent-myostatin may be measured in a subject, or biological sample therefrom, to monitor the response to a treatment for a disease or condition. It should be appreciated that the level of pro/latent-myostatin may be monitored over any suitable period of time, which may differ depending on the disease or condition, the subject has or any treatment regimen that the subject may be subject to.

Another embodiment relates to a diagnostic composition comprising any one of the above described antibodies, antigen binding fragments, polynucleotides, vectors or cells and optionally suitable means for detection. The antibodies are, for example, suited for use in immunoassays in which they can be utilized in liquid phase or bound to a solid phase carrier. Examples of immunoassays which can utilize the antibody are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies (including antigen binding fragments) provided herein may also be used in a method for evaluating pro/latent-myostatin expression in a subject by obtaining a biological sample from the subject which may be a tissue sample, a blood sample or any other appropriate body fluid sample. The procedure may comprise contacting the blood sample (whole blood, serum, plasma), a tissue sample, or protein sample isolated therefrom, with an antibody, under conditions enabling the formation of binding complexes between antibody and antigen. The level of such binding complexes may then be determined by any suitable method. In some embodiments, the biological sample is contacted with the antibody under conditions suitable for binding of the antibody to a pro/latent-myostatin protein, if the antigen is present in the sample, and formation of binding complexes consisting of antibody, bound to the antigen. This contacting step is typically performed in a reaction chamber, such as a tube, plate well, membrane bath, cell culture dish, microscope slide, and the like. In some embodiments, an antibody is immobilized on a solid support. In some embodiments, the antigen is immobilized on a solid support. In some embodiments, the solid support is the surface of the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, an antibody is immobilized on the solid support prior to contacting with the antigen. In other embodiments, immobilization of the antibody is performed after formation of binding complexes. In still other embodiments, antigen is immobilized on a solid support prior to formation of binding complexes. A detection reagent is added to the reaction chamber to detect immobilized binding complexes. In some embodiments, the detection reagent comprises a detectably labeled secondary antibody directed against the antigen. In some embodiments, the primary antibody is itself detectable labeled, and is thereby the detection reagent.

In one aspect, detection methods comprise the steps of immobilizing antibodies to a solid support; applying a sample (e.g., a biological sample or isolated protein sample) to the solid support under conditions that permit binding of antigen to the antibodies, if present in the sample; removing the excess sample from the solid support; applying detectably labeled antibodies under conditions that permit binding of the detectably labeled antibodies to the antigen-bound immobilized antibodies; washing the solid support and assaying for the presence of label on the solid support.

In some embodiments, the antigen is immobilized on the solid support, such as a PVDF membrane, prior to contacting with the antibody in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody. As disclosed herein, the detectable label may be, for example, a radioisotope, a fluorophore, a luminescent molecule, an enzyme, a biotin-moiety, an epitope tag, or a dye molecule. In some embodiments, the primary antibody is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a) detectably labeled and/or non-labeled antibodies, as antigen binding reagents (e.g., pro/latent-myostatin binding reagents); (b) a detection reagent; and, optionally, (c) complete instructions for using the reagents to detect antigens in a sample. In some embodiments, the diagnostic kit includes the antibody, and/or pro/latent-myostatin immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody. Diagnostic kits are not limited to these embodiments and other variations in kit composition will be readily apparent to one of ordinary skill in the art.

The present invention is further illustrated by the following examples, which are not intended to be limiting in any way. The entire contents of all references, patents and published patent applications cited throughout this application, as well as the Figures and Sequence Listing, are hereby incorporated herein by reference.

EXAMPLES

Example 1. Effect of Anti-Myostatin Antibody Treatment on Spinal Cord Injury in Mice Spinal Cord Injury and Test Article Treatment and Study Measures The effect of mu-Ab1 on spinal cord injury in mice was studied in a mouse severe contusion model. Adult female C57BL/6 mice (8 weeks old) were randomized to four test groups. Mice were anesthetized by intraperitoneal (i.p.) injection using a ketamine (100 mg/kg) and xylazine (10 mg/kg) cocktail, then subjected to a laminectomy between thoracic vertebrae T8 and T10 to expose the dorsal surface of the spinal cord. To induce spinal cord injury, the spinal cord at T9 was placed directly under the vertical shaft of the Infinite Horizon Impactor (IH-0400 impactor, Precision Systems Instrumentation, LLC, Virginia, USA), followed by slowly lowering of the shaft until the response peak on the force transducer reached the predetermined force level (65 kDyne). The control group was subjected to laminectomy (only) at the T9 level (sham-operation) Immediately following injury animals were administered by i.p. injection with test articles—either vehicle (20 mM Citrate and 150 mM Sodium Chloride, pH 5.5), IgG (40 mg/Kg), or GDF8 (Mu-Ab1, 40 mg/Kg). Follow-up injection of test articles was administered in the same manner 1-week post-SCI. During the two-week study multiple physical and behavior measures were used to assess the effects of anti-myostatin pharmacotherapy. Physical measures included total body weight, muscle weight, total body composition (lean body mass (LBM), fat mass, and bone mineral density) and total metabolic energy expenditure determined using indirect calorimetry. Behavioral measures were also assessed including BMS motor score, rotarod test, and grip-strength test. Between-group differences were analyzed using one-way ANOVA, followed by Tukey post hoc comparison (GraphPad, Prism). Data are expressed as mean±SEM. A significance level of $p<0.05$ was accepted as different from control.

Results and Data Analysis

Body Mass, Muscle Mass, and Body Composition

Figure 3:
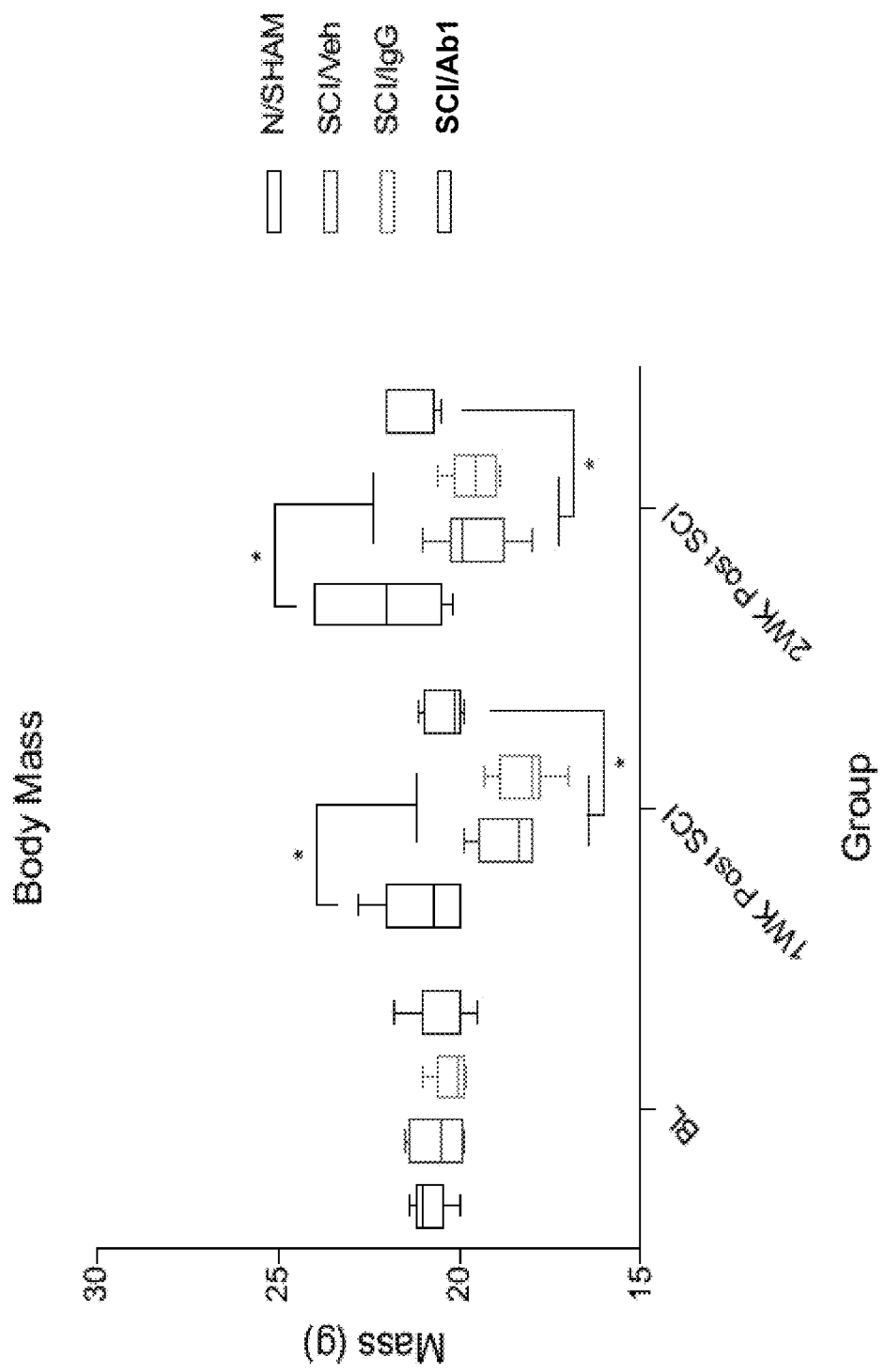
FIG. 3 depicts body mass in naïve mice, and sham, SCI-veh, SCI-IgG, SCI-Ab1 treatment groups at 1- and 2-weeks post-SCI. Asterisks * on the top reflect significant difference from sham; and asterisks * at the bottom of the bars reflect significant difference from SCI-Ab1.

Body mass was measured at the following time-points: 0 (Baseline: prior to survival surgery); 1-week post-surgery; and 2-weeks post-surgery (FIG. 3). There were no significant group differences in mass at baseline. 1-week following SCI (and treatment), there was a significant reduction in body mass in the SCI-veh ($P<0.0001$) and SCI-IgG ($P<0.0001$) groups, compared to sham control. There was no statistical difference in body mass between the sham control and SCI-GDF8 (Mu-Ab1) ($P=0.2805$) group, However, the SCI-GDF8 (Mu-Ab1) group mass was significantly greater than both SCI-veh ($P=0.004$) and SCI-IgG ($P=0.0003$) groups. 2-weeks post-SCI, body mass in SCI-veh ($P=0.0011$) and SCI-IgG ($P=0.0009$) remained significantly lower than sham-control. Body mass in the SCI-GDF8 (Mu-Ab1) group remained significantly greater than SCI-veh ($P=0.0152$) and SCI-IgG ($P=0.0123$) groups, but not different compared to sham control ($P=0.585$).

The data indicate that SCI induced a significant decrease in total body mass when compared to uninjured mice. GDF8 (Mu-Ab1) as a treatment significantly attenuated loss of body mass observed with SCI, such that group means between uninjured and GDF8 (Mu-Ab1) treated mice are qualitatively similar and statistically non-significant.

Figure 4:
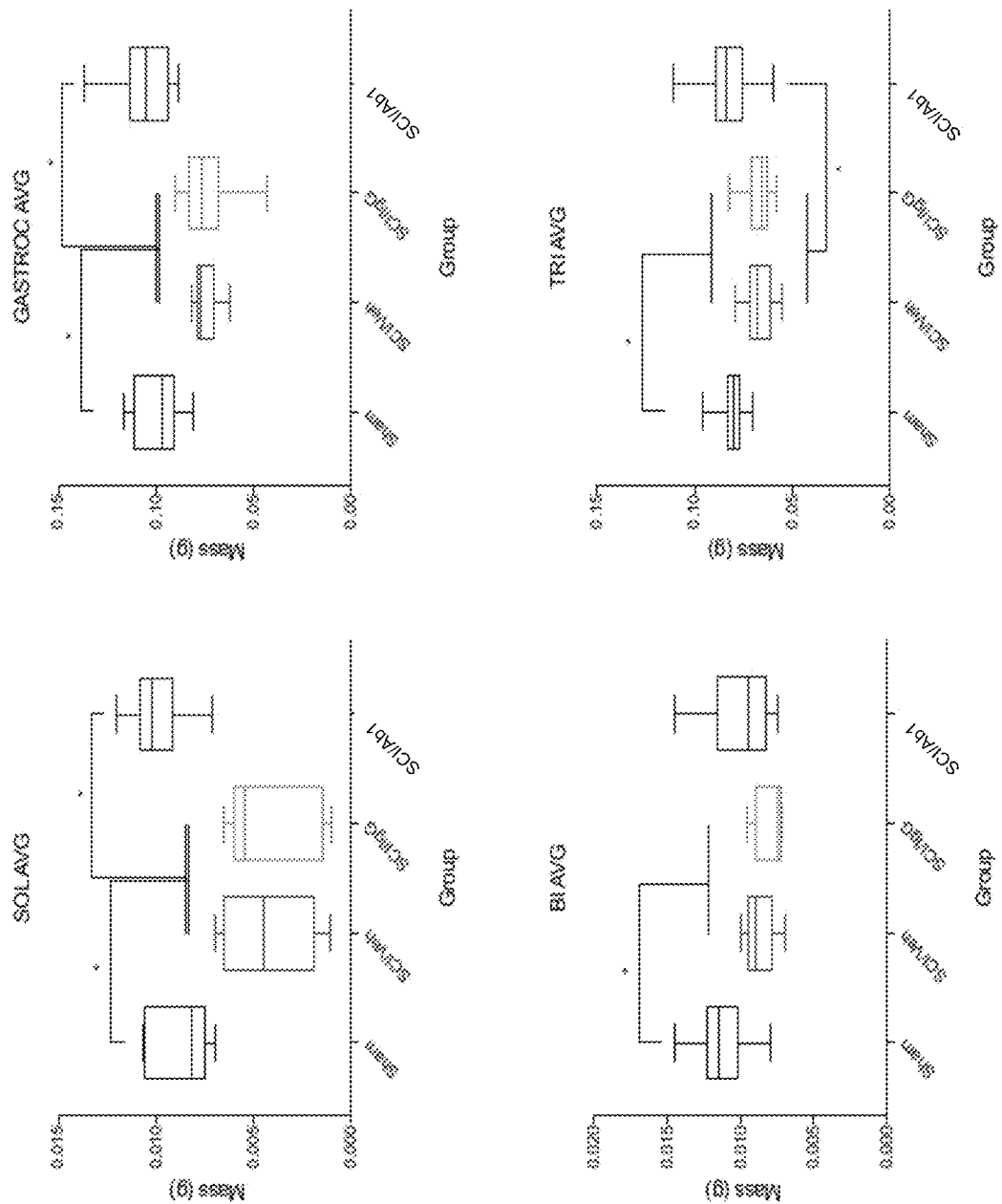
FIG. 4 depicts muscle wet weight (mass) in sham, SCI-veh, SCI-IgG, SCI-Ab1 treatment groups at 2-weeks post-SCI. Excised muscle includes sublesional soleus and gastrocnemius and supralesional biceps and triceps muscles.

At necropsy—2-weeks post-SCI—several muscle tissues (soleus, gastrocnemius, biceps and triceps) were extracted to evaluate the effect of SCI and treatment on wet weight (FIG. 4). The average weight of the soleus muscle was significantly less in the SCI-veh and SCI-IgG (both P's<0.0001) groups than the sham control. There was no statistical difference in soleus mass between the sham control and SCI-GDF8 (Mu-Ab1) (P=0.3129) group, however, the SCI-GDF8 (Mu-Ab1) group soleus mass was significantly greater than both SCI-veh and SCI-IgG (both P's<0.0001). Similarly, the average weight of the gastrocnemius muscle was significantly less in the SCI-veh and SCI-IgG (both P's<0.0001) than the sham control. There was no statistical difference in soleus mass between the sham control and SCI-GDF8 (Mu-Ab1) (P=0.3255) group, however the SCI-GDF8 (Mu-Ab1) group soleus mass was significantly greater than both SCI veh and SCI-IgG (both P's<0.0001).

The average mass of the biceps muscle was also significantly less in the SCI veh (P=0.045) and SCI-IgG (P=0.04) groups when compared to sham control. Group mean trends in biceps mass between the SCI-GDF8 (Mu-Ab1) group were greater than both SCI-veh and SCI-IgG groups. The average mass of the triceps muscle was also significantly less in the SCI-veh (P=0.007) and SCI-IgG group (P=0.0013) compared to sham control. The SCI-GDF8 (Mu-Ab1) group triceps mass was significantly greater than both SCI-veh and SCI-IgG (both P's<0.0001).

The data show that sublesional muscle mass—including the primarily oxidative soleus muscle, and the primarily glycolytic gastrocnemius muscle—was significantly reduced following SCI when compared to uninjured mice. GDF8 (Mu-Ab1) treatment surprisingly and significantly attenuated this muscle loss, where both soleus and gastrocnemius mean muscle mass was equal to the mass of uninjured mice, suggesting an effect across muscle phenotype. When examining supralesional muscle mass—including biceps and triceps muscles—there was also a significant reduction in mass with SCI compared to uninjured mice. This is likely due to an overall depression of physiological systems and global loss of mass with SCI (albeit a greater proportion of muscle mass loss is sublesional).

Figure 5:
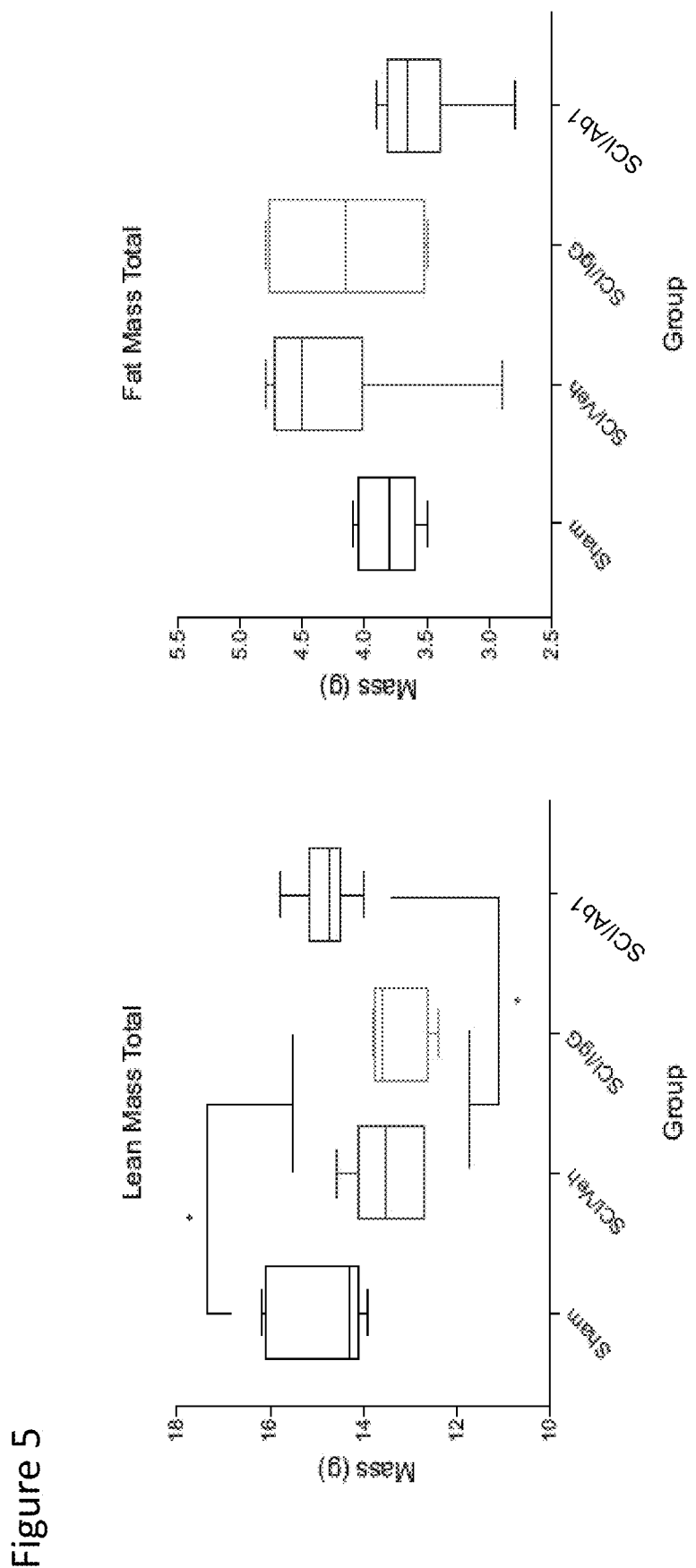
FIG. 5 depicts analysis of total fat-free (lean) and fat mass in sham, SCI-veh, SCI-IgG, and SCI-Ab1 treatment groups at 2-weeks post-SCI.
Figure 6:
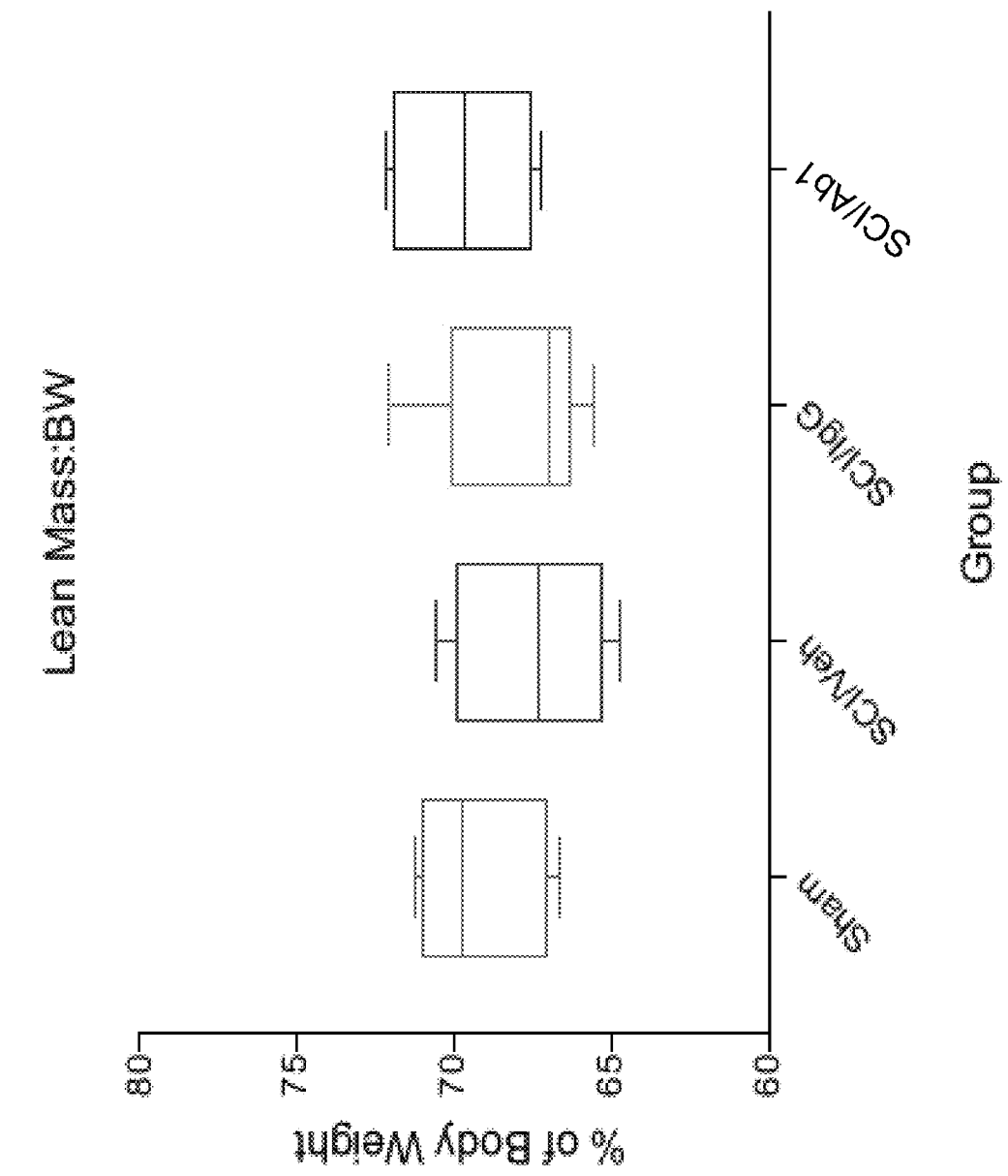
FIG. 6 depicts lean mass as a percentage of body mass in sham, SCI-veh, SCI-IgG, SCI-Ab1 treatment groups at 2-weeks post-SCI.

At 2-weeks post-SCI body composition (lean and fat mass) was assessed by dual-energy x-ray absorptiometry (DXA) densitometry (Lunar PIXImus™ densitometer (GE Medical-Lunar, Madison, Wis.)) in all experimental groups. Total body fat-free (lean) mass was significantly less in the SCI-veh (P=0.0124) and SCI-IgG (P=0.056) groups compared to sham control. The SCI-GDF8 (Mu-Ab1) group total fat-free (lean) mass was significantly greater than both the SCI-veh (P=0.0254) and SCI-IgG (P=0.0114) groups (FIG. 5), and group mean trends indicated greater fat mass in both the SCI-veh and SCI-IgG groups when compared to sham control (FIG. 5). The SCI-GDF8 (Mu-Ab1) group mean trend for whole body fat mass was also less than both the SCI-veh and SCI-IgG groups, and comparable to sham control. When examining the average fat-free (lean) mass as a percentage of body mass, there were no discernable differences between groups, suggesting that changes in body mass after SCI, and treatment effects of GDF8 (Mu-Ab1) were limited to changes in lean body mass (FIG. 6).

These data show that total—or whole body—fat free (lean) mass was significantly reduced following SCI compared to sham control. GDF8 (Mu-Ab1) treatment significantly attenuated this loss of fat-free (lean) mass after SCI, where mean fat-free (lean) mass was not different from uninjured mice, suggesting an effect on global lean tissue. Conversely, total fat mass after SCI appeared to increase compared to sham control, when examining group means. The reduction in sublesional fat-free (lean) mass, and the increase in adiposity (global and regional) is a well characterized feature of chronic SCI pathophysiology.

Intramuscular infiltration of fat/lipid following SCI was histologically analyzed. Fresh frozen gastrocnemius (GN) and soleus (SOL) muscle, harvested two-weeks post-SCI, were sectioned and stained with Oil Red O for visualization of neutral lipids.

Figure 27A:
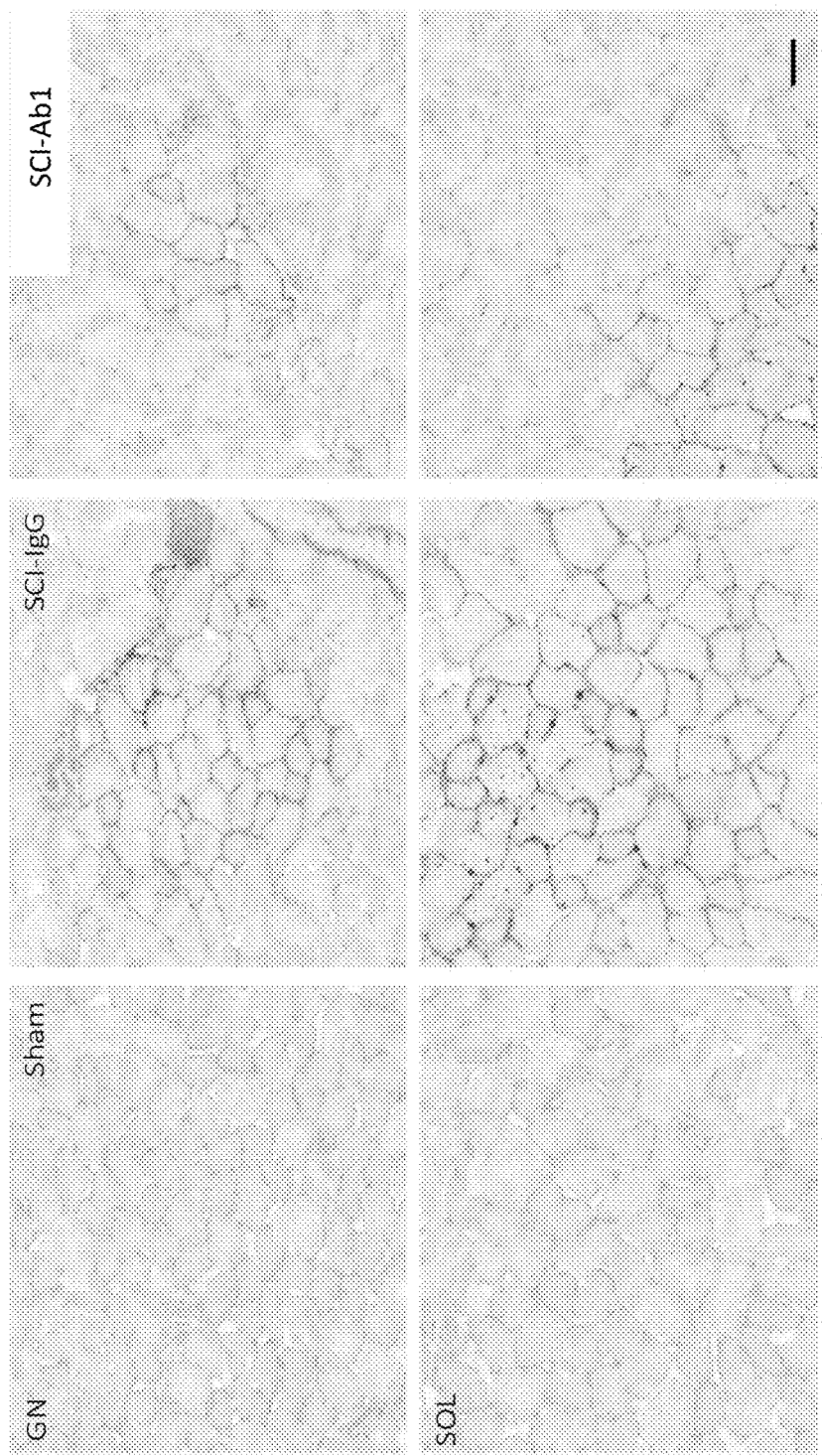
FIGS. 27A-27C demonstrate reduction of SCI-induced intramuscular fat infiltration by a monoclonal antibody that inhibits activation of myostatin.

As the images provided in FIG. 27A show, there was a significant increase in the area of Oil Red O stain in SCI-IgG and SCI-Mu-Ab1 tissue samples, as compared to sham in both muscle types. The scale bar represents 50 micrometers.

Figure 27B:
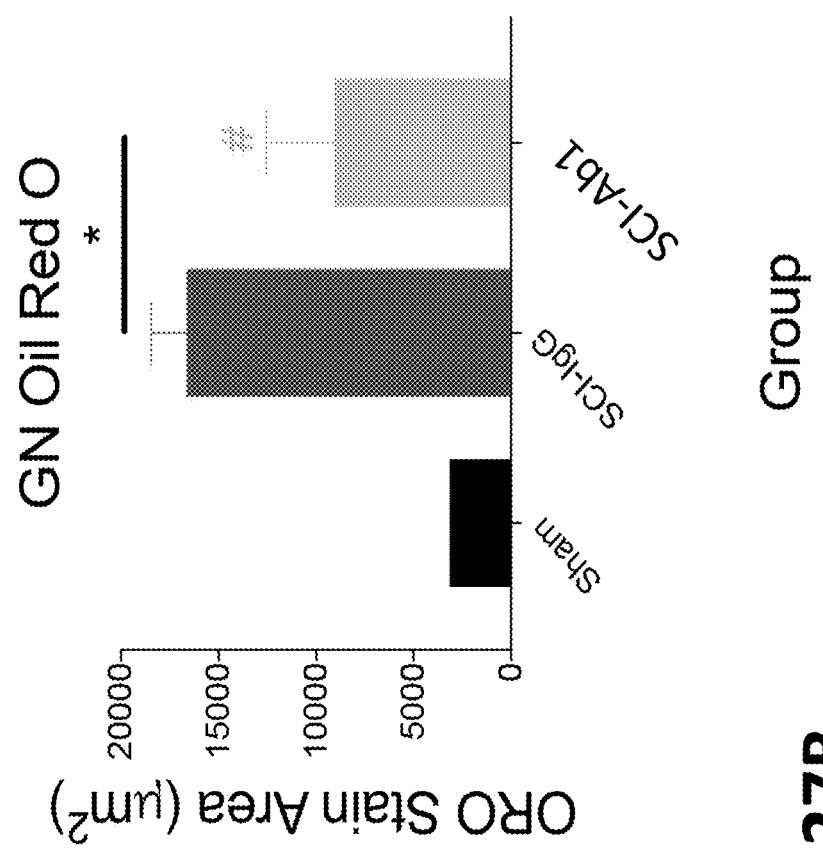
Figure 27C:
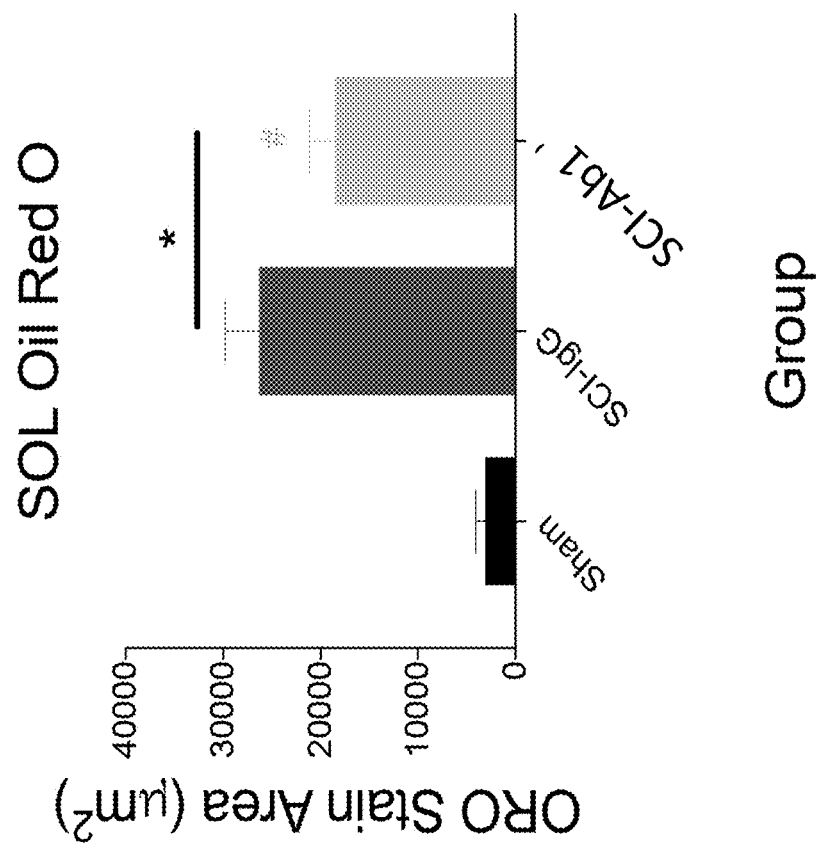

The area of Oil Red O stain in the antibody-treated group was significantly reduced as compared to SCI-IgG control for both muscle types. The results are summarized in FIG. 27B (GN) and FIG. 27C (SOL).

Metabolism and Total Energy Expenditure

Figure 7:
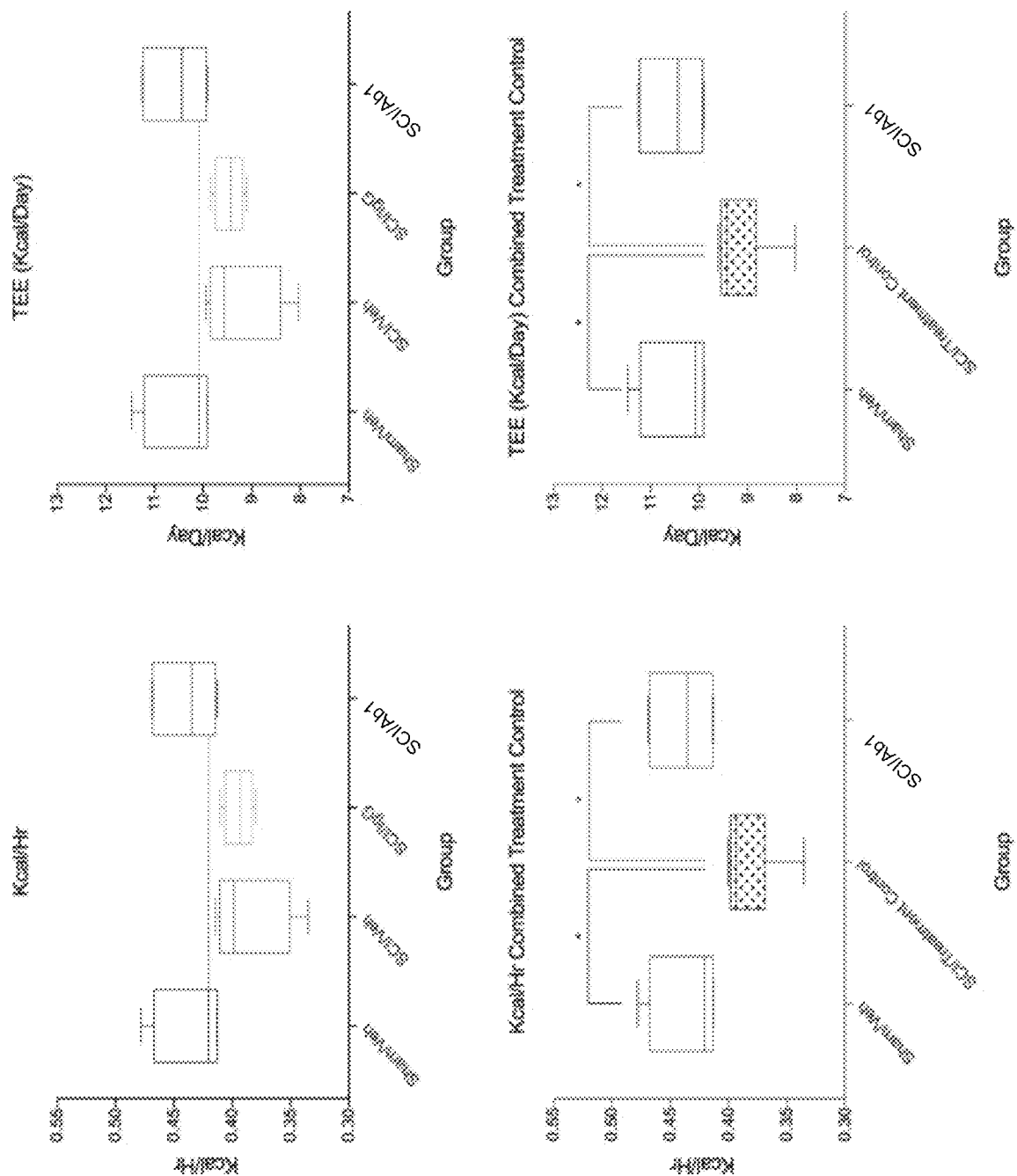
FIG. 7 depicts analysis of kcal/hr and TEE in sham, SCI-veh, SCI-IgG, and SCI-Ab1 treatment groups at 2-weeks post-SCI. In the lower graphs, the SCI/Treatment Control group represents the combined SCI/veh+SCI/IgG groups from the upper graphs.

Indirect calorimetry was performed on mice using a 12-chamber open-circuit Oxymax system of the Comprehensive Lab Animal Monitoring System (CLAMS; Columbus Instruments, Columbus, Ohio, USA). Mice were transferred to individual metabolic chambers for 3-days prior to (and including) the 2-week post-SCI analysis time-point. $VO_2$ and $VCO_2$ were measured continuously, and using indirect calorimetry, energy expenditure/hour (kcal/hr) and total energy expenditure/day (TEE) were calculated (FIG. 7). Group mean trends suggest a decrease in these measures in SCI-veh and SCI-IgG compared to sham control, and that the metabolic decrease in the SCI-veh group versus sham control approached statistical significant (P=0.075). Group means trended toward elevation in the SCI-GDF8 (Mu-Ab1) group when compared to the SCI-veh and SCI-IgG groups. Notably, the metabolic increase in the SCI-GDF8 (Mu-Ab1) compared to the SCI-veh approached statistically significant (P=0.0530), and the direction of the SCI-GDF8 group mean appeared slightly elevated compared to sham control. For additional analysis, the SCI groups not receiving the GDF8 (Mu-Ab1) treatment drug (SCI-veh+SCI-IgG) was collapsed to add group power to the SCI treatment control. In doing so, it was found that kcal/hr and TEE in the coalesced SCI-treatment control group was lower than the sham control (P=0.0159). There was no statistical difference in kcal/hr and TEE between the sham control and SCI-GDF8 (Mu-Ab1) (P=0.9764) group, however the SCI-GDF8 (Mu-Ab1) group kcal/hr and TEE was significantly greater than the coalesced SCI-treatment control (P=0.0106) group.

The results show that metabolism (as energy expenditure) was depressed following SCI, and that GDF8 (Mu-Ab1) treatment maintained resting metabolism at levels that approximate uninjured controls. These results further suggest that the biological effect of GDF8 (Mu-Ab1) on lean tissue, in particular muscle preserves levels of resting metabolism that are otherwise reduced following SCI.

Functional Measures

BMS Open Field Locomotor Test

The Basso Mouse Scale (BMS) open field locomotor test (using a 0 to 9 rating system) was used to assess recovery of hind-limb locomotor function following SCI, including (but not limited to) variables such as foot placement, weight support, and joint motion. Under blinded conditions, a team of two investigators evaluated the mice over a 4-minute time period at baseline, 1 day after SCI/sham, and weekly thereafter. The arena was divided into three zones (wall, inter and center) and mouse behavior was recorded over a 5-minute period using a high resolution, video camera. The total number of lines crossed, time spent in each zone, and stereotypical behaviors such as grooming and rearing were analyzed and expressed as number of events.

Figure 8:
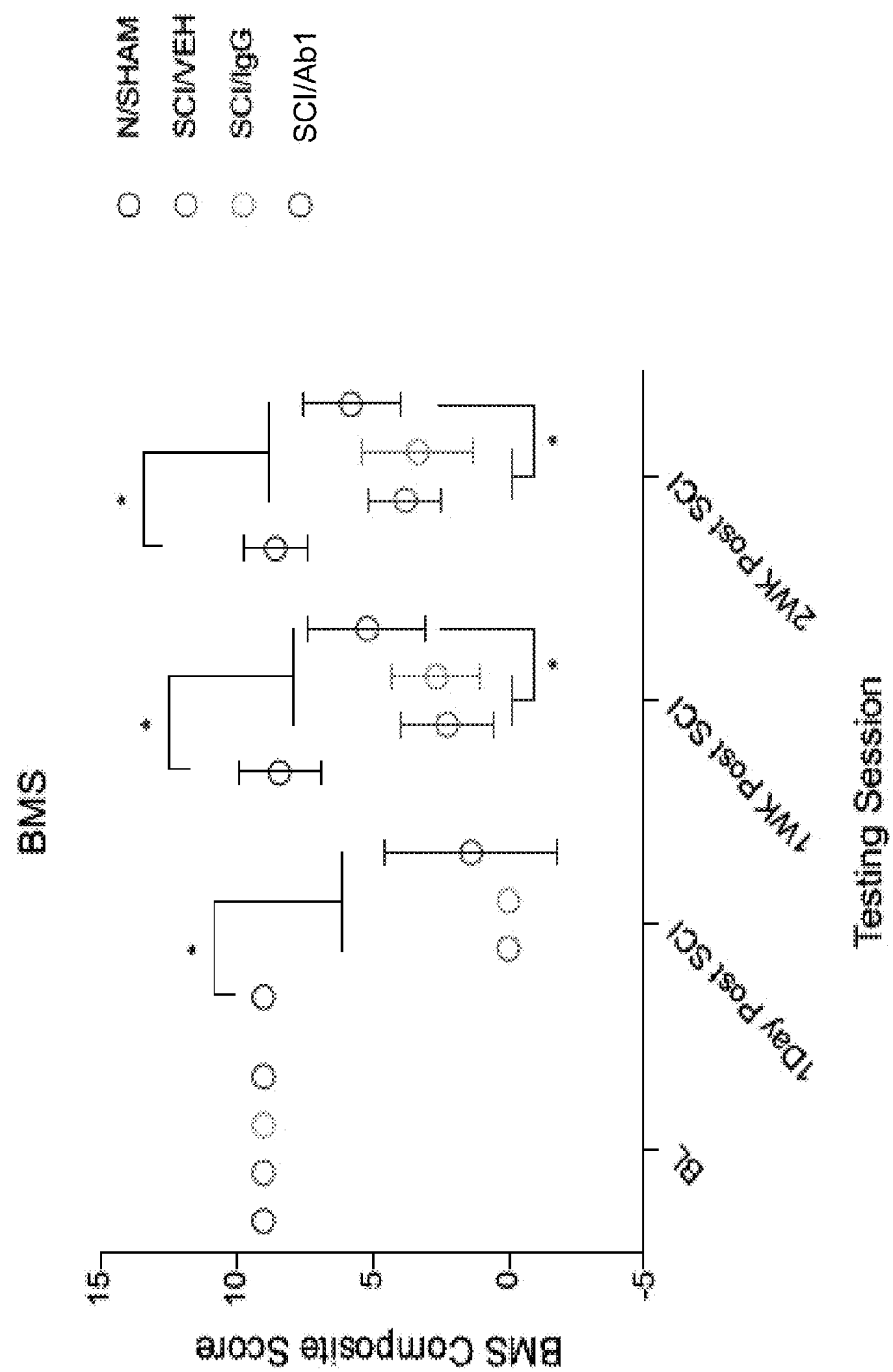
FIG. 8 depicts the BMS locomotor assessment in sham, SCI-veh, SCI-IgG, and SCI-Ab1 groups, at baseline (before survival surgery), 1-day, 1-week, and 2-weeks post-SCI. Statistical comparison at 1- and 2-weeks post-SCI reflect combined SCI-veh+SCI-IgG data.

There was a significant reduction in BMS composite score in the SCI-veh and SCI-IgG groups (both P's<0.0001) 1-day post-SCI (FIG. 8). Because of the uniformity at this timepoint in the SCI-veh and SCI-IgG groups, they were collapsed to provide additional study power at later time-points (SCI-treatment control). Also, at 1-day post-SCI, there was a significant reduction in BMS score in the SCI-GDF8 (Mu-Ab1) group (P<0.0001) compared to sham control. 1-week post-SCI, BMS scores remained significantly reduced in SCI-treatment control (P<0.0001) and SCI-GDF8 (Mu-Ab1) (P=0.0128) groups compared to sham control. However, the BMS score was significantly greater in the SCI-GDF8 (Mu-Ab1) (P=0.0148) group compared to the SCI-treatment control. Similarly, at 2-weeks post-SCI, BMS scores remained significantly reduced in both the SCI-treatment control (P<0.001) and SCI-GDF8 (Mu-Ab1) (P=0.0182) groups, but again, the SCI-GDF8 (Mu-Ab1) group had a significantly higher BMS score than the SCI treatment control (P=0.0143).

Rotarod Test

Motor coordination and balance were tested on the accelerating rotarod cylinder (Rotamex 4/8, Columbus Instruments). The procedure consisted of a 5-day pre-training (days 1 to 5) followed by the testing (1-week and 2-weeks post-SCI/sham). The cylinder rotated at increasing speed and constant acceleration (from 10 to 60 rpm over 10-minute period). The total time spent on the rod prior to fall was recorded and non-walking behaviors, such as passive clinging to the rod, were manually corrected. Each trial consisted of an average of 4 sessions.

Figure 9:
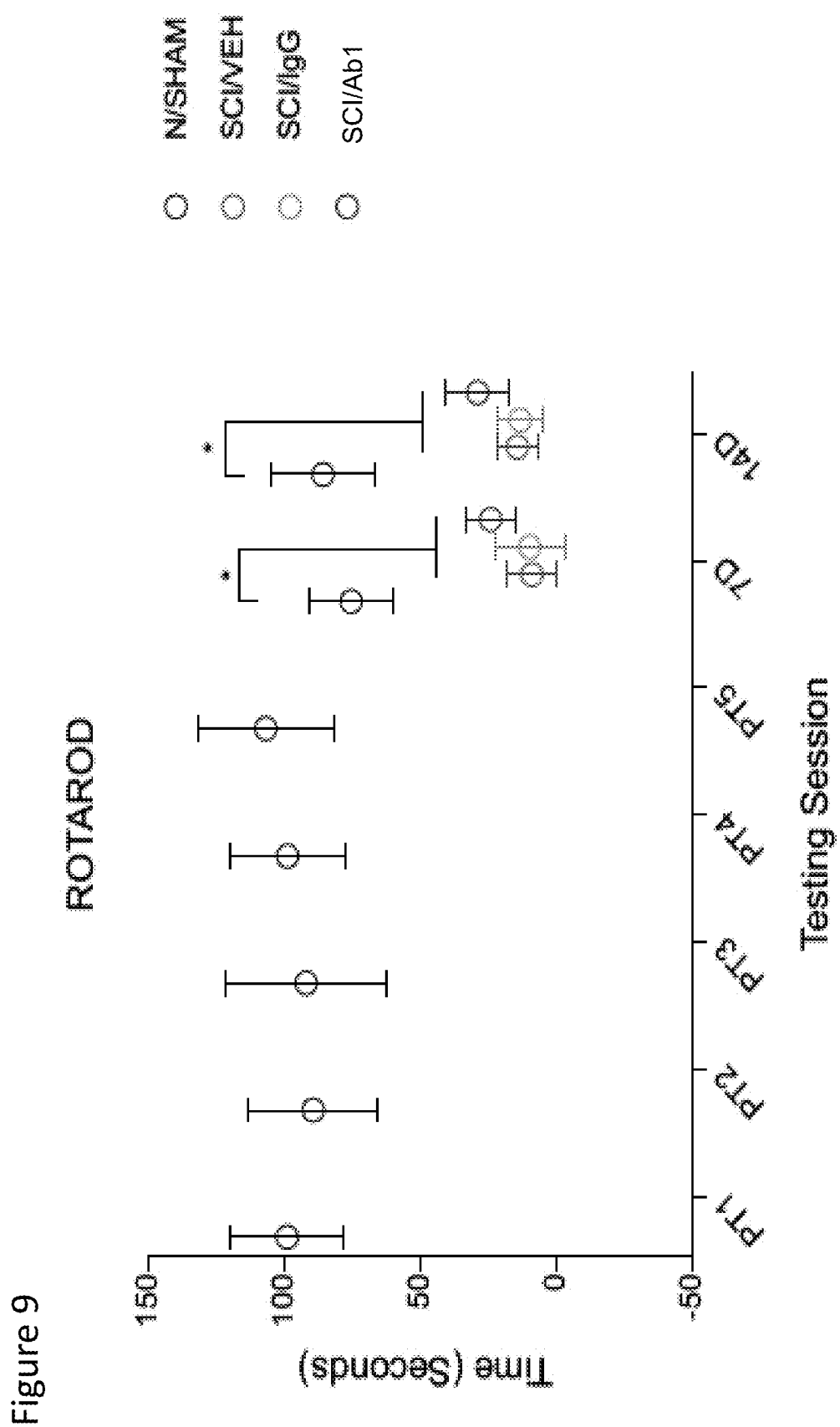
FIG. 9 depicts Rotarod time scores in sham, SCI-veh, SCI-IgG, and SCI-Ab1 groups, after pre-training (PT), 1-week, and 2-weeks post-SCI.

Using rotorod time trials as a proxy measure of motor coordination and balance this study showed that 1-week post SCI, there was a significant decrease in average rotarod time in the SCI-veh, SCI-IgG, and SCI-GDF8 groups (all P's<0.0001) compared to sham control (FIG. 9). The SCI-GDF8 (Mu-Ab1) group mean was greater than both the SCI-veh and SCI-IgG groups (P=0.118). Similarly, 2-weeks post SCI, a significant decrease persisted in average rotarod time in the SCI-veh, SCI-IgG, and SCI-GDF8 (Mu-Ab1) groups (all P's<0.0001) compared to sham control. Again, although there was no statistical difference between any of the SCI groups, the SCI-GDF8 (Mu-Ab1) group mean was greater than both the SCI-veh and SCI-IgG groups (P=0.1708).

Grip Strength Test

All animals from the sham and SCI groups underwent analysis of hindlimb peak force (muscle strength) using the grip-strength test. Hind-limb grip strength was assessed using a digital force gauge (Chatillon DFIS2, Ametek), which generates a measure of neuromuscular function as maximal muscle strength—with the unit of force measured in grams. The test consisted of a baseline assessment prior to surgery, followed by a test day at 1-week and 2-weeks post-surgery. Force values were the calculated average of 5-trials.

Figure 10:
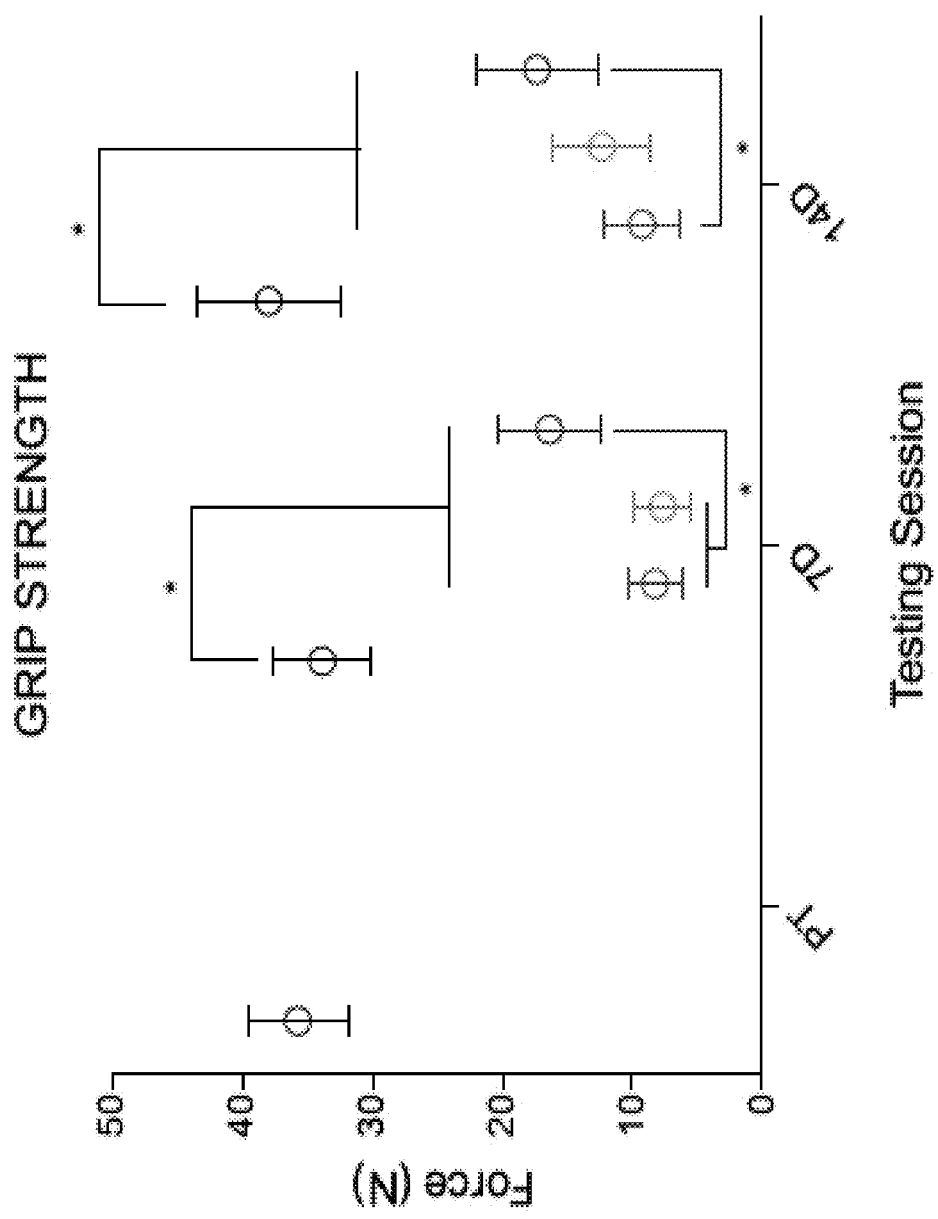
FIG. 10 depicts grip strength in sham, SCI-veh, SCI-IgG, and SCI-Ab1 groups, after pre-training (PT), 1-week, and 2-weeks post-SCI.

One week post-SCI, there was a significant decrease in grip strength in the SCI-veh, SCI-IgG, and SCI-GDF8 (Mu-Ab1) groups (all P's<0.0001) compared to sham control (FIG. 10). The SCI-GDF8 (Mu-Ab1) group grip strength was significantly greater than both the SCI-veh (P=0.0006) and SCI-IgG (P=0.0003), although the latter two groups were not different from each other. Two weeks post-SCI, there was a significant decrease in grip strength in the SCI-veh, SCI-IgG, and SCI-GDF8 (Mu-Ab1) groups (all P's<0.0001) compared to sham control. Grip strength for the SCI-GDF8 (Mu-Ab1) group was significantly greater than the SCI-veh group (P=0.0124), although not statistically different from the SCI-IgG group (however the group mean trended to greater strength; P=0.1856).

The results indicate that SCI causes a drastic reduction in hind-limb locomotor function (BMS), translating to marked reduction in motor coordination and balance (rotarod), as well as muscle strength (grip strength). GDF8 (Mu-Ab1) treatment prevented this change, as the composite BMS score for GDF8 was significantly greater than the other injury groups Animals treated with GDF8(Mu-Ab1) also had higher motor coordination and balance as assessed by the rotarod time trials.

In conclusion, these data demonstrated a profound effect of GDF8 (Mu-Ab1) treatment on the anthropometric, physiological, and functional outcome measures of mice with SCI. SCI-induced reduction in body mass and sublesional muscle mass were attenuated with GDF8 (Mu-Ab I), and metabolic abnormalities associated with SCI—related to body composition and energy expenditure—were less pronounced following GDF8 (Mu-Ab1) treatment. Further, the effects of GDF8 (Mu-Ab1) treatment translate to locomotor and functional benefits when compared to the non-treated SCI condition.

Figure 12B:
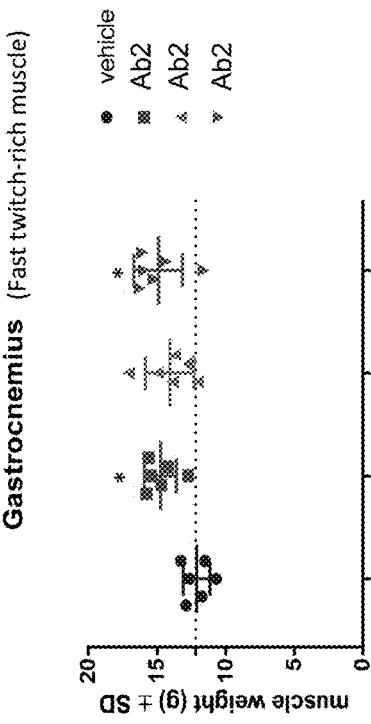
Figure 12A:
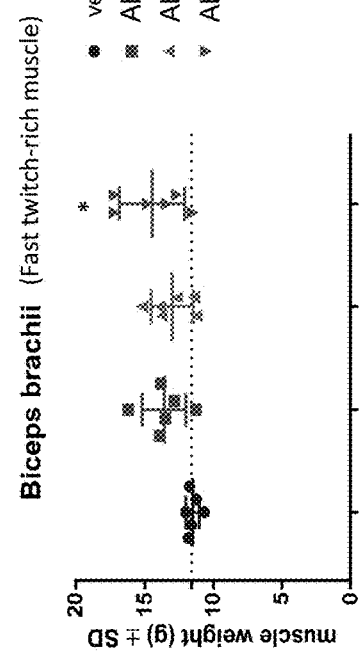

Example 2. Effects of Treatment with Ab2 on Lean Mass, Muscle Weight, and Serum Myostatin in Healthy Cynomolgus Monkeys Effects of treatment with Ab2 on change in lean mass were evaluated in healthy Cynomolgus monkeys (n=6 per treatment group). Healthy male Cynomolgus monkeys (avg age: 34 months at start of study) were dosed by intravenous injection once weekly for 8 weeks at three different dose levels of Ab2 (3 mg/kg, 10 mg/kg, and 30 mg/kg) with a 4-week recovery phase. Control animals were administered vehicle control (20 mM Citrate and 150 mM Sodium Chloride USP, pH 5.5). Lean mass was measured by Dual Energy X-Ray Absorptiometry (DEXA) at baseline and at intervals throughout the 12 week study (FIGS. 11A-11D). Treatment with Ab2 resulted in a 5-9% increase in the limb lean mass of Ab2-treated monkeys compared to vehicle control (FIGS. 11A-11D and FIG. 13). Effects of treatment with Ab2 on tissue weights from the biceps brachii and gastrocnemius muscles of healthy Cynomolgus monkeys were also measured at week 12 (FIGS. 12A-12B). Significant effects of Ab2 treatment were apparent in the weights of these muscles (FIGS. 12A-12B and FIG. 13). The gastrocnemius and biceps brachii muscles, which are rich in fast twitch fibers, were substantially larger by as much as 25% in Ab2-treated animals compared to the vehicle control (FIG. 13). Therefore, Ab2 treatment had a notable effect on muscle growth. Further, Ab2 treatment had a particularly robust effect on fast twitch-rich muscle fibers.

Figure 14A:
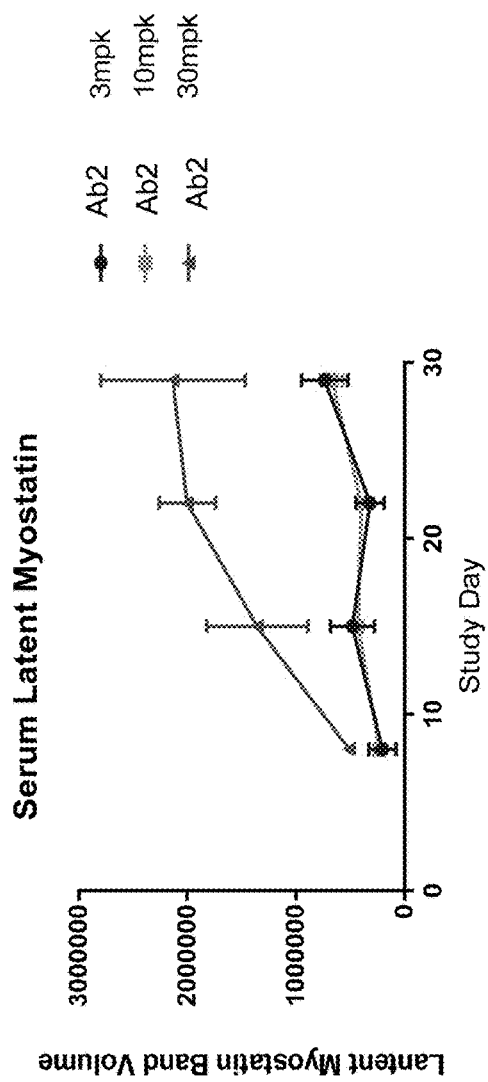
FIGS. 14A and 14B show latent Myostatin levels in serum samples of Ab2-treated healthy Cynomolgus monkeys and in control animals measured using quantitative fluorescent western blotting. Healthy male Cynomolgus monkeys were dosed by intravenous injection once weekly for 8 weeks at three different doses, 3 mg/kg, 10 mg/kg, and 30 mg/kg, with a 4-week recovery phase. Control animals were administered vehicle control (20 mM Citrate and 150 mM Sodium Chloride USP, pH 5.5). Serum samples were collected over different study days and relative levels of latent Myostatin in the serum samples were analyzed using quantitative fluorescent western blotting.
Figure 14B:
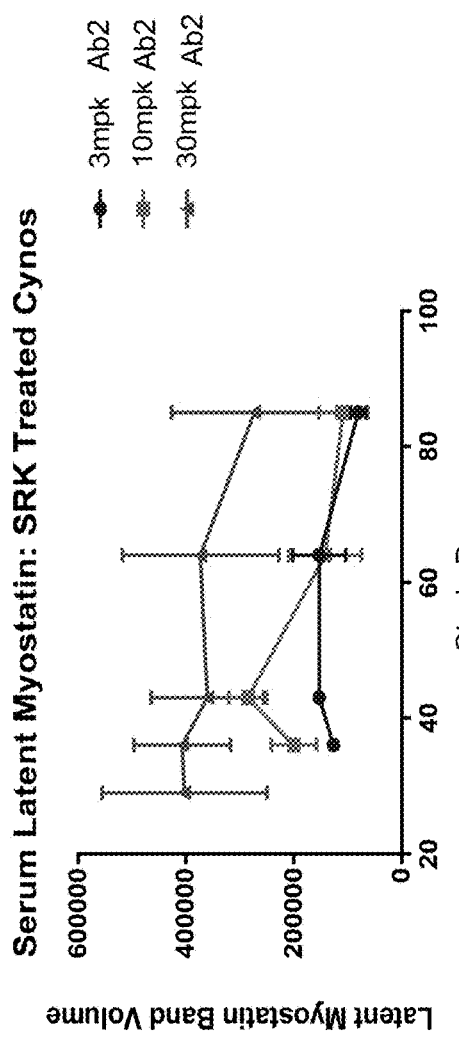

Throughout this study, serum samples for analysis of serum Myostatin levels were collected on study days 2, 4, 8, 15, 22, 29, 36, 43, 64, and 85 as indicated in FIGS. 14A-14B. Effects of treatment with Ab2 on latent Myostatin levels in the serum were also evaluated using quantitative fluorescent western blotting. Increase in Myostatin levels in Ab2-treated animals peaked and plateaued between study days 15 and 29 and declined by study day 85. Increase in latent Myostatin levels in the serum was seen with all doses of Ab2 with greatest increase seen in animals treated with 30 mg/kg of Ab2 (FIGS. 14A-14B).

Example 3. Effects of Myostatin and Myostatin Inhibition on Gene Expression

A. Natural History Study in Rats

In order to understand the effect of myostatin on signaling pathways after nerve injury, Quantigene analyses of gastrocnemius muscles and spinal cord from a rat severe contusion injury (SCI) model were performed. The study utilized negative control and SCI rats; samples were analyzed at six hours, 1 day, 3 days, 5 days, 7 days, and 14 days post-injury. Table 4 presents categories of genes that were selected for analysis, along with the rationale for selection.

TABLE 4

Genes Selected for Analysis

| Category | Gene | Synonym | Rationale |
|---|---|---|---|
| Muscle targets | MSTN | | negative regulator of muscle |
| | fbxo32 | mafbx | upregulated by pSMAD 2/3 |
| | trim63 | murf1 | upregulated by pSMAD 2/3 |
| | NRF1 | | upregulated by pgc1a; mitochondria biogenesis |
| | NFE2L2 | NRF2 | upregulated by pgc1a; mitochondria biogenesis |
| | Ppargc1a | PGC1a | mitchondria, metabolism, lipid regulator |
| | Slc2a4 | glut4 | decreased in muscle atrophy; insulin insensitivity |
| | Gadd45a | | upregulated in denervation atrophy, downregulated with FES |
| | Map3k4 | | upregulated in denervation atrophy |
| | Fndc5 | Irisin | expressed by muscle, may affect adipocyte metabolism |
| | Ddit4 | Redd1 | upregulated in immobolization and dex induced atrophy |
| | IL-6 | | upregulated in muscle with SCI; contributes to inflammation; may induce anabolic pathways |
| CNS targets | GDF5 | | upregulated following denervation; loss worsens atrophy |
| | Ntf3 | | neurotrophic |
| | Bdnf | | neurotrophic |
| | Gdnf | | neurotrophic |
| | Ngf | | neurotrophic |
| | gdf11 | | closely related to myostatin |
| | Lrrc32 | garp | regulator of TGFβ |
| | Lrrc33 | | regulator of TGFβ, upregulated in mouse spinal cord injury |
| | Ltbp1 | | regulator of TGFβ |
| | Ltbp2 | | regulator of TGFβ |
| | Ltbp3 | | regulator of TGFβ, upregulated in mouse spinal cord injury |
| | Tgfb1 | | upregulated in mouse spinal cord injury |
| | Tgfb2 | | other tgf beta |
| | Tgfb3 | | other tgf beta |
| | rtn4 | nogo | present in myelin, neurite growth inhibitor |
| | lingo-1 | | nogo receptor, upregulated in rat spinal cord 14 dpi |
| | bmp7 | | regulator of bone |
| | Serpine1 | | tgf beta transcriptional target |
| House keepers | HPRT | | House keeper |
| | GUSB | | House keeper |
| | B2M | | House keeper |
| | PPIB | | House keeper |
| | Polr2a | | House keeper |
| | txn2 | | House keeper |
| | rpl19 | | House keeper |
| | ppia | | House keeper |

In the spinal cord, Fbxo32 exhibited decreased expression initially following injury, but returned to baseline by the 14-day time point. IL-6, Gdnf, and Pai-1 exhibited increased expression within 6 hours of injury, but returned to baseline shortly thereafter. Nfe2L2, Gadd45a, TGFb1, TGFb2, TGFb3, LTBP1, LTBP3, GARP, LRRC33, and BMP7 exhibited increased expression following injury; and Ppargc1a, irisin, and Lingo1 exhibited decreased expression following injury.

In gastrocnemius, Mstn, Fbxo32, Murf1, Nrf1, Nfe2L2, Gadd45a, GDF5, TGFb2, LTBP1, and Ddit4 exhibited increased expression initially following injury, but returned to baseline by the 14 day time point. Glut-4, Irisin, Nogo, and BMP7 exhibited decreased expression following injury, but returned to baseline by the 14-day time point. Ppargc1a exhibited decreased expression following injury.

The data indicate that transcriptional changes happen early in the rat SCI model and typically return to baseline by the 14-day time point.

B. Gene Expression in Mouse SCI Model after Treatment with Myostatin Inhibitor

In a second study, Quantigene analysis of gastrocnemius from 14 days post SCI in a mouse model was performed. The mice were either administered an antibody that inhibits myostatin activation, PBS (vehicle), or IgG. Genes analyzed were Murf-1, Fbxo32, Mstn, Mt2 (metalothionein 2), and Ctsl (Cathepsin L) all showed a statistically significant increase in expression after injury. However, mice receiving treatment with the myostatin inhibitory antibody demonstrated expression levels comparable to the sham group (no injury), confirming that treatment with a myostatin inhibitor prevents upregulation of atrogenes.

C. RNASeq Data from Mice Treated with Myostatin Inhibitor

Figure 15:
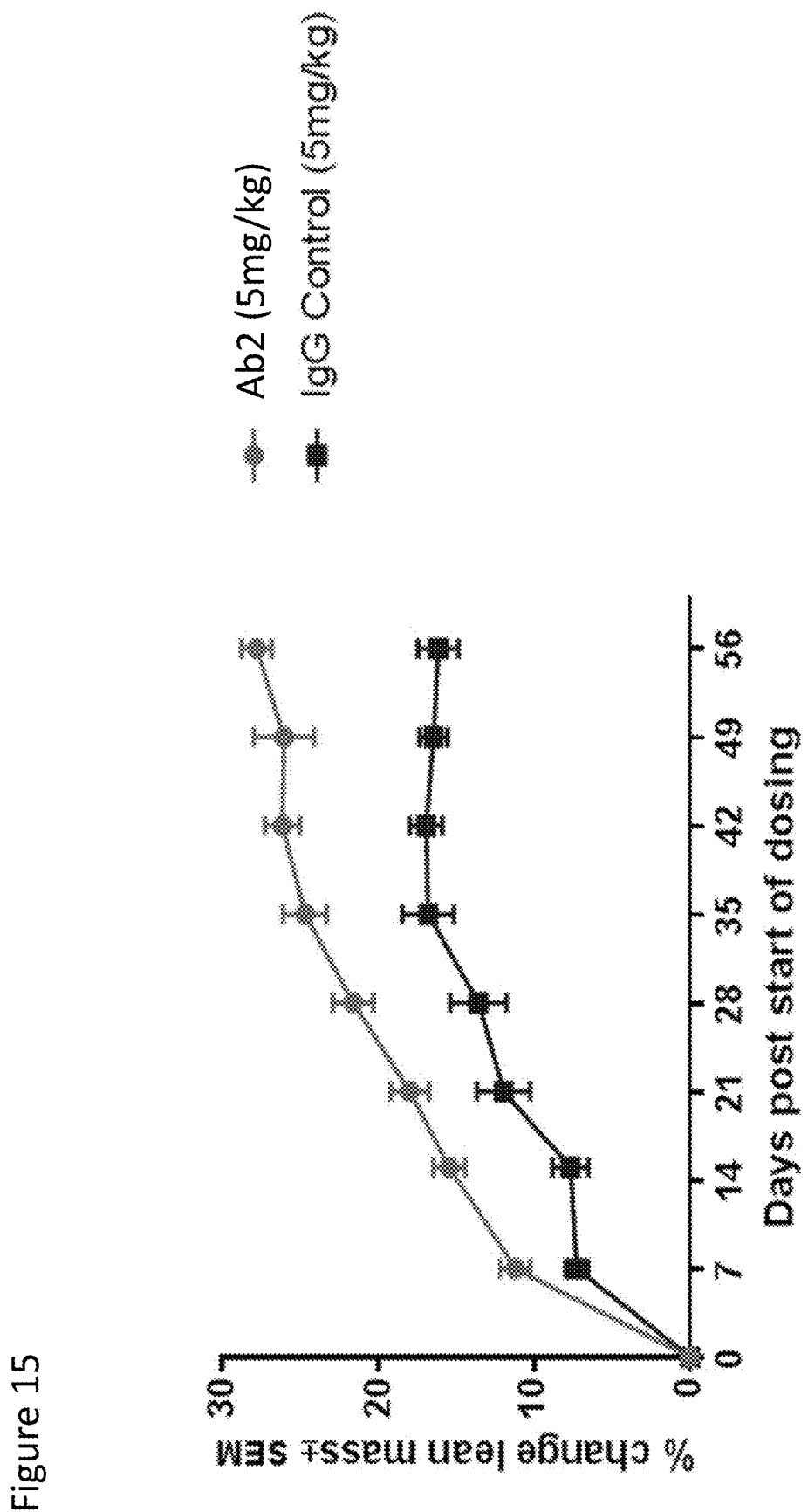
FIG. 15 depicts lean mass change by Ab2-mediated Myostatin inhibition.

To broadly profile the changes in muscle brought about by Ab2-mediated Myostatin inhibition, transcriptional profiling of RNA isolated from the tibialis anterior muscles of drug treated mice was performed. RNA was harvested from muscles tissue collected 3, 7, and 28 days after a single, 5 mg/kg dose of Ab2. This dose was sufficient to induce a marked and sustained increase in lean mass in treated mice (FIG. 15). RNA harvested from control IgG-treated mice on the day of injection (day 0) was used as a control to measure gene expression at the start of the study. For each time point, a minimum of 3 biological replicates was analyzed.

Figure 16:
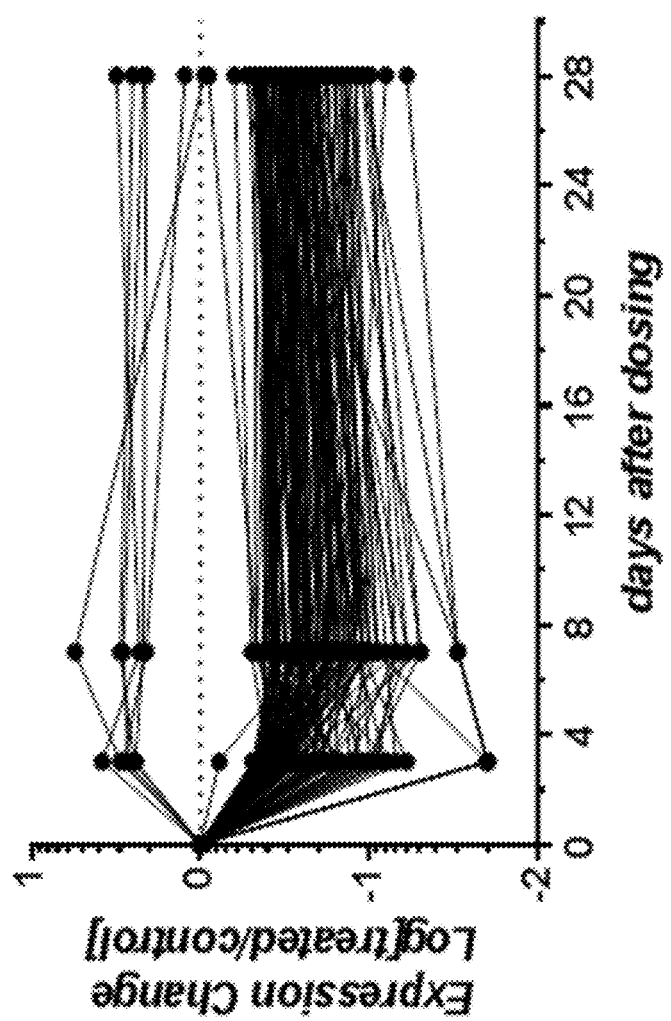
FIG. 16 depicts differentially expressed genes (DEGs) in Ab2-treated groups.

After generation of cDNA, transcriptional profiles were assessed by RNA sequencing (RNAseq). Raw sequences were generated by NextGen Sequencing (NGS) followed by alignment to reference sequences. Raw data from the groups were subsequently analyzed by NOISeq (Tarazona et al., *Genome Res.*, 2011) to identify differentially expressed genes (DEGs) in Ab2-treated groups vs. baseline controls. DEGs for each group were filtered for statistical significance, then analyzed for coordinate regulation at additional time points (e.g., DEGs upregulated in the day 3, day 7, and day 28 datasets). This yielded a total of 138 genes with differential expression vs. baseline control at all three time-points analyzed. Consistent with a biological response to an inhibitor, the majority of DEGs were downregulated, with only 6 upregulated genes (FIG. 16).

Figure 17:
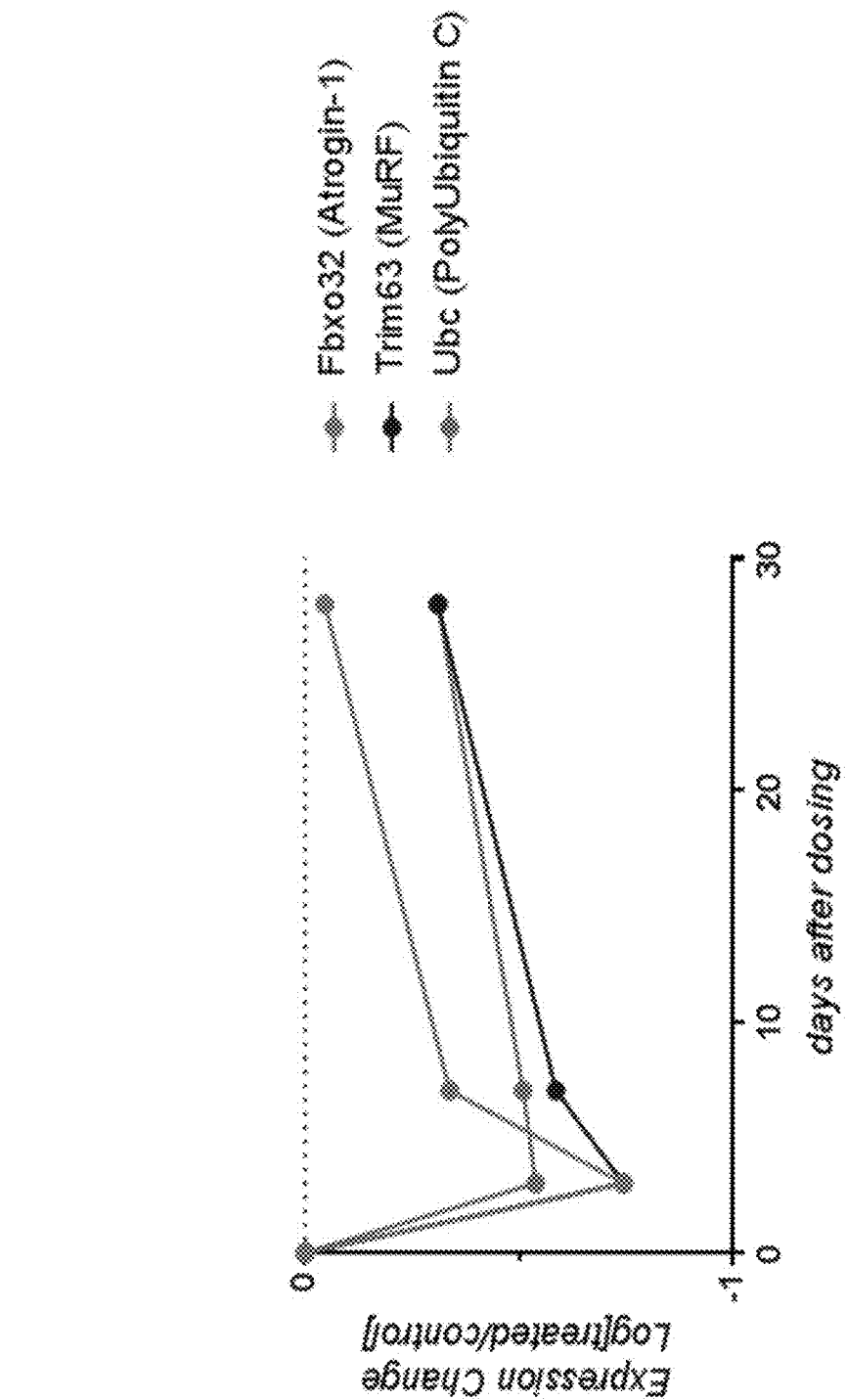
FIG. 17 depicts repression of atrogenes after Ab2-mediated myostatin inhibition.

RNAseq identified a number of genes previously identified as targets of Myostatin signaling. Among these are Fbxo32 (Atrogin-1) and Trim63 (MuRF). Both of these genes encode ubiquitin ligases that are critical drivers of muscle atrophy (Reviewed by Cohen et al., *Nat. Drug Discov.*, 2015) and whose transcription is upregulated by Myostatin signaling. These ligases, as well as one of the genes encoding ubiquitin proteins, polyubiquitin C (Ubc), are downregulated 3- to 10-fold in Ab2-treated muscles (FIG. 17), consistent with their previously described inhibition during muscle hypertrophy.

Figure 18:
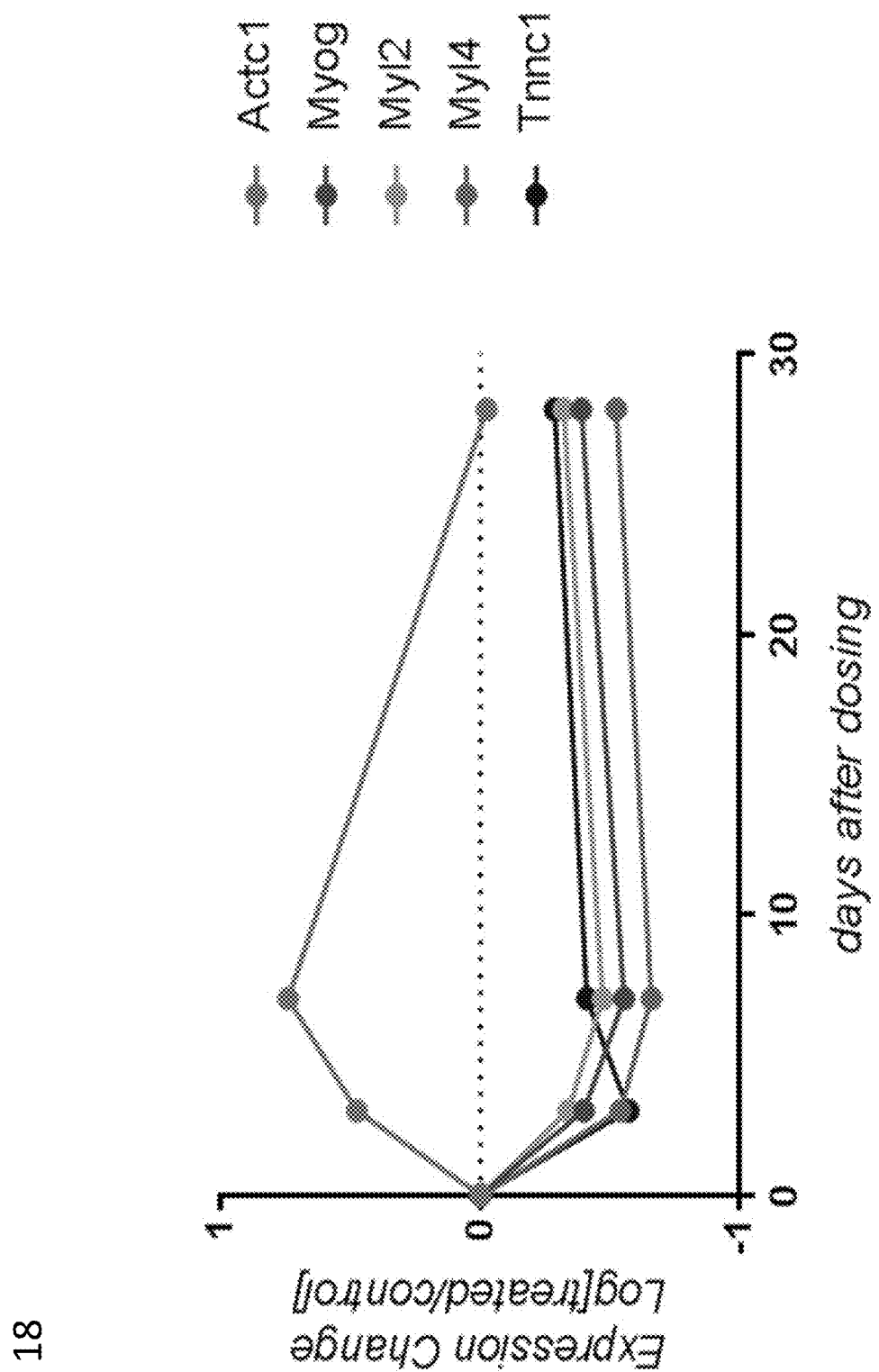
FIG. 18 depicts expression of muscle specific markers after Ab2-mediated myostatin inhibition.

The DEG dataset also included genes encoding several muscle-specific structural proteins, including early upregulation of alpha cardiac muscle actin (Actc1) (FIG. 18). This form of actin, is associated with early stages of myogenesis (Tsao et al., Stem Cell Res. Ther., 2013) and has been previously shown to be upregulated by anti-Myostatin treatment (Latres et al., Skeletal Muscle, 2015). Downregulation of Myogenin (Myog) was observed (FIG. 18), consistent with fusion of myocytes to augment existing myofibers (Reviewed by Bentzinger et al., Cold Spring Harb. Perspect. Biol., 2012). In addition, several muscle-specific proteins are downregulated by Ab2 treatment, including Myostin Light Chain 2 and 4 (Myl2 and Myl4) and Troponin C (Tnnc1). Tnnc1 and Myl2 are more closely associated with slow twitch skeletal fibers (Amann et al., Dev Biol, 2014; Lee and Hwang, Gene, 2015), while Myl4 is associated with undifferentiated and fetal muscle (Schiaffino et al., Skeletal Musc., 2015), suggesting some degree of dedifferentiation and/or fiber type switching during anti-Myostatin-driven muscle hypertrophy.

Figure 19:
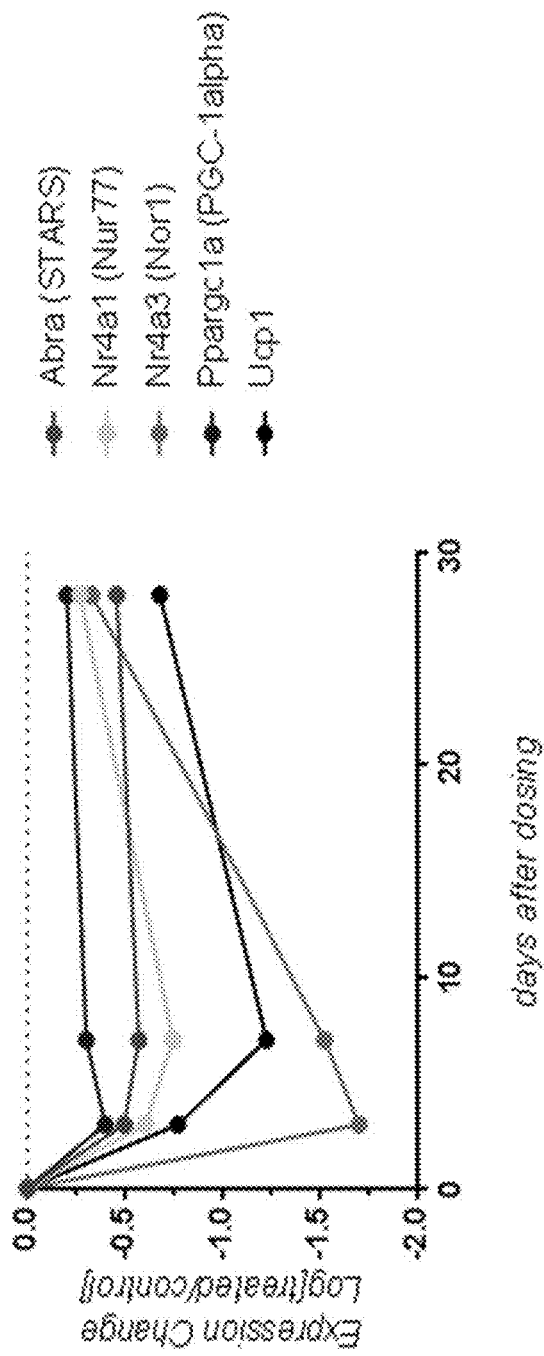
FIG. 19 depicts expression of markers of respiratory capacity after Ab2-mediated myostatin inhibition.

Several investigators have noted an inverse relationship between muscle fiber size and muscle respiratory capacity (reviewed by van Wessel et al., Eur. J. Appl. Physiol., 2010), likely reflecting the greater anaerobic demands of larger muscles. Consistent with this, a downregulation of several genes associated with respiratory capacity and mitochondrial synthesis was observed, including PGC-1α, Nor1, UCP-1, and Nur77 (FIG. 19), suggesting that anti-Myostatin treatment alters metabolic function in these hypertrophic muscles.

Figure 20:
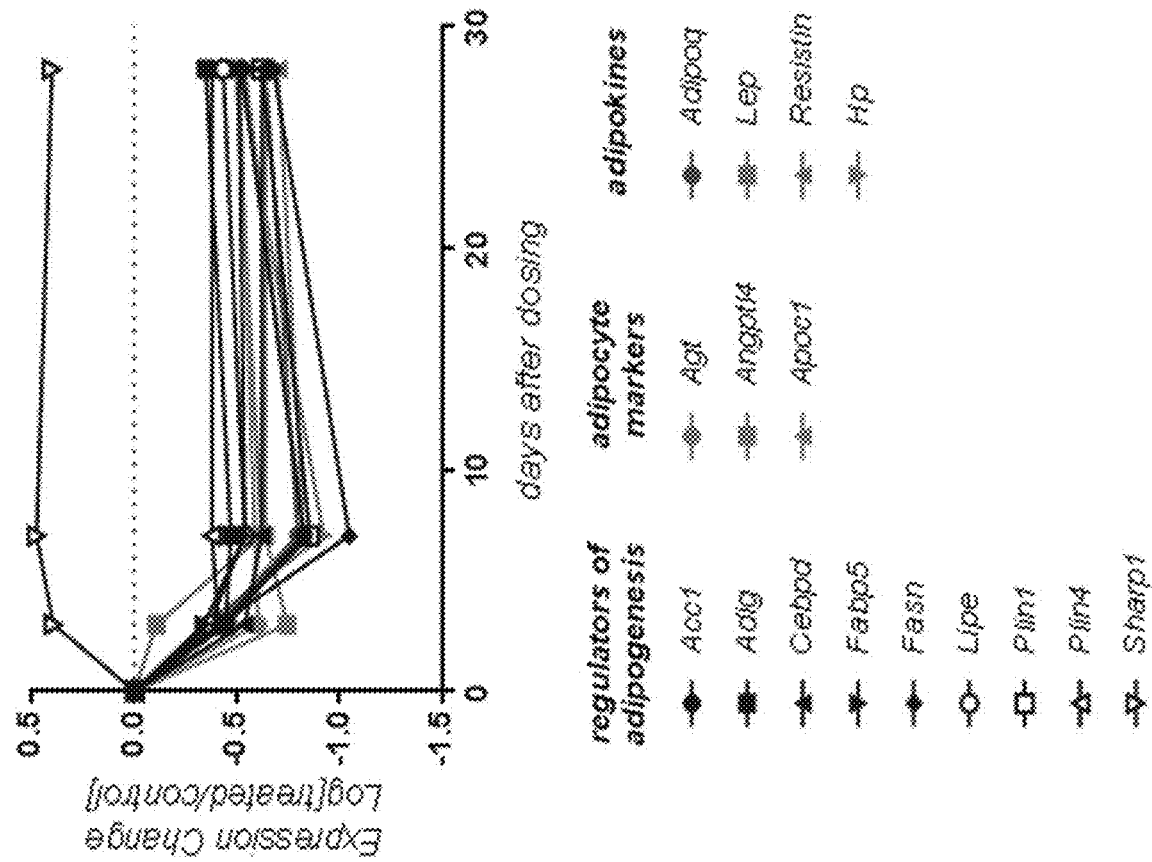
FIG. 20 depicts expression of markers of adipocytes and adipogenesis after Ab2-mediated myostatin inhibition.

A large number of DEGs in the dataset reflect changes in adipocyte differentiation and adipose deposition in Ab2 treated mice. Markers of differentiated adipocytes (Agt, Angptl4, ApoC1) and expression of adipokines (systemic signaling proteins produced by adipocytes), including adiponectin (Adipoq), Leptin (Lep), Resistin (Res), and haptoglobin (Hp) are downregulated (FIG. 20). Myostatin inhibition has previously been shown to inhibit adipocyte differentiation in vitro (reviewed by Singh et al, Front. Cell Dev. Biol., 2014), and these data are consistent with those prior results.

Reduced expression of genes associated with increased adipogenesis (Acc1, Adipogenin (Adig), Cebpd, Fatty Acid Binding Protein 5 (Fabp5), Fatty Acid Synthase (Fasn), Hormone sensitive lipase E (Lipe), and perilipn 1 and 4 (Plin1 and Plin4) was observed. In addition, we note upregulation of Sharp1, a negative regulator of adipogenesis (Gulbagci et al., EMBO Rep., 2009). Taken together, these DEGs suggest a significant decrease in the visceral fat within Ab2 treated muscle.

Myostatin inhibition has previously been shown to alter the phenotype of adipose tissue, driving white adipose tissue (WAT) towards a brown adipose tissue (BAT) phenotype (reviewed by Singh et al., Singh et al, Front. Cell Dev. Biol., 2014). One of the hallmarks of BAT is the upregulation of PGC-1α and UCP-1, while in our dataset we observe a downregulation of these markers. This may be explained, however, by the overall reduction in fat within the Ab2-treated muscle such that, even if browning of the adipose tissue is occurring, we cannot detect it within this large geneset.

Figure 21:
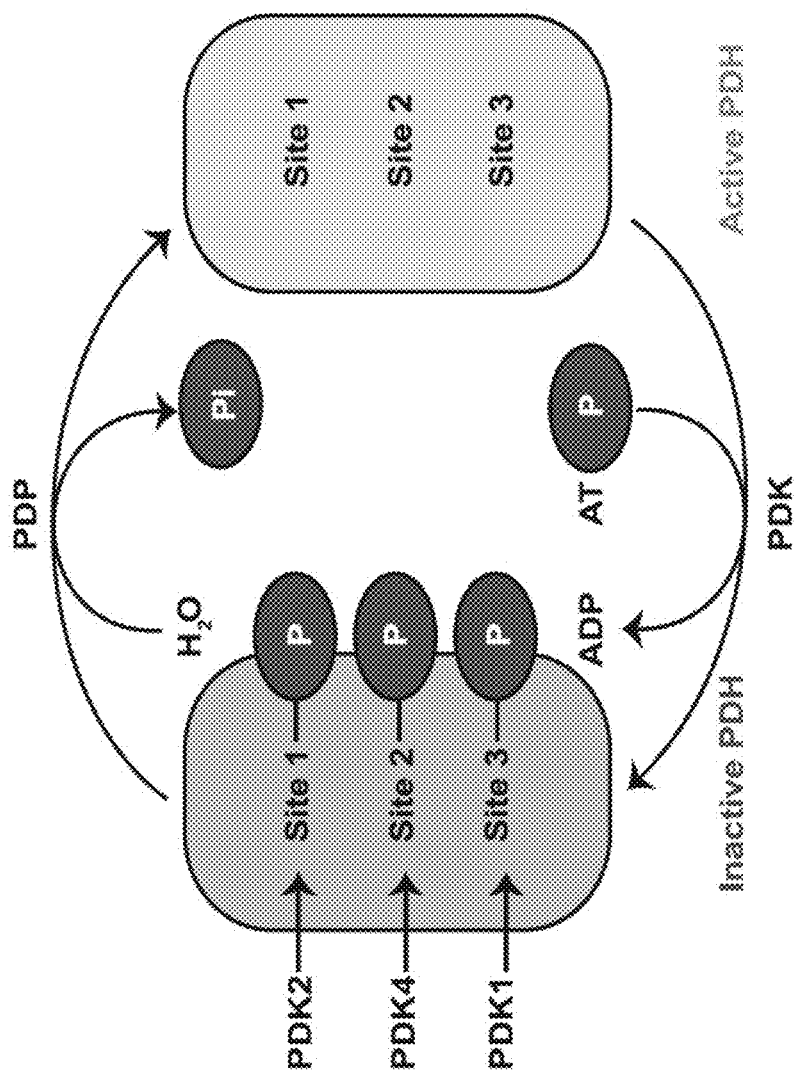
FIG. 21 depicts regulation of pyruvate dehydrogenase.

In addition to the above DEGs, we also noted changes reflecting regulation of the pyruvate dehydrogenase (PDH). PDH is a critical regulator of the Randle cycle, a biochemical mechanism that regulates cellular usage of glucose vs fatty acids as a primary source (reviewed by Hue and Taegtmeyer, Am J Physiol Endocrinol Metab, 2009). The capacity of cells to switch between metabolism of glucose and fatty acids has been termed metabolic flexibility (Storlien et al., PNAS, 2004) and has been tightly related to type 2 diabetes, obesity, and metabolic syndrome (Zhang et al., Nutrition and Metabolism, 2014). PDH activity is controlled by two regulators: pyruvate dehydrogenase kinase 4 (pdk4) and pyruvate dehydrogenase phosphatase (pdp1). Pdk4 inhibits PDH activity by phosphorylating the protein, while Pdp1 activates PDH by dephosphorylation, (FIG. 21). Inactivation of PDH limits conversion of pyruvate into acetyl-CoA in muscle, and this in turn leads to reduced synthesis of malonyl-CoA, an important inhibitor of fatty acid oxidation (Foster, J Clin Invest, 2012). Both knockdown and knockout of Pdk4 (leading to PDH inactivation) lead to improved glycemic control and glucose tolerance in mice (Tao et al., PLoS One, 2013), suggesting that PDH is critical to insulin sensitivity.

Figure 22:
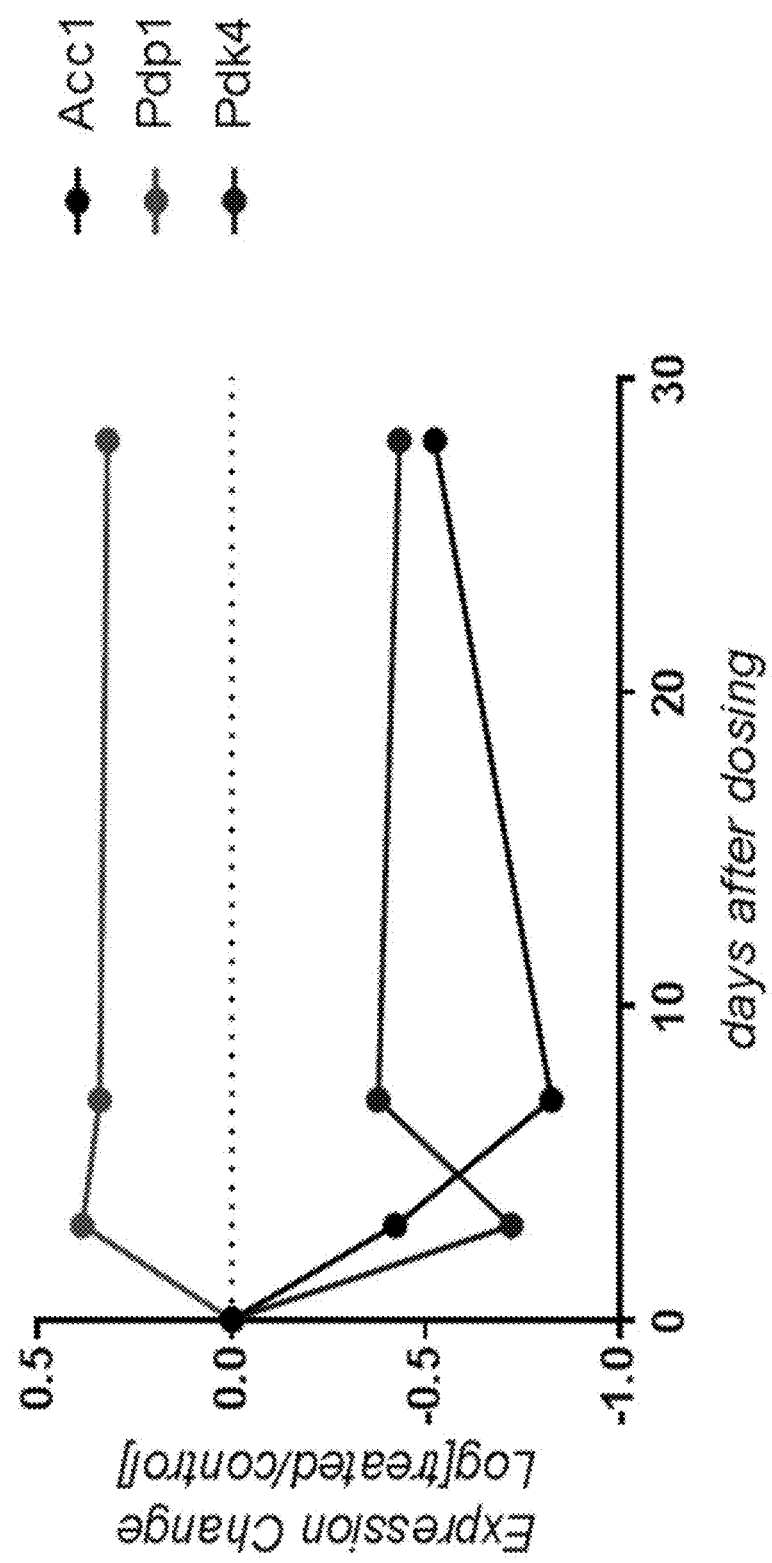
FIG. 22 depicts expression levels of regulators of pyruvate dehydrogenase and fatty acid oxidation.
Figure 23:
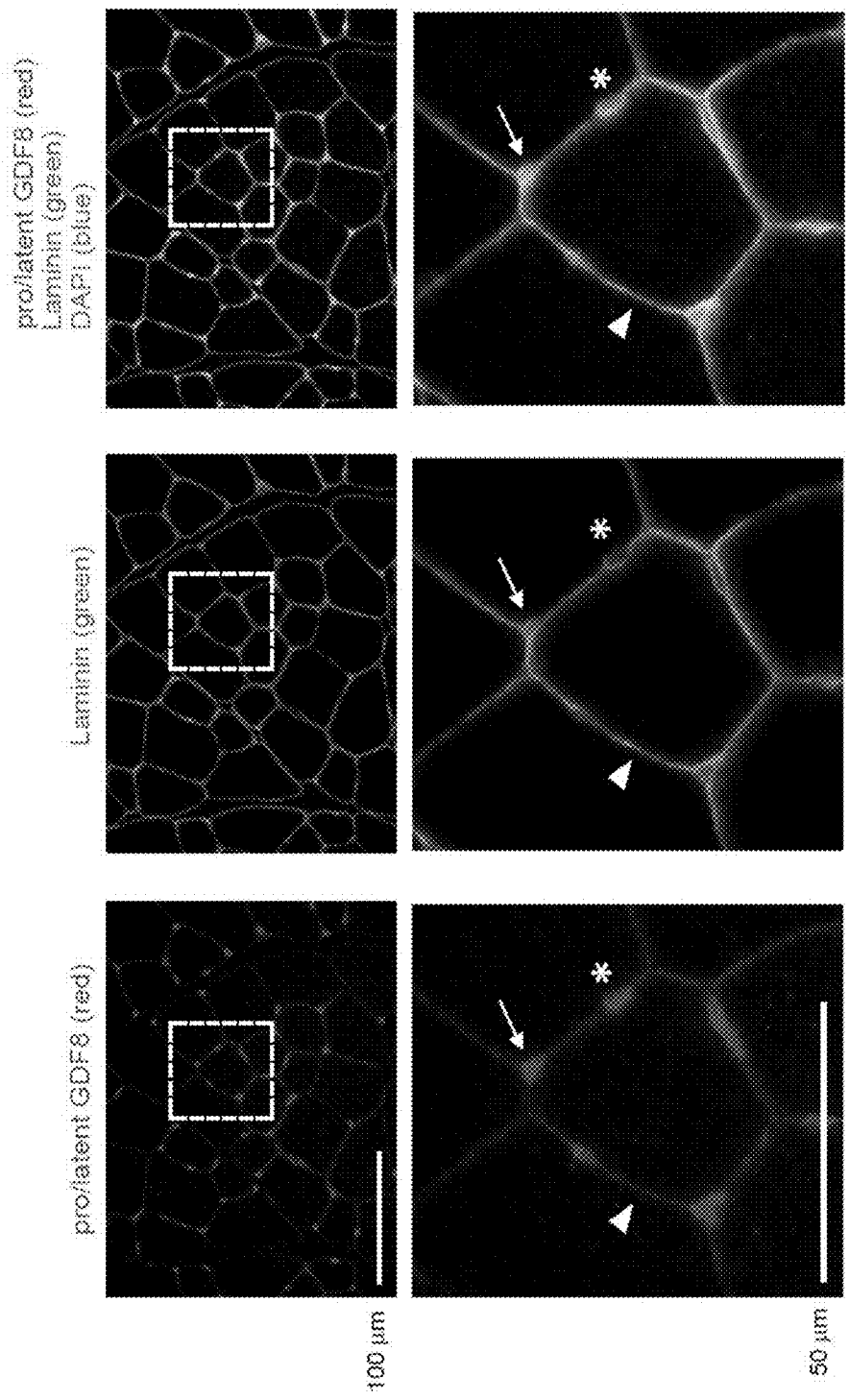
FIG. 23 depicts an immunofluorescence assay performed on cryosectioned tibialis anterior muscle from healthy mice using Ab2, and co-stained with laminin.

In Ab2-treated mice, Pdk4 is downregulated and Pdp1 is upregulated, suggesting activation of PDH (FIG. 22). This is further reflected by downregulation of Acetyl-CoA carpoxylase (Acct), an inhibitor of malonyl-CoA production (reviewed by Hue and Taegtmeyer, Am J Physiol Endocrinol Metab, 2009). Together these data suggest a shift towards fatty acid metabolism in treated mice, suggesting that at least some of the improved glycemic control observed in studies of Myostatin inhibition (Dong et al., Int J Obes, 2016) may be a consequence of direct effects on muscle rather than on cross talk between muscle and adipose tissue, as previously suggested.

Taken together, data from RNA sequencing of transcripts from Ab2-treated mice suggest that Myostatin inhibition is a powerful regulator of muscle and adipose metabolism. Furthermore, the data indicating that Myostatin regulates fatty acid oxidation through PDH suggest a potential novel use for Myostatin inhibitors in increasing metabolic flexibility in patients exhibiting insulin resistance.

Example 4: Intracellular Versus Secreted proMyostatin

Methods

Immunofluorescence

Tibialis anterior (TA) muscles were fixed in ice cold 4% paraformaldehyde (EMS), PBS for 30 min, incubated overnight in 10% sucrose, PBS at 4° C., then incubated overnight in 20% sucrose, PBS. Muscles were then mounted on cork with tragacanth (Sigma) and frozen in liquid nitrogen cooled isopentane (Sigma) for cryosectioning. 10 µm sections of TA muscle were permeabilized with 0.1% Triton-X 100 (Sigma), PBS for 20 minutes, washed once with 0.05% Triton-X 100, PBS (PBS/T), and then incubated in Mouse IgG blocking reagent (Vector Lab) diluted at 1 drop per 1.5 mL PBS/T for 1 h. Sections were washed once with PBS/T and then incubated in 10% Normal Goat Serum (Sigma), 1% Blocking powder (Perkin Elmer), PBS/T (NGB) for 30 minutes at room temperature. Primary antibodies (Rabbit anti-laminin, 1:5000, Abcam; Ab10, 50 µg/mL; HuNeg, 50 µg/mL,) were diluted in NGB and applied to sections overnight at 4° C. Sections were washed 3 times with PBS/T, and then incubated in secondary antibodies (Alexa Fluor 488 conjugated Goat anti-Rabbit, 1:1000, Invitrogen; Alexa Fluor 594 conjugated Goat anti-Human IgG FC ϒ, 1:500, Jackson ImmunoResearch) diluted in NGB for 1 h. Sections were then incubated in 350 nM DAPI (Thermo), PBS/T for 5 minutes, washed twice with PBS/T, and then mounted with Vectashield (Vector Laboratories). For recombinant protein absorption experiments, 50 µg/mL Ab10 was incubated overnight alone or with 10× molar excess of either rGDF8 or rGDF11 (both murine) in NGB, and then used as primary antibody.

Microscopy

Fluorescent images were captured with a Leica DM4 B equipped with 40×/0.80 Fluotar objective using Leica Application Suite X software. Images were then processed with Fiji (Schindelin, J.; Arganda-Carreras, I. & Frise, E. et al. (2012), "Fiji: an open-source platform for biological-image analysis", Nature methods 9(7): 676-682, PMID 22743772).

Results

Previous data suggested that the majority of myostatin found in the muscle is stored as pro-myostatin. However, these methods cannot discriminate between intracellular and secreted stores of pro-myostatin. To address this, immunofluorescence was performed on cryosectioned TA muscle from healthy mice using antibody Ab10 that specifically detects pro- and latent myostatin.

Figure 24A:
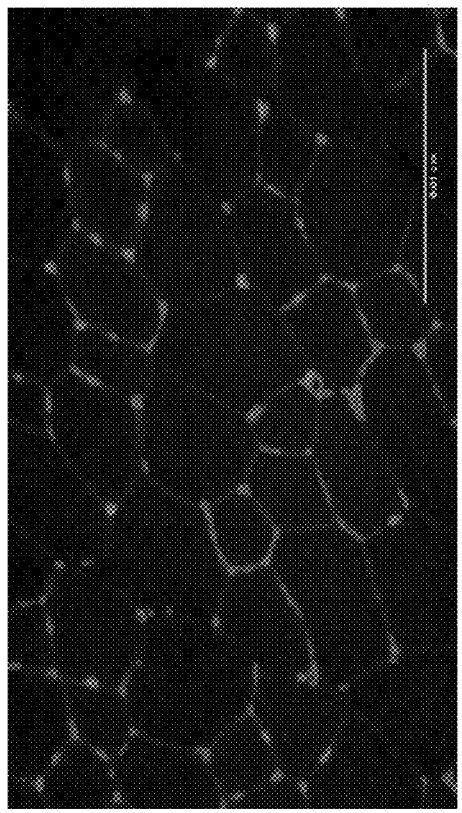
FIGS. 24A-24B show cross sections of tibilias anterior muscle probed with anti-pro/latent GDF8 antibody, Ab10 or non-specific targeting antibody, is shown in FIG. 24A, HuNeg is shown in FIG. 24B, and each of the figures are counterstained with DAPI. The scale bar is 0.01 cm.
Figure 24B:
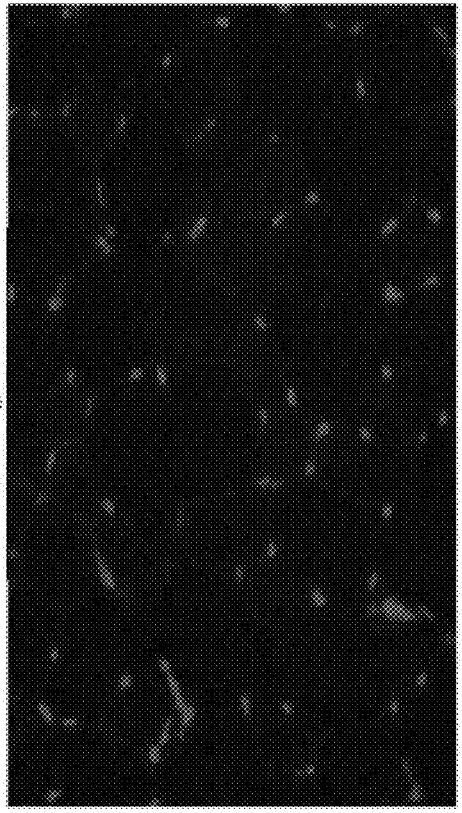
Figures 25A, 25B, 25C:
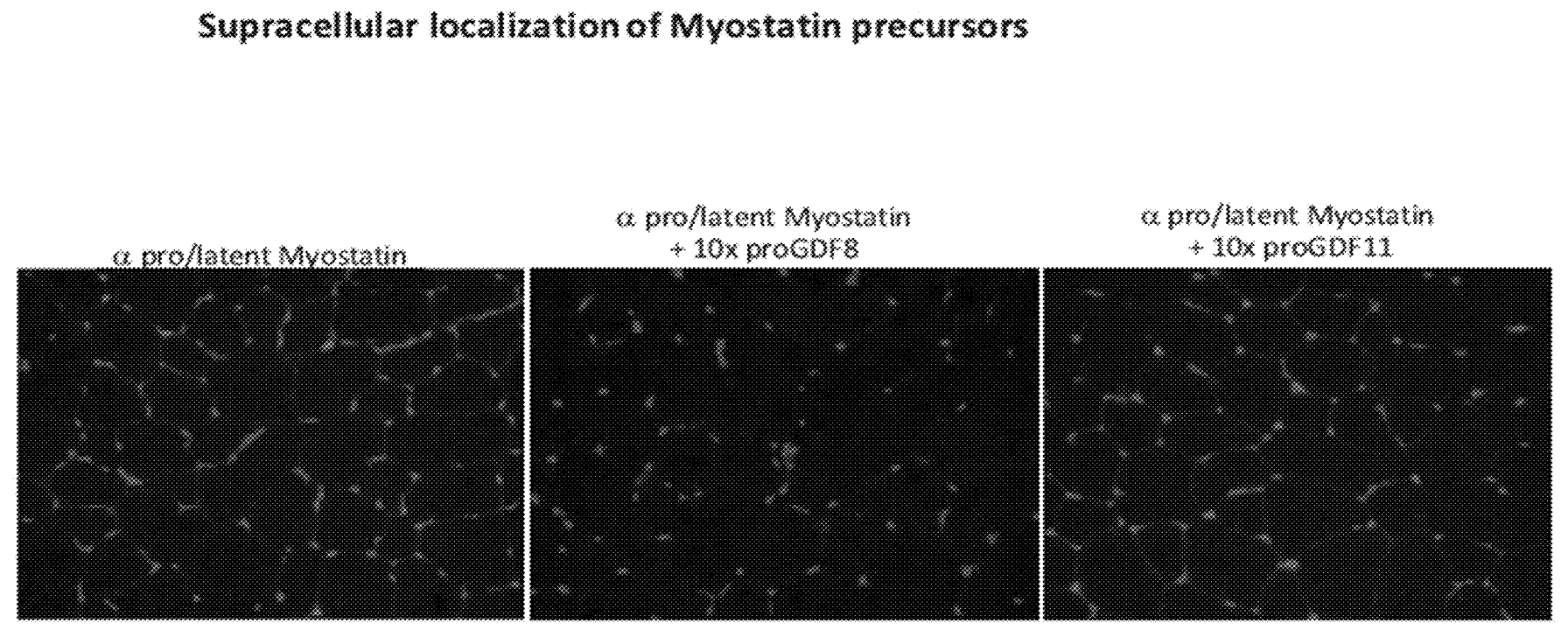
Figures 26A, 26B, 26C:
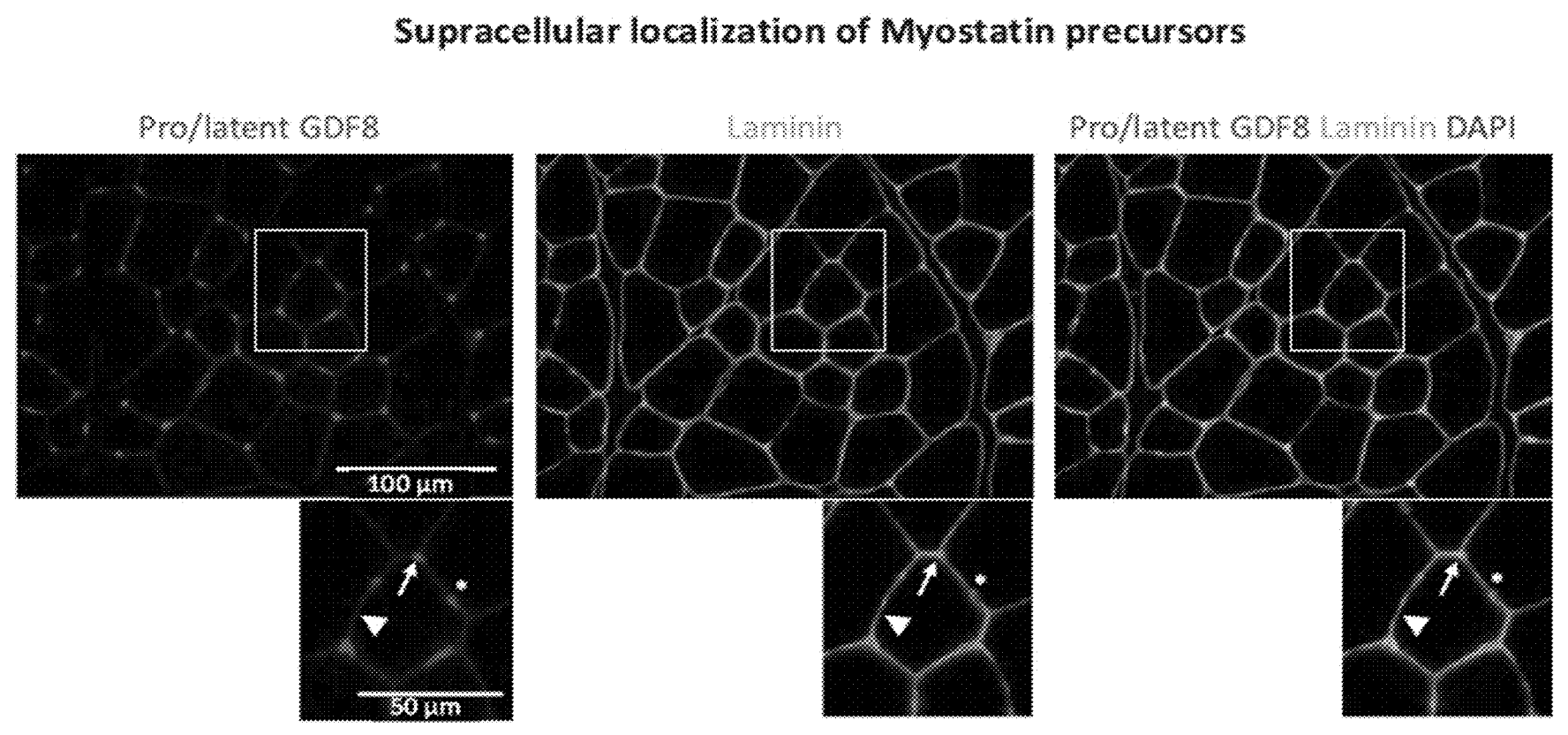

Control experiments to test the specificity of anti-pro/latent GDF8 antibody, Ab10, are shown in FIGS. 24A-24B and FIGS. 25A-25C. FIGS. 24A-24B show cross sections of TA muscle probed with anti-pro/latent GDF8 antibody, Ab10, or a non-specific targeting antibody. Ab10 is shown in FIG. 24A, HuNeg is shown in FIG. 24B, each of the figures are counterstained with DAPI. The scale bar is 0.01 cm. FIGS. 25A-25C show cross sections of TA muscle probed with anti-pro/latent GDF8 antibody, Ab10, that had been incubated in blocking buffer alone (FIG. 25A), incubated in blocking buffer with 10-fold molar excess a recombinant mouse GDF8 (FIG. 25B), or incubated in blocking buffer with 10-fold molar excess of recombinant mouse GDF11 (FIG. 25C). FIGS. 26A-26C are counterstained with DAPI.

Co-staining of anti-pro/latent GDF8 antibody, Ab10, with laminin, an extracellular matrix marker, demonstrated that the majority of myostatin precursors detected in muscle are in the extracellular space with little signal detected intracellularly. FIGS. 23 and 26A-26C show cross sections of TA muscle probed with anti-pro/latent GDF8 antibody, Ab10, and anti-laminin, and counterstained with DAPI. Pro/latent GDF8 and laminin colocalize in the interstitial space at muscle fiber vertices (arrow), between muscle fibers (arrow head), and around interstitial nuclei (asterisk). Thus, in healthy muscle, pro-myostatin lies dormant in a supracellular space, and Ab10 recognizes the major forms of myostatin found in muscle.

Example 5: Effects of Myostatin Inhibition on Bone in an Injury Model

A monoclonal antibody that specifically binds pro/latent forms of myostatin and blocks the activation of mature myostatin was evaluated for its in vivo effects on bone in a cardiotoxin (CTX)-induced Tibialis anterior (TA) acute injury model in mice. Following a 7-day acclimation, animals (n=19 per group) were treated with weekly doses of 40 mg/kg for four weeks. The first dose was given pre-injury (one day before CTX treatment). Doses 2-4 were administered post-injury. Tibia tissues were harvested for bone microCT scan (5 mice per time point).

Raw microCT images of proximal tibia showed a visibly clear increase in trabecular bone in the antibody-treated mice as compared to control mice (images now shown). Results from quantitative analyses are provided in FIG. 28.

Figure 28A:
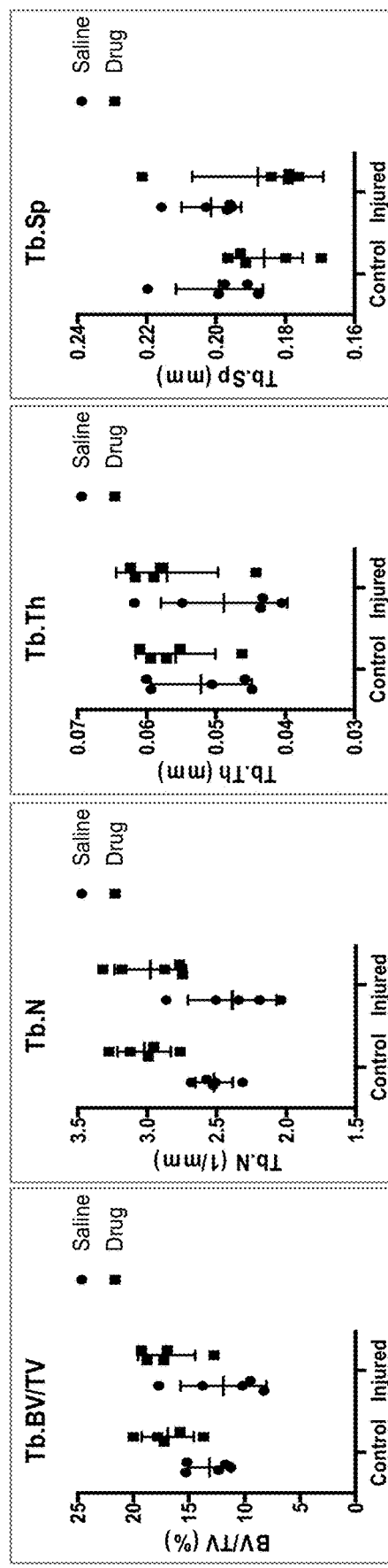
FIGS. 28A-28B show effects of a monoclonal antibody that inhibits activation of myostatin in a cardiotoxin-induced injury model.

FIG. 28A shows that mice treated with the antibody that inhibits myostatin activation increased trabecular bone in proximal tibia. Notably, muscle injury had little impact on trabecular bone; yet, the pro/latent myostatin-targeting drug increased trabecular bone mass.

Figure 28B:
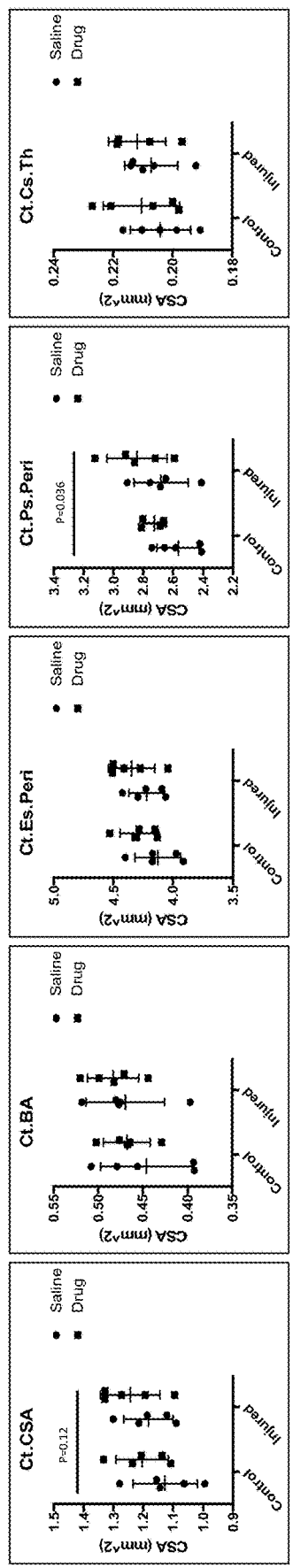

FIG. 28B provides effects on cortical bone in proximal tibia. Cortical bone effects in the antibody-treated animals was present but less pronounced than seen in proximal tibia. An increase in the cross sectional area and outer (periosteal) perimeter of the cortical bone in the antibody-treated animals was seen. It should be noted that cortical bone tends to exhibit smaller changes in bone quality relative to trabecular bone.

Example 6: Effects of Myostatin Inhibition in Murine Model of Mild SMA

To assess the effects of an antibody which inhibits myostatin activation on both muscle function and bone in SMA, a variant of a pharmacological model of SMA, in which the severity of the disease can be moderated through administration of varying amounts of the small molecule SMN2 splice modulator SMN-C1, was used. The foundation of this model is the Δ7 mouse model of severe SMA. This mouse, which lacks the sole endogenous murine SMN gene, expresses two copies of human SMN2 as well as two copies of SMN lacking exon 7 (Smn−/−; hSMN2; SMNΔ7). Due to the severity of disease in this model, the median survival of this mouse is 13 days, which is an insufficient amount of time to assess efficacy of potential therapeutic agents.

Treatment with a high dose of SMN-C1, 3 mg/kg/day, results in a mild form of SMA, with the mice appearing largely healthy and displaying only modest deficits in body weight and motor function. Specifically, treatment with this high dose of SMN-C1 results in significant correction of disease and mimics mild presentations of SMA, such as ambulatory Type 111 or Type IV SMA. In this study, at PND24 mice began treatment with Ab1 (20 mg/kg/week).

Bone Effects

Cortical bone mean crossectional tissue area, mean total crossectional bone area, mean total crossectional tissue perimeter, mean total crossectional bone perimeter, cortical thickness, bone volume, and cortical porosity were measured by micro CT. Trabecular bone volume, trabecular thickness, trabecular number, and trabecular separation/spacing were also measured.

Figure 31:
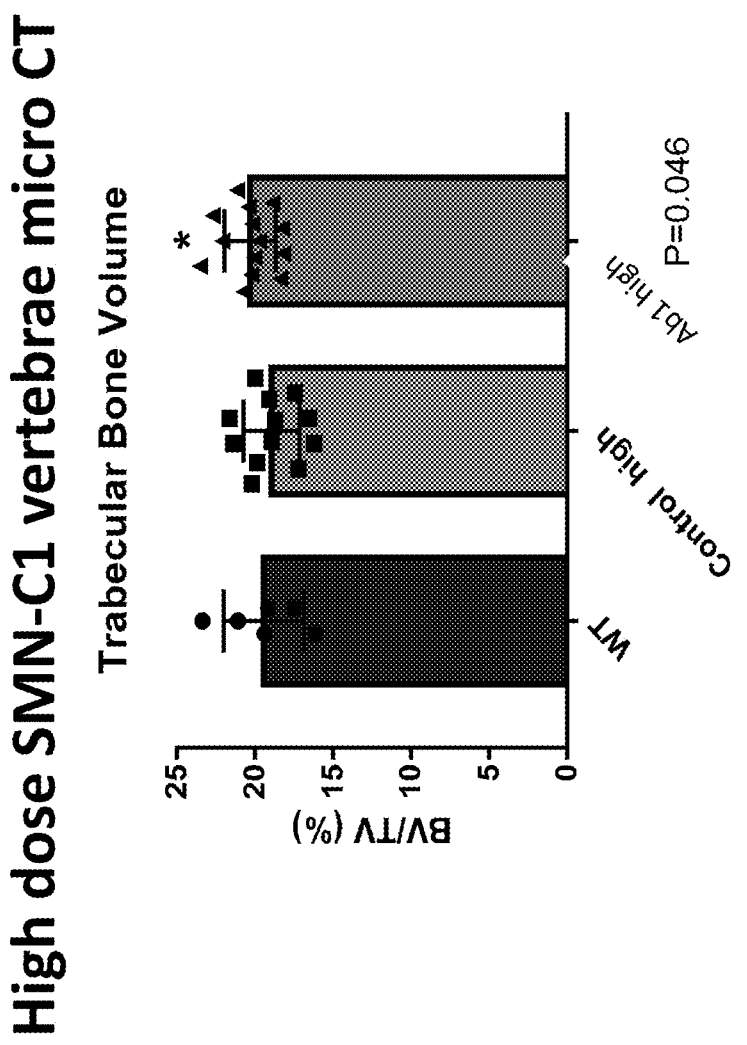
FIG. 31 demonstrates that animals treated with the myostatin inhibitor demonstrated an increase in bone volume in non-weight bearing bone, e.g., the vertebrae.

MicroCT analysis of cortical bone and trabecular bone showed statistically significant increases in the antibody-treated animals as compared to control mice. Results are shown in FIGS. 29-31. FIG. 29 shows that antibody-treated animals exhibited a statistically significant increase in mean total crossectional bone area and cortical thickness as compared to control (PBS). FIG. 30 shows that antibody-treated animals exhibited an increase in trabecular bone volume, trabecular thickness, and trabecular number as compared to control. Additionally, antibody-treated animals showed a decrease in trabecular separation as compared to control.

It is well known in the art that weight-bearing activity is an important stimulus for bone mass accrual. Surprisingly, animals treated with the myostatin antibody demonstrated not only an increase in weight-bearing bone (FIGS. 29 and 30) but also demonstrated an increase in bone volume in non-weight bearing bone, e.g., the vertebrae (FIG. 31). This increase in non-weight bearing bone further demonstrates that the myostatin inhibitors disclosed herein act not only to increase bone volume through, for example, increased muscle stimulation, but also act as a key regulator to increase general metabolic effects, including bone health.

Muscle Effects

Figure 32:
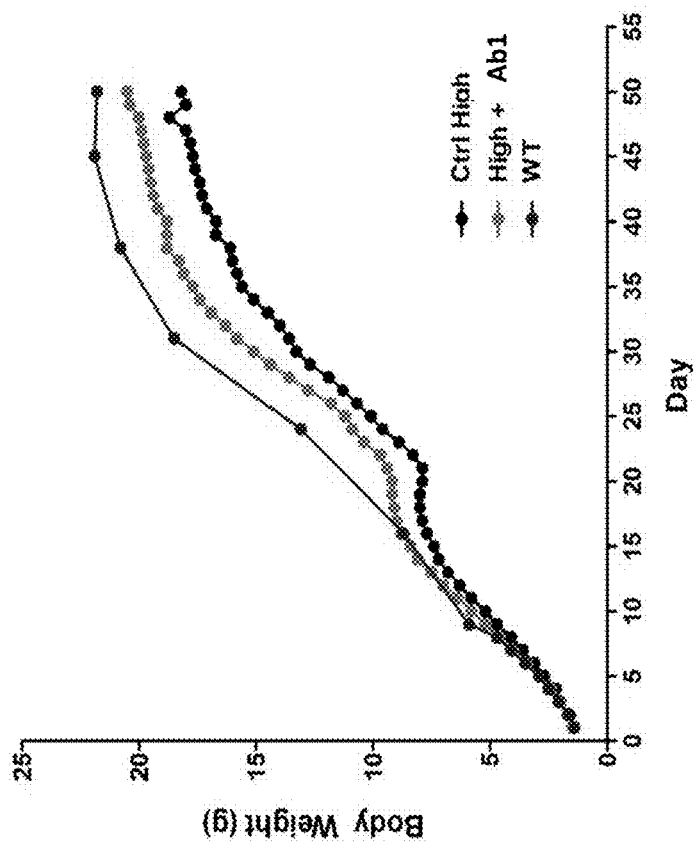
FIG. 32 demonstrates that mice treated with Ab1 exhibited a 14.4% increase in body weight at day 50 as compared to control mice (PBS treatment).
Figure 33:
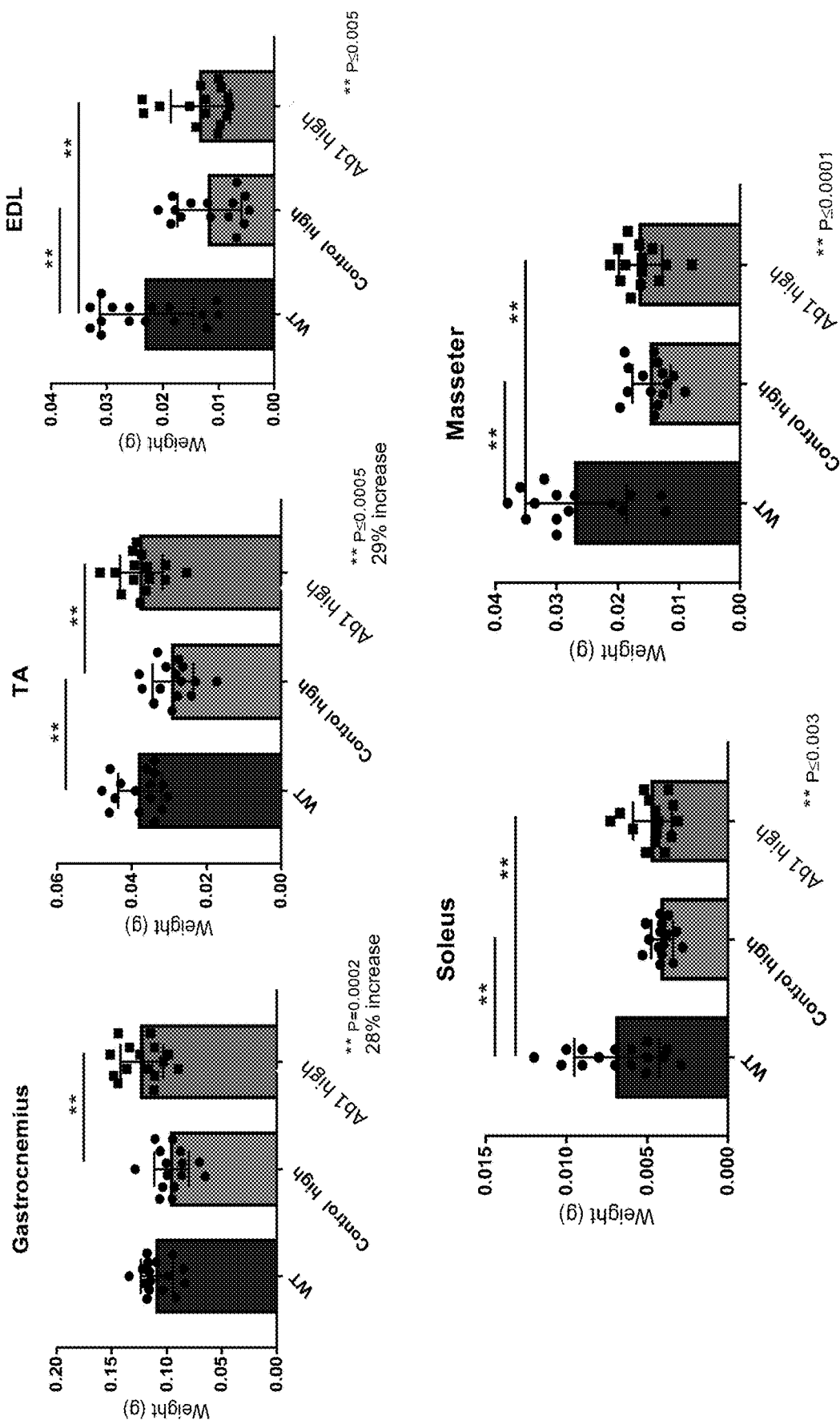
FIG. 33 depicts the increase in weight of several muscles: gastrocnemius, TA, EDL, soleus, and masseter, after treatment with Ab1.
Figure 34A:
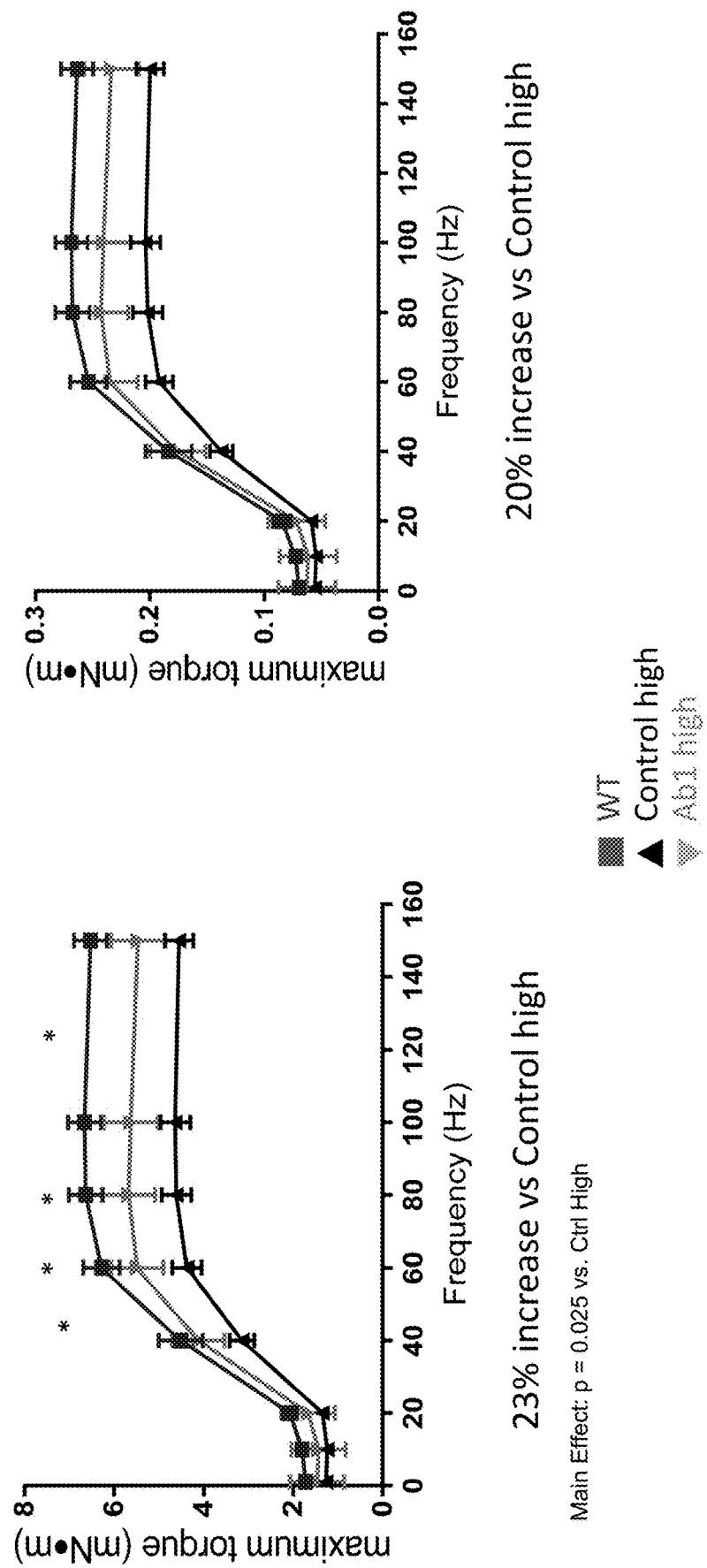
FIG. 34A depicts an increase of 23% in plantarflexor force (maximum torque) after treatment with Ab1 versus PBS control, and a 20% increase in plantarflexor force maximum torque/limb length after treatment with Ab1 versus PBS control.
Figure 34B:
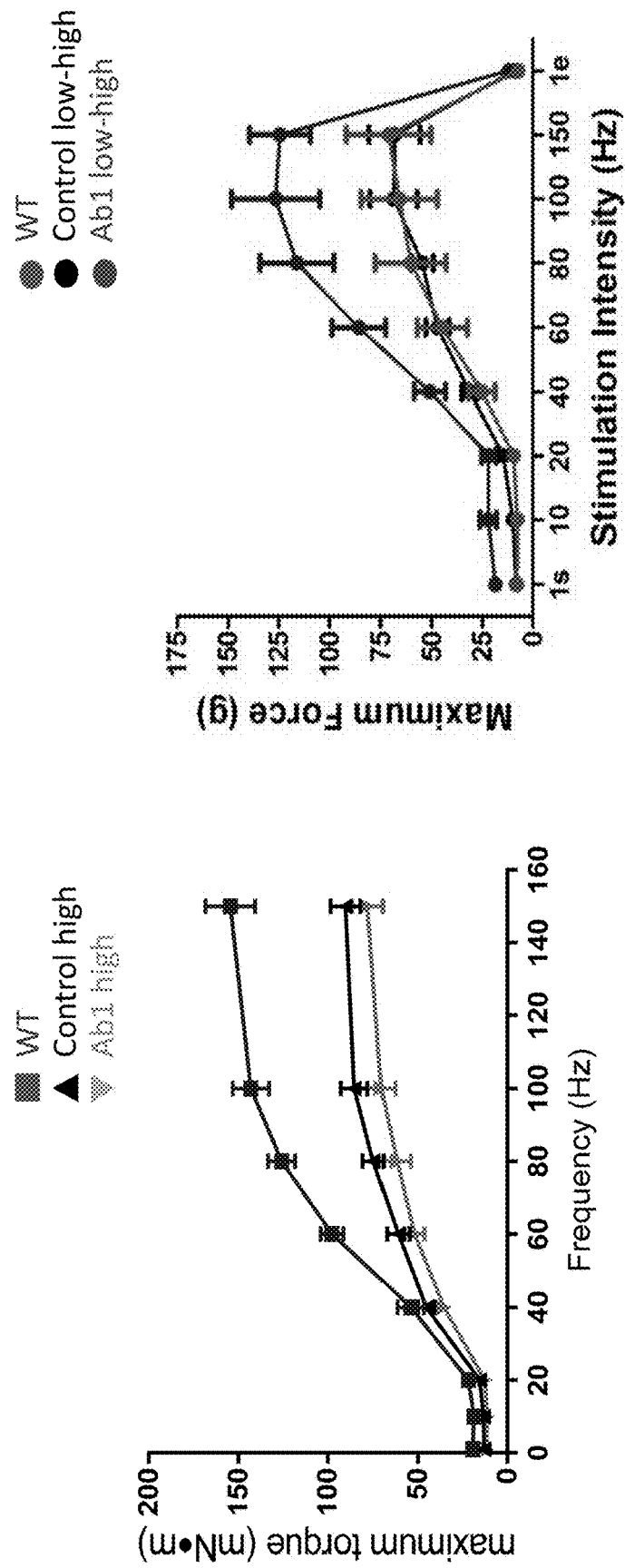
FIG. 34B depicts masseter force after treatment with Ab1 versus controls.

The same pharmacological model of SMA was also used to assess muscle function in animals treated with an inhibitor of myostatin activation versus control. Total body weight, specific muscle weights, muscle force, and muscle fiber type and cross sectional areas were measured. FIG. 32 demonstrates that mice treated with Ab1 exhibited a 14.4% increase in body weight at day 50 as compared to control mice (PBS treatment), and FIG. 33 depicts the increase in weight of several muscles: gastrocnemius, TA, EDL, soleus, and masseter, after treatment with Ab1. FIG. 34A depicts an increase of 23% in plantarflexor force (maximum torque) after treatment with Ab1 versus PBS control, and a 20% increase in plantarflexor force maximum torque/limb length after treatment with Ab1 versus PBS control. FIG. 34B depicts masseter force in Ab1-treated mice as compared to controls.

The differential efficacy of antibody treatment on the gastrocnemius (which constitutes the bulk of the plantarflexor group) and the masseter may be attributed to many facets of SMA disease pathology. For example, among other factors, it is known that myostatin inhibition preferentially results in hypertrophy of fast glycolytic muscle fibers (Type IIB in the mouse) (see PCT/US2017/037332, the entire contents of which are incorporated herein by reference). While the mouse gastrocnemius muscle consists primarily of Type IIB fibers (~75%), the masseter has significantly fewer, between 10 and 25%. Therefore, it is not surprising that masseter weight and force did not increase after treatment with the myostatin antibody.

Figure 35:
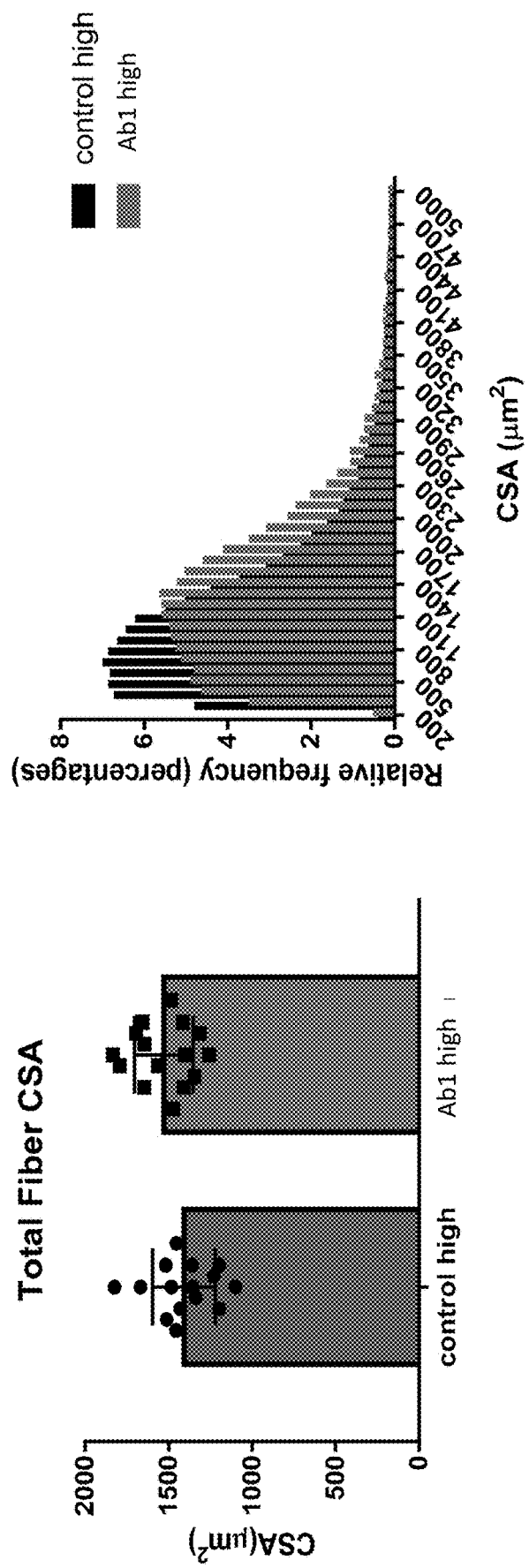
FIG. 35 depicts histology data from a high-dose SMN-C1 cohort and shows the total fiber cross sectional area (CSA) and a histogram of CSA distribution in control (vehicle) versus Ab1 treated animals, demonstrating an increasing trend in fiber CSA. This trend was attributed entirely to type IIb fibers (data not shown).

FIG. 35 depicts histology data from the high-dose SMN-C1 cohorts. Specifically, FIG. 35 shows the total fiber cross sectional area (CSA) and a histogram of CSA distribution in control (vehicle) versus Ab1 treated animals, demonstrating an increasing trend in fiber CSA. This increase was attributed entirely to type IIb fibers (data not shown).

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The invention claimed is:

1. A method of making a pharmaceutical composition comprising a myostatin-selective inhibitor, the method comprising:
   (i) screening for an antibody or an antigen-binding fragment thereof that selectively binds to myostatin and/or a protein complex comprising myostatin and is capable of decreasing expression of pyruvate dehydrogenase kinase 4 (PDK4) and increasing expression of pyruvate dehydrogenase phosphatase 1 (PDP1) in a human subject after administration to the subject;
   (ii) culturing host cells comprising one or more polynucleotides encoding the antibody or antigen-binding fragment under conditions that allow for expression of the antibody or antigen-binding fragment;
   (iii) purifying the antibody or antigen-binding fragment from the culture; and,
   (iv) formulating the antibody or antigen-binding fragment into a pharmaceutical composition suitable for administration to the subject, wherein the composition further comprises a pharmaceutically acceptable carrier or excipient.

2. The method of claim 1, wherein the host cells are CHO cells, 293 cells, or NSO cells.

3. The method of claim 1, wherein the pharmaceutical composition is formulated for subcutaneous administration to a subject.

4. The method of claim 1, wherein the antibody or antigen-binding fragment is screened for the ability to bind to Activin A, wherein the antibody or antigen-binding fragment does not bind to Activin A.

5. The method of claim 1, wherein the pharmaceutical composition further comprises an insulin secretion-promoting agent.

6. The method of claim 1, wherein the subject has or is at risk of developing a metabolic disease, wherein optionally the metabolic disease is obesity.

7. The method of claim 6, wherein the obesity is obesity associated with type II diabetes.

* * * * *